(12) United States Patent  
Forsblom et al.

(10) Patent No.: US 8,188,101 B2
(45) Date of Patent: May 29, 2012

(54) DIHYDROPYRIDOPYRIMIDINES FOR THE TREATMENT OF AB-RELATED PATHOLOGIES

(75) Inventors: Rickard Forsblom, Södertälje (SE); Kim Paulsen, Södertälje (SE); Didier Rotticci, Södertälje (SE); Ellen Santangelo, Södertälje (SE); Magnus Waldman, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 217 days.

(21) Appl. No.: 12/613,935

(22) Filed: Nov. 6, 2009

(65) Prior Publication Data

US 2010/0130495 A1 May 27, 2010

Related U.S. Application Data

(60) Provisional application No. 61/111,786, filed on Nov. 6, 2008, provisional application No. 61/179,088, filed on May 18, 2009, provisional application No. 61/179,459, filed on May 19, 2009.

(51) Int. Cl.
*A61K 31/519* (2006.01)

(52) U.S. Cl. .................................... 514/264.1; 544/279

(58) Field of Classification Search .................. 544/279
See application file for complete search history.

(56) References Cited

U.S. PATENT DOCUMENTS

| 2005/0197361 A1 | 9/2005 | Jirgensons et al. |
| 2006/0004013 A1 | 1/2006 | Kimura et al. |
| 2008/0171771 A1 | 7/2008 | Arnold et al. |
| 2008/0280948 A1 | 11/2008 | Baumann et al. |
| 2009/0099195 A1 | 4/2009 | Bayrakdarian et al. |
| 2009/0099217 A1 | 4/2009 | Berg et al. |
| 2009/0203697 A1 | 8/2009 | Kimura et al. |
| 2010/0105904 A1 | 4/2010 | Kimura et al. |
| 2010/0292210 A1 | 11/2010 | Lo-Alfredsson et al. |

FOREIGN PATENT DOCUMENTS

| EP | 1352659 A1 | 10/2003 |
| EP | 1348707 B1 | 8/2010 |
| WO | 2004073705 A1 | 9/2004 |
| WO | 2004110350 A2 | 12/2004 |
| WO | 2005012304 A2 | 2/2005 |
| WO | 2005013985 A1 | 2/2005 |
| WO | 2005054193 A1 | 6/2005 |
| WO | 2005115990 A1 | 12/2005 |
| WO | 2007035873 A1 | 3/2007 |
| WO | 2007042299 A1 | 4/2007 |
| WO | 2007044698 A1 | 4/2007 |
| WO | 2007114771 A1 | 10/2007 |
| WO | 2007125364 A1 | 11/2007 |
| WO | 2007135969 A1 | 11/2007 |
| WO | 2007139149 A1 | 12/2007 |
| WO | 2007149033 A1 | 12/2007 |
| WO | 2008006103 A2 | 1/2008 |
| WO | 2008097538 A1 | 8/2008 |
| WO | 2008099210 A1 | 8/2008 |
| WO | 2008100412 A1 | 8/2008 |
| WO | 2008136756 A1 | 11/2008 |
| WO | 2009020580 A1 | 2/2009 |
| WO | 2009032277 A1 | 3/2009 |
| WO | 2009073777 A1 | 6/2009 |
| WO | 2009073779 A1 | 6/2009 |
| WO | 2009076337 A1 | 6/2009 |
| WO | 2009087127 A1 | 7/2009 |
| WO | 2009103652 A1 | 8/2009 |
| WO | 2010070008 A1 | 6/2010 |
| WO | 2010075204 A2 | 7/2010 |
| WO | 2010083141 A1 | 7/2010 |
| WO | 2010089292 A1 | 8/2010 |
| WO | 2010094647 A1 | 8/2010 |
| WO | 2010132015 A1 | 11/2010 |

OTHER PUBLICATIONS

Aharony et al, J Pharmacol Exp Ther 1995, 274(3), 1216-1221.
Beher, Curr top Med Chem 2008, 8(1), 34-37.
Maggi et al, J Pharmacol Exp Ther 1994, 271(3), 1489-1500.
Weggen et al, Nature 2001, 414(6860), 212-216.

*Primary Examiner* — James O Wilson
*Assistant Examiner* — Brian McDowell
(74) *Attorney, Agent, or Firm* — Kenneth F. Mitchell

(57) ABSTRACT

Dihydropyridopyrimidine compounds of formula (Ia)

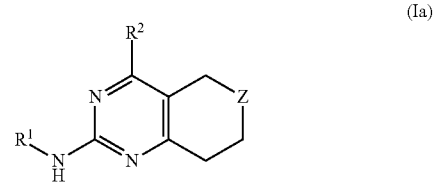

(Ia)

and therapeutically acceptable salts thereof, wherein $R^1$, $R^2$ and Z are as defined in the specification; processes for making them and methods for using them in the treatment of Aβ-related pathologies.

5 Claims, No Drawings

DIHYDROPYRIDOPYRIMIDINES FOR THE TREATMENT OF AB-RELATED PATHOLOGIES

This application claims the benefit of US Provisional Patent Applications Numbered 61/111,786 filed 6 Nov. 2008, 61/179,088 filed 18 May 2009 and 61/179,459 filed 19May 2009.

TECHNICAL FIELD OF THE INVENTION

The present invention relates to novel compounds and pharmaceutically acceptable salt thereof. Furthermore, the present invention also relates to pharmaceutical compositions comprising said compounds, processes for making said compounds and their use as medicaments for treatment and or prevention of various diseases. In particular, the present invention relates to compounds, which interfer with γ-secretase and or its substrate and hence modulate the formation of Aβ peptides. These compounds are used for treatment and or prevention of Aβ-related pathologies, such as Alzheimer's disease, Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

BACKGROUND OF THE INVENTION

The prime neuropathological event distinguishing Alzheimer's disease (AD) is deposition of the amyloid β-peptide (Aβ) in brain parenchyma and cerebral vessels. A large body of genetic, biochemical and in vivo data support a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ, mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Aβ can be found in both plasma, cerebrospinal fluid (CSF), and in the medium from cultured cells, and is generated as a result of APP proteolysis. There are two main cleavages of APP that results in Aβ production, the so-called β-, and γ-cleavages. The β-cleavage, which generates the N terminus of Aβ, is catalyzed by the transmembrane aspartyl protease BACE1. The γ-cleavage, generating the Aβ C termini and subsequent release of the peptide, is effected by a multi-subunit aspartyl protease named γ-secretase. Both BACE1 and γ-secretase processes APP at different sites, resulting in Aβ peptides of different lengths and heterologous N- and C-termini. The invention described herein covers all N-terminal variants of Aβ. Therefore, for the sake of simplicity, all N-terminal variants will be covered by the denotation Aβ.

The activity of γ-secretase causes the liberation of many Aβ peptides, such as Aβ37, Aβ38, Aβ39, Aβ40, Aβ42 and Aβ43, of which Aβ40 is the most common These peptides show a different propensity to aggregate, and in particular Aβ42 is prone to form oligomers and fibrillar deposits. Intriguingly, human genetics strongly support a key role for Aβ42 as a key mediator of Alzheimer pathogenesis. Indeed, more than 150 different mutations causing familial Alzheimer's disease either result in an increase in the ratio of Aβ 42/40 peptides produced or affect the intrinsic aggregation behaviour of Aβ. Based on this knowledge, Aβ42 has become a prime target for therapeutic intervention in AD (Beher D, *Curr Top Med Chem* 2008; 8(1):34-7). Targeting Aβ42 at the level of γ-secretase activity must however be conducted with caution since γ-secretase catalyses proteolysis of many proteins, which have important physiological functions. Among its many substrates is the Notch receptor family, which signaling is essential for many different cell fate determination processes e.g. during embryogenesis and in the adult. As such, Aβ42 lowering strategies at the level of γ-secretase must be compatible with maintained Notch signaling.

Encouragingly, an enormous scientific effort and progress have suggested that it is indeed possible to combine γ-secretase interference and lowered Aβ42 production without obtaining toxic side effects due to impaired Notch signaling There have for instance been reports, which postulate that allosteric modulation of γ-secretase combines lowered Aβ42 production with maintained Notch signaling (Weggen et al. Nature 414(6860), 212-216 (2003)). In addition, a number of compounds interfering with γ-secretase and Aβ production have been suggested, in e.g. WO2005/054193, WO2005/001398, WO2004/073705, WO2007/135969, WO2007/139149, WO2005/115990, WO2008/097538, WO2008/099210, WO2008/100412, WO2007/125364 and WO2009/103652.

The present invention describes a new class of compounds, said compounds will inhibit the Aβ40 and 42 production, increase Aβ37 and Aβ38 levels and maintaining Notch signaling. These compounds will thus be useful in the prevention and/or treatment of Alzheimer's Disease (AD).

DISCLOSURE OF THE INVENTION

It has been found that compounds of the Formula (I), herein also referred to as the compounds of the (present) invention, are affecting the γ-secretase mediated processing of APP and thereby lowering the secretion of Aβ42 and Aβ40 peptides while causing an increase in the secreted levels of Aβ37 and Aβ38 and maintaining Notch signaling. These compounds can be used for treatment and/or prevention of Aβ-related pathologies.

Hence, the present invention relates to a compound according to formula (I)

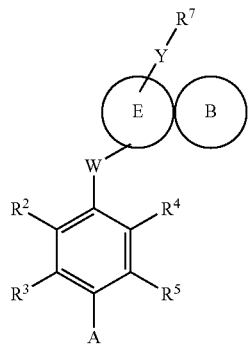

wherein
E is

wherein X and V are independently selected from nitrogen or CH and wherein at least one of X or V is nitrogen;
W is —C($R^6$)$_2$—, —O— or —N($R^6$)—;
$R^6$ is hydrogen, $C_{1-4}$alkyl or $C_{1-4}$alkoxy, wherein said $C_{1-4}$alkyl is substituted with halogen, cyano, hydroxy, amino, NH$C_{1-4}$alkyl, N($C_{1-4}$alkyl)$_2$, heterocyclyl, NC(O)$C_{1-4}$alkyl, C(O)$C_{1-4}$alkoxy or SO$_2C_{1-6}$alkyl;
Y is —C($R^{12}$)($R^{13}$)—, —N($R^8$)— or —O—;
$R^{12}$ and $R^{13}$ are independently selected from hydrogen, halogen, $C_{1-6}$alkyl, $C_{1-6}$alkylO$C_{1-6}$alkyl, carbocyclyl, heterocyclyl and $C_{1-6}$alkoxy, wherein said $C_{1-6}$alkyl, $C_{1-6}$alkylO$C_{1-6}$alkyl, carbocyclyl, heterocyclyl or $C_{1-6}$alkoxy is optionally substituted with one or more substituents selected from halogen, cyano, hydroxy, heterocyclyl, N($C_{0-4}$alkyl)$_2$, NC(O)$C_{1-4}$alkyl;
or
$R^{12}$ and $R^{13}$ may form together with the carbon atom they are attached to a saturated, partially unsaturated or saturated ring system, wherein said ring system may contain one or more heteroatoms selected from N, O and S, and wherein if said ring system contains an nitrogen atom that nitrogen may optionally be substituted with a group selected from $C_{1-6}$alkyl and C(O)$C_{1-6}$alkyl and wherein said ring is optionally substituted with one or more groups selected from halogen, cyano, hydroxy;
or
$R^{12}$ and $R^7$ may form together a saturated, partially unsaturated or saturated bicyclic ring system, wherein said bicyclic ring system may contain zero to three heteroatoms selected from N, O and S, and wherein said bicyclic ring system is optionally substituted with one to three substituents selected from halogen, cyano, hydroxy, $C_{1-6}$alkoxy, amino, NH$C_{1-4}$alkyl, N($C_{1-6}$alkyl)$_2$, NC(O)$C_{1-6}$alkyl, SO$_2C_{1-6}$alkyl and heterocyclyl, and wherein if said bicyclic ring system contains an nitrogen atom that nitrogen may optionally be substituted by a group selected from $C_{1-6}$alkyl and C(O)$C_{1-6}$alkyl;
$R^8$ is selected from hydrogen, $C_{1-6}$alkyl, $C_{1-6}$alkylO$C_{1-6}$alkyl, C(O)$C_{1-6}$alkyl, C(O) cycloalkyl, heterocyclyl, carbocyclyl, C(O) heterocyclyl or SO$_2C_{1-6}$alkyl, wherein said $C_{1-6}$alkyl, heterocyclyl, carbocyclyl or $C_{1-6}$alkylO$C_{1-6}$alkyl is optionally substituted with one to three substituents selected from halogen, cyano, hydroxy, amino, NH$C_{1-4}$alkyl, N($C_{1-6}$alkyl)$_2$, NC(O)$C_{1-6}$alkyl, C(O)$C_{1-6}$alkoxy, SO$_2C_{1-6}$alkyl and heterocyclyl;
$R^7$ is selected from hydrogen, aryl, heteroaryl, $C_{1-4}$alkylaryl, $C_{1-4}$alkylheteroaryl, $C_{1-4}$alkylcarbocyclyl, $C_{1-4}$alkylheterocyclyl and carbocyclyl, wherein said aryl, heteroaryl, $C_{1-4}$alkylcarbocyclyl, $C_{1-4}$alkylheterocyclyl, $C_{1-4}$alkylaryl, carbocyclyl or $C_{1-4}$alkylheteroaryl is optionally substituted with one or more substituents selected from halogen, cyano, hydroxy, nitro, $C_{1-6}$alkyl, $C_{1-6}$alkoxy, carbocyclyl, heterocyclyl, CF$_3$, OCF$_3$, O$C_{1-6}$alkyl, C(O)$C_{1-6}$alkyl, $C_{1-6}$alkylO$C_{1-6}$alkyl, SO$_2C_{1-6}$alkyl, SO$_2$NH$C_{1-6}$ alkyl, SO$_2$N($C_{1-6}$alkyl)$_2$, SO$_2$N-heterocyclyl, C(O)NH$_2$, C(O)NH$C_{1-6}$alkyl, C(O)N($C_{1-6}$alkyl)$_2$, C(O)N-heterocyclyl, $C_{2-6}$alkenyl and $C_{2-6}$alkynyl, wherein said $C_{1-6}$alkyl, $C_{1-6}$alkoxy, $C_{1-6}$alkylO$C_{1-6}$alkyl, heterocyclyl, carbocyclyl, $C_{2-6}$alkenyl or $C_{2-6}$alkynyl is optionally substituted with cyano, hydroxy, methoxy, halogen, SO$_2C_{1-4}$ alkyl, amino, NH$C_{1-4}$alkyl, N($C_{1-4}$alkyl)$_2$, heterocyclyl or aryl;
or
$R^8$ and $R^7$ may, when Y is NR$^8$, optionally form together with the nitrogen atom a saturated, partially saturated or unsaturated ring system, wherein said ring system is optionally substituted with one or more groups selected from halogen, hydroxy, cyano, $C_{1-4}$alkylO$C_{1-4}$alkyl and $C_{1-4}$alkyl, wherein said $C_{1-4}$alkylO$C_{1-4}$alkyl or $C_{1-4}$alkyl is optionally substituted with halogen, cyano, hydroxy;
$R^1$ is selected from hydrogen, $C_{1-6}$alkyl, $C_{1-6}$alkoxy, $C_{2-6}$alkenyl, $C_{2-6}$alkynyl, carbocyclyl, heterocyclyl, C(O)$R^9$, C(O)N($R^9$)$_2$, C(O)CH$_2$N($R^9$)$_2$, C(O)heterocyclyl, C(O)carbocyclyl, C(O)O$R^9$, SO$_2R^9$, SO$_2$heterocyclyl, SO$_2$carbocyclyl and SO$_2$N($R^9$)$_2$, wherein said $C_{1-6}$alkyl, $C_{1-6}$alkoxy, $C_{2-6}$alkenyl, $C_{2-6}$alkynyl, carbocyclyl or heterocyclyl is optionally substituted with one or more substituents selected from halogen, hydroxy, cyano, amino, C(O)O$R^9$, NH$C_{1-6}$alkyl, NH$C_{1-6}$alkoxy, N($C_{1-6}$alkyl)$_2$, N($C_{1-6}$alkoxy)$_2$, S$C_{1-6}$alkyl, SO$C_{1-6}$alkyl, SO$_2C_{1-6}$alkyl, $C_{1-6}$alkyl, $C_{1-6}$alkoxy, heterocyclyl and carbocyclyl;
$R^9$ is selected from hydrogen, hydroxy, halogen, cyano, $C_{1-6}$alkyl, $C_{1-6}$alkoxy, carbocyclyl and heterocyclyl, wherein said $C_{1-6}$alkyl, $C_{1-6}$alkoxy, cycloalkyl or heterocyclyl is optionally substituted with one or more substituents selected from halogen, cyano, hydroxy or methoxy;
$R^4$, $R^5$, $R^3$ and $R^2$ are independently selected from hydrogen, cyano, $C_{1-4}$alkoxy, $C_{1-4}$alkoxy, halogen, OCH$_3$, OCF$_3$, OCF$_2$H, OCFH$_2$ and hydroxy;
A is a 5-7 membered heteroaryl, wherein at least one of the ring forming atoms is selected from nitrogen and the remaining ring forming atoms are selected from carbon, nitrogen, sulphur and oxygen, and wherein said A is optionally substituted with one or more substituents selected from halogen, $C_{1-4}$alkyl, S$R^{10}$, N$R^{10}R^{11}$, O$R^{10}$, $C_{2-4}$alkenyl and $C_{2-4}$alkynyl and wherein said $C_{1-4}$alkyl, $C_{2-4}$alkenyl or $C_{2-4}$alkynyl is optionally substituted with halogen, hydroxy, cyano or $C_{1-4}$alkoxy;
$R^{10}$ and $R^{11}$ are independently selected from hydrogen, $C_{1-4}$alkyl, CF$_3$, CF$_2$H and CFH$_2$;
B is a 5 to 7 membered non-aromatic saturated ring, wherein one of the ring forming atom is selected from —N($R^1$)—, —C($R^9$)—, —S(O)$_n$— or —O— and the other ring forming atoms are carbon, wherein one —CH$_2$— group can optionally be replaced by a —C(O)— and wherein said ring is optionally substituted with one to three substituents selected from halogen, cyano, hydroxy, amino, $C_{1-4}$alkyl, $C_{1-4}$alkoxy, $NHC_{1-6}$alkyl, $NHC_{1-6}$alkylOC$_{1-6}$alkyl, $N(C_{1-6}$alkyl)$_2$, $N(C_{1-6}$alkylOC$_{1-6}$alkyl)$_2$, carbocyclyl and heterocyclyl, wherein said $C_{1-4}$alkyl, $C_{1-4}$alkoxy, $NHC_{1-6}$alkyl, $NHC_{1-6}$alkylOC$_{1-6}$alkyl, $N(C_{1-6}$alkyl)$_2$, $N(C_{1-6}$alkylOC$_{1-6}$alkyl)$_2$, carbocyclyl or heterocyclyl is optionally substituted with one or more substituents selected from halogen, hydroxy or cyano;

n is selected from 0, 1, 2;

E and B will together form a bicyclic ring system;

provided that the following compounds are excluded:

a compound according to formula (I), wherein V and X are N, Y is NR$^8$; B contains a —N(R$^1$)— moiety, R$^8$ is hydrogen, alkyl or cycloalkyl, and R$^7$ is arylalkyl, optionally substituted with a group containing a linker selected from O or S; and as a free base or a pharmaceutically acceptable salt thereof.

The present invention also relates to a compound according to formula (I)

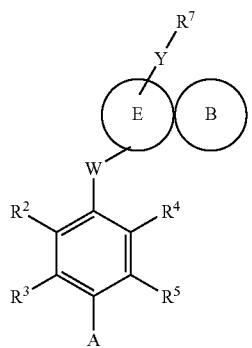

(I)

wherein
E is

wherein X and V are independently selected from nitrogen or CH and wherein at least one of X or V is nitrogen;

W is —C(R$^6$)$_2$—, —O— or —N(R$^6$)—;

R$^6$ is hydrogen, $C_{1-4}$alkyl or $C_{1-4}$alkoxy, wherein said $C_{1-4}$alkyl is substituted with halogen, cyano, hydroxy, amino, $NHC_{1-4}$alkyl, $N(C_{1-4}$alkyl)$_2$, heterocyclyl, NC(O)$C_{1-4}$alkyl, $C(O)C_{1-4}$alkoxy or $SO_2C_{1-6}$alkyl;

Y is —C(R$^{12}$)(R$^{13}$)—, —N(R$^8$)— or —O—;

R$^{12}$ and R$^{13}$ are independently selected from hydrogen, halogen, $C_{1-6}$alkyl, $C_{1-6}$alkylOC$_{1-6}$alkyl, carbocyclyl, heterocyclyl and $C_{1-6}$alkoxy, wherein said $C_{1-6}$alkyl, $C_{1-6}$alkylOC$_{1-6}$alkyl, carbocyclyl, heterocyclyl or $C_{1-6}$alkoxy is optionally substituted with one or more substituents selected from halogen, cyano, hydroxy, heterocyclyl, $N(C_{0-4}$alkyl)$_2$, NC(O)$C_{1-4}$alkyl;

or

R$^{12}$ and R$^{13}$ may form together with the cabon atom they are attached to a saturated, partially unsaturated or saturated ring system, wherein said ring system may contain one or more heteroatoms selected from N, O and S, and wherein if said ring system contains an —NH— moiety that nitrogen may optionally be substituted with a group selected from $C_{1-6}$alkyl and $C(O)C_{1-6}$alkyl and wherein said ring is optionally substituted with one or more groups selected from halogen, cyano, hydroxy;

or

R$^{12}$ and R$^7$ may form together a saturated, partially unsaturated or saturated bicyclic ring system, wherein said bicyclic ring system may contain zero to three heteroatoms selected from N, O and S, and wherein said bicyclic ring system is optionally substituted with one to three substituents selected from halogen, cyano, hydroxy, $C_{1-6}$alkoxy, amino, $NHC_{1-4}$alkyl, $N(C_{1-6}$alkyl)$_2$, NC(O)$C_{1-6}$alkyl, $SO_2C_{1-6}$alkyl and heterocyclyl, and wherein if said bicyclic ring system contains an —NH— moiety that nitrogen may optionally be substituted by a group selected from $C_{1-6}$alkyl and $C(O)C_{1-6}$alkyl;

R$^8$ is selected from hydrogen, $C_{1-6}$alkyl, $C_{1-6}$alkylOC$_{1-6}$alkyl, $C(O)C_{1-6}$alkyl, C(O) cycloalkyl, heterocyclyl, carbocyclyl, C(O) heterocyclyl or $SO_2C_{1-6}$alkyl, wherein said $C_{1-6}$alkyl, heterocyclyl, carbocyclyl or $C_{1-6}$alkylOC$_{1-6}$alkyl is optionally substituted with one to three substituents selected from halogen, cyano, hydroxy, amino, $NHC_{1-4}$alkyl, $N(C_{1-6}$alkyl)$_2$, NC(O)$C_{1-6}$alkyl, $C(O)C_{1-6}$alkoxy, $SO_2C_{1-6}$alkyl and heterocyclyl;

R$^7$ is selected from hydrogen, aryl, heteroaryl, $C_{1-4}$alkylaryl, $C_{1-4}$alkylheteroaryl, $C_{1-4}$alkylcarbocyclyl, $C_{1-4}$alkylheterocyclyl, wherein said aryl, heteroaryl, $C_{1-4}$alkylcarbocyclyl, $C_{1-4}$alkylheterocyclyl, $C_{1-4}$alkylaryl, carbocyclyl or $C_{1-4}$alkylheteroaryl is optionally substituted with one or more substituents selected from halogen, cyano, hydroxy, nitro, $C_{1-6}$alkyl, $C_{1-6}$alkoxy, carbocyclyl, heterocyclyl, $CF_3$, $OCF_3$, $OC_{1-6}$alkyl, $C(O)C_{1-6}$alkyl, $C_{1-6}$alkylOC$_{1-6}$alkyl, $SO_2C_{1-6}$alkyl, $SO_2NHC_{1-6}$alkyl, $SO_2N(C_{1-6}$alkyl)$_2$, $SO_2N$-heterocyclyl, $C(O)NH_2$, $C(O)NHC_{1-6}$alkyl, $C(O)N(C_{1-6}$alkyl)$_2$, $C(O)N$-heterocyclyl, $C_{2-6}$alkenyl and $C_{2-6}$alkynyl, wherein said $C_{1-6}$alkyl, $C_{1-6}$alkoxy, $C_{1-6}$alkylOC$_{1-6}$alkyl, heterocyclyl, carbocyclyl, $C_{2-6}$alkenyl or $C_{2-6}$alkynyl is optionally substituted with cyano, hydroxy, methoxy, halogen, $SO_2C_{1-4}$alkyl, amino, $NHC_{1-4}$alkyl, $N(C_{1-4}$alkyl)$_2$, heterocyclyl or aryl;

or

R$^8$ and R$^7$ may, when Y is NR$^8$, optionally form together with the nitrogen atom a saturated, partially saturated or unsaturated ring system, wherein said ring system is optionally substituted with one or more groups selected from halogen, hydroxy, cyano, $C_{1-4}$alkylOC$_{1-4}$alkyl and $C_{1-4}$alkyl, wherein said $C_{1-4}$alkylOC$_{1-4}$alkyl or $C_{1-4}$alkyl is optionally substituted with halogen, cyano, hydroxy;

R$^1$ is selected from hydrogen, $C_{1-6}$alkyl, $C_{1-6}$alkoxy, $C_{2-6}$alkenyl, $C_{2-6}$alkynyl, carbocyclyl, heterocyclyl, C(O)R$^9$, $C(O)N(R^9)_2$, $C(O)CH_2N(R^9)_2$, C(O)heterocyclyl, C(O) carbocyclyl, C(O)OR$^9$, $SO_2R^9$, $SO_2$heterocyclyl, $SO_2$carbocyclyl and $SO_2N(R^9)_2$, wherein said $C_{1-6}$alkyl, $C_{1-6}$alkoxy, $C_{2-6}$alkenyl, $C_{2-6}$alkynyl, carbocyclyl or heterocyclyl is optionally substituted with one or more substituents selected from halogen, hydroxy, cyano, amino, C(O)OR$^9$, $NHC_{1-6}$alkyl, $NHC_{1-6}$alkoxy, $N(C_{1-6}$alkyl)$_2$, $N(C_{1-6}$alkoxy)$_2$, $SC_{1-6}$alkyl, $SOC_{1-6}$alkyl, $SO_2C_{1-6}$alkyl, $C_{1-6}$alkyl, $C_{1-6}$alkoxy, heterocyclyl and carbocyclyl;

R$^9$ is selected from hydrogen, hydroxy, halogen, cyano, $C_{1-6}$alkyl, $C_{1-6}$alkoxy, carbocyclyl and heterocyclyl, wherein said $C_{1-6}$alkyl, $C_{1-6}$alkoxy, cycloalkyl or heterocyclyl is optionally substituted with one or more substituents selected from halogen, cyano, hydroxy or methoxy;

R$^4$, R$^5$, R$^3$ and R$^2$ are independently selected from hydrogen, cyano, $C_{1-4}$alkyl, $C_{1-4}$alkoxy, halogen, $OCH_3$, $OCF_3$, $OCF_2H$, $OCFH_2$ and hydroxy;

A is a 5-7 membered heteroaryl, wherein at least one of the ring forming atoms is selected from nitrogen and the remaining ring forming atoms are selected from carbon, nitrogen, sulphur and oxygen, and wherein said A is optionally substituted with one or more substituents selected from halogen, $C_{1-4}$alkyl, $SR^{10}$, $NR^{10}R^{11}$, $OR^{10}$, $C_{2-4}$alkenyl and $C_{2-4}$ alkynyl and wherein said $C_{1-4}$alkyl, $C_{2-4}$alkenyl or $C_{2-4}$alkynyl is optionally substituted with halogen, hydroxy, cyano or $C_{1-4}$alkoxy;

$R^{10}$ and $R^{11}$ are independently selected from hydrogen, $C_{1-4}$alkyl, $CF_3$, $CF_2H$ and $CFH_2$;

B is a 5 to 7 membered non-aromatic ring, wherein one of the ring forming atom is selected from —$N(R^1)$—, —$C(R^9)$—, —$S(O)_n$— or —O— and the other ring forming atoms are carbon, wherein one —$CH_2$— group can optionally be replaced by a —C(O)— and wherein said ring is optionally substituted with one to three substituents selected from halogen, cyano, hydroxy, amino, $C_{1-4}$alkyl, $C_{1-4}$alkoxy, $NHC_{1-6}$alkyl, $NHC_{1-6}$alkylO$C_{1-6}$alkyl, $N(C_{1-6}$alkyl$)_2$, $N(C_{1-6}$alkylO$C_{1-6}$alkyl$)_2$, carbocyclyl and heterocyclyl, wherein said $C_{1-4}$alkyl, $C_{1-4}$alkoxy, $NHC_{1-6}$alkyl, $NHC_{1-6}$alkylO$C_{1-6}$alkyl, $N(C_{1-6}$alkyl$)_2$, $N(C_{1-6}$alkylO$C_{1-6}$alkyl$)_2$, carbocyclyl or heterocyclyl is optionally substituted with one or more substituents selected from halogen, hydroxy or cyano;

n is selected from 0, 1, 2;

E and B will together form a bicyclic ring system;

provided that the following compounds are excluded:

a compound according to formula (I), wherein V and X are N; Y is $NR^8$; $R^8$ is hydrogen, alkyl or cycloalkyl, and $R^7$ is arylalkyl, optionally substituted with a group containing a linker selected from O or S and B contains a —$N(R^1)$— moiety and a compound according to formula (I), wherein V and X are N; Y is $NR^8$; $R^8$ is hydrogen, alkyl or cycloalky and $R^7$ is arylalkyl and wherein $R^7$ and $R^8$ will together form a ring, said ring is piperidyl, piperazinyl or morpholinyl and is optionally substituted with hydroxy, oxo or a group containing —C(O) and B contains a —$N(R^1)$— moiety;

as a free base or a pharmaceutically acceptable salt thereof.

According to one embodiment of the present invention, X is nitrogen.

According to one embodiment of the present invention, V is nitrogen.

According to one embodiment of the present invention, X and V are nitrogen.

According to one embodiment of the present invention, W is $NR^6$.

According to another embodiment of the present invention, $R^6$ is hydrogen.

According to one embodiment of the present invention, Y is —$N(R^8)$—.

According to another embodiment of the present invention, $R^8$ is selected from hydrogen, $C_{1-6}$alkyl, $C_{1-6}$alkylO$C_{1-6}$alkyl, C(O)$C_{1-6}$alkyl, heterocyclyl and carbocyclyl, wherein said $C_{1-6}$alkyl, heterocyclyl, carbocyclyl or $C_{1-6}$alkylO$C_{1-6}$alkyl is optionally substituted with one to three substituents selected from halogen, cyano, hydroxy, amino, $NHC_{1-4}$alkyl, $N(C_{1-6}$alkyl$)_2$, NC(O)$C_{1-6}$alkyl and heterocyclyl;

According to another embodiment of the present invention, $R^8$ and $R^7$ will form together with the nitrogen atom a partially saturated or unsaturated ring system, wherein said ring system is optionally substituted with one or more groups selected from halogen, hydroxy, cyano, $C_{1-4}$alkylO$C_{1-4}$alkyl and $C_{1-4}$alkyl, wherein said $C_{1-4}$alkylO$C_{1-4}$alkyl or $C_{1-4}$alkyl is optionally substituted with hydroxy.

According to one embodiment of the present invention, Y is —O—.

According to one embodiment of the present invention, Y is —$C(R^{12})(R^{13})$—.

According to another embodiment of the present invention, $R^{12}$ and $R^{13}$ are independently selected from hydrogen, halogen, $C_{1-6}$alkyl, $C_{1-6}$alkylO$C_{1-6}$alkyl, carbocyclyl and heterocyclyl y, wherein said $C_{1-6}$alkyl, $C_{1-6}$alkylO$C_{1-6}$alkyl, carbocyclyl or heterocyclyl is optionally substituted with one or more substituents selected from halogen, cyano, hydroxy, heterocyclyl, $N(C_{0-4}$alkyl$)_2$, NC(O)$C_{1-4}$alkyl.

According to one embodiment of the present invention, $R^2$ and $R^4$ are hydrogen.

According to one embodiment of the present invention, $R^3$ is selected from hydrogen, cyano, $C_{1-4}$alkyl, halogen and $C_{1-4}$alkoxy.

According to one embodiment of the present invention, $R^5$ is selected from hydrogen, cyano, $C_{1-4}$alkyl, halogen and $C_{1-4}$alkoxy.

According to one embodiment of the present invention, A is selected from oxazolyl, imidazolyl, pyrazolyl, isoxazolyl, oxadiazolyl, pyridinyl, pyrimidinyl, pyrryl, thiazolyl, triazolyl and thiadiazolyl.

According to another embodiment of the present invention, A is selected from oxazolyl, imidazolyl and pyrazolyl.

According to another embodiment of the present invention, A is substituted with $C_{1-4}$alkyl or halogen.

According to one embodiment of the present invention, B is a non-aromatic 6 membered ring, wherein one of the ring forming atom is $N(R^1)$ and five of the ring forming atoms are carbon.

According to one embodiment of the present invention, B is a non-aromatic 6 membered ring, wherein one of the ring forming atom is O and five of the ring forming atoms are carbon.

According to one embodiment of the present invention, B is a non-aromatic 6 membered ring, wherein one of the ring forming atom is $C(R^9)$ and five of the ring forming atoms are carbon, and wherein $R^9$ is selected from hydrogen and $C_{1-4}$alkyl wherein said $C_{1-4}$alkyl is optionally substituted with one or more substituents selected from halogen.

According to one embodiment of the present invention, the ring system formed by E and B is selected from 5,6,7,8-tetrahydropyrido[4,3-d]pyrimidine;
5,6,7,8-tetrahydropyrido[3,4-d]pyrimidine;
6,7-dihydro-5H-pyrrolo[3,4-d]pyrimidine;
6,7,8,9-tetrahydro-5H-pyrimido[4,5-d]azepine;
6,7,8,9-tetrahydro-5H-pyrimido[4,5-c]azepine;
6,7,8,9-tetrahydro-5H-pyrimido[5,4-c]azepine;
5,6,7,8-tetrahydropyrido[2,3-d]pyrimidine;
5,6,7,8-tetrahydroquinazoline;
7,8-dihydro-5H-thiopyrano[4,3-d]pyrimidine 6-oxide;
7,8-Dihydro-5H-pyrano[4,3-d]pyrimidine;
and 6,7-dihydro-5H-pyrrolo[2,3-d]pyrimidine.

According to another embodiment of the present invention, said ring system is
5,6,7,8-tetrahydropyrido[4,3-d]pyrimidine
5,6,7,8-tetrahydroquinazoline;
7,8-dihydro-5H-thiopyrano[4,3-d]pyrimidine 6-oxide;
7,8-Dihydro-5H-pyrano[4,3-d]pyrimidine;
or 5,6,7,8-tetrahydropyrido[3,4-d]pyrimidine.

According to one embodiment of the present invention, E is

W is —N($R^6$)—;
$R^6$ is hydrogen;
Y is —C($R^{12}$)($R^{13}$)—, —N($R^8$)— or —O—;
$R^{12}$ and $R^{13}$ are independently selected from hydrogen, halogen, $C_{1-6}$alkyl, $C_{1-6}$alkylO$C_{1-6}$alkyl, carbocyclyl and heterocyclyl, wherein said $C_{1-6}$alkyl, $C_{1-6}$alkylO$C_{1-6}$alkyl, carbocyclyl or heterocyclyl is optionally substituted with one or more substituents selected from halogen, cyano, hydroxy, heterocyclyl, N($C_{0-4}$alkyl)$_2$, NC(O)$C_{1-4}$alkyl;
$R^8$ is selected from hydrogen, $C_{1-6}$alkyl, $C_{1-6}$alkylO$C_{1-6}$alkyl, C(O)$C_{1-6}$alkyl, C(O) cycloalkyl, heterocyclyl, carbocyclyl and C(O)heterocyclyl, wherein said $C_{1-6}$alkyl, heterocyclyl, carbocyclyl or $C_{1-6}$alkylO$C_{1-6}$alkyl is optionally substituted with one to three substituents selected from halogen, cyano, hydroxy, amino, NH$C_{1-4}$alkyl, N($C_{1-6}$alkyl)$_2$, NC(O)$C_{1-6}$alkyl, C(O)$C_{1-6}$alkoxy, SO$_2C_{1-6}$alkyl and heterocyclyl;
$R^7$ is selected from hydrogen, aryl, heteroaryl, $C_{1-4}$alkylaryl, $C_{1-4}$alkylheteroaryl, $C_{1-4}$alkylcarbocyclyl, $C_{1-4}$alkylheterocyclyl and carbocyclyl, wherein said aryl, heteroaryl, $C_{1-4}$alkylcarbocyclyl, $C_{1-4}$alkylheterocyclyl, $C_{1-4}$alkylaryl, carbocyclyl or $C_{1-4}$alkylheteroaryl is optionally substituted with one or more substituents selected from halogen, cyano, hydroxy, nitro, $C_{1-6}$alkyl, $C_{1-6}$alkoxy, carbocyclyl, heterocyclyl, CF$_3$, OCF$_3$, O$C_{1-6}$alkyl, C(O)$C_{1-6}$alkyl, $C_{1-6}$alkylO$C_{1-6}$alkyl, SO$_2C_{1-6}$alkyl, SO$_2$NH$C_{1-6}$ alkyl, SO$_2$N($C_{1-6}$alkyl)$_2$, SO$_2$N-heterocyclyl, C(O)NH$_2$, C(O)NH$C_{1-6}$alkyl, C(O)N($C_{1-6}$alkyl)$_2$, C(O)N-heterocyclyl, $C_{2-6}$alkenyl and $C_{2-6}$alkynyl, wherein said $C_{1-6}$alkyl, $C_{1-6}$alkoxy, $C_{1-6}$alkylO$C_{1-6}$alkyl, heterocyclyl, carbocyclyl, $C_{2-6}$alkenyl or $C_{2-6}$alkynyl is optionally substituted with cyano, hydroxy, methoxy, halogen, SO$_2C_{1-4}$alkyl, amino, NH$C_{1-4}$alkyl, N($C_{1-4}$alkyl)$_2$, heterocyclyl or aryl;
or
$R^8$ and $R^7$ may, when Y is N$R^8$, optionally form together with the nitrogen atom a saturated, partially saturated or unsaturated ring system, wherein said ring system is optionally substituted with one or more groups selected from halogen, hydroxy, cyano, $C_{1-4}$alkylO$C_{1-4}$alkyl and $C_{1-4}$alkyl, wherein said $C_{1-4}$alkylO$C_{1-4}$alkyl or $C_{1-4}$alkyl is optionally substituted with halogen, cyano, hydroxy;
$R^1$ is selected from hydrogen, $C_{1-6}$alkyl, $C_{1-6}$alkoxy, carbocyclyl, heterocyclyl, C(O)$R^9$, C(O)N($R^9$)$_2$, C(O)CH$_2$N($R^9$)$_2$, C(O)heterocyclyl, C(O)carbocyclyl, C(O)O$R^9$, SO$_2R^9$, wherein said $C_{1-6}$alkyl, $C_{1-6}$alkoxy, carbocyclyl or heterocyclyl is optionally substituted with one or more substituents selected from halogen, hydroxy, cyano, amino, C(O)O$R^9$, NH$C_{1-6}$alkyl, NH$C_{1-6}$alkoxy, N($C_{1-6}$alkyl)$_2$, N($C_{1-6}$alkoxy)$_2$, S$C_{1-6}$alkyl, SO$C_{1-6}$alkyl, SO$_2C_{1-6}$alkyl, $C_{1-6}$alkyl, $C_{1-6}$alkoxy, heterocyclyl and carbocyclyl;
$R^9$ is selected from hydrogen, hydroxy, halogen, cyano, $C_{1-6}$alkyl, $C_{1-6}$alkoxy, carbocyclyl and heterocyclyl, wherein said $C_{1-6}$alkyl, $C_{1-6}$alkoxy, cycloalkyl or heterocyclyl is optionally substituted with one or more substituents selected from halogen, cyano, hydroxy or methoxy;
$R^4$, $R^5$, $R^3$ and $R^2$ are independently selected from hydrogen, $C_{1-4}$alkyl, $C_{1-4}$alkoxy, halogen and hydroxy;

A is a 5 membered heteroaryl, wherein at least one of the ring forming atoms is selected from nitrogen and the remaining ring forming atoms are selected from carbon, nitrogen, and oxygen, and wherein said A is optionally substituted with one or more substituents selected from halogen or $C_{1-4}$alkyl and wherein said $C_{1-4}$alkyl is optionally substituted with halogen, hydroxy, cyano or $C_{1-4}$alkoxy;
B is a 6 membered non-aromatic ring, wherein one of the ring forming atom is selected from —N($R^1$)— or —O— and the other ring forming atoms are carbon, wherein said ring is optionally substituted with one to three substituents selected from halogen, cyano, hydroxy, amino, $C_{1-4}$alkyl, $C_{1-4}$alkoxy, NH$C_{1-6}$alkyl, NH$C_{1-6}$alkylO$C_{1-6}$alkyl, N($C_{1-6}$alkyl)$_2$, N($C_{1-6}$alkylO$C_{1-6}$alkyl)$_2$, carbocyclyl and heterocyclyl According to one embodiment of the present invention, E is

wherein X and V are nitrogen;
W is —O— or —N($R^6$)—;
$R^6$ is hydrogen;
Y is —C($R^{12}$)($R^{13}$)—, —N($R^8$)— or —O—;
$R^{12}$ and $R^{13}$ are independently selected from hydrogen, $C_{1-6}$alkyl, $C_{1-6}$alkylO$C_{1-6}$alkyl, wherein said $C_{1-6}$alkyl or $C_{1-6}$alkylO$C_{1-6}$alkyl is optionally substituted with one or more substituents selected from halogen, cyano, hydroxy, heterocyclyl, N($C_{0-4}$alkyl)$_2$, NC(O)$C_{1-4}$alkyl;
$R^8$ is selected from hydrogen, $C_{1-6}$alkyl and carbocyclyl, wherein said $C_{1-6}$alkyl, is optionally substituted with one to three substituents selected from cyano, hydroxy and heterocyclyl;
$R^7$ is selected from hydrogen, aryl, $C_{1-4}$alkylaryl, $C_{1-4}$alkylheteroaryl, $C_{1-4}$alkylcarbocyclyl, $C_{1-4}$alkylheterocyclyl and carbocyclyl, wherein said aryl, $C_{1-4}$alkylcarbocyclyl, $C_{1-4}$alkylheterocyclyl, $C_{1-4}$alkylaryl, carbocyclyl or $C_{1-4}$alkylheteroaryl is optionally substituted with one or more substituents selected from hydroxy, halogen, $C_{1-6}$alkyl, C(O)$C_{1-6}$alkyl, wherein said $C_{1-6}$alkyl is optionally substituted with hydroxy;
or
$R^8$ and $R^7$ may, when Y is N$R^8$, optionally form together with the nitrogen atom a saturated, partially saturated or unsaturated ring system, wherein said ring system is optionally substituted with one or more groups selected from $C_{1-4}$alkylO$C_{1-4}$alkyl and $C_{1-4}$alkyl, wherein said $C_{1-4}$alkylO$C_{1-4}$alkyl or $C_{1-4}$alkyl is optionally substituted with hydroxy;
$R^1$ is selected from hydrogen, $C_{1-6}$alkyl, C(O)$R^9$, C(O)N($R^9$)$_2$, C(O)CH$_2$N($R^9$)$_2$, C(O)O$R^9$ and SO$_2R^9$, wherein said $C_{1-6}$alkyl, is optionally substituted with one hydroxy or heterocyclyl;
$R^9$ is selected from $C_{1-6}$alkyl and carbocyclyl, wherein said $C_{1-6}$alkyl is optionally substituted with one or more substituents selected from halogen, cyano, hydroxy or methoxy;
$R^4$, $R^5$, $R^3$ and $R^2$ are independently selected from hydrogen and $C_{1-4}$alkoxy;
A is a 5 membered heteroaryl, wherein at least one of the ring forming atoms is selected from nitrogen and the remaining ring forming atoms are selected from carbon, nitrogen, sulphur and oxygen, and wherein said A is optionally substituted with one or more substituents selected from halogen, $C_{1-4}$alkyl, $SR^{10}$, $NR^{10}R^{11}$, $OR^{10}$, $C_{2-4}$alkenyl and $C_{2-4}$alkynyl and wherein said $C_{1-4}$alkyl, $C_{2-4}$alkenyl or $C_{2-4}$alkynyl is optionally substituted with halogen, hydroxy, cyano or $C_{1-4}$alkoxy;

B is a 6 membered non-aromatic ring, wherein one of the ring forming atom is selected from —N($R^1$)—, —C($R^9$)—, —S(O)$_n$— or —O— and the other ring forming atoms are carbon, wherein one —CH$_2$— group can optionally be replaced by a —C(O)— and wherein said ring is optionally substituted with one to three substituents selected from halogen, cyano, hydroxy, amino, $C_{1-4}$alkyl, $C_{1-4}$alkoxy, NHC$_{1-6}$alkyl, NHC$_{1-6}$alkylOC$_{1-6}$alkyl, N(C$_{1-6}$alkyl)$_2$, N(C$_{1-6}$alkylOC$_{1-6}$alkyl)$_2$, carbocyclyl and heterocyclyl wherein said $C_{1-4}$alkyl, $C_{1-4}$alkoxy, NHC$_{1-6}$alkyl, NHC$_{1-6}$alkylOC$_{1-6}$alkyl, N(C$_{1-6}$alkyl)$_2$, N(C$_{1-6}$alkylOC$_{1-6}$alkyl)$_2$, carbocyclyl or heterocyclyl is optionally substituted with one or more substituents selected from halogen, hydroxy and cyano;

n is 1.

According to one embodiment of the present invention, E is

wherein X and V are nitrogen;

W is —O— or —N($R^6$)—;

$R^6$ is hydrogen;

Y is —C($R^{12}$)($R^{13}$)—, —N($R^8$)— or —O—;

$R^{12}$ and $R^{13}$ are independently selected from hydrogen, $C_{1-4}$alkyl, $C_{1-4}$alkylalkoxy;

$R^8$ is selected from hydrogen, $C_{1-6}$alkyl and carbocyclyl, wherein said $C_{1-6}$alkyl, is optionally substituted with one to three substituents selected from cyano, hydroxy and heterocyclyl;

$R^7$ is selected from hydrogen, aryl, $C_{1-4}$alkylaryl, $C_{1-4}$alkylheteroaryl, $C_{1-4}$alkylcarbocyclyl, $C_{1-4}$alkylheterocyclyl and carbocyclyl, wherein said aryl, $C_{1-4}$alkylcarbocyclyl, $C_{1-4}$alkylheterocyclyl, $C_{1-4}$alkylaryl, carbocyclyl or $C_{1-4}$alkylheteroaryl is optionally substituted with one or more substituents selected from hydroxy, halogen, $C_{1-6}$alkyl, C(O)C$_{1-6}$alkyl, wherein said C$_{1-6}$alkyl is optionally substituted with hydroxy;

or $R^8$ and $R^7$ may, when Y is $NR^8$, optionally form together with the nitrogen atom a saturated, partially saturated or unsaturated ring system, wherein said ring system is optionally substituted with one or more groups selected from $C_{1-4}$alkylOC$_{1-4}$alkyl and $C_{1-4}$alkyl, wherein said $C_{1-4}$alkylOC$_{1-4}$alkyl or $C_{1-4}$alkyl is optionally substituted with hydroxy;

$R^1$ is selected from hydrogen, $C_{1-6}$alkyl, C(O)$R^9$, C(O)N($R^9$)$_2$, C(O)CH$_2$N($R^9$)$_2$, C(O)O$R^9$ and SO$_2R^9$, wherein said $C_{1-6}$alkyl, is optionally substituted with one hydroxy or heterocyclyl;

$R^9$ is selected from $C_{1-6}$alkyl and carbocyclyl, wherein said $C_{1-6}$alkyl is optionally substituted with one or more substituents selected from hydroxy or methoxy;

$R^4$, $R^5$, $R^3$ and $R^2$ are independently selected from hydrogen and $C_{1-4}$alkoxy;

$R^{14}$ is hydrogen or $C_{1-4}$alkyl wherein said $C_{1-4}$alkyl is optionally substituted with one or more substituents selected from halogen A is a 5 membered heteroaryl, wherein at least one of the ring forming atoms is selected from nitrogen and the remaining ring forming atoms are selected from carbon, nitrogen and oxygen, and wherein said A is optionally substituted with one $C_{1-4}$alkyl;

B is a 6 non-aromatic ring, wherein one of the ring forming atom is selected from —N($R^1$)—, —O—, —S(O)—, —C($R^{14}$)— and the other ring forming atoms are carbon, and wherein said ring is optionally substituted with one to three substituents selected from $C_{1-4}$alkyl.

According to one embodiment of the present invention, E is

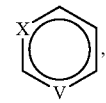

wherein X and V are nitrogen;

W is —O— or —N($R^6$)—;

$R^6$ is hydrogen;

Y is —C($R^{12}$)($R^{13}$)—, —N($R^8$)— or —O—;

$R^{12}$ and $R^{13}$ are hydrogen;

$R^8$ is selected from hydrogen, $C_{1-6}$alkyl and carbocyclyl, wherein said $C_{1-6}$alkyl, is optionally substituted with one to three substituents selected from cyano, hydroxy and heterocyclyl;

$R^7$ is selected from hydrogen, aryl, $C_{1-4}$alkylaryl, $C_{1-4}$alkylheteroaryl, $C_{1-4}$alkylheterocyclyl and carbocyclyl, wherein said aryl, $C_{1-4}$alkylaryl or carbocyclyl is optionally substituted with one substituent selected from hydroxy, $C_{1-6}$alkyl and C(O)$C_{1-6}$alkyl, wherein said $C_{1-6}$alkyl is optionally substituted with hydroxy;

or $R^8$ and $R^2$ may, when Y is $NR^8$, optionally form together with the nitrogen atom a saturated, partially saturated or unsaturated ring system, wherein said ring system is optionally substituted with one or more groups selected from $C_{1-4}$alkyl, wherein said $C_{1-4}$alkyl is optionally substituted with hydroxy;

$R^1$ is selected from hydrogen, $C_{1-6}$alkyl, C(O)$R^9$, C(O)N($R^9$)$_2$, C(O)CH$_2$N($R^9$)$_2$, C(O)O$R^9$ and SO$_2R^9$, wherein said $C_{1-6}$alkyl, is optionally substituted with one hydroxy or heterocyclyl;

$R^9$ is $C_{1-6}$alkyl or carbocyclyl, wherein said $C_{1-6}$alkyl is optionally substituted with one e substituent selected from hydroxy or methoxy;

$R^4$, $R^5$, $R^3$ and $R^2$ are independently selected from hydrogen and $C_{1-4}$alkoxy;

A is a 5 membered heteroaryl, wherein at least one of the ring forming atoms is selected from nitrogen and the remaining ring forming atoms are selected from carbon, nitrogen and oxygen, and wherein said A is optionally substituted with one $C_{1-4}$alkyl;

B is a 6 membered non-aromatic ring, wherein one of the ring forming atom is selected from —O—, or —N($R^1$)— and the other ring forming atoms are carbon.

The present invention also relates to a compound according to formula (Ia)

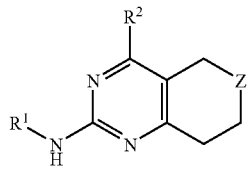

wherein R¹ is selected from phenyl substituted by a heteroaryl group and wherein the phenyl group and the heteroaryl group are optionally and independently substituted by one to three R' groups;
R² is Y—R⁷;
Y is —C(R¹²)(R¹³)—, —N(R⁸)—, —O—, —C(R¹²)(R¹³)—N(R⁸)—, —N(R⁸)—C(R¹²)(R¹³)—, —C(R¹²)(R¹³)—O—, or —O—C(R¹²)(R¹³)—;
R' is selected from halogen, C₁₋₆alkyl, halogenated C₁₋₆alkyl, C₁₋₆alkoxy, halogenated C₁₋₆alkoxy;
R⁸ is selected from hydrogen, C₁₋₆alkyl, halogenated C₁₋₆alkyl and C₃₋₆carbocyclyl, wherein said C₁₋₆alkyl, is optionally substituted with one to three substituents selected from cyano, hydroxy and heterocyclyl;
R⁷ is selected from hydrogen, aryl, heteroaryl, C₁₋₄alkylaryl, C₁₋₄alkylheteroaryl, C₁₋₄alkylheterocyclyl, halogenated C₁₋₆alkyl, C₁₋₆alkyl and C₃₋₆carbocyclyl, wherein said aryl, heteroaryl, C₁₋₆alkyl or carbocyclyl is optionally and independently substituted with one to three R' groups, fluoro, hydroxy, alkoxy, cyano, hydroxyalkyl or C(O)C₁₋₆alkyl, wherein said C₁₋₆alkyl is optionally substituted with hydroxy; or
R⁸ and R⁷ may, when Y is NR⁸, optionally form together with the nitrogen atom a saturated, partially saturated or unsaturated ring system, wherein said ring system is optionally and independently substituted by one to three R' groups
R¹² and R¹³ are independently selected from C₁₋₄alkyl, halogenated C₁₋₄alkyl, C₁₋₄alkoxy, halgogenated C₁₋₄alkoxy;
Z is selected from CH—(R³ᵃ), N—(R³ᵇ), O, S, S(O), and S(O)₂;
R³ᵃ is selected from C₁₋₆alkyl and halgonated C₁₋₆alkyl;
R³ᵇ is selected from hydrogen, C₁₋₆alkyl, cyano substituted C₁₋₆alkyl, halogenated C₁₋₆alkyl, C₁₋₆alkanoyl, hydroxy substituted C₁₋₆alkanoyl, dialkylamino substituted C₁₋₆alkanoyl, C₁₋₆alkoxy substituted C₁₋₆alkanoyl, C₃₋₆carbocyclyl-carbonyl, (C₁₋₆alkyl)₂carbamoyl, C₁₋₆alkylsulfonyl, C₁₋₆alkoxycarbonyl,
or a pharmaceutically acceptable salt thereof.
Further, one embodiment of the present invention is a compound of formula Ia wherein R¹ is selected from phenyl substituted by a heteroaryl group and wherein the phenyl group and the heteroaryl group are optionally and independently substituted by one to three R' groups;
R² is Y—R⁷;
Y is —C(R¹²)(R¹³)—, —N(R⁸)—, —O—, —C(R¹²)(R¹³)—N(R⁸)—, —N(R⁸)—C(R¹²)(R¹³)—, —C(R¹²)(R¹³)—O—, or —O—C(R¹²)(R¹³)—;
R' is selected from halogen, C₁₋₆alkyl, halogenated C₁₋₆alkyl, C₁₋₆alkoxy, halogenated C₁₋₆alkoxy;
R⁸ is selected from hydrogen, C₁₋₆alkyl, halogenated C₁₋₆alkyl and C₃₋₆carbocyclyl, wherein said C₁₋₆alkyl, is optionally substituted with one to three substituents selected from cyano, hydroxy and heterocyclyl;
R⁷ is selected from hydrogen, aryl, heteroaryl, C₁₋₄alkylaryl, C₁₋₄alkylheteroaryl, C₁₋₄alkylheterocyclyl, C₁₋₆alkyl, halogenatedC₁₋₆alkyl, and C₃₋₆carbocyclyl, wherein said aryl, heteroaryl, C₁₋₆alkyl or carbocyclyl is optionally and independently substituted with one to three R' groups, fluoro, hydroxy, alkoxy, cyano, hydroxyalkyl, or C(O)C₁₋₆alkyl, wherein said C₁₋₆alkyl is optionally substituted with hydroxy;
or
R⁸ and R⁷ may, when Y is NR⁸, optionally form together with the nitrogen atom a saturated, partially saturated or unsaturated ring system, wherein said ring system is optionally and independently substituted by one to three R' groups;
R¹² and R¹³ are independently selected from C₁₋₄alkyl, halogenated C₁₋₄alkyl, C₁₋₄alkoxy, halgogenated C₁₋₄alkoxy;
Z is selected from CH—(R³ᵃ), N—(R³ᵇ), O, S, S(O), and S(O)₂;
R³ᵃ is selected from C₁₋₆alkyl and halogenated C₁₋₆alkyl;
R³ᵇ is selected from hydrogen, C₁₋₆alkyl, cyano substituted C₁₋₆alkyl, C₁₋₆alkanoyl, hydroxy substituted C₁₋₆alkanoyl, amino substituted C₁₋₆alkanoyl, C₁₋₆alkoxy substituted C₁₋₆alkanoyl, C₃₋₆carbocyclyl-carbonyl, (C₁₋₆alkyl)₂carbamoyl, C₁₋₆alkylsulfonyl, C₁₋₆alkoxy-carbonyl,
or a pharmaceutically acceptable salt thereof.
Further, one embodiment of the present invention is a compound of formula Ia wherein R¹ is selected from phenyl substituted by a heteroaryl group and wherein the phenyl group is further optionally substituted with a C₁₋₄alkoxy group or a halogenated C₁₋₄alkoxy group and the heteroaryl group is optionally substituted by a C₁₋₄alkyl group or a halogenated C₁₋₄alkyl group;
R² is Y—R⁷;
Y is —C(R¹²)(R¹³)— or C(R¹²)(R¹³)—O—;
R⁷ is selected from hydrogen, aryl, heteroaryl, C₁alkylaryl, C₁alkylheteroaryl, C₁alkylheterocyclyl, C₁₋₆alkyl, halogenatedC₁₋₆alkyl and C₃₋₆carbocyclyl, wherein said aryl, heteroaryl, C₁₋₄alkylaryl, C₁₋₆alkyl, halogenatedC₁₋₆alkyl or carbocyclyl is optionally substituted with one substituent selected from hydroxy, alkoxy, cyano, C₁₋₆alkyl, halogenated C₁₋₆alkyl and C(O)C₁₋₆alkyl, wherein said C₁₋₆alkyl is optionally substituted with hydroxy;
R¹² and R¹³ are independently selected from C₁₋₄alkyl, halogenated C₁₋₄alkyl, C₁₋₄alkoxy, halgogenated C₁₋₄alkoxy;
Z is selected from CH—(R³ᵃ), N—(R³ᵇ) and O;
R³ᵃ is selected from C₁₋₆alkyl and halogenated C₁₋₆alkyl; and
R³ᵇ is selected from hydrogen, C₁₋₆alkyl, cyano substituted C₁₋₆alkyl, C₁₋₆alkanoyl, hydroxy substituted C₁₋₆alkanoyl, amino substituted C₁₋₆alkanoyl, C₁₋₆alkoxy substituted C₁₋₆alkanoyl, C₃₋₆carbocyclyl-carbonyl, (C₁₋₆alkyl)₂carbamoyl, C₁₋₆alkylsulfonyl, C₁₋₆alkoxy-carbonyl,
or a pharmaceutically acceptable salt thereof.
Further, one embodiment of the present invention is a compound of formula Ia wherein R¹ is selected from 3-methoxy-4-(4-methylimidazol-1-yl)phenyl, 4-(1-methylpyrazol-4-yl) phenyl, 4-(2-methylimidazol-1-yl)phenyl, or 4-oxazol-5-ylphenyl;
R² is selected from [2-fluoro-1-(fluoromethyl)ethoxy]methyl, (2-fluorophenyl)methyl, (2-hydroxy-2-phenylethyl)-methyl-amino, (2R)-2-(hydroxymethyl)indolin-1-yl, (2S)-2-(hydroxymethyl)indolin-1-yl, (3-acetylphenyl) amino, (3-methoxyphenyl)methyl, (4-fluorophenyl) methyl, (4-fluorophenyl)-methyl-amino, [(2R)-norbornan-2-yl]amino, [(2R)-tetrahydrofuran-2-yl] methylamino, [(2S)-tetrahydrofuran-2-yl]methylamino, [1-(hydroxymethyl)cyclopentyl]amino, [2-(hydroxymethyl)phenyl]methyl-methyl-amino, [3-(hydroxymethyl) phenyl]amino, 1-(3,5-dimethylpyrazol-1-yl)ethyl, 1-hydroxy-1-methyl-ethyl, 1-phenylethyl, 2-(2-oxopyrrolidin-1-yl)ethyl, 2-(3-fluorophenyl)ethyl, 2-(hydroxymethyl)-1-piperidyl, 2-cyanoethyl-cyclopropyl-amino, 2-cyclohexylethyl, 2-hydroxyethyl-phenyl-amino, 2-tetrahydrofuran-2-ylethyl, 3-(hydroxymethyl)-1-piperidyl, 4,4-difluoro-1-piperidyl, benzyl, benzyl-(2-hydroxyethyl)amino, benzylamino, benzyloxy, cyclohexylamino, cyclohexyl-methyl-amino, cyclopentoxymethyl, cyclopentylmethyl, ethyl-(tetrahydrofuran-2-ylmethyl)amino, indolin-1-yl, methoxy-phenyl-methyl, methyl-(2-pyridylmethyl)amino, methyl-(3-pyridylmethyl)amino, p-tolylmethyl, tetrahydropyran-4-ylmethyl, and tetrahydropyran-4-ylmethylamino;

Z is selected from CH—($R^{3a}$), N—($R^{3b}$), and O;

$R^{3a}$ is trifluoromethyl; and $R^{3b}$ is selected from hydrogen, (2S)-2-hydroxypropanoyl, 2-dimethylaminoacetyl, 2-hydroxyacetyl, 2-hydroxyethyl, 2-methoxyacetyl, acetyl, cyanomethyl, cyclopropane-carbonyl, dimethylcarbamoyl, ethoxycarbonyl, ethylsulfonyl, methoxycarbonyl, methyl, methylsulfonyl, propanoyl, and propyl;

or a pharmaceutically acceptable salt thereof.

Further, one embodiment of the present invention is a compound of formula Ia wherein $R^1$ is selected from 3-methoxy-4-(4-methylimidazol-1-yl)phenyl, 4-(1-methylpyrazol-4-yl) phenyl, 4-(2-methylimidazol-1-yl)phenyl, or 4-oxazol-5-ylphenyl;

$R^2$ is selected from [2-fluoro-1-(fluoromethyl)ethoxy]methyl, (2-fluorophenyl)methyl, (2-hydroxy-2-phenyl-ethyl)-methyl-amino, (2R)-2-(hydroxymethyl)indolin-1-yl, (2S)-2-(hydroxymethyl)indolin-1-yl, (3-acetylphenyl)amino, (3-methoxyphenyl)methyl, (4-fluorophenyl)methyl, (4-fluorophenyl)-methyl-amino, [(2R)-norbornan-2-yl]amino, [(2R)-tetrahydrofuran-2-yl]methylamino, [(2S)-tetrahydrofuran-2-yl]methylamino, [1-(hydroxymethyl)cyclopentyl]amino, [2-(hydroxymethyl)phenyl]methyl-methyl-amino, [3-(hydroxymethyl)phenyl]amino, 1-(3,5-dimethylpyrazol-1-yl)ethyl, 1-hydroxy-1-methyl-ethyl, 1-phenylethyl, 2-(2-oxopyrrolidin-1-yl)ethyl, 2-(3-fluorophenyl)ethyl, 2-(hydroxymethyl)-1-piperidyl, 2-cyanoethyl-cyclopropyl-amino, 2-cyclohexylethyl, 2-hydroxyethyl-phenyl-amino, 2-tetrahydrofuran-2-ylethyl, 3-(hydroxymethyl)-1-piperidyl, 4,4-difluoro-1-piperidyl, benzyl, benzyl-(2-hydroxyethyl)amino, benzylamino, benzyloxy, cyclohexylamino, cyclohexyl-methyl-amino, cyclopentoxymethyl, cyclopentylmethyl, ethyl-(tetrahydrofuran-2-ylmethyl)amino, indolin-1-yl, methoxy-phenyl-methyl, methyl-(2-pyridylmethyl)amino, methyl-(3-pyridylmethyl)amino, p-tolylmethyl, tetrahydropyran-4-ylmethyl, and tetrahydropyran-4-ylmethylamino;

Z is selected from CH—$R^{3a}$, N—$R^{3b}$, O and S;

$R^{3a}$ is trifluoromethyl; and $R^{3b}$ is selected from hydrogen, (2S)-2-hydroxypropanoyl, 2-dimethylaminoacetyl, 2-hydroxyacetyl, 2-hydroxyethyl, 2-methoxyacetyl, acetyl, cyanomethyl, cyclopropane-carbonyl, dimethylcarbamoyl, ethoxycarbonyl, ethylsulfonyl, methoxycarbonyl, methyl, methylsulfonyl, propanoyl, and propyl;

or a pharmaceutically acceptable salt thereof.

The present invention also relates to a compound selected from 2-((2-(4-(oxazol-5-yl)phenylamino)-5,6,7,8-tetrahydropyrido[4,3-d]pyrimidin-4-yl)(phenyl)amino)ethanol 2-((6-methyl-2-(4-(oxazol-5-yl)phenylamino)-5,6,7,8-tetrahydropyrido[4,3-d]pyrimidin-4-yl)(phenyl)amino)ethanol N2-(4-(oxazol-5-yl)phenyl)-N4-phenyl-5,6,7,8-tetrahydropyrido[4,3-d]pyrimidine-2,4-diamine 6-methyl-N2-(4-(oxazol-5-yl)phenyl)-N4-phenyl-5,6,7,8-tetrahydropyrido[4,3-d]pyrimidine-2,4-diamine N4-benzyl-N2-(4-(oxazol-5-yl)phenyl)-5,6,7,8-tetrahydropyrido[3,4-d]pyrimidine-2,4-diamine N4-benzyl-N2-(4-(oxazol-5-yl)phenyl)-5,6,7,8-tetrahydropyrido[4,3-d]pyrimidine-2,4-diamine N2-(3-methoxy-4-(4-methyl-1H-imidazol-1-yl)phenyl)-N4-phenyl-5,6,7,8-tetrahydropyrido[4,3-d]pyrimidine-2,4-diamine 2-(2-(3-methoxy-4-(4-methyl-1H-imidazol-1-yl)phenylamino)-4-(phenylamino)-7,8-dihydropyrido[4,3-d]pyrimidin-6(5H)-yl)ethanol (S)-(1-(6-methyl-2-(4-(2-methyl-1H-imidazol-1-yl)phenylamino)-5,6,7,8-tetrahydropyrido[4,3-d]pyrimidin-4-yl)indolin-2-yl)methanol N4-((2R)-bicyclo[2.2.1]heptan-2-yl)-6-methyl-N2-(4-(2-methyl-1H-imidazol-1-yl)phenyl)-5,6,7,8-tetrahydropyrido[4,3-d]pyrimidine-2,4-diamine N4-cyclohexyl-N4,6-dimethyl-N2-(4-(2-methyl-1H-imidazol-1-yl)phenyl)-5,6,7,8-tetrahydropyrido[4,3-d]pyrimidine-2,4-diamine 4-(benzyloxy)-N-(4-(oxazol-5-yl)phenyl)-5,6,7,8-tetrahydropyrido[4,3-d]pyrimidin-2-amine (R)-(1-(6-methyl-2-(4-(2-methyl-1H-imidazol-1-yl)phenylamino)-5,6,7,8-tetrahydropyrido[4,3-d]pyrimidin-4-yl)indolin-2-yl)methanol 2-((2-(4-(oxazol-5-yl)phenylamino)-6-propyl-5,6,7,8-tetrahydropyrido[4,3-d]pyrimidin-4-yl)(phenyl)amino)ethanol 1-(4-((2-hydroxyethyl)(phenyl)amino)-2-(4-(oxazol-5-yl)phenylamino)-7,8-dihydropyrido[4,3-d]pyrimidin-6(5H)-yl)propan-1-one Cyclopropyl(4-((2-hydroxyethyl)(phenyl)amino)-2-(4-(oxazol-5-yl)phenylamino)-7,8-dihydropyrido[4,3-d]pyrimidin-6(5H)-yl)methanone 2-(dimethylamino)-1-(4-((2-hydroxyethyl)(phenyl)amino)-2-(4-(oxazol-5-yl)phenylamino)-7,8-dihydropyrido[4,3-d]pyrimidin-6(5H)-yl)ethanone 1-(4-((2-hydroxyethyl)(phenyl)amino)-2-(4-(oxazol-5-yl)phenylamino)-7,8-dihydropyrido[4,3-d]pyrimidin-6(5H)-yl)-2-methoxyethanone 2-hydroxy-1-(4-((2-hydroxyethyl)(phenyl)amino)-2-(4-(oxazol-5-yl)phenylamino)-7,8-dihydropyrido[4,3-d]pyrimidin-6(5H)-yl)ethanone (S)-2-hydroxy-1-(4-((2-hydroxyethyl)(phenyl)amino)-2-(4-(oxazol-5-yl)phenylamino)-7,8-dihydropyrido[4,3-d]pyrimidin-6(5H)-yl)propan-1-one 2-((6-(methylsulfonyl)-2-(4-(oxazol-5-yl)phenylamino)-5,6,7,8-tetrahydropyrido[4,3-d]pyrimidin-4-yl)(phenyl)amino)ethanol 2-((6-(ethylsulfonyl)-2-(4-(oxazol-5-yl)phenylamino)-5,6,7,8-tetrahydropyrido[4,3-d]pyrimidin-4-yl)(phenyl)amino)ethanol methyl 4-((2-hydroxyethyl)(phenyl)amino)-2-(4-(oxazol-5-yl)phenylamino)-7,8-dihydropyrido[4,3-d]pyrimidine-6(5H)-carboxylate ethyl 4-((2-hydroxyethyl)(phenyl)amino)-2-(4-(oxazol-5-yl)phenylamino)-7,8-dihydropyrido[4,3-d]pyrimidine-6(5H)-carboxylate 4-((2-hydroxyethyl)(phenyl)amino)-N,N-dimethyl-2-(4-(oxazol-5-yl)phenylamino)-7,8-dihydropyrido[4,3-d]pyrimidine-6(5H)-carboxamide 1-(4-(cyclohexylamino)-2-(4-(oxazol-5-yl)phenylamino)-7,8-dihydropyrido[4,3-d]pyrimidin-6(5H)-yl)ethanone (S)-1-(2-(4-(oxazol-5-yl)phenylamino)-4-((tetrahydrofuran-2-yl)methylamino)-7,8-dihydropyrido[4,3-d]pyrimidin-6(5H)-yl)ethanone 1-(4-((2-hydroxyethyl)(phenyl)amino)-2-(4-(oxazol-5-yl)phenylamino)-7,8-dihydropyrido[4,3-d]pyrimidin-6(5H)-yl)ethanone 1-(4-(3-(hydroxymethyl)phenylamino)-2-(4-(oxazol-5-yl)phenylamino)-7,8-dihydropyrido[4,3-d]pyrimidin-6(5H)-yl)ethanone (S)-1-(4-(2-(hydroxymethyl)indolin-1-yl)-2-(4-(oxazol-5-yl)phenylamino)-7,8-dihydropyrido[4,3-d]pyrimidin-6(5H)-yl)ethanone 3-((6-acetyl-2-(4-(oxazol-5-yl)phenylamino)-5,6,7,8-tetrahydropyrido[4,3-d]pyrimidin-4-yl)(cyclopropyl)amino)propanenitrile 1-(4-(benzyl(2-hydroxyethyl)amino)-2-(4-(oxazol-5-yl)phenylamino)-7,8-dihydropyrido[4,3-d]pyrimidin-6(5H)-yl)ethanone 1-(3-(6-acetyl-2-(4-(oxazol-5-yl)phenylamino)-5,6,7,8-tetrahydropyrido[4,3-d]pyrimidin-4-ylamino)phenyl)ethanone 1-(4-((2-hydroxy-2-phenylethyl)(methyl)amino)-2-(4-(oxazol-5-yl)phenylamino)-7,8-dihydropyrido[4,3-d]pyrimidin-6(5H)-yl)ethanone 1-(4-(1-(hydroxymethyl)cyclopentylamino)-2-(4-(oxazol-5-yl)phenylamino)-7,8-dihydropyrido[4,3-d]pyrimidin-6(5H)-yl)ethanone 1-(4-(methyl(pyridin-3-ylmethyl)amino)-2-(4-(oxazol-5-yl)phenylamino)-7,8-dihydropyrido[4,3-d]pyrimidin-6(5H)-yl)ethanone (R)-1-(4-(2-(hydroxymethyl)indolin-1-yl)-2-(4-(oxazol-5-yl)phenylamino)-7,8-dihydropyrido[4,3-d]pyrimidin-6(5H)-yl)ethanone 2-((6-methyl-2-(4-(1-methyl-1H-pyrazol-4-yl)phenylamino)-5,6,7,8-tetrahydropyrido[4,3-d]pyrimidin-4-yl)(phenyl)amino)ethanol 2-((2-(4-(1-methyl-1H-pyrazol-4-yl)phenylamino)-6-propyl-5,6,7,8-tetrahydropyrido[4,3-d]pyrimidin-4-yl)(phenyl)amino)ethanol 2-(4-benzyl-2-(4-(2-methyl-1H-imidazol-1-yl)phenylamino)-7,8-dihydropyrido[4,3-d]pyrimidin-6(5H)-yl)ethanol 4-benzyl-6-methyl-N-(4-(2-methyl-1H-imidazol-1-yl)phenyl)-5,6,7,8-tetrahydropyrido[4,3-d]pyrimidin-2-amine 4-benzyl-N-(3-methoxy-4-(4-methyl-1H-imidazol-1-yl)phenyl)-7,8-dihydro-5H-pyrano[4,3-d]pyrimidin-2-amine 4-(4-fluorobenzyl)-N-[3-methoxy-4-(4-methyl-1H-imidazol-1-yl)phenyl]-7,8-dihydro-5H-thiopyrano[4,3-d]pyrimidin-2-amine 6-oxide 4-benzyl-N-(4-(2-methyl-1H-imidazol-1-yl)phenyl)-7,8-dihydro-5H-pyrano[4,3-d]pyrimidin-2-amine N-(4-(2-methyl-1H-imidazol-1-yl)phenyl)-4-((tetrahydro-2H-pyran-4-yl)methyl)-7,8-dihydro-5H-thiopyrano[4,3-d]pyrimidin-2-amine 2-(4-(2-cyclohexylethyl)-2-(4-(2-methyl-1H-imidazol-1-yl)phenylamino)-7,8-dihydropyrido[4,3-d]pyrimidin-6(5H)-yl)ethanol 2-(2-(4-(2-methyl-1H-imidazol-1-yl)phenylamino)-4-(4-methylbenzyl)-7,8-dihydropyrido[4,3-d]pyrimidin-6(5H)-yl)ethanol 2-(4-(3-fluorophenethyl)-2-(4-(2-methyl-1H-imidazol-1-yl)phenylamino)-7,8-dihydropyrido[4,3-d]pyrimidin-6(5H)-yl)ethanol 6-methyl-N-(4-(2-methyl-1H-imidazol-1-yl)phenyl)-4-(4-methylbenzyl)-5,6,7,8-tetrahydropyrido[4,3-d]pyrimidin-2-amine 4-(3-fluorophenethyl)-6-methyl-N-(4-(2-methyl-1H-imidazol-1-yl)phenyl)-5,6,7,8-tetrahydropyrido[4,3-d]pyrimidin-2-amine 4-(2-fluorobenzyl)-6-methyl-N-(4-(2-methyl-1H-imidazol-1-yl)phenyl)-5,6,7,8-tetrahydropyrido[4,3-d]pyrimidin-2-amine 4-(3-methoxybenzyl)-6-methyl-N-(4-(2-methyl-1H-imidazol-1-yl)phenyl)-5,6,7,8-tetrahydropyrido[4,3-d]pyrimidin-2-amine 4-(2-cyclohexylethyl)-6-methyl-N-(4-(2-methyl-1H-imidazol-1-yl)phenyl)-5,6,7,8-tetrahydropyrido[4,3-d]pyrimidin-2-amine 4-(cyclopentylmethyl)-6-methyl-N-(4-(2-methyl-1H-imidazol-1-yl)phenyl)-5,6,7,8-tetrahydropyrido[4,3-d]pyrimidin-2-amine 2-(4-(2-fluorobenzyl)-2-(4-(2-methyl-1H-imidazol-1-yl)phenylamino)-7,8-dihydropyrido[4,3-d]pyrimidin-6(5H)-yl)ethanol 2-(4-(3-methoxybenzyl)-2-(4-(2-methyl-1H-imidazol-1-yl)phenylamino)-7,8-dihydropyrido[4,3-d]pyrimidin-6(5H)-yl)ethanol 1-(4-(2-cyclohexylethyl)-2-(4-(2-methyl-1H-imidazol-1-yl)phenylamino)-7,8-dihydropyrido[4,3-d]pyrimidin-6(5H)-yl)ethanone 1-(2-(4-(2-methyl-1H-imidazol-1-yl)phenylamino)-4-(4-methylbenzyl)-7,8-dihydropyrido[4,3-d]pyrimidin-6(5H)-yl)ethanone 1-(4-(3-fluorophenethyl)-2-(4-(2-methyl-1H-imidazol-1-yl)phenylamino)-7,8-dihydropyrido[4,3-d]pyrimidin-6(5H)-yl)ethanone 6-methyl-N-(4-(2-methyl-1H-imidazol-1-yl)phenyl)-4-((tetrahydro-2H-pyran-4-yl)methyl)-5,6,7,8-tetrahydropyrido[4,3-d]pyrimidin-2-amine 2-(2-(4-(2-methyl-1H-imidazol-1-yl)phenylamino)-4-((tetrahydro-2H-pyran-4-yl)methyl)-7,8-dihydropyrido[4,3-d]pyrimidin-6(5H)-yl)ethanol 1-(2-(4-(2-methyl-1H-imidazol-1-yl)phenylamino)-4-((tetrahydro-2H-pyran-4-yl)methyl)-7,8-dihydropyrido[4,3-d]pyrimidin-6(5H)-yl)ethanone 4-(4-fluorobenzyl)-N-[4-(2-methyl-1H-imidazol-1-yl)phenyl]-7,8-dihydro-5H-thiopyrano[4,3-d]pyrimidin-2-amine 6-oxide 4-(methoxy(phenyl)methyl)-N-(4-(2-methyl-1H-imidazol-1-yl)phenyl)-7,8-dihydro-5H-pyrano[4,3-d]pyrimidin-2-amine 4-[methoxy(phenyl)methyl]-N-[4-(2-methyl-1H-imidazol-1-yl)phenyl]-7,8-dihydro-5H-thiopyrano[4,3-d]pyrimidin-2-amine 6,6-dioxide N-(4-(2-methyl-1H-imidazol-1-yl)phenyl)-4-((tetrahydro-2H-pyran-4-yl)methyl)-7,8-dihydro-5H-pyrano[4,3-d]pyrimidin-2-amine 4-benzyl-N-(3-methoxy-4-(4-methyl-1H-imidazol-1-yl)phenyl)-6-methyl-5,6,7,8-tetrahydropyrido[4,3-d]pyrimidin-2-amine N4-cyclohexyl-6-methyl-N2-(4-(2-methyl-1H-imidazol-1-yl)phenyl)-5,6,7,8-tetrahydropyrido[4,3-d]pyrimidine-2,4-diamine 6-Methyl-N-(4-(2-methyl-1H-imidazol-1-yl)phenyl)-4-(1-phenylethyl)-5,6,7,8-tetrahydropyrido[4,3-d]pyrimidin-2-amine 6-Methyl-N-(4-(2-methyl-1H-imidazol-1-yl)phenyl)-4-(1-phenylethyl)-5,6,7,8-tetrahydropyrido[4,3-d]pyrimidin-2-amine (S)-(1-(6-methyl-2-(methyl(4-(2-methyl-1H-imidazol-1-yl)phenyl)amino)-5,6,7,8-tetrahydropyrido[4,3-d]pyrimidin-4-yl)indolin-2-yl)methanol (S)-6-methyl-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine (R)-6-methyl-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine 2-(4-benzyl-2-(3-methoxy-4-(4-methyl-1H-imidazol-1-yl)phenylamino)-7,8-dihydropyrido[4,3-d]pyrimidin-6(5H)-yl)ethanol 2-(benzyl(6-methyl-2-(4-(2-methyl-1H-imidazol-1-yl)phenylamino)-5,6,7,8-tetrahydropyrido[4,3-d]pyrimidin-4-yl)amino)ethanol 2-(4-(ethyl((tetrahydrofuran-2-yl)methyl)amino)-2-(4-(2-methyl-1H-imidazol-1-yl)phenylamino)-7,8-dihydropyrido[4,3-d]pyrimidin-6(5H)-yl)ethanol 3-(cyclopropyl(6-methyl-2-(4-(2-methyl-1H-imidazol-1-yl)phenylamino)-5,6,7,8-tetrahydropyrido[4,3-d]pyrimidin-4-yl)amino)propanenitrile 6-methyl-N2-(4-(2-methyl-1H-imidazol-1-yl)phenyl)-N4-((tetrahydro-2H-pyran-4-yl)methyl)-5,6,7,8-tetrahydropyrido[4,3-d]pyrimidine-2,4-diamine (R)-2-(2-(4-(oxazol-5-yl)phenylamino)-4-((tetrahydrofuran-2-yl)methylamino)-7,8-dihydropyrido[4,3-d]pyrimidin-6(5H)-yl)ethanol 2-(4-(ethyl((tetrahydrofuran-2-yl)methyl)amino)-2-(4-(oxazol-5-yl)phenylamino)-7,8-dihydropyrido[4,3-d]pyrimidin-6(5H)-yl)ethanol N4-ethyl-6-methyl-N2-(4-(oxazol-5-yl)phenyl)-N4-((tetrahydrofuran-2-yl)methyl)-5,6,7,8-tetrahydropyrido[4,3-d]pyrimidine-2,4-diamine (S)-6-methyl-N2-(4-(oxazol-5-yl)phenyl)-N4-((tetrahydrofuran-2-yl)methyl)-5,6,7,8-tetrahydropyrido[4,3-d]pyrimidine-2,4-diamine (R)-6-methyl-N2-(4-(oxazol-5-yl)phenyl)-N4-((tetrahydrofuran-2-yl)methyl)-5,6,7,8-tetrahydropyrido[4,3-d]pyrimidine-2,4-diamine 6-methyl-N2-(4-(oxazol-5-yl)phenyl)-N4-((tetrahydro-2H-pyran-4-yl)methyl)-5,6,7,8-tetrahydropyrido[4,3-d]pyrimidine-2,4-diamine 2-(2-(4-(oxazol-5-yl)phenylamino)-4-((tetrahydro-2H-pyran-4-yl)methylamino)-7,8-dihydropyrido[4,3-d]pyrimidin-6(5H)-yl)ethanol 4-Methyl-N-(4-(2-methyl-1H-imidazol-1-yl)phenyl)-6-(1-phenylethyl)pyrimidin-2-amine 1-(4-(cyclohexyl(methyl)amino)-2-(4-(oxazol-5-yl)phenylamino)-7,8-dihydropyrido[4,3-d]pyrimidin-6(5H)-yl)ethanone 1-(4-((4-fluorophenyl)(methyl)amino)-2-(4-(oxazol-5-yl)phenylamino)-7,8-dihydropyrido[4,3-d]pyrimidin-6(5H)-yl)ethanone 1-(4-(indolin-1-yl)-2-(4-(oxazol-5-yl)phenylamino)-7,8-dihydropyrido[4,3-d]pyrimidin-6(5H)-yl)ethanone 1-(4-((2-(hydroxymethyl)benzyl)(methyl)amino)-2-(4-(oxazol-5-yl)phenylamino)-7,8-dihydropyrido[4,3-d]pyrimidin-6(5H)-yl)ethanone 1-(4-(methyl(pyridin-2-ylmethyl)amino)-2-(4-(oxazol-5-yl)phenylamino)-7,8-dihydropyrido[4,3-d]pyrimidin-6(5H)-yl)ethanone 1-(4-(3-(hydroxymethyl)piperidin-1-yl)-2-(4-(oxazol-5-yl)phenylamino)-7,8-dihydropyrido[4,3-d]pyrimidin-6(5H)-yl)ethanone 1-(4-(2-(hydroxymethyl)piperidin-1-yl)-2-(4-(oxazol-5-yl)phenylamino)-7,8-dihydropyrido[4,3-d]pyrimidin-6(5H)-yl)ethanone N-(3-methoxy-4-(4-methyl-1H-imidazol-1-yl)phenyl)-4-(3-methoxybenzyl)-6-methyl-5,6,7,8-tetrahydropyrido[4,3-d]pyrimidin-2-amine 1-(2-(3-methoxy-4-(4-methyl-1H-imidazol-1-yl)phenylamino)-4-(3-methoxybenzyl)-7,8-dihydropyrido[4,3-d]pyrimidin-6(5H)-yl)ethanone 1-(4-(3-methoxybenzyl)-2-(4-(2-methyl-1H-imidazol-1-yl)phenylamino)-7,8-dihydropyrido[4,3-d]pyrimidin-6(5H)-yl)ethanone 1-(4-(2-fluorobenzyl)-2-(4-(2-methyl-1H-imidazol-1-yl)phenylamino)-7,8-dihydropyrido[4,3-d]pyrimidin-6(5H)-yl)ethanone 4-(4-fluorobenzyl)-N-(4-(2-methyl-1H-imidazol-1-yl)phenyl)-6-(trifluoromethyl)-5,6,7,8-tetrahydroquinazolin-2-amine N-(3-methoxy-4-(4-methyl-1H-imidazol-1-yl)phenyl)-4-(3-methoxybenzyl)-7,8-dihydro-5H-pyrano[4,3-d]pyrimidin-2-amine 4-(Methoxy(phenyl)methyl)-N-(3-methoxy-4-(4-methyl-1H-imidazol-1-yl)phenyl)-7,8-dihydro-5H-pyrano[4,3-d]pyrimidin-2-amine N-(3-Methoxy-4-(4-methyl-1H-imidazol-1-yl)phenyl)-4-(2-(tetrahydrofuran-2-yl)ethyl)-7,8-dihydro-5H-pyrano[4,3-d]pyrimidin-2-amine 2-(2-(3-methoxy-4-(4-methyl-1H-imidazol-1-yl)phenylamino)-7,8-dihydro-5H-pyrano[4,3-d]pyrimidin-4-yl)propan-2-ol 4-(1-(3,5-dimethyl-1H-pyrazol-1-yl)ethyl)-N-(3-methoxy-4-(4-methyl-1H-imidazol-1-yl)phenyl)-7,8-dihydro-5H-pyrano[4,3-d]pyrimidin-2-amine 2-(4-benzyl-2-(3-methoxy-4-(4-methyl-1H-imidazol-1-yl)phenylamino)-7,8-dihydropyrido[4,3-d]pyrimidin-6(5H)-yl)acetonitrile 4-benzyl-N-(3-methoxy-4-(4-methyl-1H-imidazol-1-yl)phenyl)-5,6,7,8-tetrahydropyrido[4,3-d]pyrimidin-2-amine 1-(4-benzyl-2-(3-methoxy-4-(4-methyl-1H-imidazol-1-yl)phenylamino)-7,8-dihydropyrido[4,3-d]pyrimidin-6(5H)-yl)ethanone 1-(4-(1-(3,5-dimethyl-1H-pyrazol-1-yl)ethyl)-2-(3-methoxy-4-(4-methyl-1H-imidazol-1-yl)phenylamino)-7,8-dihydropyrido[4,3-d]pyrimidin-6(5H)-yl)ethanone 4-(cyclopentyloxymethyl)-N-(3-methoxy-4-(4-methyl-1H-imidazol-1-yl)phenyl)-7,8-dihydro-5H-pyrano[4,3-d]pyrimidin-2-amine 1-(2-(2-(3-methoxy-4-(4-methyl-1H-imidazol-1-yl)phenylamino)-7,8-dihydro-5H-pyrano[4,3-d]pyrimidin-4-yl)ethyl)pyrrolidin-2-one 1-(2-(3-methoxy-4-(4-methyl-1H-imidazol-1-yl)phenylamino)-4-(2-(tetrahydrofuran-2-yl)ethyl)-7,8-dihydropyrido[4,3-d]pyrimidin-6(5H)-yl)ethanone N-(3-methoxy-4-(4-methyl-1H-imidazol-1-yl)phenyl)-6-methyl-4-(2-(tetrahydrofuran-2-yl)ethyl)-5,6,7,8-tetrahydropyrido[4,3-d]pyrimidin-2-amine 4-((1,3-difluoropropan-2-yloxy)methyl)-N-(3-methoxy-4-(4-methyl-1H-imidazol-1-yl)phenyl)-7,8-dihydro-5H-pyrano[4,3-d]pyrimidin-2-amine 4-benzyl-N-[4-(2-methyl-1H-imidazol-1-yl)phenyl]-7,8-dihydro-5H-thiopyrano[4,3-d]pyrimidin-2-amine 6-oxide as a free base or a pharmaceutically acceptable salt thereof.

The definitions set forth in this application are intended to clarify terms used throughout this application. The term "herein" means the entire application.

As used herein, "alkyl", used alone or as a suffix or prefix, is intended to include both branched and straight chain saturated aliphatic hydrocarbon groups having from 1 to 12 carbon atoms or if a specified number of carbon atoms is provided then that specific number would be intended. For example "$C_{1-6}$ alkyl" denotes alkyl having 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl. In the case where a subscript is the integer 0 (zero) the group to which the subscript refers to indicates that the group may be absent, i.e. there is a direct bond between the groups.

As used herein, "alkenyl", used alone or as a suffix or prefix, is intended to include both branched and straight chain aliphatic hydrocarbon groups comprising at least one carbon-carbon double bond (—C═C—) and having from 2 to 12 carbon atoms or if a specified number of carbon atoms is provided then that specific number would be intended. For example "$C_{2-6}$ alkenyl" denotes alkenyl having 2, 3, 4, 5 or 6 carbon atoms.

As used herein, "alkynyl", ", used alone or as a suffix or prefix, is intended to include both branched and straight chain aliphatic hydrocarbon groups comprising at least one carbon-carbon triple bond (—C≡C—) and having from 2 to 12 carbon atoms or if a specified number of carbon atoms is provided then that specific number would be intended. For example "$C_{2-6}$ alkynyl" denotes alkynyl having 2, 3, 4, 5 or 6 carbon atoms.

As used herein, "carbocyclyl", used alone or as suffix or prefix, is intended to include cyclic non-aromatic hydrocarbon groups from 3 to 14 ring carbon atoms, wherein a —$CH_2$— group can optionally be replaced by a —C(O)—. In one embodiment, "carbocyclyl" is a monocyclic ring containing 5 or 6 atoms or a bicyclic ring containing 9 or 10 atoms. Examples of carbocyclyls include cyclopropyl, cyclobutyl, cyclopentyl, cyclohexyl, cycloheptyl 1-oxocyclopentyl, cyclopentyl, cyclopentenyl, cyclohexyl, cyclohexenyl, phenyl, naphthyl, tetralinyl, indanyl or 1-oxoindanyl. According to one embodiment, the cycloalkyl group can comprise cycloalkyl groups that are substituted with other rings including fused ring. Example of cycloalkyl groups that are substituted with fused rings include, but are not limited to, adamantly, bornyl, camphenyl, bicycle[2.2.2]octyl, tetrahydronaphthyl and indanyl groups.

The term "alkoxy", unless stated otherwise, refers to radicals of the general formula —O—R, wherein R is selected from a hydrocarbon radical. For example "$C_{1-6}$ alkoxy" denotes alkoxy having 1, 2, 3, 4, 5 or 6 carbon atoms. Examples of alkoxy include, but are not limited to, methoxy, ethoxy, propoxy, isopropoxy, butoxy, t-butoxy and isobutoxy.

As used herein, the term "aryl" refers to an aromatic ring structure made up of from 5 to 14 carbon atoms. Ring structures containing 5, 6, 7 and 8 carbon atoms would be single-ring aromatic groups, for example, phenyl. Ring structures containing 8, 9, 10, 11, 12, 13, or 14 would be polycyclic, for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic and, for example, the other cyclic rings can be cycloalkyls, cycloalkenyls, cycloalkynyls, aryls and/or heterocyclyls.

As used herein, "halo" or "halogen" or "halogenated" refers to fluoro, chloro, bromo, and iodo. "Counterion" is used to represent a small, negatively charged species such as chloride, bromide, hydroxide, acetate, sulfate, tosylate, benezensulfonate, and the like.

As used herein, "heteroaryl" refers to a heteroaromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl (i.e., pyridinyl), pyrimidinyl, pyrazinyl, pyridazinyl, triazinyl, furyl (i.e. furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, imidazothiazolyl and the like. In some embodiments, the heteroaryl group has from 1 to 16 carbon atoms, and in further embodiments from 3 to 16 carbon atoms. In some embodiments, the heteroaryl group contains 3 to 14, 4 to 14, 3 to 7, or 5 to 6 ring-forming atoms. In some embodiments, the heteroaryl group has 1 to 4, 1 to 3, or 1 to 2 heteroatoms. In some embodiments, the heteroaryl group has 1 heteroatom.

A "heterocyclyl" is a saturated or partially unsaturated monocyclic ring containing 4-7 atoms of which at least one atom is chosen from nitrogen, sulphur or oxygen, which may, unless otherwise specified, be carbon or nitrogen linked, wherein a —$CH_2$— group can optionally be replaced by a —C(O)—, or a ring nitrogen and/or sulphur atom may be optionally oxidised to form the N-oxide and or the S-oxides. In one aspect of the present invention, "heterocyclyl" is a saturated monocyclic ring containing 4 or 5 or 6 atoms. Examples of heterocyclic groups include without limitation areazetidyl, morpholino, piperidyl, tetrahydropyranyl, 1,4-dioxanyl, 1,3-dioxolanyl, 1,2-oxathiolanyl, piperazinyl, pyrrolidinyl, tetrahydrofuranyl and thiomorpholino.

As used herein, the phrase "protecting group" means temporary substituents, which protect a potentially reactive functional group from undesired chemical transformations. Examples of such protecting groups include esters of carboxylic acids, silyl ethers of alcohols, and acetals and ketals of aldehydes and ketones respectively. The field of protecting group chemistry has been extensively reviewed (e.g. Jarowicki, K; Kocienski, P. Perkin Trans. 1, 2001, issue 18, p. 2109).

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the non-toxic salts or the quaternary ammonium salts of the parent compound formed, for example, from non-toxic inorganic or organic acids. For example, such non-toxic salts include those derived from inorganic acids such as hydrochloric acid.

The pharmaceutically acceptable salts of the present invention can be synthesized from the parent compound that contains a basic or acidic moiety by chemical methods. Generally, such salts can be prepared by reacting the free acid or base forms of these compounds with a stoichiometric amount of the appropriate base or acid in water or in an organic solvent, or in a mixture of the two; generally, nonaqueous media like diethyl ether, ethyl acetate, ethanol, isopropanol, or acetonitrile are used.

A variety of compounds in the present invention may exist in particular geometric or stereoisomeric forms. The present invention takes into account all such compounds, including cis- and trans isomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. Many geometric isomers of olefins, C=N double bonds, and the like can also be present in the compounds described herein, and all such stable isomers are contemplated in the present invention. C is and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

As used herein, "tautomer" means other structural isomers that exist in equilibrium resulting from the migration of a hydrogen atom. For example, keto-enol tautomerism where the resulting compound has the properties of both a ketone and an unsaturated alcohol.

Compounds of the invention further include hydrates and solvates.

The present invention further includes isotopically-labeled compounds of the invention. An "isotopically" or "radio-labeled" compound is a compound of the invention where one or more atoms are replaced or substituted with an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radiolabeled compounds will depend on the specific application of that radio-labeled compound. For example, for in vitro receptor labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from the group consisting of $^3$H, $^{14}$C, $^{125}$I, $^{35}$S and $^{82}$Br.

The present invention also relates to the use of a compound according to formula (I)

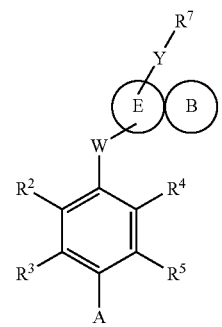

wherein
E is

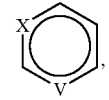

X and V are independently selected from nitrogen or CH and wherein at least one of X or V is nitrogen;

W is —C(R$^6$)$_2$—, —O— or —N(R$^6$)—;

R$^6$ is hydrogen, C$_{1-4}$alkyl or C$_{1-4}$alkoxy, wherein said C$_{1-4}$alkyl is substituted with halogen, cyano, hydroxy, amino, NHC$_{1-4}$alkyl, N(C$_{1-4}$alkyl)$_2$, heterocyclyl, NC(O)C$_{1-4}$alkyl, C(O)C$_{1-4}$alkoxy or SO$_2$C$_{1-6}$alkyl;

Y is —C(R$^{12}$)(R$^{13}$)—, —N(R$^8$)— or —O—;

R$^{12}$ and R$^{13}$ are independently selected from hydrogen, halogen, C$_{1-6}$alkyl, C$_{1-6}$alkylOC$_{1-6}$alkyl, carbocyclyl, heterocyclyl and C$_{1-6}$alkoxy, wherein said C$_{1-6}$alkyl, C$_{1-6}$alkylOC$_{1-6}$alkyl, carbocyclyl, heterocyclyl or C$_{1-6}$alkoxy is optionally substituted with one or more substituents selected from halogen, cyano, hydroxy, heterocyclyl, N(C$_{0-4}$alkyl)$_2$, NC(O)C$_{1-4}$alkyl;

or

R$^{12}$ and R$^{13}$ may form together with the cabon atom they are attached to a saturated, partially unsaturated or saturated ring system, wherein said ring system may contain one or more heteroatoms selected from N, O and S, and wherein if said ring system contains an —NH— moiety that nitrogen may optionally be substituted with a group selected from C$_{1-6}$alkyl and C(O)C$_{1-6}$alkyl and wherein said ring is optionally substituted with one or more groups selected from halogen, cyano, hydroxy;

or

R$^{12}$ and R$^7$ may form together a saturated, partially unsaturated or saturated bicyclic ring system, wherein said bicyclic ring system may contain zero to three heteroatoms selected from N, O and S, and wherein said bicyclic ring system is optionally substituted with one to three substituents selected from halogen, cyano, hydroxy, C$_{1-6}$alkoxy, amino, NHC$_{1-4}$alkyl, N(C$_{1-6}$alkyl)$_2$, NC(O)C$_{1-6}$alkyl, SO$_2$C$_{1-6}$alkyl and heterocyclyl, and wherein if said bicyclic ring system contains an —NH— moiety that nitrogen may optionally be substituted by a group selected from C$_{1-6}$alkyl and C(O)C$_{1-6}$alkyl;

R$^8$ is selected from hydrogen, C$_{1-6}$alkyl, C$_{1-6}$alkylOC$_{1-6}$alkyl, C(O)C$_{1-6}$alkyl, C(O)C$_{3-8}$cycloalkyl, heterocyclyl, carbocyclyl, C(O)C$_{3-6}$heterocyclyl or SO$_2$C$_{1-6}$alkyl, wherein said C$_{1-6}$alkyl, heterocyclyl, carbocyclyl or C$_{1-6}$alkylOC$_{1-6}$alkyl is optionally substituted with one to three substituents selected from halogen, cyano, hydroxy, amino, NHC$_{1-4}$alkyl, N(C$_{1-6}$alkyl)$_2$, NC(O)C$_{1-6}$alkyl, C(O)C$_{1-6}$alkoxy, SO$_2$C$_{1-6}$alkyl and heterocyclyl;

R$^7$ is selected from hydrogen, aryl, heteroaryl, C$_{1-4}$alkylaryl, C$_{1-4}$alkylheteroaryl, C$_{1-4}$alkylcarbocyclyl, C$_{1-4}$alkylheterocyclyl and carbocyclyl, wherein said aryl, heteroaryl, C$_{1-4}$alkylcarbocyclyl, C$_{1-4}$alkylheterocyclyl, C$_{1-4}$alkylaryl, carbocyclyl or C$_{1-4}$alkylheteroaryl is optionally substituted with one or more substituents selected from halogen, cyano, hydroxy, nitro, C$_{1-6}$alkyl, C$_{1-6}$alkoxy, carbocyclyl, heterocyclyl, CF$_3$, OCF$_3$, OC$_{1-6}$alkyl, C(O)C$_{1-6}$alkyl, C$_{1-6}$alkylOC$_{1-6}$alkyl, SO$_2$C$_{1-6}$alkyl, SO$_2$NHC$_{1-6}$ alkyl, SO$_2$N(C$_{1-6}$alkyl)$_2$, SO$_2$N-heterocyclyl, C(O)NH$_2$, C(O)NHC$_{1-6}$alkyl, C(O)N(C$_{1-6}$alkyl)$_2$, C(O)N-heterocyclyl, C$_{2-6}$alkenyl and C$_{2-6}$alkynyl, wherein said C$_{1-6}$alkyl, C$_{1-6}$alkoxy, C$_{1-6}$alkylOC$_{1-6}$alkyl, heterocyclyl, carbocyclyl, C$_{2-6}$alkenyl or C$_{2-6}$alkynyl is optionally substituted with cyano, hydroxy, methoxy, halogen, SO$_2$C$_{1-4}$alkyl, amino, NHC$_{1-4}$alkyl, N(C$_{1-4}$alkyl)$_2$, heterocyclyl or aryl;

or

R$^8$ and R$^7$ may, when Y is NR$^8$, optionally form together with the nitrogen atom a saturated, partially saturated or unsaturated ring system, wherein said ring system is optionally substituted with one or more groups selected from halogen, hydroxy, cyano, C$_{1-4}$alkylOC$_{1-4}$alkyl and C$_{1-4}$alkyl, wherein said C$_{1-4}$alkylOC$_{1-4}$alkyl and C$_{1-4}$alkyl is optionally substituted with halogen, cyano, hydroxy;

R$^1$ is selected from hydrogen, C$_{1-6}$alkyl, C$_{1-6}$alkoxy, C$_{2-6}$alkenyl, C$_{2-6}$alkynyl, carbocyclyl, heterocyclyl, C(O)R$^9$, C(O)N(R$^9$)$_2$, C(O)CH$_2$N(R$^9$)$_2$, C(O)heterocyclyl, C(O)carbocyclyl, C(O)OR$^9$, SO$_2$R$^9$, SO$_2$heterocyclyl, SO$_2$carbocyclyl and SO$_2$N(R$^9$)$_2$, wherein said C$_{1-6}$alkyl, C$_{1-6}$alkoxy, C$_{2-6}$alkenyl, C$_{2-6}$alkynyl, carbocyclyl or heterocyclyl is optionally substituted with one or more substituents selected from halogen, hydroxy, cyano, amino, C(O)OR$^9$, NHC$_{1-6}$alkyl, NHC$_{1-6}$alkoxy, N(C$_{1-6}$alkyl)$_2$, N(C$_{1-6}$alkoxy)$_2$, SC$_{1-6}$alkyl, SOC$_{1-6}$alkyl, SO$_2$C$_{1-6}$alkyl, C$_{1-6}$alkyl, C$_{1-6}$alkoxy, heterocyclyl and carbocyclyl;

R$^9$ is selected from hydrogen, hydroxy, halogen, cyano, C$_{1-6}$alkyl, C$_{1-6}$alkoxy, carbocyclyl and heterocyclyl, wherein said C$_{1-6}$alkyl, C$_{1-6}$alkoxy, cycloalkyl or heterocyclyl is optionally substituted with one or more substituents selected from halogen, cyano, hydroxy or methoxy;

R$^4$, R$^5$, R$^3$ and R$^2$ are independently selected from hydrogen, cyano, C$_{1-4}$alkyl, C$_{1-4}$alkoxy, halogen, OCH$_3$, OCF$_3$, OCF$_2$H, OCFH$_2$ and hydroxy;

A is a 5-7 membered heteroaryl, wherein at least one of the ring forming atoms is selected from nitrogen and the remaining ring forming atoms are selected from carbon, nitrogen, sulphur and oxygen, and wherein said A is optionally substituted with one or more substituents selected from halogen, C$_{1-4}$alkyl, SR$^{10}$, NR$^{10}$R$^{11}$, OR$^{10}$, C$_{2-4}$alkenyl and C$_{2-4}$alkynyl and wherein said C$_{1-4}$alkyl, C$_{2-4}$alkenyl or C$_{2-4}$alkynyl is optionally substituted with halogen, hydroxy, cyano or C$_{1-4}$alkoxy;

R$^{10}$ and R$^{11}$ are independently selected from hydrogen, C$_{1-4}$alkyl, CF$_3$, CF$_2$H and CFH$_2$;

B is a 5 to 7 membered saturated or partly saturated ring, wherein one of the ring forming atom is selected from —N(R$^1$)—, —C(R$^9$)—, —S(O)$_n$— or —O— and the other ring forming atoms are carbon, wherein one —CH$_2$— group can optionally be replaced by a —C(O)— and wherein said ring is optionally substituted with one to three substituents selected from halogen, cyano, hydroxy, amino, C$_{1-4}$alkyl, C$_{1-4}$alkoxy, NHC$_{1-6}$alkyl, NHC$_{1-6}$alkylOC$_{1-6}$alkyl, N(C$_{1-6}$alkyl)$_2$, N(C$_{1-6}$alkylOC$_{1-6}$alkyl)$_2$, carbocyclyl and heterocyclyl wherein said C$_{1-4}$alkyl, C$_{1-4}$alkoxy, NHC$_{1-6}$alkyl, NHC$_{1-6}$alkylOC$_{1-6}$alkyl, N(C$_{1-6}$alkyl)$_2$, N(C$_{1-6}$alkylOC$_{1-6}$alkyl)$_2$, carbocyclyl or heterocyclyl is optionally substituted with one or more substituents selected from halogen, hydroxy, cyano;

n is selected from 0, 1, 2;

E and B will together form a bicyclic ring system;

as a free base or a pharmaceutically acceptable salt thereof;

for the manufacture of a medicament for treating or preventing an Aβ-related pathology.

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

The quantity of the compound to be administered will vary for the patient being treated and will vary from about 100 ng/kg of body weight to 100 mg/kg of body weight per day and preferably will be from 10 pg/kg to 50 mg/kg per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

The treatment of Aβ-related pathology defined herein may be applied as a sole therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents or atypical antipsychotic agents. Cognitive enhancing agents, memory enhancing agents and acetyl choline esterase inhibitors includes, but not limited to, onepezil (Aricept), galantamine (Reminyl or Razadyne), rivastigmine (Exelon), tacrine (Cognex) and memantine (Namenda, Axura or Ebixa). Atypical antipsychotic agents includes, but not limited to, Olanzapine (marketed as Zyprexa), Aripiprazole (marketed as Abilify), Risperidone (marketed as Risperdal), Quetiapine (marketed as Seroquel), Clozapine (marketed as Clozaril), Ziprasidone (marketed as Geodon) and Olanzapine/Fluoxetine (marketed as Symbyax).

Such conjoint treatment may be achieved by way of the simultaneous, sequential or separate dosing of the individual components of the treatment. Such combination products employ the compounds of the invention.

Additional conventional therapy may include one or more of the following categories of agents:

(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine and equivalents and pharmaceutically active isomer(s) and metabolite(s) thereof.

(ii) atypical antipsychotics including for example quetiapine and pharmaceutically active isomer(s) and metabolite(s) thereof.
(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof.
(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof.
(v) anticonvulsants including for example carbamazepine, valproate, lamotrigine, gabapentin and equivalents and pharmaceutically active isomer(s) and metabolite(s) thereof.
(vi) Alzheimer's therapies including for example donepezil, memantine, tacrine and equivalents and pharmaceutically active isomer(s) and metabolite(s) thereof.
(vii) Parkinson's therapies including for example deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof.
(viii) migraine therapies including for example almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof.
(ix) stroke therapies including for example abciximab, activase, NXY-059, citicoline, crobenetine, desmoteplase,r-epinotan, traxoprodil and equivalents and pharmaceutically active isomer(s) and metabolite(s) thereof.
(x) urinary incontinence therapies including for example darafenacin, falvoxate, oxybutynin, propiverine, robalzotan, solifenacin, tolterodine and and equivalents and pharmaceutically active isomer(s) and metabolite(s) thereof.
(xi) neuropathic pain therapies including for example gabapentin, lidoderm, pregablin and equivalents and pharmaceutically active isomer(s) and metabolite(s) thereof.
(xii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof.
(xiii) insomnia therapies including for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem and equivalents and pharmaceutically active isomer(s) and metabolite(s) thereof.
(xiv) mood stabilizers including for example carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combination products employ the compounds of this invention within the dosage range described herein and the other pharmaceutically active compound or compounds within approved dosage ranges and/or the dosage described in the publication reference.

Methods of Preparation for Compounds of the Present Invention

Preparation of the compounds of formula (I) will be illustrated below.

In each of the following preparation methods, when a defined group changes under reaction conditions or is not suitable for carrying out the method, the preparation can be easily carried out by subjecting the group to a procedure conventionally employed in organic synthetic chemistry, such as protection and/or deprotection of a functional group (for example see, Protection Groups in Organic Synthesis, T. W. Green, Wiley & Sons Inc. (1999)).

Where necessary the order of reation process steps such as introduction of substituents can be altered. Solvent, temperature, pressure, and other reaction conditions may readily be selected by one of ordinary skill of the art. Starting materials are commercially available or readily prepared by one skilled in the art. Compounds of formula (I) can be prepared, for example, using the Methods of Preparation 1 to 4.

Compounds of formula (AI) can be prepared, for example, by using the Methods of Preparation 1 to 5. In the method of preparation below, PG represents a protective group or any suitable $R^1$ defined as in formula (I). PG can be replaced or exchanged prior to, during or immediately following the processing mentioned below.

Method of Preparation 1:

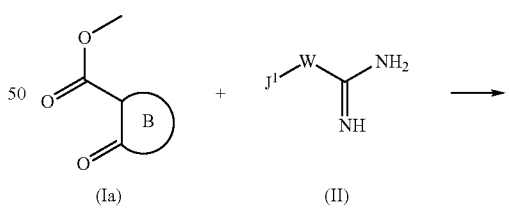

(Ia)    (II)

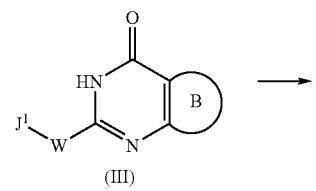

(III)

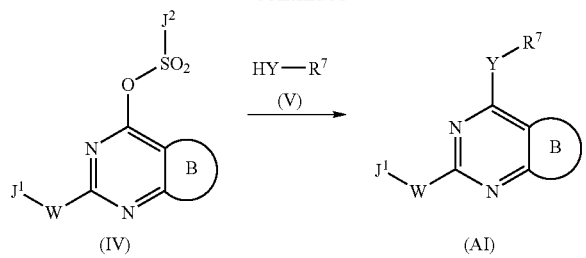

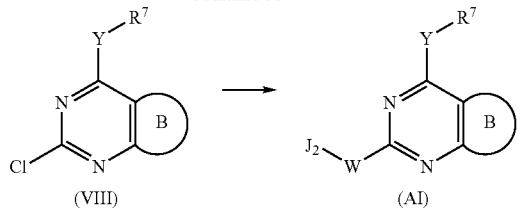

wherein $J^1$-W is a substituted $ArNR^6$, ArO or $ArC(R^6)_2$ $J^2$ is $CF_3$, $CH_3$ or aryl.

Y, $R^6$, $R^7$ and B are as defined for the compound of formula (I) above.

Condensation of cyclic beta-keto ester of formula (Ia) with an appropriate substituted guanidine or substituted acetamide of formula (II) in presence of a suitable base (such as sodium or potassium alkoxides) provides pyrimidinone of formula (III). Pyrimidinone of formula (III) is converted into the sulfonate of formula (IV) using reagents (such as triflate anhydride or 1,1,1-trifluoro-N-phenyl-N-(trifluoromethylsulfonyl)methanesulfonamide or sulphonyl chloride) in presence of a suitable base (such as 1,8-diazabicyclo[5.4.0]undec-7-ene and triethylamine).

Displacement of the sulphonate of formula (IV) in presence of an appropriate nucleophile (V) such as amine, alcohol and thiol afford compounds of formula (AI). The conditions for displacing the sulphonate of formula (IV) will depend on the nature of the reactivity of formula (V) and are generally by the skilled person (see for examples European J. Med. Chem; 2007, 42, 256, and Synlett; 1997, 12; 1400; and Org. Lett., 2000, 2 , 927).

Cross-coupling reaction is an alternative method for converting a compound of formula (IV) into a compound of formula (I). Compounds of formula (IV) and of formula (V) are heated in presence of a catalyst (such as $Pd(OAc)_2$ and $Pd(dba)_2$, a ligand (such as BINAP, dppf and Xantphos), a suitable base (such as potassium tert-butoxide and $CsCO_3$) in a suitable solvent (see for examples Accounts of Chemical Research, 2002, 35, 717; and J. Am. Chem. Soc. 2003, 125, 6653).

Method of Preparation 2:

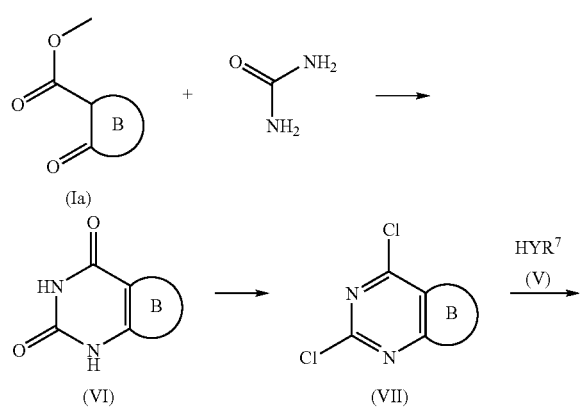

wherein $J^2W$ is a substituted $ArNR^6$ or ArO;

Y, B, $R^6$ and $R^7$ are as defined for the compound of formula (I) above.

Compounds of formula (VI) can be prepared, for example, according to the method described in US 2007/0037834. Thus, compound of formula (VI) can be obtained by reacting a beta-keto ester of formula (Ia) with one equivalent to an excess of urea in the presence of a base (such as sodium or potassium alkoxides). Compounds of formula (VII) can be prepared by reacting a compound of formula (VI) with an excess of a chlorinating agent. Examples of chlorinating agents are phosphorus oxychloride and phosphorus pentachloride. Compounds of formula (VIII) can be prepared by reacting compounds of formula (VII) with one equivalent to a large excess of a compound of formula (V) optionally in presence of a base. Examples of suitable bases are triethylamine, pyridine and sodium carbonates.

Compound of formula (VIII) can also be obtained by using the "Buchwald-Hartwig cross-coupling" method as an alternative to the thermal displacement mentioned above. In said method are compounds of formula (VII) reacted with a reactant of formula (V), which may be an amine, thiol or alcohol in the presence of a suitable base (such as $CsCO_3$ or potassium tert-butoxide), a suitable catalyst (such as $Pd(OAc)_2$) and a suitable ligand (such as triphenylphosphine or BINAP) to provide compound of formula (VIII) (see for examples Acc. Chem. Res. 1998, 31, 803-818 and J. Am. Chem. Soc., 125, 6653).

Method of Preparation 3:

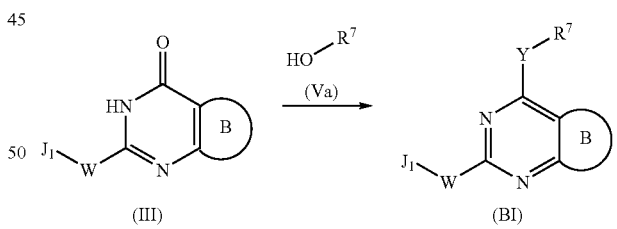

wherein $J^1W$ is a substituted $ArNR^6$, ArO or $ArC(R^6)_2$;

B, $R^6$ and $R^7$ are as defined for the compounds of formula (I) above.

Compounds of formula (BI) can be prepared in one step using the "Mitsunobu" method (see for examples Tetra. Lett. 1994, 35, 2819 and Synlett. 2005, 18, 2808). Trialkyl or triaryl phosphine (such as triphenyphosphine or tributylphosphine) and a suitable dialkyl azodicarboxylate (such as DEAD) are added to a compound of formula (II) in the presence of an appropriate alcohol of formula (Va) in a suitable solvent (such as THF) to afford compound of formula (BI).

Method of Preparation 4:

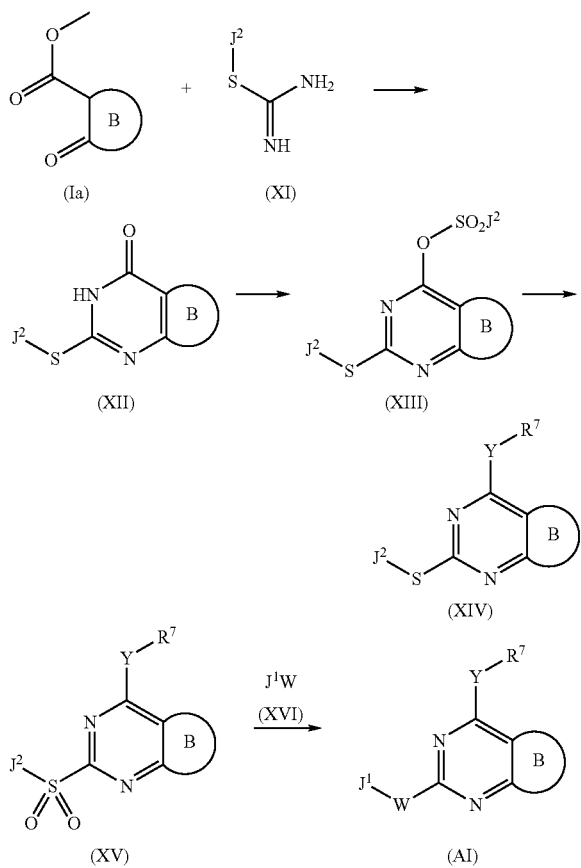

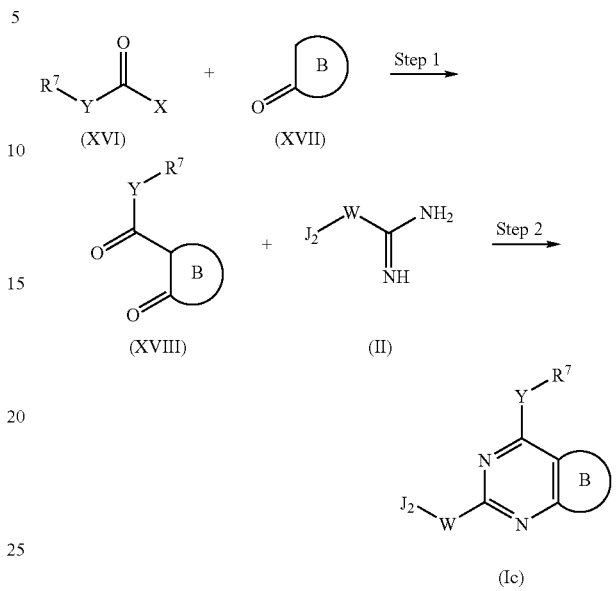

wherein J¹W is a substituted ArNR⁶ or ArO;
J² is alkyl or arylalkyl;
B, R⁷, R⁶ and Y are as defined for the compound of formula (I) above.

Condensation of cyclic beta-keto ester of formula (Ia) with an appropriate thiourea of formula (XI) in presence of a suitable base (such as sodium or potassium alkoxides) provides a compound of formula (XII). A compound of formula (XII) is converted into the sulphonate of formula (XIII) using reagents (such as triflate anhydride, 1,1,1-trifluoro-N-phenyl-N-(trifluoromethylsulfonyl)methanesulfonamide or a sulphonyl chloride) in presence of an suitable base (such as 1,8-diazabicyclo[5.4.0]undec-7-ene or triethylamine). Displacement of the sulphonate of formula (XIII) in presence of an appropriate nucleophile of formula (V) such as amine, alcohol and thiol affords a compound of formula (XIV).

The compound of formula (XIV) can also be obtained by the "Buchwald-Hartwig cross-coupling" method as an alternative to the thermal displacement mentioned above. Compound of formula (XIII) is reacted with a reactant of formula (V), which may be an amine, thiol or alcohol, in the presence of a suitable base (such as CsCO₃ or potassium tert-butoxide), a suitable catalyst (such as Pd(OAc)₂) and a suitable ligand (such as triphenylphosphine or BINAP) to provide the compound of formula (VIII).

Conversion of compound of formula (XIV) to the corresponding sulphone of formula (XV) can be obtained by reacting a compound of formula (XIV) with an oxidation agent (such as m-chloroperbenzoic acid) in a suitable solvent. Displacement of a compound of formula (XV) with a suitable nucleophile of formula (XVI) such as amine, alcohol and thio, provides compound of formula (AI).

Method of Preparation 5 wherein
Y is —C(R¹²)(R¹³), —C(R¹²)(R¹³)—O—, —C(R¹²)(R¹³)—N(R⁸)—;
J² is a substituted aryl;
W is carbon or nitrogen;
X is Cl or imidazolyl;
B is as defined for the compound of formula (I) above;
R¹³, R¹³ and R⁸ are as defined for the compound of formula (Ia) above;

Step 1
A suitable base (such as lithium diisoprylamide, lithium bis(trimethylsilyl)amide) is added to a solution of ketone of formula (XVII) in a suitable solvent (such as hexane, THF) preferably below room temperature followed by addition of the acid chloride or other activated form such as imidazolyl of formula (XVI) to afford a diketone of formula (XVIII).

Step 2
Condensation of diketone of formula (XVIII) with an appropriate compound of formula (II) in presence of a suitable base (such as sodium or potassium alkoxides) provides a compound of formula (Ic). Condensation is preferably performed between rt and 150° C. in a suitable solvent (such as ethanol or DMF).

Examples have been named using CambridgeSoft MedChem ELN v2.1.

ABBREVIATIONS app apparent
aq. Aqueous
Ar Argon (or Argon atmosphere)
br broadened
BINAP 2,2'-bis(diphenylphosphino)-1,1'-binaphthyl
CI chemical ionization
δ chemical shift in parts per million (ppm) downfield from the standard
d doublet
DCM dichloromethane
DIPEA N,N-diisopropylethylamine DMA N,N-dimethylacetamide
DMF N,N-dimethylformamide
DME 1,2-dimethoxyethane
DMSO dimethyl sulfoxide
dppf 1,1'-bis(diphenylphosphino)ferrocene
EI electron impact
eq equivalents
ES electro-spray
ELS electro-spray
Et$_2$O diethyl ether
EtOH ethanol
HCl hydrochloric acid
HBTU O-Benzotriazol-1-yl-N,N,N',N'-tetra-methyluronium hexafluorophosphate
HPLC high performance liquid chromatography
LC liquid chromatography
LHMDS lithium hexamethyldisilazide
m multiplet
mCPBA meta-chloroperbenzoic acid
MeCN acetonitrile
MeOH methanol
MP-CNBH$_3$ Macroporous cyanoborohydride
MS mass spectroscopy
NMR nuclear magnetic resonance
o.n. Over-night
Pd(dba)$_2$ bis(dibenzylideneacetone)palladium
Pd(OAc)$_2$ palladium(II) acetate
Pd(PPh$_3$)$_4$ tetrakis(triphenylphosphine)palladium(0)
PDA photodiode array detector
prep. Preparative
q quartet
r.t. Room temperature (ca 21-25° C.)
s singlet
t triplet
THF tetrahydrofuran
TEA triethylamine
TFA trifluoroacetic acid
TLC thin layer chromatography
UV ultra violet
Xantphos 4,5-bis(diphenylphosphino)-9,9-dimethylxanthene

EXAMPLES

Below follows a number of non-limiting examples of compounds of the invention.

General Procedure for the Preparation of Pyrimidines

The diketone (1 eq), the guanidine (1 eq) and potassium carbonate (2 eq) was slurrified in EtOH. The reaction was heated to 130° C. in the microwave oven. DCM and water were added and the organic phase was separated. The crude products were used as such or purified by preparative HPLC.

General Procedure for the Preparation of Diketones

The ketone were dissolved in toluene and cooled to 0° C. LHMDS (1.1 eq) was added and after 2 min the acid chlorides were added. The reactions were quenched after 5 min with 5 eq acetic acid in water. The organic phase was separated and reduced under vacuum. The crude products were purified with flash column chromatography (a gradient of EtOAc in Heptane).

General Procedure for Reductive Amination

To the amine, the aldehyde, 0.1 eq acetic acid and 2 eq MP-cyanoborohydride were added 2 ml MeOH. After 2 h stirring at rt the solid reagent was filtered off and the solvent was evaporated. The crude products were purified on MS-triggered preparative HPLC.

General Procedure for Boc Deprotection of Amines

The boc protected amines were dissolved in DCM (5 mL). TFA (10 eq) was added and the reactions were heated to reflux for 2 h. The mixtures were neutralized with sat NaHCO$_3$ and the phases were separated. The organic phases, in all cases except two, contained the deprotected products. The organic phases were separated, dried with MgSO$_4$ and the solvents were evaporated. Where the deproteced product could be found in the aqueous phase both phases were evaporated together and used as such.

General Procedure for N-acetylation

Acetic anhydride (1 eq) was added to a solution of the secondary amine (1 eq) in DCM (and in some cases a few drops of MeOH). After 2 hours the solvents were evaporated and the residues redissolved in MeOH (1 mL) and then transferred into a 48 pos MTP. The products were purified on UV or MS-triggered preparative HPLC.

General Procedure for Preparation of Acid Chlorides

The carboxylic acid (1 eq) was dissolved in thionyl chloride (3 eq) and heated to reflux for 1 h. The excess thionyl chloride was evaporated and used as such.

Example 1

2-((2-(4-(Oxazol-5-yl)phenylamino)-5,6,7,8-tetrahydropyrido[4,3-d]pyrimidin-4-yl)(phenyl)aminoethanol

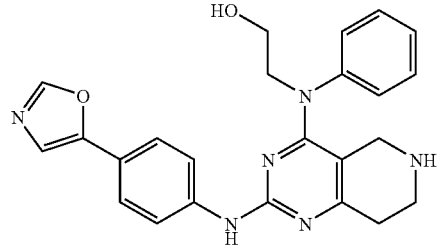

Hydrochloric acid (2 M, 2 ml) was added to a solution of tert-butyl 4-((2-hydroxyethyl)(phenyl)amino)-2-(4-(oxazol-5-yl)phenylamino)-7,8-dihydropyrido[4,3-d]pyrimidine-6 (5H)-carboxylate (150 mg, 0.28 mmol, Example 1a) in methanol (4 mL). Water (2 mL) was added and the solution was stirred at 70° C. for 30 min. The residual solvent was evaporated under reduced pressure and the crude product dissolved in DMSO. Purification by preparative HPLC afforded 2-((2-(4-(oxazol-5-yl)phenylamino)-5,6,7,8-tetrahydropyrido[4,3-d]pyrimidin-4-yl)(phenyl)amino)ethanol (72 mg, 54.8%). MS (ESI+)/(ESI−) m/z 429/427

$^1$H NMR (500 MHz, DMSO-d$_6$) δ ppm 2.56 (t, 2 H) 2.73 (s, 2 H) 2.78 (t, 2 H) 3.66 (t, 2 H) 4.02 (t, 2 H) 4.83 (br. s., 1 H) 7.10-7.20 (m, 3 H) 7.31-7.38 (m, 2 H) 7.50 (s, 1 H) 7.60 (d, 2 H) 7.87 (d, Hz, 2 H) 8.35 (s, 1 H) 9.44 (s, 1 H)

Example 1a tert-Butyl 4-((2-hydroxyethyl)(phenyl)amino)-2-(4-(oxazol-5-yl)phenylamino)-7,8-dihydropyrido[4,3-d]pyrimidine-6(5H)-carboxylate

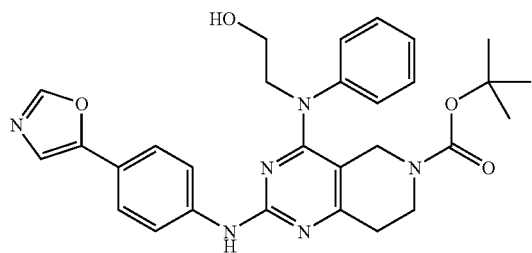

2-(Phenylamino)ethanol (0.051 g, 0.37 mmol) was added to tert-butyl 2-(4-(oxazol-5-yl)phenylamino)-4-(trifluoromethylsulfonyloxy)-7,8-dihydropyrido[4,3-d]pyrimidine-6(5H)-carboxylate (0.2 g, 0.37 mmol, Example 1b) in DMSO (3 mL). The reaction mixture was heated in a microwave reactor at 70° C. for 3 h. Water (1 mL) was added to the solution and the precipitate was washed with water and filtered to give tert-butyl 4-((2-hydroxyethyl)(phenyl)amino)-2-(4-(oxazol-5-yl)phenylamino)-7,8-dihydropyrido[4,3-d]pyrimidine-6(5H)-carboxylate (150 mg, 77%). No further purification. MS (ESI+)/(ESI−) m/z 529/527

Example 1b tert-Butyl 2-(4-(oxazol-5-yl)phenylamino)-4-(trifluoromethylsulfonyloxy)-7,8-dihydropyrido[4,3-d]pyrimidine-6(5H)-carboxylate

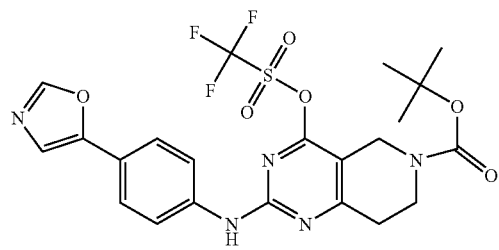

1,1,1-Trifluoro-N-phenyl-N-(trifluoromethylsulfonyl)methanesulfonamide (1.396 g, 3.91 mmol) was added to tert-butyl 4-hydroxy-2-(4-(oxazol-5-yl)phenylamino)-7,8-dihydropyrido[4,3-d]pyrimidine-6(5H)-carboxylate (1.6 g, 3.91 mmol, Example 3b) and 1,8-diazabicyclo[5.4.0]undec-7-ene (0.589 ml, 3.91 mmol) in DCM (20 mL). 4-Dimethylaminopyridine (0.01 g, 0.08 mmol) was added and the solution was stirred for 30 minutes at rt. The solvent was removed under reduced pressure and the crude was redissolved in DCM, washed with H$_2$O, dried (MgSO$_4$), filtered and concentrated under reduced pressure. The crude mixture was recrystallized from in ethanol with the addition of a few drops of water to give tert-butyl 2-(4-(oxazol-5-yl)phenylamino)-4-(trifluoromethylsulfonyloxy)-7,8-dihydropyrido[4,3-d]pyrimidine-6(5H)-carboxylate (1.700 g, 80%). MS (ESI+)/(ESI−) m/z 542/540

Example 1c tert-Butyl 4-hydroxy-2-(4-(oxazol-5-yl)phenylamino)-7,8-dihydropyrido[4,3-d]pyrimidine-6(5H)-carboxylate

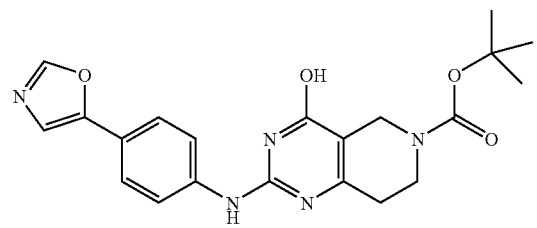

Sodium ethoxide (0.106 g, 1.55 mmol) was added to 1-tert-butyl 3-methyl 4-oxopiperidine-1,3-dicarboxylate (0.400 g, 1.55 mmol, Example 3c) and 1-(4-(oxazol-5-yl)phenyl)guanidine (obtained from Example 1e, 0.314 g, 1.55 mmol) in ethanol (4 mL) and heated in a microwave reactor at 100° C. for 15 minutes. The suspension was diluted with ethanol (5 mL) and the precipitated product was filtered off and washed with cold ethanol to give tert-butyl 4-hydroxy-2-(4-(oxazol-5-yl)phenylamino)-7,8-dihydropyrido[4,3-d]pyrimidine-6(5H)-carboxylate (0.480 g, 75%). No further purification. MS (ESI+)/(ESI−) M/Z 410/408

Example 1d 1-tert-Butyl 3-methyl 4-oxopiperidine-1,3-dicarboxylate

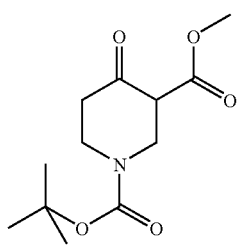

Di-tert-butyl dicarbonate (2.227 g, 10.20 mmol) was added to a solution of methyl 4-oxopiperidine-3-carboxylate (2.000 g, 10.20 mmol) and triethylamine (2.84 mL, 20.41 mmol) in DCM (20 mL) cooled on an ice-bath. One DMAP crystal was added and the suspension was stirred for 15 minutes. The solution was poured onto ice and washed with saturated aq. NaHCO$_3$ and H$_2$O. The organic layer was dried (MgSO$_4$) filtered and concentrated to give 1-tert-butyl 3-methyl 4-oxopiperidine-1,3-dicarboxylate (2.500 g, 95%). No further purification. MS (ESI+)/(ESI−) m/z 258/256

Example 1e

1-(4-(Oxazol-5-yl)phenyl)guanidine

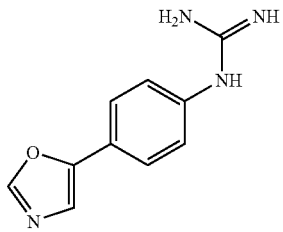

Hydrochloric acid (4.04 mL, 24.35 mmol) was added to a solution of 4-(oxazol-5-yl)aniline (5 g, 31.22 mmol) and carbodiimide (1.444 g, 34.34 mmol) in ethanol (50 mL). The resulting mixture was heated to reflux for 5 h. The reaction mixture was concentrated under reduced pressure and potassium carbonate (2.59 g, 18.73 mmol) in water (50.00 mL) was added. The formed crystals were filtered off, washed with several portions of potassium carbonate (aq) and dried over night under reduced pressure. The crude solid was slurried in DCM and filtered to give 1-(4-(oxazol-5-yl)phenyl)guanidine (7.00 g, 86%). No further purification. MS (ESI+)/(ESI−) m/z 203/201

Example 2

2-((6-Methyl-2-(4-(oxazol-5-yl)phenylamino)-5,6,7,8-tetrahydropyrido[4,3-d]pyrimidin-4-yl)(phenyl)amino)ethanol

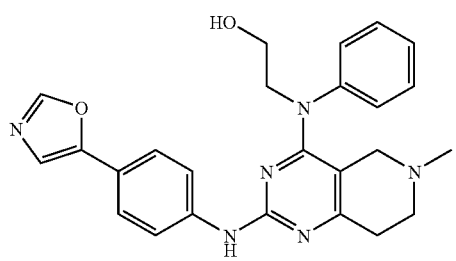

Triethylamine (0.038 ml, 0.27 mmol) was added to 2-((2-(4-(oxazol-5-yl)phenylamino)-5,6,7,8-tetrahydropyrido[4,3-d]pyrimidin-4-yl)(phenyl)amino)ethanol (0.058 g, 0.14 mmol, Example 1) in DMF (2 mL). Methyl iodide (9.28 µl, 0.15 mmol) was added and the reaction mixture was stirred for 1 h at 25° C. The solution was concentrated under reduced pressure and the product purified by preparative HPLC to give 2-((6-methyl-2-(4-(oxazol-5-yl)phenylamino)-5,6,7,8-tetrahydropyrido[4,3-d]pyrimidin-4-yl)(phenyl)amino)ethanol (0.022 g, 36.7%). MS (ESI+)/(ESI−) m/z 443/441

$^1$H NMR (500 MHz, MeOD) δ ppm 2.17 (s, 3 H) 2.64 (s, 2 H) 2.69 (t, 2 H) 2.84 (t, 2 H) 3.80 (t, 2 H) 4.15 (t, 2 H) 7.20-7.27 (m, 3 H) 7.36-7.45 (m, 3 H) 7.66 (d, 2 H) 7.81 (d, 2 H) 8.20 (s, 1 H)

Example 3

N2-(4-(Oxazol-5-yl)phenyl)-N4-phenyl-5,6,7,8-tetrahydropyrido[4,3-d]pyrimidine-2,4-diamine

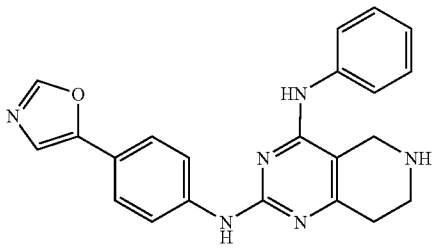

Aniline (0.017 mL, 0.18 mmol) was added to tert-butyl 2-(4-(oxazol-5-yl)phenylamino)-4-(trifluoromethylsulfonyloxy)-7,8-dihydropyrido[4,3-d]pyrimidine-6(5H)-carboxylate (0.1 g, 0.18 mmol, Example 1b) in DMSO (4 mL). The solution was heated in a microwave reactor at 80° C. for 1 h. HCl (2M aq, 1.5 mL) was added and the reaction was stirred in an open vessel at 76° C. for 30 min. The reaction was allowed to cool and DMSO was added to the solution. The product was purified by preparative HPLC to give N2-(4-(oxazol-5-yl)phenyl)-N4-phenyl-5,6,7,8-tetrahydropyrido[4,3-d]pyrimidine-2,4-diamine (0.017 g, 24%).

$^1$H NMR (500 MHz, DMSO-d$_6$) δ ppm 2.55-2.60 (m, 2 H) 2.96-3.03 (m, 2 H) 3.69-3.75 (m, 2 H) 7.11 (t, 1 H) 7.36 (t, 2 H) 7.46-7.51 (m, 3 H) 7.64 (d, 2 H) 7.80 (d, 2 H) 8.20 (s, 1 H) 8.35 (s, 1 H) 9.26 (s, 1 H) MS (ESI+)/(ESI−) m/z 385/383

Example 4

6-Methyl-N2-(4-(oxazol-5-yl)phenyl)-N4-phenyl-5,6,7,8-tetrahydropyrido[4,3-d]pyrimidine-2,4-diamine

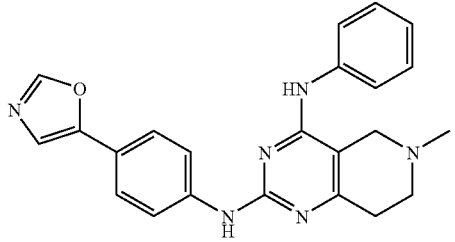

Triethylamine (0.022 mL, 0.16 mmol) was added to N2-(4-(oxazol-5-yl)phenyl)-N4-phenyl-5,6,7,8-tetrahydropyrido[4,3-d]pyrimidine-2,4-diamine (0.06 g, 0.16 mmol, Example 3) in DMF (1 mL) and dioxane (1 mL). Iodomethane (0.031 g, 0.22 mmol) was added and the reaction stirred at 25° C. for 1 h. Solvent was removed under reduced pressure and the crude product redissolved in DMSO. The crude product was purified by preparative HPLC to give 6-methyl-N2-(4-(oxazol-5-yl)phenyl)-N4-phenyl-5,6,7,8-tetrahydropyrido[4,3-d]pyrimidine-2,4-diamine (0.014 g, 23%).

¹H NMR (500 MHz, MeOD) δ ppm 2.60 (s, 3 H) 2.83 (d, 2 H) 2.88 (d, 2 H) 3.55 (s, 2 H) 7.17 (t, 1 H) 7.32-7.41 (m, 3 H) 7.50 (d, 2 H) 7.58 (d, 2 H) 7.68 (d, 2 H) 8.19 (s, 1 H) MS (ESI+)/(ESI−) m/z 399/397

Example 5

N4-Benzyl-N2-(4-(oxazol-5-yl)phenyl)-5,6,7,8-tetrahydropyrido[3,4-d]pyrimidine-2,4-diamine

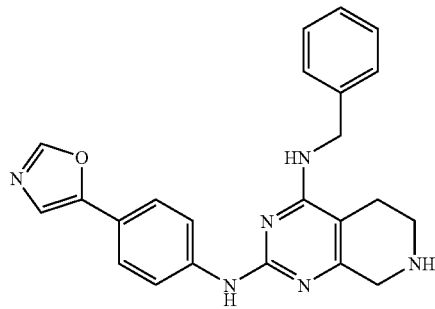

Hydrogen chloride (2 mL, 0.20 mmol, 2M aq) was added to a solution of tert-butyl 4-(benzylamino)-2-(4-(oxazol-5-yl)phenylamino)-5,6-dihydropyrido[3,4-d]pyrimidine-7(8H)-carboxylate (0.1 g, 0.20 mmol, Example 5a) in MeOH (5 mL) and heated in an open reaction vessel to 76° C. for 1 h. The residual solvent was removed under reduced pressure, the crude product was redissolved in DMSO and purified by preparative HPLC to give N4-benzyl-N2-(4-(oxazol-5-yl)phenyl)-5,6,7,8-tetrahydropyrido[3,4-d]pyrimidine-2,4-diamine (38 mg, 47.5%). MS (ESI+)/(ESI−) m/z 399/397

¹H NMR (600 MHz, DMSO-d₆) δ ppm 2.33 (t, 2 H) 2.97 (t, 2 H) 3.55 (s, 2 H) 4.65 (d, 2 H) 7.17-7.28 (m, 2 H) 7.30-7.37 (m, 4 H) 7.42-7.49 (m, 3 H) 7.71 (d, 2 H) 8.33 (s, 1 H) 9.05 (s, 1 H)

Example 5a tert-Butyl 4-(benzylamino)-2-(4-(oxazol-5-yl)phenylamino)-5,6-dihydropyrido[3,4-d]pyrimidine-7(8H)-carboxylate

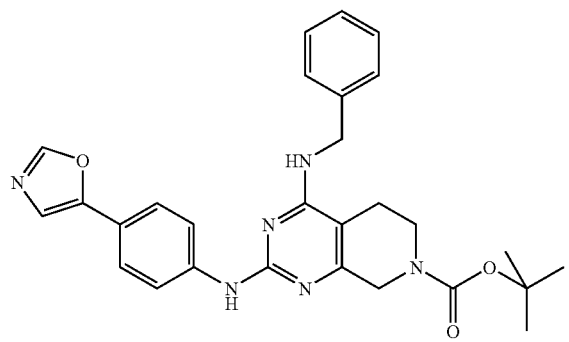

Benzylamine (0.030 g, 0.28 mmol) was added to tert-butyl 2-(4-(oxazol-5-yl)phenylamino)-4-(trifluoromethylsulfonyloxy)-5,6-dihydropyrido[3,4-d]pyrimidine-7(8H)-carboxylate (0.15 g, 0.28 mmol, Example 5b) in dioxane (10 mL) and DMF (0.5 mL). The reaction was stirred at rt over night. The solvent was removed under reduced pressure and the crude product redissolved in EtOAc, washed with saturated NaHCO₃ and H₂O. The organic layer was dried (MgSO₄), filtered and concentrated to give tert-butyl 4-(benzylamino)-2-(4-(oxazol-5-yl)phenylamino)-5,6-dihydropyrido[3,4-d]pyrimidine-7(8H)-carboxylate (0.120 g, 87%). No further purification.

MS (ESI+)/(ESI−) m/z 499/497

Example 5b tert-Butyl 2-(4-(oxazol-5-yl)phenylamino)-4-(trifluoromethylsulfonyloxy)-5,6-dihydropyrido[3,4-d]pyrimidine-7(8H)-carboxylate

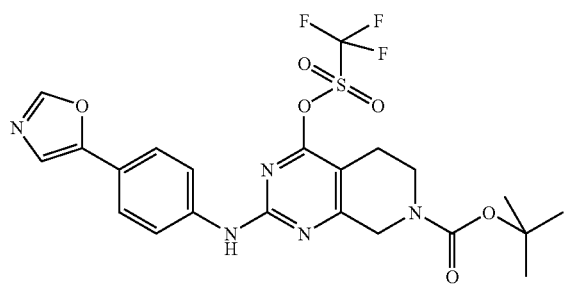

1,1,1-Trifluoro-N-phenyl-N-(trifluoromethylsulfonyl)methanesulfonamide (0.698 g, 1.95 mmol) was added to tert-butyl 4-hydroxy-2-(4-(oxazol-5-yl)phenylamino)-5,6-dihydropyrido[3,4-d]pyrimidine-7(8H)-carboxylate (0.8 g, 1.95 mmol) and 1,8-diazabicyclo[5.4.0]undec-7-ene (0.292 mL, 1.95 mmol) in DCM (30 mL). 4-Dimethylaminopyridine (0.024 g, 0.20 mmol) was added and the solution was stirred for 30 minutes. Solvent was removed under reduced pressure and the crude product dissolved in DCM and washed with H₂O. The organic layer was dried (MgSO₄), filtered and concentrated. The crude mixture was dissolved in ethanol and precipitated upon addition of a few drops of water to give tert-butyl 2-(4-(oxazol-5-yl)phenylamino)-4-(trifluoromethylsulfonyloxy)-5,6-dihydropyrido[3,4-d]pyrimidine-7(8H)-carboxylate (0.850 g, 80%). No further purification. MS (ESI+)/(ESI−) m/z 542/540

Example 5c tert-Butyl 4-hydroxy-2-(4-(oxazol-5-yl)phenylamino)-5,6-dihydropyrido[3,4-d]pyrimidine-7(8H)-carboxylate

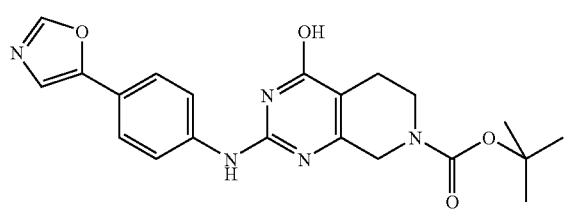

Sodium ethoxide (0.476 g, 7.00 mmol) was added to 1-tert-butyl 4-ethyl 3-oxopiperidine-1,4-dicarboxylate (1.899 g, 7.00 mmol, Example 1d) and 1-(4-(oxazol-5-yl)phenyl)guanidine (1.415 g, 7.00 mmol, Example 1e) in ethanol (10 mL). The reaction vial was heated a microwave reactor at 100° C. for 15 minutes. The suspension was diluted with ethanol (5 ml) and the precipitated crude product was filtered off and washed with cold ethanol to give tert-butyl 4-hydroxy-2-(4-(oxazol-5-yl)phenylamino)-5,6-dihydropyrido[3,4-d]pyrimidine-7(8H)-carboxylate (1.200 g, 41.9%). No further purification. MS (ESI+)/(ESI−) m/z 410/408

Example 5d 1-tert-Butyl 4-ethyl 3-oxopiperidine-1,4-dicarboxylate

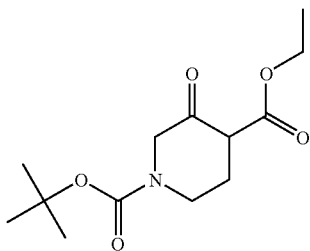

Di-tert-butyl dicarbonate (3.19 g, 14.60 mmol) was added to a solution of ethyl 3-oxopiperidine-4-carboxylate (2.5 g, 14.60 mmol) and triethylamine (2.030 mL, 14.60 mmol) in DCM (50 mL) cooled on an ice-bath. One DMAP crystal was added and the suspension was stirred for 15 minutes. The solution was poured onto ice and neutralised with HCl (2M, aq). The organic layer was washed with HCl (0.1M), H₂O, dried (MgSO₄), filtered and concentrated to give 1-tert-butyl 4-ethyl 3-oxopiperidine-1,4-dicarboxylate (2.60 g, 65.6%). MS (ESI−) m/z 270

Example 6

N4-Benzyl-N2-(4-(oxazol-5-yl)phenyl)-5,6,7,8-tetrahydropyrido[4,3-d]pyrimidine-2,4-diamine

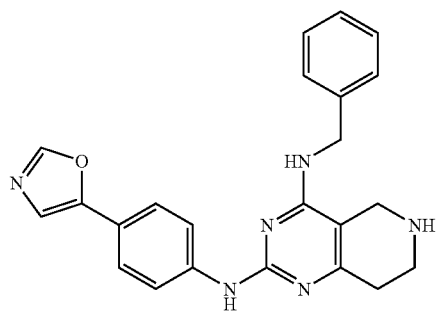

Hydrochloric acid (2M aq, 2 ml) was added to a solution of tert-butyl 4-(benzylamino)-2-(4-(oxazol-5-yl)phenylamino)-7,8-dihydropyrido[4,3-d]pyrimidine-6(5H)-carboxylate (0.15 g, 0.30 mmol, Example 6a) in MeOH (4 mL). The reaction was heated in an open reaction vessel to 76° C. for 1 h and the product precipitated out from the solution as it was cooled. The crude product was filtered off and washed with water. The crude salt was dissolved in water and precipitated when saturated NaHCO₃ was added. The product was filtered off and purified by preparative HPLC to give N4-benzyl-N2-(4-(oxazol-5-yl)phenyl)-5,6,7,8-tetrahydropyrido[4,3-d]pyrimidine-2,4-diamine (0.090 g, 75%). MS (ESI+)/(ESI−) m/z 399/397

$^1$H NMR (600 MHz, DMSO-d₆) δ ppm 2.47 (t, 2 H) 2.94 (t, 2 H) 3.57 (s, 2 H) 4.64 (d, 2 H) 7.14 (t, 1 H) 7.21 (t, 1 H) 7.29-7.39 (m, 4 H) 7.42-7.49 (m, 3 H) 7.71 (d, 2 H) 8.33 (s, 1 H) 9.06 (s, 1 H)

Example 6a tert-Butyl 4-(benzylamino)-2-(4-(oxazol-5-yl)phenylamino)-7,8-dihydropyrido[4,3-d]pyrimidine-6(5H)-carboxylate

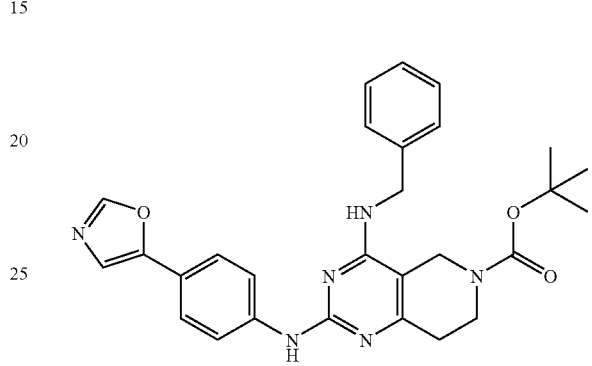

Benzylamine (0.061 mL, 0.55 mmol) was added to tert-butyl 2-(4-(oxazol-5-yl)phenylamino)-4-(trifluoromethylsulfonyloxy)-7,8-dihydropyrido[4,3-d]pyrimidine-6(5H)-carboxylate (0.3 g, 0.55 mmol, Example 3c) in dioxane (4 mL) and the reaction mixture was stirred over night at 25° C. The solvent was removed under reduced pressure and the reaction mixture was redissolved in DCM and washed with water. The organic layer was dried (MgSO₄), filtered and concentrated to give tert-butyl 4-(benzylamino)-2-(4-(oxazol-5-yl)phenylamino)-7,8-dihydropyrido[4,3-d]pyrimidine-6(5H)-carboxylate (0.238 g, 86%). MS (ESI+)/(ESI−) m/z 499/497

Example 7

N2-(3-Methoxy-4-(4-methyl-1H-imidazol-1-yl)phenyl)-N4-phenyl-5,6,7,8-tetrahydropyrido[4,3-d]pyrimidine-2,4-diamine

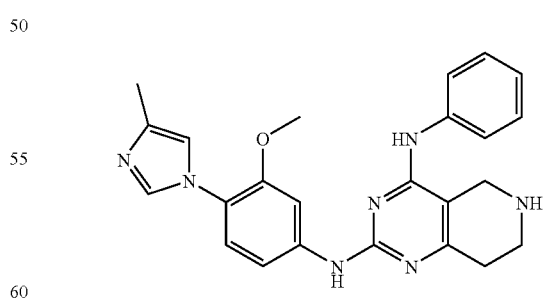

Aniline (0.032 g, 0.34 mmol) was added to a solution of tert-butyl 2-(3-methoxy-4-(4-methyl-1H-imidazol-1-yl)phenylamino)-4-(trifluoromethylsulfonyloxy)-7,8-dihydropyrido[4,3-d]pyrimidine-6(5H)-carboxylate (0.2 g, 0.34 mmol, Example 7a) in DMF (2 mL). The solution was stirred at 70° C. for 1 h. HCl 2M aq (2 ml) was added and the solution heated to 76° C. for 1 h. Solvent was concentrated under reduced pressure and purified on preparative HPLC to give N2-(3-methoxy-4-(4-methyl-1H-imidazol-1-yl)phenyl)-N4-phenyl-5,6,7,8-tetrahydropyrido[4,3-d]pyrimidine-2,4-diamine (0.060 g, 41.0%). MS (ESI+)/(ESI−) m/z 428/426

$^1$H NMR (500 MHz, DMSO-$d_6$) δ ppm 2.13 (s, 3 H) 2.56 (t, 2 H) 2.97 (t, 2 H) 3.52 (s, 3 H) 3.70 (s, 2 H) 6.99 (s, 1 H) 7.01-7.11 (m, 2 H) 7.28-7.38 (m, 3 H) 7.61 (d, 1 H) 7.65 (d, 2 H) 7.70 (s, 1 H) 8.16 (s, 1 H) 9.18 (s, 1 H)

Example 7a tert-Butyl 2-(3-methoxy-4-(4-methyl-1H-imidazol-1-yl)phenylamino)-4-(trifluoromethylsulfonyloxy)-7,8-dihydropyrido[4,3-d]pyrimidine-6(5H)-carboxylate

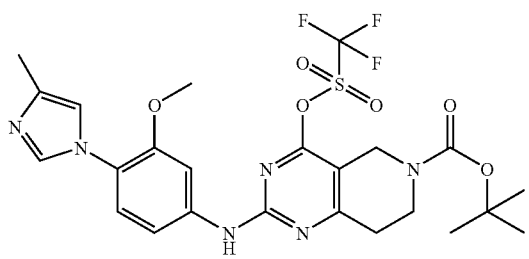

tert-Butyl 4-hydroxy-2-(3-methoxy-4-(4-methyl-1H-imidazol-1-yl)phenylamino)-7,8-dihydropyrido[4,3-d]pyrimidine-6(5H)-carboxylate (0.5 g, 1.10 mmol, Example 7b), 1,1,1-trifluoro-N-phenyl-N-(trifluoromethylsulfonyl)methanesulfonamide (0.395 g, 1.10 mmol), 1,8-diazabicyclo[5.4.0]undec-7-ene (0.165 ml, 1.10 mmol) and 4-dimethylaminopyridine (0.013 g, 0.11 mmol) in DCM (20 mL) were stirred at rt for 1 h. Solvent was evaporated under reduced pressure and the crude product was purified on a silica gel column using DCM/MeOH (9/1) as eluent. Collected fractions were pooled and solvent evaporated under reduced pressure to give tert-butyl 2-(3-methoxy-4-(4-methyl-1H-imidazol-1-yl)phenylamino)-4-(trifluoromethylsulfonyloxy)-7,8-dihydropyrido[4,3-d]pyrimidine-6(5H)-carboxylate (0.400 g, 61.9%). MS (ESI+) m/z 585

Example 7b tert-Butyl 4-hydroxy-2-(3-methoxy-4-(4-methyl-1H-imidazol-1-yl)phenylamino)-7,8-dihydropyrido[4,3-d]pyrimidine-6(5H)-carboxylate

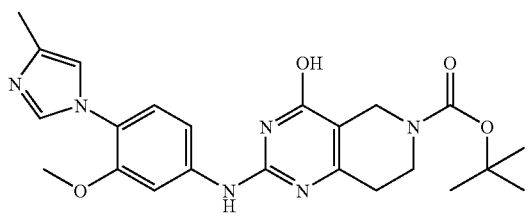

In a microwave vial was 1-tert-butyl 3-methyl 4-oxopiperidine-1,3-dicarboxylate (0.577 g, 2.24 mmol, Example 7c), Sodium ethoxide (0.153 g, 2.24 mmol), and 1-(3-methoxy-4-(4-methyl-1H-imidazol-1-yl)phenyl)guanidine (0.55 g, 2.24 mmol) added in ethanol (10 mL) to give a suspension. The reaction was heated in the microwave oven for 20 min at 100° C. Solvent was evaporated under reduced pressure. The crude was dissolved in minimal volume of EtOH and few drops of water added to allow the product to precipitate. The precipitated product was filtered and dried to give tert-butyl 4-hydroxy-2-(3-methoxy-4-(4-methyl-1H-imidazol-1-yl)phenylamino)-7,8-dihydropyrido[4,3-d]pyrimidine-6(5H)-carboxylate (0.400 g, 39.4%). MS (ESI+)/(ESI−) m/z 453/450

Example 7c 1-(3-Methoxy-4-(4-methyl-1H-imidazol-1-yl)phenyl)guanidine

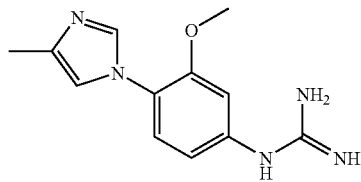

3-Methoxy-4-(4-methyl-1H-imidazol-1-yl)aniline hydrochloride (3 g, 12.52 mmol), cyanamide (0.684 g, 16.27 mmol) and hydrochloric acid (1.564 mL, 18.77 mmol) in ethanol (20 mL) were heated to reflux o.n. The reaction mixture was concentrated under reduced pressure before the resulting mixture was poured on a solution of potassium carbonate (1.730 g, 12.52 mmol) in water (60 mL) and left in refrigerator o.n. The formed carbonate-salt was filtered off, and dried in vacuum oven o.n. The solid was washed with several portions of DCM, dried and used as such in next step.

MS (ESI+)/(ESI−) m/z 246/244

Example 7d

3-Methoxy-4-(4-methyl-imidazol-1-yl)-phenylamine

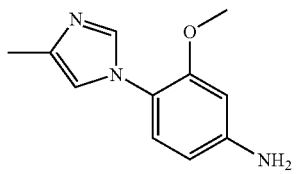

10% Pd/C was added to a solution of 1-(2-methoxy-4-nitro-phenyl)-4-methyl-1H-imidazole (616 mg, 2.6 mmol, Example 7e) in ethyl acetate (20 mL). The resulting mixture was shaken under hydrogen atmosphere overnight at 35 psi and room temperature. The mixture was filtered through a pad of celite and washed with ethyl acetate (2×15 mL). The filtrate was concentrated to 10 mL and diluted with ether (50 mL). 2M HCl in dioxane (2 mL) was added to the resulting solution at 0° C. under stirring and continued the stirring for another hour at room temperature. The separated solid was filtered, washed with ether (3×15 mL) and dried under high vacuum to afford the title compound as HCl salt (603 mg, 95%).

$^1$H NMR (400 MHz, methanol-$d_4$) δ ppm 2.42 (s, 3 H) 3.93 (s, 3 H), 6.91 (dd, 1 H), 7.05 (d, 1 H), 7.44-7.67 (m, 2 H), 9.10 (d, 1 H), Mol. Formula: $C_{11}H_{13}N_3O \cdot 1.8$ HCl Elemental Analysis: Found C 48.99, H 5.86, N 15.27; Calcd. C 49.14, H 5.55, N 15.63 MS m/z [M+H] 204

Example 7e 1-(2-Methoxy-4-nitro-phenyl)-4-methyl-1H-imidazole and 1-(2-methoxy-4-nitro-phenyl)-5-methyl-1H-imidazole

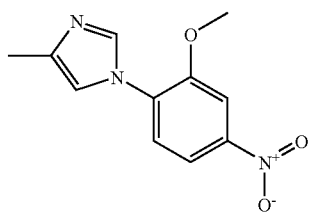

A mixture of 4-methyl imidazole (500 mg, 6 mmol), 2-fluoro-5-nitro anisole (1.02 g, 5.9 mmol) and potassium carbonate (1.68 g, 12 mmol) in DMF (15 mL) was heated overnight at 85° C. in a sealed tube. The reaction mixture was cooled, transferred into a round bottom flask using ethyl acetate and concentrated under high vacuum to 5 mL volume. The residue was suspended in water and extracted with dichloromethane (3×25 mL). The organic extracts were combined, washed with brine, dried over anhydrous MgSO$_4$, filtered and concentrated to give an orange solid. The solid was dissolved in dichloromethane (10 mL) and diluted with hexane until the solution became slightly turbid. The turbid solution was left at room temperature. The separated orange solid was filtered, washed with hexane to give 1-(2-methoxy-4-nitro-phenyl)-4-methyl-1H-imidazole and 1-(2-methoxy-4-nitro-phenyl)-5-methyl-1H-imidazole (577 mg, 43%).

$^1$H NMR (400 MHz, methanol-d$_4$) δ ppm 2.25 (s, 3 H) 4.02 (s, 3 H) 7.21 (s, 1 H) 7.62 (d, 1 H) 7.92-8.02 (m, 2 H) 8.04 (s, 1 H)

Example 8

2-(2-(3-Methoxy-4-(4-methyl-1H-imidazol-1-yl) phenylamino)-4-(phenylamino)-7,8-dihydropyrido[4,3-d]pyrimidin-6(5H)-yl)ethanol

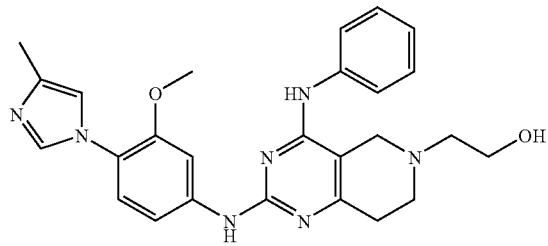

Acetic acid (0.803 μL, 0.01 mmol) was added to a solution of N2-(3-methoxy-4-(4-methyl-1H-imidazol-1-yl)phenyl)-N4-phenyl-5,6,7,8-tetrahydropyrido[4,3-d]pyrimidine-2,4-diamine (Example 7, 0.03 g, 0.07 mmol) and 2-hydroxyacetaldehyde (4.21 mg, 0.07 mmol) in MeOH (5 mL). The reaction mixture was stirred for 10 min and sodium cyanoborohydride (4.41 mg, 0.07 mmol) added. The reaction was stirred for an additional 15 min and solvent evaporated under reduced pressure. The crude product was dissolved in MeOH/DMSO and purified by preparative HPLC to give 2-(2-(3-methoxy-4-(4-methyl-1H-imidazol-1-yl)phenylamino)-4-(phenylamino)-7,8-dihydropyrido[4,3-d]pyrimidin-6(5H)-yl)ethanol (0.018 g, 53.5%). MS (ESI+)/(ESI−) m/z 472/470

$^1$H NMR (500 MHz, DMSO-d$_6$) δ ppm 2.13 (s, 3 H) 2.64 (t, 2 H) 2.68 (t, 2 H) 2.76 (t, 2 H) 3.45 (s, 2 H) 3.51 (s, 3 H) 3.64 (q, 2 H) 4.51 (t, 1 H) 6.99 (s, 1 H) 7.03-7.10 (m, 2 H) 7.29-7.38 (m, 3 H) 7.59-7.66 (m, 3 H) 7.68 (br. s., 1 H) 8.25 (s, 1 H) 9.20 (s, 1 H)

Example 9

(S)-(1-(6-methyl-2-(4-(2-methyl-1H-imidazol-1-yl) phenylamino)-5,6,7,8-tetrahydropyrido[4,3-d]pyrimidin-4-yl)indolin-2-yl)methanol

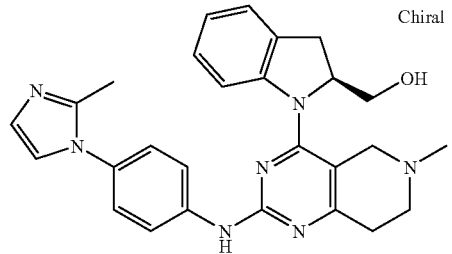

(S)-Indolin-2-ylmethanol (25.5 mg, 0.17 mmol) was added to a solution of 6-methyl-2-(4-(2-methyl-1H-imidazol-1-yl)phenylamino)-5,6,7,8-tetrahydropyrido[4,3-d]pyrimidin-4-yl trifluoromethanesulfonate (80 mg, 0.17 mmol, Example 9a) in DMSO (1 mL). The reaction was heated to 80° C. for 2 h. The solution was allowed to cool down, filtered and the product was purified on preparative HPLC to give (S)-(1-(6-methyl-2-(4-(2-methyl-1H-imidazol-1-yl)phenylamino)-5,6,7,8-tetrahydropyrido[4,3-d]pyrimidin-4-yl)indolin-2-yl)methanol (22.00 mg, 27.6%). MS (ESI+)/(ESI−) m/z 468/466

$^1$H NMR (500 MHz, MeOD) δ ppm 2.31 (s, 3 H) 2.41 (s, 3 H) 2.66 (s, 1 H) 2.80-2.87 (m, 1 H) 2.87-2.94 (m, 1 H) 2.98 (t, 2 H) 3.13 (dd, 1 H) 3.23-3.28 (m, 1 H) 3.42 (d, 1 H) 3.65 (dd, 1 H) 3.82 (dd, 1 H) 4.73-4.80 (m, 1 H) 6.65 (d, 1 H) 6.85 (t, 1 H) 6.93 (d, 1 H) 7.07 (t, 1 H) 7.12 (d, 1 H) 7.21 (d, 1 H) 7.24-7.29 (m, 2 H) 7.78-7.89 (m, 2 H)

Example 9a

6-Methyl-2-(4-(2-methyl-1H-imidazol-1-yl)phenylamino)-5,6,7,8-tetrahydropyrido[4,3-d]pyrimidin-4-yl trifluoromethanesulfonate

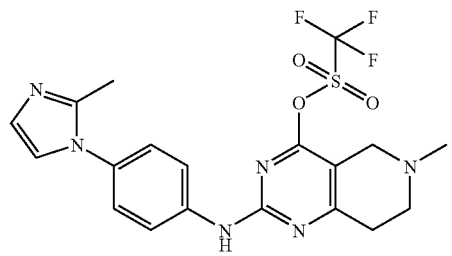

6-Methyl-2-(4-(2-methyl-1H-imidazol-1-yl)phenylamino)-5,6,7,8-tetrahydropyrido[4,3-d]pyrimidin-4-ol (0.4 g, 1.19 mmol, Example 9b), 1,1,1-trifluoro-N-phenyl-N-(trifluoromethylsulfonyl)methanesulfonamide (0.425 g, 1.19 mmol), 1,8-diazabicyclo[5.4.0]undec-7-ene (0.179 mL, 1.19 mmol) and 4-dimethylaminopyridine (0.015 g, 0.12 mmol) in DCM (10 mL) was stirred at room temperature for 30 min. Solvent was evaporated under reduced pressure and the crude dissolved in minimal volume of EtOH, the desired product precipitated when a few drops of water were added. The precipitate was filtered and washed carefully with ice-cold ethanol to give 6-methyl-2-(4-(2-methyl-1H-imidazol-1-yl)phenylamino)-5,6,7,8-tetrahydropyrido[4,3-d]pyrimidin-4-yl trifluoromethanesulfonate (0.500 g, 90%). MS (ESI+)/(ESI−) m/z 469/467

Example 9b

6-Methyl-2-(4-(2-methyl-1H-imidazol-1-yl)phenylamino)-5,6,7,8-tetrahydropyrido[4,3-d]pyrimidin-4-ol

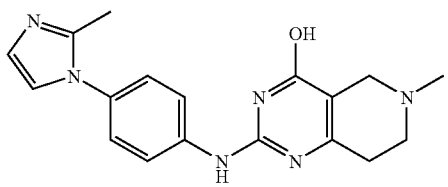

A suspension of 2-(4-(2-methyl-1H-imidazol-1-yl)phenylamino)-5,6,7,8-tetrahydropyrido[4,3-d]pyrimidin-4-ol (1.4 g, 4.34 mmol, Example 9c), formaldehyde (0.423 g, 5.21 mmol) and acetic acid (0.025 mL, 0.43 mmol) in MeOH (25 mL) was stirred for 10 min. Sodium cyanoborohydride (0.273 g, 4.34 mmol) was added and the reaction was stirred for an additional 10 min after which water (2 mL) was added. Solvent was evaporated and EtOAc (2 mL) was added followed by the addition of potassium carbonate solution (sat. aq., 1 mL). The solution was stirred and the formed precipitate was filtered off to give 6-methyl-2-(4-(2-methyl-1H-imidazol-1-yl)phenylamino)-5,6,7,8-tetrahydropyrido[4,3-d]pyrimidin-4-ol (0.500 g, 34.2%).
MS (ESI+)/(ESI−) m/z 337/335

Example 9c 2-(4-(2-Methyl-1H-imidazol-1-yl)phenylamino)-5,6,7,8-tetrahydropyrido[4,3-d]pyrimidin-4-ol

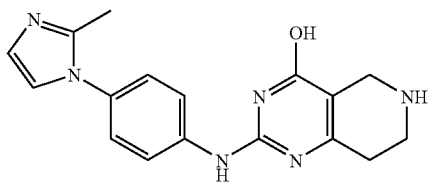

tert-Butyl 4-hydroxy-2-(4-(2-methyl-1H-imidazol-1-yl)phenylamino)-7,8-dihydropyrido[4,3-d]pyrimidine-6(5H)-carboxylate (2.3 g, 5.44 mmol, Example 9d) was added to a solution of hydrogen chloride (10 mL, 5.44 mmol) in ethanol (20 mL). The solution was stirred at 75° C. for 30 min allowing the EtOH to evaporate. The solution was made basic with potassium carbonate (s) and EtOAc (20 mL) was added. After stirring 10 min the precipitated product was filtered off and dried to give 2-(4-(2-methyl-1H-imidazol-1-yl)phenylamino)-5,6,7,8-tetrahydropyrido[4,3-d]pyrimidin-4-ol (1.300 g, 74.1%). MS (ESI+)/(ESI−) m/z 323/321

Example 9d tert-Butyl 4-hydroxy-2-(4-(2-methyl-1H-imidazol-1-yl)phenylamino)-7,8-dihydropyrido[4,3-d]pyrimidine-6(5H)-carboxylate

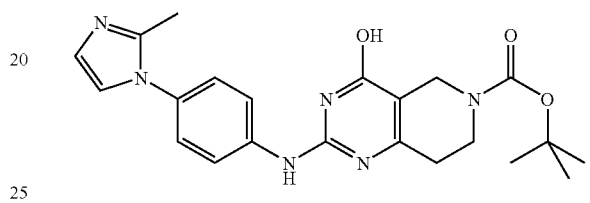

1-(4-(2-Methyl-1H-imidazol-1-yl)phenyl)guanidine (1.4 g, 6.50 mmol, Example 9e), 1-tert-butyl-3-methyl 4-oxopiperidine-1,3-dicarboxylate (1.673 g, 6.50 mmol) and sodium ethoxide (0.443 g, 6.50 mmol) were placed in a microwave vial and ethanol (1 mL) added. The vial was heated in a microwave oven at 100° C. for 20 min. Solvent was evaporated under reduced pressure and the crude dissolved in EtOAc. The organic solution was washed with sat NaHCO₃ and H₂O. The organic layer was dried over Na₂SO₄, filtered and evaporated to give tert-butyl-4-hydroxy-2-(4-(2-methyl-1H-imidazol-1-yl)phenylamino)-7,8-dihydropyrido[4,3-d]pyrimidine-6(5H)-carboxylate (2.300 g, 84%). MS (ESI+)/(ESI−) m/z 423/421

Example 9e 1-(4-(2-methyl-1H-imidazol-1-yl)phenyl)guanidine

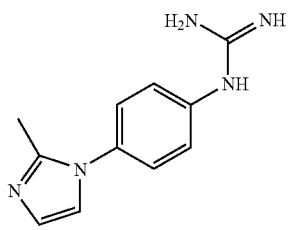

To a solution of 4-(2-methyl-1H-imidazol-1-yl)aniline (2 g, 11.55 mmol) in ethanol (25 mL) was added cyanamide (0.728 g, 17.32 mmol) and hydrochloric acid (1.422 mL, 17.32 mmol). The reaction mixture was refluxed for 4 h. An additional 1 eq of hydrochloric acid (1.422 ml, 17.32 mmol) was added and precipitation occurred. The precipitated product was filtered off and washed with DCM to give 1-(4-(2-methyl-1H-imidazol-1-yl)phenyl)guanidine (1.600 g, 64.4%). MS (ESI+)/(ESI−) m/z 216/214

Example 10

N4-((2R)-bicyclo[2.2.1]heptan-2-yl)-6-methyl-N2-(4-(2-methyl-1H-imidazol-1-yl)phenyl)-5,6,7,8-tetrahydropyrido[4,3-d]pyrimidine-2,4-diamine

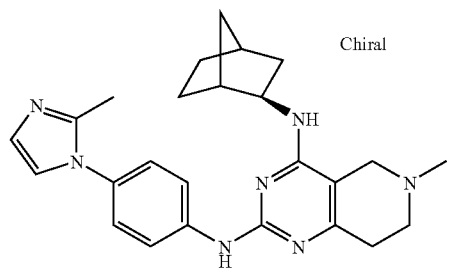

exo-2-Aminonorbornane (20.24 μl, 0.17 mmol) was added to a solution of 6-methyl-2-(4-(2-methyl-1H-imidazol-1-yl)phenylamino)-5,6,7,8-tetrahydropyrido[4,3-d]pyrimidin-4-yl trifluoromethanesulfonate (80 mg, 0.17 mmol, Example 9a) in DCM (10 mL). The reaction was stirred at 35° C. for 2 h. Solvent was evaporated and the crude mixture dissolved in MeOH/DMSO and purified on preparative HPLC to give N4-((2R)-bicyclo[2.2.1]heptan-2-yl)-6-methyl-N2-(4-(2-methyl-1H-imidazol-1-yl)phenyl)-5,6,7,8-tetrahydropyrido[4,3-d]pyrimidine-2,4-diamine (40.0 mg, 47.8%).

MS (ESI+)/(ESI−) m/z 430/428

$^1$H NMR (500 MHz, DMSO-$d_6$) δ ppm 1.07 (d, 1 H) 1.10-1.19 (m, 1 H) 1.26-1.34 (m, 1 H) 1.45 (t, 1 H) 1.50-1.57 (m, 2 H) 1.64 (d, 2 H) 2.24 (s, 4 H) 2.29 (d, 1 H) 2.37 (s, 3 H) 2.58 (br. s., 4 H) 3.11-3.21 (m, 2 H) 3.85 (q, 1 H) 6.02 (d, 1 H) 6.86 (d, 1 H) 7.19-7.24 (m, 3 H) 7.95 (d, 2 H) 9.19 (s, 1 H)

Example 11

N4-Cyclohexyl-N4,6-dimethyl-N2-(4-(2-methyl-1H-imidazol-1-yl)phenyl)-5,6,7,8-tetrahydropyrido[4,3-d]pyrimidine-2,4-diamine

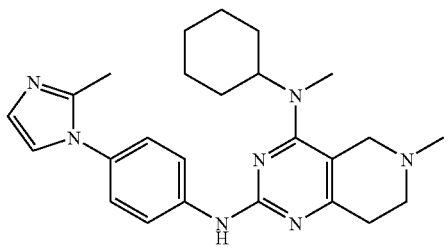

N-Methylcyclohexanamine (9.67 mg, 0.09 mmol) was added to a solution of 6-methyl-2-(4-(2-methyl-1H-imidazol-1-yl)phenylamino)-5,6,7,8-tetrahydropyrido[4,3-d]pyrimidin-4-yl trifluoromethanesulfonate (40 mg, 0.09 mmol, Example 9a) in DMSO (1 mL) and the reaction was stirred at 80° C. for 2 h. Solvent was allowed to cool down, filtered and the product purified on preparative HPLC to give N4-cyclohexyl-N4,6-dimethyl-N2-(4-(2-methyl-1H-imidazol-1-yl)phenyl)-5,6,7,8-tetrahydropyrido[4,3-d]pyrimidine-2,4-diamine (22.00 mg, 59.7%). MS (ESI+)/(ESI−) m/z 432/430

$^1$H NMR (500 MHz, DMSO-$d_6$) δ ppm 1.06-1.17 (m, 1 H) 1.35 (q, 2 H) 1.51-1.66 (m, 3 H) 1.70-1.84 (m, 4 H) 2.24 (s, 3 H) 2.34 (s, 3 H) 2.59-2.65 (m, 2 H) 2.69 (t, 2 H) 2.85 (s, 3 H) 3.30 (s, 2 H) 3.76-3.84 (m, 1 H) 6.86 (d, 1 H) 7.20 (s, 1 H) 7.25 (d, 2 H) 7.88 (d, 2 H) 9.28 (s, 1 H)

Example 12

4-(Benzyloxy)-N-(4-(oxazol-5-yl)phenyl)-5,6,7,8-tetrahydropyrido[4,3-d]pyrimidin-2-amine

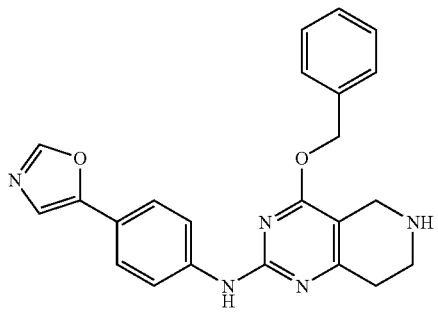

tert-Butyl-4-hydroxy-2-(4-(oxazol-5-yl)phenylamino)-7,8-dihydropyrido[4,3-d]pyrimidine-6(5H)-carboxylate (0.2 g, 0.49 mmol, Example 3d), phenylmethanol (0.063 ml, 0.61 mmol) and triphenylphosphine (0.160 g, 0.61 mmol) in THF (5 mL) was stirred for 10 min. Diisopropyl azodicarboxylate (0.119 mL, 0.61 mmol) was added and reaction was stirred at 50° C. over night. HCl (2M aq, 2 mL) was added and the solution was heated to 75° C. for 1 h, allowing THF to evaporate. The remaining solvent was evaporated under reduced pressure. The crude product was dissolved in MeOH/DMSO and purified on preparative HPLC to give 4-(benzyloxy)-N-(4-(oxazol-5-yl)phenyl)-5,6,7,8-tetrahydropyrido[4,3-d]pyrimidin-2-amine (0.089 g, 39.7%).

$^1$H NMR (500 MHz, DMSO-$d_6$) δ ppm 2.56-2.61 (m, 2 H) 2.94-3.02 (m, 2 H) 3.65 (br. s., 2 H) 5.47 (s, 2 H) 7.33 (t, 1 H) 7.41 (t, 2 H) 7.47 (d, 2 H) 7.52 (s, 1 H) 7.60 (d, 2 H) 7.82 (d, 2 H) 8.37 (s, 1 H) 9.61 (br. s., 1 H)

MS (ESI+)/(ESI−) m/z 400/398

Example 13

(R)-(1-(6-Methyl-2-(4-(2-methyl-1H-imidazol-1-yl)phenylamino)-5,6,7,8-tetrahydropyrido[4,3-d]pyrimidin-4-yl)indolin-2-yl)methanol

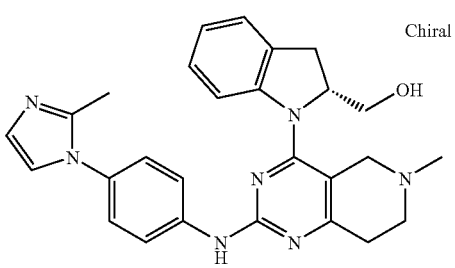

6-Methyl-2-(4-(2-methyl-1H-imidazol-1-yl)phenylamino)-5,6,7,8-tetrahydropyrido[4,3-d]pyrimidin-4-yl trifluoromethanesulfonate (65 mg, 0.14 mmol, Example 9a) and (R)-indolin-2-ylmethanol (20.70 mg, 0.14 mmol) in DMSO (3 mL) were heated to 80° C. in a microwave reactor for 2 h. The reaction mixture was filtered and purified by preparative HPLC, yielding (R)-(1-(6-methyl-2-(4-(2-methyl-1H-imidazol-1-yl)phenylamino)-5,6,7,8-tetrahydropyrido[4,3-d]pyrimidin-4-yl)indolin-2-yl)methanol (31.0 mg, 47.8%).

HPLC, ms detection: (ESI) (M+1) m/z 468.3;

$^1$H NMR (500 MHz, chloroform-d) δ ppm 2.35 (s, 3 H) 2.35 (s, 3 H) 2.63-2.73 (m, 1 H) 2.82-2.93 (m, 2 H) 2.97-3.04 (m, 2 H) 3.07 (d, 1 H) 3.15-3.21 (m, 1 H) 3.35 (dd, 1 H) 3.65 (dd, 1 H) 3.77 (dd, 1 H) 4.68 (tt, 1 H) 6.58 (d, 1 H) 6.90 (t, 1 H) 6.99 (d, 2 H) 7.12 (t, 1 H) 7.17-7.23 (m, 4 H) 7.70 (d, 2 H)

Example 14

2-((2-(4-(Oxazol-5-yl)phenylamino)-6-propyl-5,6,7,8-tetrahydropyrido[4,3-d]pyrimidin-4-yl)(phenyl)amino)ethanol

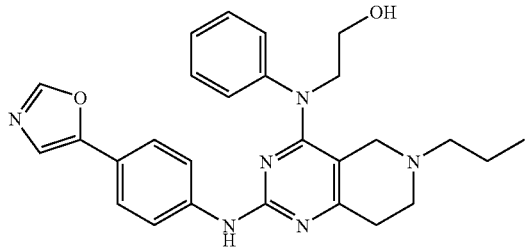

2-((2-(4-(Oxazol-5-yl)phenylamino)-5,6,7,8-tetrahydropyrido[4,3-d]pyrimidin-4-yl)(phenyl)amino)ethanol (25 mg, 0.06 mmol, Example 1) was dissolved in methanol (1 mL). Acetic acid (0.013 mL, 0.23 mmol) and propionaldehyde (4.25 µL, 0.06 mmol) was added and the reaction mixture was stirred at room temperature for 10 minutes. Sodium cyanoborohydride (3.67 mg, 0.06 mmol) was added and after 15 minutes the solvent was evaporated under reduced pressure. The crude was dissolved in few drops of dimethylformamide and acetonitrile, filtered and purified by preparative HPLC yielding 2-((2-(4-(oxazol-5-yl)phenylamino)-6-propyl-5,6,7,8-tetrahydropyrido[4,3-d]pyrimidin-4-yl)(phenyl)amino)ethanol (6.3 mg, 22.95%).

HPLC, ms detection: (ESI) (M+1) m/z 471;

$^1$H NMR (500 MHz, chloroform-d) δ ppm 0.82 (t, 3 H) 1.33 (br. s., 2 H) 2.04 (s, 1 H) 2.19 (br. s., 2 H) 2.60 (br. s., 2 H) 2.65 (br. s., 2 H) 2.87 (br. s., 2 H) 3.75 (t, 2 H) 4.18 (t, 2 H) 7.17 (d, 1 H) 7.22 (t, 1 H) 7.27 (s, 1 H) 7.37 (t, 2 H) 7.63 (m, 2 H) 7.69 (m, 2 H) 7.89 (s, 1 H)

Example 15

1-(4-((2-Hydroxyethyl)(phenyl)amino)-2-(4-(oxazol-5-yl)phenylamino)-7,8-dihydropyrido[4,3-d]pyrimidin-6(5H)-yl)propan-1-one

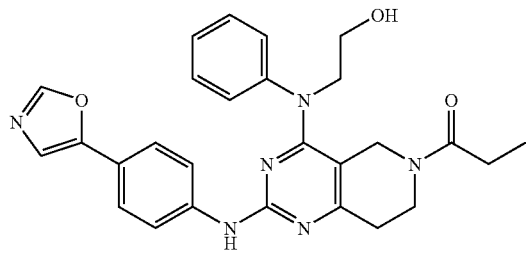

2-((2-(4-(Oxazol-5-yl)phenylamino)-5,6,7,8-tetrahydropyrido[4,3-d]pyrimidin-4-yl)(phenyl)amino)ethanol (85 mg, 0.20 mmol, Example 1) was dissolved in DMF (0.5 mL) and dichloromethane (4 mL). Triethylamine (0.028 mL, 0.20 mmol) was added followed by propionyl chloride (0.021 mL, 0.24 mmol). The reaction mixture was stirred at room temperature for 2 h and the solvent was evaporated under reduced pressure. The crude was dissolved in dimethylformamide and acetonitrile, filtered and purified by preparative HPLC yielding 1-(4-((2-hydroxyethyl)(phenyl)amino)-2-(4-(oxazol-5-yl)phenylamino)-7,8-dihydropyrido[4,3-d]pyrimidin-6(5H)-yl)propan-1-one (8.0 mg, 8.32%).

MS m/z (ES+), (M+H)+=485;

Mixture of rotamers:

$^1$H NMR (500 MHz, chloroform-d) δ ppm 0.98 (t) 1.10 (t) 1.94 (t) 2.12 (s) 2.31 (q) 2.73-2.86 (m) 3.53 (s) 3.59 (t) 3.68 (s) 3.71 (t) 3.77 (dt) 4.20 (dt) 7.20-7.26 (m) 7.28 (s) 7.36-7.47 (m) 7.60-7.66 (m) 7.68-7.73 (m) 7.90 (s))

Total no of protons in spectrum: 28

Ratio major:minor: 1.2:1.5

Example 16

Cyclopropyl(4-((2-hydroxyethyl)(phenyl)amino)-2-(4-(oxazol-5-yl)phenylamino)-7,8-dihydropyrido[4,3-d]pyrimidin-6(5H)-yl)methanone

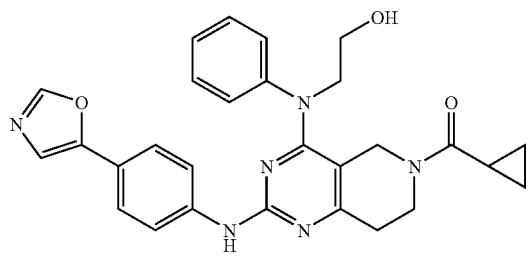

2-((2-(4-(Oxazol-5-yl)phenylamino)-5,6,7,8-tetrahydropyrido[4,3-d]pyrimidin-4-yl)(phenyl)amino)ethanol (50 mg, 0.12 mmol, Example 1) was dissolved in DMF (3 mL). Cyclopropanecarbonyl chloride (10.59 µL, 0.12 mmol) was added and the reaction was stirred at room temperature for 4 h. An extra equivalent of cyclopropanecarbonyl chloride was added and the reaction was stirred for 2 h. The solvent was evaporated, the crude dissolved in few drops dimethylformamide and acetonitrile, filtered and purified by preparative HPLC yielding cyclopropyl(4-((2-hydroxyethyl)(phenyl)amino)-2-(4-(oxazol-5-yl)phenylamino)-7,8-dihydropyrido[4,3-d]pyrimidin-6(5H)-yl)methanone (1.8 mg, 2.96%).

Mixture of rotamers:

HPLC, ms detection: (ESI) (M+1) m/z 497;

Mixture of rotamers:

$^1$H NMR (500 MHz, chloroform-d) δ ppm 0.62 (d, 1 H) 0.74 (d, 1 H) 0.87 (br. s., 1 H) 0.92 (br. ., 1 H) 2.12 (s, 2 H) 2.78 (br. s., 1 H) 2.89 (t, 1 H) 3.65-3.85 (m, 5 H) 4.15-4.26 (m, 2 H) 7.18-7.26 (m, 2 H) 7.28 (s, 1 H) 7.35-7.45 (m, 2 H) 7.60-7.67 (m, 2 H) 7.67-7.73 (m, 2 H) 7.90 (s, 1 H)

Total no of protons in spectrum: 26

Ratio major:minor: 1.3:1

Example 17

2-(Dimethylamino)-1-(4-((2-hydroxyethyl)(phenyl)amino)-2-(4-(oxazol-5-yl)phenylamino)-7,8-dihydropyrido[4,3-d]pyrimidin-6(5H)-yl)ethanone

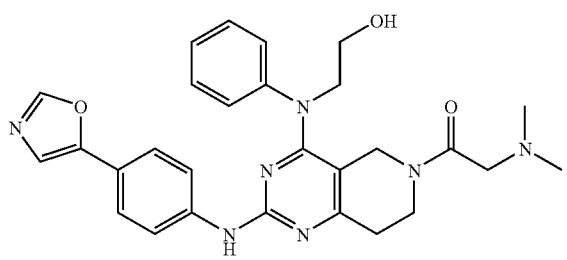

2-((2-(4-(Oxazol-5-yl)phenylamino)-5,6,7,8-tetrahydropyrido[4,3-d]pyrimidin-4-yl)(phenyl)amino)ethanol (100 mg, 0.23 mmol, Example 1) was dissolved in methanol (0.5 mL) and dichloromethane (5 mL). Triethylamine (0.033 mL, 0.23 mmol) was added followed by dimethylaminoacetyl chloride hydrochloride (43.4 mg, 0.23 mmol). The reaction mixture was stirred at room temperature for 1 h and the solvent was evaporated under reduced pressure. The crude was dissolved in dimethylformamide filtered and purified by preparative HPLC yielding 2-(dimethylamino)-1-(4-((2-hydroxyethyl)(phenyl)amino)-2-(4-(oxazol-5-yl)phenylamino)-7,8-dihydropyrido[4,3-d]pyrimidin-6(5H)-yl)ethanone (27.3 mg, 20.39%).

HPLC, ms detection: (ESI) (M+1) m/z 514.3;

$^1$H NMR (500 MHz, chloroform-d) δ ppm 2.09 (br. s., 2 H) 2.25 (s, 6 H) 2.77 (t, 1 H) 2.84 (t, 1 H) 2.91 (s, 1 H) 3.12 (s, 1 H) 3.59-3.72 (m, 4 H) 3.75 (t, 1 H) 3.80 (t, 1 H) 4.19 (ddd, 2 H) 7.17-7.26 (m, 3 H) 7.39 (ddd, 2 H) 7.61 (d, 2 H) 7.71 (dd, 2 H) 7.89 (s, 1 H)

Example 18

1-(4-((2-Hydroxyethyl)(phenyl)amino)-2-(4-(oxazol-5-yl)phenylamino)-7,8-dihydropyrido[4,3-d]pyrimidin-6(5H)-yl)-2-methoxyethanone

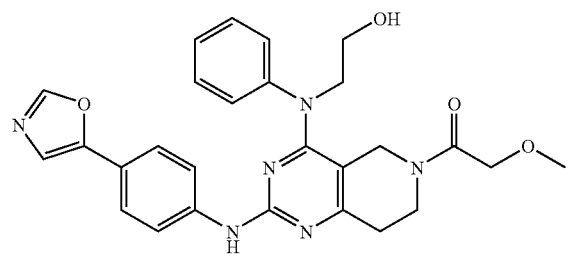

2-((2-(4-(Oxazol-5-yl)phenylamino)-5,6,7,8-tetrahydropyrido[4,3-d]pyrimidin-4-yl)(phenyl)amino)ethanol (40 mg, 0.09 mmol, Example 1) was dissolved in methanol (0.5 mL) and dichloromethane (3 mL). Triethylamine (0.013 mL, 0.09 mmol) was added followed by methoxyacetyl chloride (8.55 μL, 0.09 mmol). The reaction mixture was stirred at room temperature for 2 h and the solvent was evaporated under reduced pressure. The crude was dissolved in few drops of dimethylformamide and acetonitrile, filtered and purified by preparative HPLC yielding 1-(4-((2-hydroxyethyl)(phenyl)amino)-2-(4-(oxazol-5-yl)phenylamino)-7,8-dihydropyrido[4,3-d]pyrimidin-6(5H)-yl)-2-methoxyethanone (8.4 mg, 16.96%). HPLC, ms detection: (ESI) (M+1) m/z 501;

Mixture if rotamers:

$^1$H NMR (500 MHz, CHLOROFORM-d) δ ppm 2.77-2.89 (m) 3.27 (s, H) 3.37 (s) 3.57 (s) 3.62 (t) 3.66 (s) 3.70-3.82 (m) 4.06 (s) 4.16-4.24 (m) 7.17-7.32 (m, partly overlapped with solvent signal) 7.41 (m) 7.63 (d, H) 7.67-7.73 (m) 7.81 (m) 7.90 (s).

Total number of protons in spectrum: 27

Ratio rotamer 1:rotamer 2: 1:1

Example 19

2-Hydroxy-1-(4-((2-hydroxyethyl)(phenyl)amino)-2-(4-(oxazol-5-yl)phenylamino)-7,8-dihydropyrido[4,3-d]pyrimidin-6(5H)-yl)ethanone

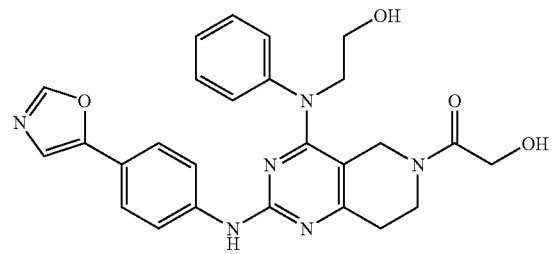

2-((2-(4-(Oxazol-5-yl)phenylamino)-5,6,7,8-tetrahydropyrido[4,3-d]pyrimidin-4-yl)(phenyl)amino)ethanol (100 mg, 0.23 mmol, Example 1) was dissolved in DMF (5 mL).

N-Ethyldiisopropylamine (0.081 mL, 0.47 mmol) was added followed by O-(1H-Benzotriazol-1-yl)-N,N,N',N'-tetramethyluronium hexafluorophosphate (115 mg, 0.30 mmol) and glycolic acid (0.025 mL, 0.23 mmol). The reaction mixture was stirred at room temperature overnight. The solvent was evaporated and the crude dissolved in DMF and acetonitrile, filtered and purified by prep. HPLC. The fractions containing the title compound were pulled together and freezed-dried over the weekend yielding 2-hydroxy-1-(4-((2-hydroxyethyl)(phenyl)amino)-2-(4-(oxazol-5-yl)phenylamino)-7,8-dihydropyrido[4,3-d]pyrimidin-6(5H)-yl)ethanone (21.0 mg, 18.49%).

MS m/z (ES−) 485.2 (M−H)−

$^1$H NMR (500 MHz, CHLOROFORM-d) δ ppm 2.12 (s, 2 H) 2.82 (ddd, 2 H) 3.33 (s, 1 H) 3.43 (t, 1 H) 3.71 (d, 2 H) 3.73-3.82 (m, 3 H) 4.15 (s, 1 H) 4.19 (dt, 2 H) 7.23 (t, 2 H) 7.28 (s, 1 H) 7.37-7.48 (m, 2 H) 7.63 (m, 2 H) 7.71 (m, 2 H) 7.90 (s, 2 H)

Example 20

(S)-2-Hydroxy-1-(4-((2-hydroxyethyl)(phenyl)amino)-2-(4-(oxazol-5-yl)phenylamino)-7,8-dihydropyrido[4,3-d]pyrimidin-6(5H)-yl)propan-1-one

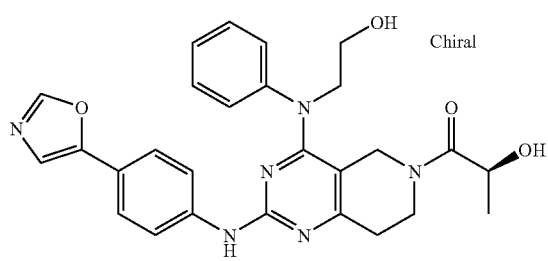

2-((2-(4-(Oxazol-5-yl)phenylamino)-5,6,7,8-tetrahydropyrido[4,3-d]pyrimidin-4-yl)(phenyl)amino)ethanol (100 mg, 0.23 mmol, Example 1) was dissolved in DMF (5 mL). N-Ethyldiisopropylamine (0.081 mL, 0.47 mmol) was added followed by O-(1H-Benzotriazol-1-yl)-N,N,N',N'-tetramethyluronium hexafluorophosphate (115 mg, 0.30 mmol) and L-lactic acid (21.02 mg, 0.23 mmol). The reaction mixture was stirred at room temperature overnight. The solvent was evaporated under reduced pressure, the crude dissolved in MeOH and acetonitrile, filtered and purified by preparative HPLC yielding (S)-2-hydroxy-1-(4-((2-hydroxyethyl)(phenyl)amino)-2-(4-(oxazol-5-yl)phenylamino)-7,8-dihydropyrido[4,3-d]pyrimidin-6(5H)-yl)propan-1-one (30.0 mg, 26%).

MS (ESI) (M+1) m/z 501.3

$^1$H NMR (500 MHz, CHLOROFORM-d) δ ppm 0.99 (d, 2 H) 1.30 (d, 1 H) 2.12 (s, 1 H) 2.76-2.89 (m, 1 H) 3.37 (d, 1 H) 3.47-3.60 (m, 2 H) 3.70 (d, 1 H) 3.76 (ddd, 2 H) 3.93-4.02 (m, 1 H) 4.12-4.27 (m, 2 H) 7.20 (d, 1 H) 7.24 (t, 1 H) 7.28 (s, 1 H) 7.31 (t, 1 H) 7.39 (t, 1 H) 7.45 (t, 1 H) 7.63 (d, 2 H) 7.71 (dd, 2 H) 7.79 (d, 1 H) 7.90 (s, 1 H)

Example 21

2-((6-(Methylsulfonyl)-2-(4-(oxazol-5-yl)phenylamino)-5,6,7,8-tetrahydropyrido[4,3-d]pyrimidin-4-yl)(phenyl)amino)ethanol

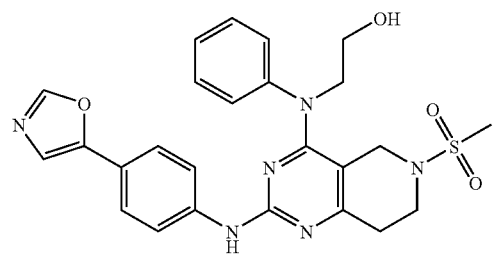

2-((2-(4-(Oxazol-5-yl)phenylamino)-5,6,7,8-tetrahydropyrido[4,3-d]pyrimidin-4-yl)(phenyl)amino)ethanol (40 mg, 0.09 mmol, Example 1) was dissolved in methanol (0.5 mL) and dichloromethane (3 mL). Triethylamine (0.013 mL, 0.09 mmol) and methanesulfonyl chloride (7.23 μL, 0.09 mmol) were added and the reaction mixture was stirred at room temperature, under nitrogen atmosphere, for 3 h. The solvent was evaporated under reduced pressure, the crude dissolved in few drops of dimethylformamide and acetonitrile, filtered and purified by preparative HPLC yielding 2-((6-(methylsulfonyl)-2-(4-(oxazol-5-yl)phenylamino)-5,6,7,8-tetrahydropyrido[4,3-d]pyrimidin-4-yl)(phenyl)amino)ethanol (5.2 mg, 10.15%).

MS (ESI) (M+1) m/z 507

$^1$H NMR (500 MHz, chloroform-d) δ ppm 2.12 (s, 2 H) 2.56 (s, 3 H) 2.91 (t, 2 H) 3.31 (s, 2 H) 3.42 (t, 2 H) 3.77 (t, 2 H) 4.20 (t, 2 H) 7.22 (d, 2 H) 7.27-7.31 (m, 2 H) 7.42 (t, 2 H) 7.64 (m, 2 H) 7.71 (m, 2 H) 7.90 (s, 1 H)

Example 22

2-((6-(Ethylsulfonyl)-2-(4-(oxazol-5-yl)phenylamino)-5,6,7,8-tetrahydropyrido[4,3-d]pyrimidin-4-yl)(phenyl)amino)ethanol

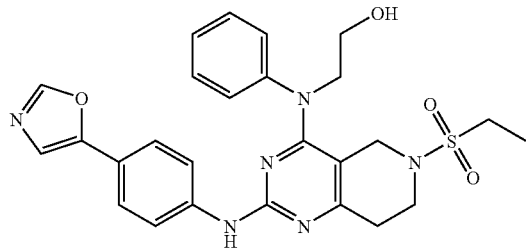

2-((2-(4-(Oxazol-5-yl)phenylamino)-5,6,7,8-tetrahydropyrido[4,3-d]pyrimidin-4-yl)(phenyl)amino)ethanol (100 mg, 0.23 mmol, Example 1) was dissolved in MeOH (0.5 mL) and dichloromethane (5 mL). Triethylamine (0.033 mL, 0.23 mmol) was added followed by ethanesulphonyl chloride (0.022 mL, 0.23 mmol). The reaction mixture was stirred at room temperature for 1 h before the solvent was evaporated under reduced pressure. The crude was dissolved in dimethylformamide and acetonitrile and purified by preparative HPLC yielding 2-((6-(ethylsulfonyl)-2-(4-(oxazol-5-yl)phenylamino)-5,6,7,8-tetrahydropyrido[4,3-d]pyrimidin-4-yl)(phenyl)amino)ethanol (22.0 mg, 18.11%). MS (ESI) (M+1) m/z 521;

$^1$H NMR (500 MHz, chloroform-d) δ ppm 1.19 (t, 3 H) 2.75 (q, 2 H) 2.87 (t, 2 H) 3.37 (s, 2 H) 3.47 (t, 2 H) 3.76 (t, 2 H) 4.19 (t, 2 H) 7.21 (d, 2 H) 7.28 (s, 2 H) 7.40 (t, 2 H) 7.63 (m, 2 H) 7.71 (m, 2 H) 7.90 (s, 1 H) 8.12 (br. s., 1 H)

Example 23

Methyl 4-((2-hydroxyethyl)(phenyl)amino)-2-(4-(oxazol-5-yl)phenylamino)-7,8-dihydropyrido[4,3-d]pyrimidine-6(5H)-carboxylate

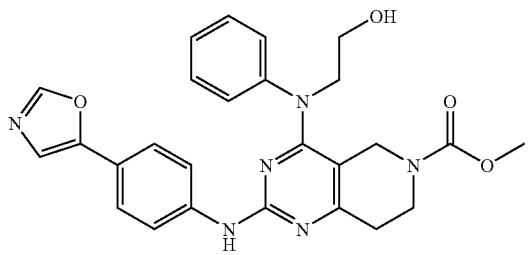

2-((2-(4-(Oxazol-5-yl)phenylamino)-5,6,7,8-tetrahydropyrido[4,3-d]pyrimidin-4-yl)(phenyl)amino)ethanol (80 mg, 0.19 mmol, Example 1) was dissolved in DMF (5 mL). Methyl chloroformate (0.014 mL, 0.19 mmol) was added and the reaction was stirred for 2 h. The solvent was evaporated, the crude dissolved in few drops of dimethylformamide and acetonitrile, filtered and purified by HPLC. The fractions containing the title compound were pulled together and freezed-dried overnight, yielding methyl 4-((2-hydroxyethyl)(phenyl)amino)-2-(4-(oxazol-5-yl)phenylamino)-7,8-dihydropyrido[4,3-d]pyrimidine-6(5H)-carboxylate (28.0 mg, 30.8%).

MS (ESI) (M+1) m/z 487;

$^1$H NMR (500 MHz, chloroform-d) δ ppm 2.12 (s, 1 H) 2.82 (t, 2 H) 3.53 (br. s., 2 H) 3.59 (br. s., 3 H) 3.65 (br. s., 2 H) 3.74-3.81 (m, 2 H) 4.20 (t, 2 H) 7.17-7.26 (m, 2 H) 7.30 (s, 2 H) 7.42 (t, 2 H) 7.67 (m, 4 H) 7.90 (s, 1 H)

Example 24

Ethyl 4-((2-hydroxyethyl)(phenyl)amino)-2-(4-(oxazol-5-yl)phenylamino)-7,8-dihydropyrido[4,3-d]pyrimidine-6(5H)-carboxylate

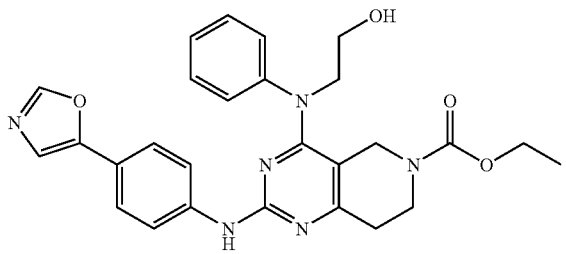

2-((2-(4-(Oxazol-5-yl)phenylamino)-5,6,7,8-tetrahydropyrido[4,3-d]pyrimidin-4-yl)(phenyl)amino)ethanol (100 mg, 0.23 mmol, Example 1) was dissolved in MeOH (0.5 mL) and dichloromethane (5 mL). Triethylamine (0.033 mL, 0.23 mmol) was added followed by ethyl carbonochloridate (0.022 mL, 0.23 mmol). The reaction mixture was stirred at room temperature for 1 h and the solvent was evaporated under reduced pressure. The crude was dissolved in dimethylformamide and acetonitrile, filtered and purified by preparative HPLC yielding ethyl 4-((2-hydroxyethyl)(phenyl)amino)-2-(4-(oxazol-5-yl)phenylamino)-7,8-dihydropyrido[4,3-d]pyrimidine-6(5H)-carboxylate (28.0 mg, 24%).

MS (ESI) (M+1) m/z 501;

$^1$H NMR (500 MHz, chloroform-d) δ ppm 1.20 (br. s., 3 H) 2.13 (s, 1 H) 2.77 (t, 2 H) 3.46-3.65 (m, 4 H) 3.75 (br. s., 2 H) 4.05 (d, 2 H) 4.18 (br. s., 2 H) 7.20 (d, 3 H) 7.39 (br. s., 2 H) 7.62 (m, 2 H) 7.71 (m, 2 H) 7.89 (s, 1 H)

Example 25

4-((2-Hydroxyethyl)(phenyl)amino)-N,N-dimethyl-2-(4-(oxazol-5-yl)phenylamino)-7,8-dihydropyrido[4,3-d]pyrimidine-6(5H)-caroxamide

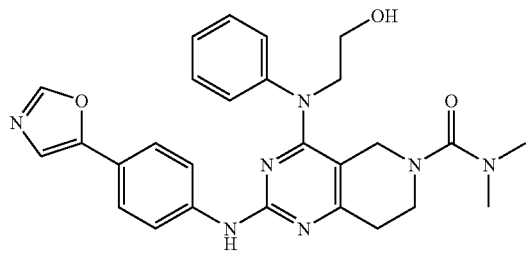

2-((2-(4-(Oxazol-5-yl)phenylamino)-5,6,7,8-tetrahydropyrido[4,3-d]pyrimidin-4-yl)(phenyl)amino)ethanol (50 mg, 0.12 mmol, Example 1) was dissolved in dichloromethane (5 mL) and methanol (1 mL). Triethylamine (0.016 mL, 0.12 mmol) was added followed by dimethylcarbamyl chloride (10.72 μL, 0.12 mmol). The reaction mixture was stirred at room temperature for 2 h. The solvent was evaporated under reduced pressure, the crude dissolved in few drops of dimethylformamide and acetonitrile, filtered and purified by HPLC yielding 4-((2-hydroxyethyl)(phenyl)amino)-N,N-dimethyl-2-(4-(oxazol-5-yl)phenylamino)-7,8-dihydropyrido[4,3-d]pyrimidine-6(5H)-carboxamide (19.0 mg, 33%).

HPLC, ms detection: (ESI) (M+1) m/z 500;

$^1$H NMR (500 MHz, chloroform-d) δ ppm 2.12 (s, 2 H) 2.69 (s, 6 H) 2.85 (t, 2 H) 3.33 (s, 2 H) 3.38 (t, 2 H) 3.77 (t, 2 H) 4.21 (t, 2 H) 7.22 (d, 2 H) 7.29 (s, 1 H) 7.40 (t, 2 H) 7.63 (m, 2 H) 7.70 (m, 2 H) 7.90 (s, 1 H)

Example 26

1-(4-(Cyclohexylamino)-2-(4-(oxazol-5-yl)phenylamino)-7,8-dihydropyrido[4,3-d]pyrimidin-6(5H)-yl)ethanone

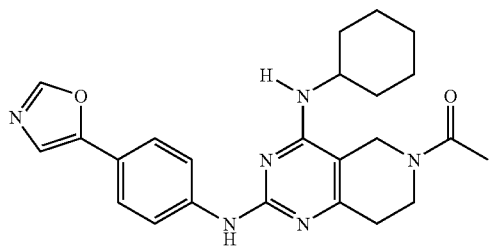

6-Acetyl-2-(4-(oxazol-5-yl)phenylamino)-5,6,7,8-tetrahydropyrido[4,3-d]pyrimidin-4-yl trifluoromethanesulfonate (35 mg, 0.07 mmol) in DMSO (1 mL) was dispensed in a library plate. Cyclohexanamine (6.94 mg, 0.07 mmol) was added and the reaction mixture was stirred overnight at 80° C. before it was filtered and purified by preparative HPLC to give 1-(4-(cyclohexylamino)-2-(4-(oxazol-5-yl)phenylamino)-7,8-dihydropyrido[4,3-d]pyrimidin-6(5H)-yl)ethanone (11.2 mg, 36%).

MS m/z (ES−), (M−H)−=431.2

Mixture of rotamers:

$^1$H NMR (500 MHz, CDCl$_3$) δ ppm 1.18-1.35 (m), 1.40-1.53 (m), 1.70-1.91 (m), 2.09-2.18 (m), 2.20-2.27 (m) 2.68-2.82 (m), 3.69-3.78 (m), 3.84-3.92 (m), 3.98-4-12 (m), 4.15-4.25 (m), 4.34 (s), 7.27-7.29 (m), 7.56-7.62 (m), 7.70-7.72 (m), 7.89 (s)

Total no of protons in spectrum: 27
Ratio major:minor: 0.7:0.4

Example 26a

6-Acetyl-2-(4-(oxazol-5-yl)phenylamino)-5,6,7,8-tetrahydropyrido[4,3-d]pyrimidin-4-yl trifluoromethanesulfonate

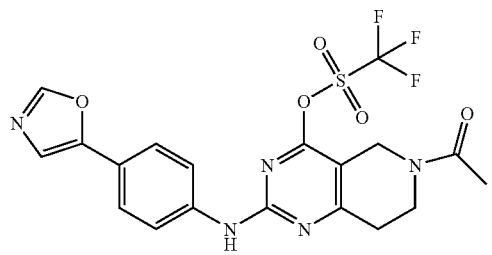

1-(4-Hydroxy-2-(4-(oxazol-5-yl)phenylamino)-7,8-dihydropyrido[4,3-d]pyrimidin-6(5H)-yl)ethanone (2.9 g, 8.25 mmol) was dissolved in dichloromethane (50 mL) and 1,8-diazabicyclo[5.4.0]undec-7-ene (1.232 mL, 8.25 mmol). N-phenyltrifluoromethane-sulfonimide (3.24 g, 9.08 mmol) was added followed by 4-dimethylaminopyridine (1.01 mg, 8.25 μmol). The reaction mixture was stirred at room temperature for 4 h. The solvent was evaporated under reduced pressure and the crude dissolved in ethanol. Water was added until the product precipitated. The solid obtained was filtered and dried in a vacuum oven overnight at 40° C. yielding 6-acetyl-2-(4-(oxazol-5-yl)phenylamino)-5,6,7,8-tetrahydropyrido[4,3-d]pyrimidin-4-yl trifluoromethanesulfonate (0.720 g, 18%).

MS (ESI) (M+1) m/z 484.2

Example 26b 1-(4-Hydroxy-2-(4-(oxazol-5-yl)phenylamino)-7,8-dihydropyrido[4,3-d]pyrimidin-6(5H)-yl)ethanone

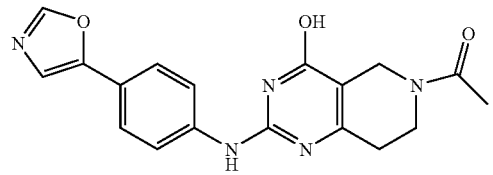

1-(4-(Oxazol-5-yl)phenyl)guanidine (2.7 g, 13.35 mmol), methyl 1-acetyl-4-oxopiperidin-3-carboxylate (2.66 g, 13.35 mmol) and sodium ethoxide (0.946 g, 13.35 mmol) in ethanol (15 mL) were heated in a microwave reactor at 100° C. for 15 minutes. The reaction mixture was allowed to reach room temperature and water was added. The solid obtained was filtered, washed with water and dried in a vaccum oven yielding 1-(4-hydroxy-2-(4-(oxazol-5-yl)phenylamino)-7,8-dihydropyrido[4,3-d]pyrimidin-6(5H)-yl)ethanone (2.90 g, 61.8%).

MS (ESI) (M+1) m/z 352.2

$^1$H NMR (500 MHz, MeOD) δ ppm 1.90 (s, 7 H) 2.20 (d, 3 H) 2.63 (t, 1 H) 2.72 (t, 1 H) 3.74-3.85 (m, 3 H) 4.41 (d, 2 H) 7.34-7.43 (m, 3 H) 7.56 (s, 1 H) 7.64 (dd, 2 H) 7.75-7.85 (m, 4 H) 8.20 (d, 1 H) 8.28 (s, 1 H)

Example 26c

Methyl 1-acetyl-4-oxopiperidine-3-carboxylate

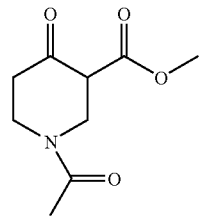

Methyl 4-oxo-3-piperidinecarboxylate hydrochloride (10 g, 51.65 mmol) was dissolved in dichloromethane (130 mL). Triethylamine (7.20 mL, 51.65 mmol) was added followed by acetic anhydride (4.87 mL, 51.65 mmol). The reaction mixture was stirred at room temperature for 2 h. The organic phase was washed with water, dried over MgSO$_4$, filtered and concentrated to give methyl 1-acetyl-4-oxopiperidine-3-carboxylate (6.10 g, 59.3%), which was used in the next step as such.

MS (ESI) (M+1) m/z 200.1

Example 27

(S)-1-(2-(4-(Oxazol-5-yl)phenylamino)-4-((tetrahydrofuran-2-yl)methylamino)-7,8-dihydropyrido[4,3-d]pyrimidin-6(5H)-yl)ethanone

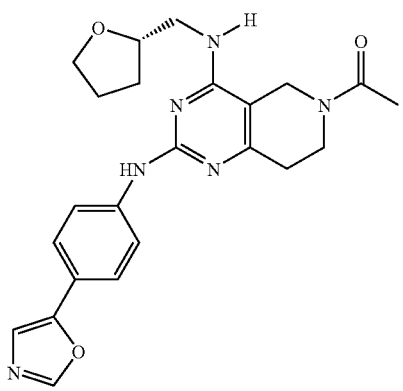

6-Acetyl-2-(4-(oxazol-5-yl)phenylamino)-5,6,7,8-tetrahydropyrido[4,3-d]pyrimidin-4-yl trifluoromethanesulfonate (35 mg, 0.07 mmol, Example 26a) in DMSO (1 mL) was dispensed in a library plate. (S)-(tetrahydrofuran-2-yl)methanamine (7.08 mg, 0.07 mmol) was added to the plate and it was left to shake overnight at 80° C., filtered and purified by preparative HPLC to give (S)-1-(2-(4-(oxazol-5-yl)phenylamino)-4-((tetrahydrofuran-2-yl)methylamino)-7,8-dihydropyrido[4,3-d]pyrimidin-6(5H)-yl)ethanone (12.7 mg, 40.4%).

MS m/z (ES−) 433 (M−H)−

$^1$H NMR (500 MHz, DMSO-$d_6$) δ ppm 1.65 (ddd, 1 H) 1.76-2.00 (m, 4 H) 2.11 (s, 3 H) 2.64-2.67 (m, 1 H) 3.39-3.56 (m, 3 H) 3.58-3.74 (m, 3 H) 3.76-3.85 (m, 1 H) 4.08-4.17 (m, 1 H) 4.21-4.33 (m, 2 H) 6.93-7.02 (m, 1 H) 7.50 (s, 1 H) 7.56 (dd, 2 H) 7.88 (d, 2 H) 8.35 (s, 1 H) 9.19-9.28 (m, 1 H)

Example 28

1-(4-((2-Hydroxyethyl)(phenyl)amino)-2-(4-(oxazol-5-yl)phenylamino)-7,8-dihydropyrido[4,3-d]pyrimidin-6(5H)-yl)ethanone

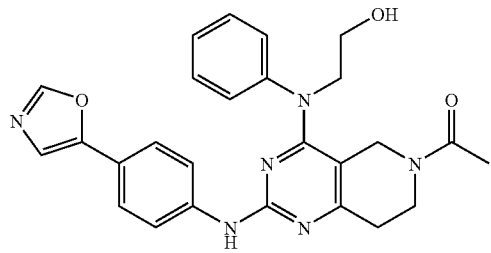

2-((2-(4-(Oxazol-5-yl)phenylamino)-5,6,7,8-tetrahydropyrido[4,3-d]pyrimidin-4-yl)(phenyl)amino)ethanol (30 mg, 0.07 mmol, Example 26a) was dissolved in dichloromethane (1 mL) and THF (1 mL). Acetic anhydride (6.61 μL, 0.07 mmol) was added and the reaction mixture was stirred for 3 h at room temperature. The solvent was evaporated under reduced pressure, the crude was dissolved in dimethylformamide and acetonitrile, filtered and purified by preparative HPLC yielding 1-(4-((2-hydroxyethyl)(phenyl)amino)-2-(4-(oxazol-5-yl)phenylamino)-7,8-dihydropyrido[4,3-d]pyrimidin-6(5H)-yl)ethanone (5.9 mg, 17.91%).

MS (ESI) (M+1) m/z 471

$^1$H NMR (500 MHz, chloroform-d) δ ppm 1.75 (s, 1 H) 2.06 (s, 2 H) 2.12 (s, 1 H) 2.80 (t, 1 H) 2.88 (t, 1 H) 3.52 (s, 1 H) 3.59 (t, 1 H) 3.63 (br. s., 1 H) 3.70 (t, 1 H) 3.79 (ddd, 2 H) 4.21 (ddd, 2 H) 7.27-7.35 (m, 4 H) 7.39-7.49 (m, 2 H) 7.62-7.72 (m, 4 H) 7.91 (s, 1 H)

Example 29

1-(4-(3-(Hydroxymethyl)phenylamino)-2-(4-(oxazol-5-yl)phenylamino)-7,8-dihydropyrido[4,3-d]pyrimidin-6(5H)-yl)ethanone

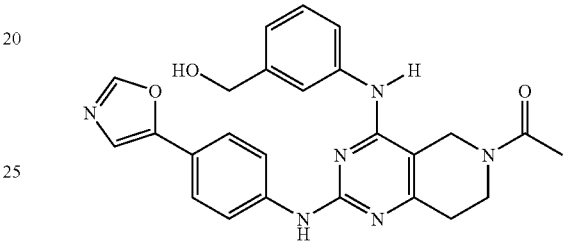

6-Acetyl-2-(4-(oxazol-5-yl)phenylamino)-5,6,7,8-tetrahydropyrido[4,3-d]pyrimidin-4-yl trifluoromethanesulfonate (35 mg, 0.07 mmol, Example 26a) in DMSO (1 mL) was dispensed in a library plate. (3-aminophenyl)methanol (8.62 mg, 0.07 mmol) was added to the funnel and the plate was left to shake overnight at 80° C. before it was filtered and purified by preparative HPLC to give 1-(4-(3-(hydroxymethyl)phenylamino)-2-(4-(oxazol-5-yl)phenylamino)-7,8-dihydropyrido[4,3-d]pyrimidin-6(5H)-yl)ethanone (7.2 mg, 22%).

MS (ESI) (M+1) m/z 457

Mixture of rotamers:

$^1$H NMR (500 MHz, DMSO-$d_6$) δ ppm 2.10-2.20 (m), 2.57-2.65 (m), 3.70-3.80 (q), 4.48-4.54 (m), 5.18-5.26 (m), 7.05-7.13 (m), 7.29-7.38 (m), 7.45-7.60 (m), 7.50-7.81 (m), 8.14 (s, 1 H), 8.41-8.61 (m), 9.10-9.18 (m)

Total no of protons in spectrum: 24

Ratio major:minor=1:0.7

Example 30

(S)-1-(4-(2-(Hydroxymethyl)indolin-1-yl)-2-(4-(oxazol-5-yl)phenylamino)-7,8-dihydropyrido[4,3-d]pyrimidin-6(5H)-yl)ethanone

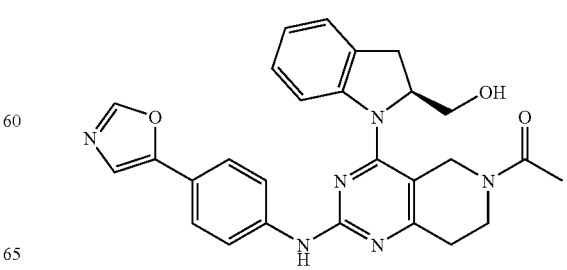

6-Acetyl-2-(4-(oxazol-5-yl)phenylamino)-5,6,7,8-tetrahydropyrido[4,3-d]pyrimidin-4-yl trifluoromethanesulfonate (35 mg, 0.07 mmol, Example 26a) in DMSO (1 mL) was dispensed in a library plate. (S)-indolin-2-ylmethanol (10.44 mg, 0.07 mmol) was added and it was left to shake overnight at 80° C. before filtered and purified by preparative HPLC to yield (11.5 mg, 24%).

MS (ESI) (M+1) m/z 483

Mixture of rotamers:

$^1$H NMR (500 MHz, CDCl$_3$) δ ppm 1.95 (s), 2.14 (s), 2.81-3.07 (m), 3.30-3.46 (m), 3.62-4.00 (m), 4.02-4.42 (m), 4.67-4.81 (m), 6.49-6.61 (m), 6.86-7.00 (m), 7.07-7.17 (m), 7.20-7.24 (m), 7.27-7.30 (m), 7.58-7.69 (m), 7.89 (s)

Total no of protons in spectrum: 26

Ratio major:minor: 1:0.6

Example 31

3-((6-Acetyl-2-(4-(oxazol-5-yl)phenylamino)-5,6,7,8-tetrahydropyrido[4,3-d]pyrimidin-4-yl)(cyclopropyl)amio)propanenitrile

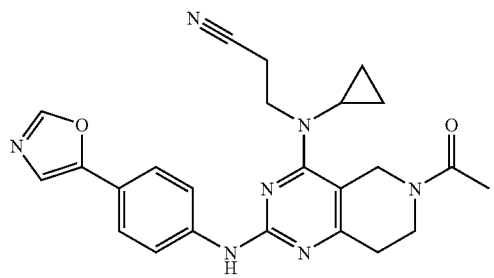

6-Acetyl-2-(4-(oxazol-5-yl)phenylamino)-5,6,7,8-tetrahydropyrido[4,3-d]pyrimidin-4-yl trifluoromethanesulfonate (35 mg, 0.07 mmol, Example 26a) in DMSO (1 mL) was dispensed in a library plate. 3-(cyclopropylamino)propanenitrile (7.71 mg, 0.07 mmol) was added and it was left to shake overnight at 80° C. before filtered and purified by preparative HPLC to yield 3-((6-Acetyl-2-(4-(oxazol-5-yl)phenylamino)-5,6,7,8-tetrahydropyrido[4,3-d]pyrimidin-4-yl)(cyclopropyl)amino)propanenitrile (15.5 mg, 48%).

MS (ESI) (M+1) m/z 444

Mixture of rotamers:

$^1$H NMR (500 MHz, DMSO-d$_6$) δ ppm 0.63 (d, 2 H) 0.89 (d, 2 H) 2.07 (d, 3 H) 2.70 (t, 1H) 2.82 (t, 1 H) 2.86-2.97 (m, 2 H) 3.02-3.16 (m, 1 H) 3.73 (q, 2 H) 3.77-3.87 (m, 2 H) 4.66 (d, 2 H) 7.49 (s, 1 H) 7.59 (d, 2 H) 7.79 (dd, 2 H) 8.36 (s, 1 H) 9.43 (d, 1 H)

Total no of protons in spectrum: 25

Ratio major:minor: 0.5:0.6

Example 32

1-(4-(Benzyl(2-hydroxyethyl)amino)-2-(4-(oxazol-5-yl)phenylamino)-7,8-dihydropyrido[4,3-d]pyrimidin-6(5H)-yl)ethanone

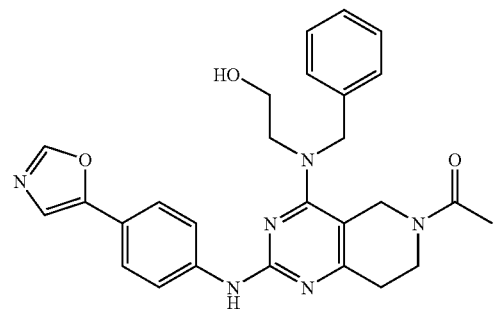

6-Acetyl-2-(4-(oxazol-5-yl)phenylamino)-5,6,7,8-tetrahydropyrido[4,3-d]pyrimidin-4-yl trifluoromethanesulfonate (35 mg, 0.07 mmol, Example 26a) in DMSO (1 mL) was dispensed in a library plate. 1-(3-aminophenyl)ethanone (-, 0.07 mmol) was added and it was left to shake overnight at 80° C. before filtered and purified by preparative HPLC to yield 1-(4-(benzyl(2-hydroxyethyl)amino)-2-(4-(oxazol-5-yl)phenylamino)-7,8-dihydropyrido[4,3-d]pyrimidin-6(5H)-yl)ethanone (16.5 mg, 49%).

MS (ESI) (M+1) m/z 485

$^1$H NMR (500 MHz, DMSO-d$_6$) δ ppm 1.80 (s, 1 H) 2.06 (s, 2 H) 2.64-2.70 (m, 1 H) 2.80 (t, 1 H) 3.46 (t, 1 H) 3.53 (t, 1 H) 3.61-3.77 (m, 4 H) 4.53 (d, 2 H) 4.73-4.83 (m, 2 H) 7.20-7.28 (m, 1 H) 7.28-7.39 (m, 4 H) 7.44-7.57 (m, 3 H) 7.72 (t, 2 H) 8.35 (d, 1 H) 9.36 (d, 1 H)

Example 33

1-(3-(6-Acetyl-2-(4-(oxazol-5-yl)phenylamino)-5,6,7,8-tetrahydropyrido[4,3-d]pyrimidin-4-ylamino)phenyl)ethanone

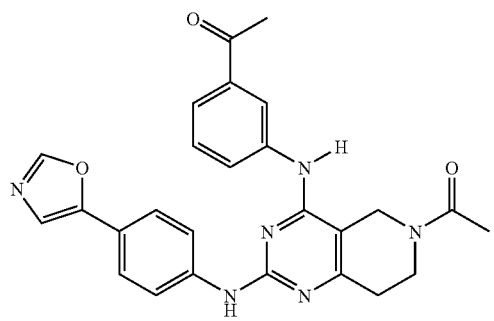

6-Acetyl-2-(4-(oxazol-5-yl)phenylamino)-5,6,7,8-tetrahydropyrido[4,3-d]pyrimidin-4-yl trifluoromethanesulfonate (35 mg, 0.07 mmol, Example 26a) in DMSO (1 mL) dispensed in a library plate. 1-(3-aminophenyl)ethanone (9.5 mg, 0.07 mmol) was added and it was left to shake overnight at 80° C. before filtered and purified by preparative HPLC to yield 1-(3-(6-acetyl-2-(4-(oxazol-5-yl)phenylamino)-5,6,7,8-tetrahydropyrido[4,3-d]pyrimidin-4-ylamino)phenyl)ethanone (17.5 mg, 49%).

MS (ESI) (M+1) m/z 469

Mixture of rotamers:

$^1$H NMR (500 MHz, DMSO-$d_6$) δ ppm 2.12-2.20 (m) 2.54 (s) 2.56 (s) 2.60-2.66 (m) 2.77 (t) 3.75 (m) 4.53 (d) 7.41-7.49 (m) 7.50-7.58 (m) 7.71 (m) 7.75 (m) 8.02 (m) 8.13 (s) 8.36 (s) 9.36-9.45 (m)

Total no of protons in spectrum: 24

Ratio major:minor: 1:0.4

Example 34

1-(4-((2-Hydroxy-2-phenylethyl)(methyl)amino)-2-(4-(oxazol-5-yl)phenylamino)-7,8-dihydropyrido[4,3-d]pyrimidin-6(5H)-yl)ethanone

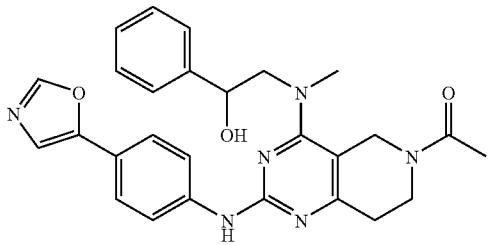

6-Acetyl-2-(4-(oxazol-5-yl)phenylamino)-5,6,7,8-tetrahydropyrido[4,3-d]pyrimidin-4-yl trifluoromethanesulfonate (35 mg, 0.07 mmol, Example 26a) in DMSO (1 mL) dispensed in a library plate. 2-(methylamino)-1-phenylethanol (10.58 mg, 0.07 mmol) was added and it was left to shake overnight at 80° C. before filtered and purified by preparative HPLC to yield 1-(4-((2-hydroxy-2-phenylethyl)(methyl)amino)-2-(4-(oxazol-5-yl)phenylamino)-7,8-dihydropyrido[4,3-d]pyrimidin-6(5H)-yl)ethanone (21.9 mg, 63%).

MS (ESI) (M+1) m/z 485

$^1$H NMR (500 MHz, DMSO-$d_6$) δ ppm 2.01-2.11 (m, 3 H) 2.59-2.66 (m, 1 H) 2.77 (t, 1H) 3.12 (s, 3 H) 3.55-3.79 (m, 4 H) 4.46-4.53 (m, 1 H) 4.53-4.61 (m, 1 H) 4.84-4.96 (m, 1 H) 5.51 (d, 1 H) 7.21-7.29 (m, 1 H) 7.29-7.35 (m, 2 H) 7.36-7.43 (m, 2 H) 7.47-7.52 (m, 1 H) 7.55 (t, 2 H) 7.79-7.86 (m, 2 H) 8.36 (s, 1 H) 9.29 (s, 1 H)

Example 35

1-(4-(1-(Hydroxymethyl)cyclopentylamino)-2-(4-(oxazol-5-yl)phenylamino)-7,8-dihydropyrido[4,3-d]pyrimidin-6(5H)-yl)ethanone

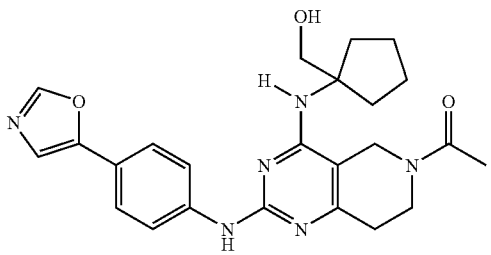

6-Acetyl-2-(4-(oxazol-5-yl)phenylamino)-5,6,7,8-tetrahydropyrido[4,3-d]pyrimidin-4-yl trifluoromethanesulfonate (35 mg, 0.07 mmol, Example 26a) in DMSO (1 mL) dispensed in a library plate. (1-aminocyclopentyl)methanol (8.06 mg, 0.07 mmol) was added and it was left to shake overnight at 80° C. before filtered and purified by preparative HPLC to yield 1-(4-(1-(hydroxymethyl)cyclopentylamino)-2-(4-(oxazol-5-yl)phenylamino)-7,8-dihydropyrido[4,3-d]pyrimidin-6(5H)-yl)ethanone (8.5 mg, 26%).

MS (ESI) (M+1) m/z 449.3

$^1$H NMR (500 MHz, DMSO-$d_6$) δ ppm 1.35 (s, 1 H) 1.49 (d, 2 H) 1.56-1.70 (m, 6 H) 1.91-2.00 (m, 3 H) 2.07-2.15 (m, 5 H) 2.61 (t, 1 H) 3.54 (d, 2 H) 3.68 (q, 3 H) 4.44 (d, 2 H) 6.12 (d, 1 H) 7.57-7.61 (m, 2 H) 7.63 (d, 2 H) 7.66 (d, 1 H) 7.82-7.86 (m, 1 H) 8.34-8.38 (m, 1 H) 8.38-8.42 (m, 1 H)

Example 36

1-(4-(Methyl(pyridin-3-ylmethyl)amino)-2-(4-(oxazol-5-yl)phenylamino)-7,8-dihydropyrido[4,3-d]pyrimidin-6(5H)-yl)ethanone

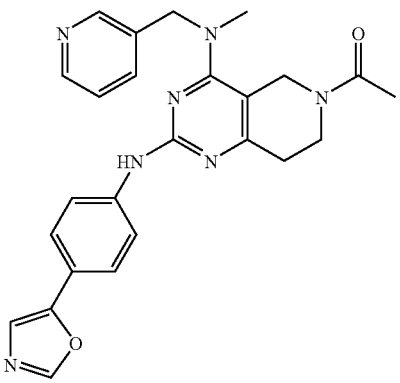

6-Acetyl-2-(4-(oxazol-5-yl)phenylamino)-5,6,7,8-tetrahydropyrido[4,3-d]pyrimidin-4-yl trifluoromethanesulfonate (35 mg, 0.07 mmol, Example 26a) in DMSO (1 mL) was dispensed in a library plate. N-methyl-1-(pyridin-3-yl)methanamine (8.55 mg, 0.07 mmol) was added and it was left to shake overnight at 80° C. before filtered and purified by preparative HPLC to yield 1-(4-(Methyl(pyridin-3-ylmethyl)amino)-2-(4-(oxazol-5-yl)phenylamino)-7,8-dihydropyrido[4,3-d]pyrimidin-6(5H)-yl)ethanone (17 mg, 52%).

MS (ESI) (M+1) m/z 456.3

Mixture of rotamers:

$^1$H NMR (500 MHz, DMSO-$d_6$) δ ppm 1.93 (s) 2.07 (s) 2.67 (t) 2.81 (t) 3.03 (s) 3.09 (s) 3.67-3.79 (m) 4.52 (s) 4.59 (s) 4.68-4.76 (m) 7.35-7.43 (m) 7.44-7.53 (m) 7.65-7.80 (m) 8.35 (s) 8.45-8.51 (m) 8.51-8.62 (m) 9.35-9.46 (m)

Total no of protons in spectrum: 25

Ratio major:minor: 1.4:0.7

Example 37

(R)-1-(4-(2-(Hydroxymethyl)indolin-1-yl)-2-(4-(oxazol-5-yl)phenylamino)-7,8-dihydropyrido[4,3-d]pyrimidin-6(5H)-yl)ethanone

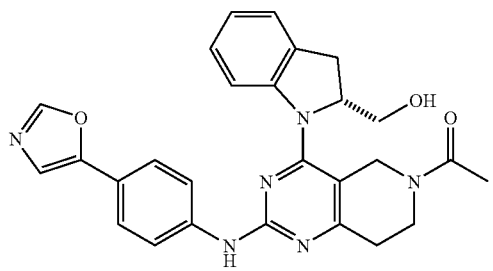

6-Acetyl-2-(4-(oxazol-5-yl)phenylamino)-5,6,7,8-tetrahydropyrido[4,3-d]pyrimidin-4-yl trifluoromethanesulfonate (35 mg, 0.07 mmol, Example 26a) in DMSO (1 mL) was dispensed in a library plate. (R)-indolin-2-ylmethanol (10.44 mg, 0.07 mmol) was added to it and the reaction mixture was left to shake overnight at 80° C. before filtered and purified by preparative HPLC to yield (R)-1-(4-(2-(Hydroxymethyl)indolin-1-yl)-2-(4-(oxazol-5-yl)phenylamino)-7,8-dihydropyrido[4,3-d]pyrimidin-6(5H)-yl)ethanone (12.7 mg, 36%).

MS (ESI) (M+1) m/z 483.3
$^1$H NMR (500 MHz, DMSO-$d_6$) δ ppm 1.35 (s, 1 H) 1.96 (s, 1 H) 2.05-2.12 (m, 2H) 2.89-2.96 (m, 1 H) 3.08-3.27 (m, 3 H) 3.44-3.57 (m, 1 H) 3.57-3.70 (m, 1 H) 3.74 (ddd, 1 H) 4.17 (d, 1 H) 4.35 (d, 1 H) 4.50 (d, 1 H) 4.72 (br. s., 1 H) 4.83-4.89 (m, 1 H) 6.60-6.68 (m, 1 H) 6.79-6.86 (m, 1 H) 7.04 (t, 1 H) 7.19-7.26 (m, 1 H) 7.49-7.53 (m, 1 H) 7.57-7.63 (m, 2 H) 7.81-7.89 (m, 2 H) 8.34-8.39 (m, 1 H)

Example 38

2-((6-Methyl-2-(4-(1-methyl-1H-pyrazol-4-yl)phenylamino)-5,6,7,8-tetrahydropyrido[4,3-d]pyrimidin-4-yl)(phenyl)amino)ethanol

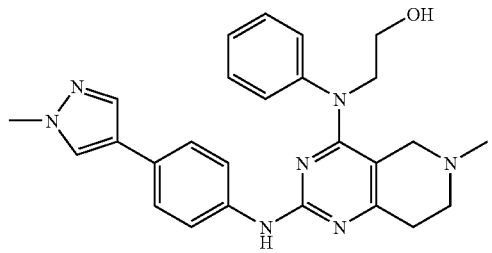

2-((2-(4-(1-Methyl-1H-pyrazol-4-yl)phenylamino)-5,6,7,8-tetrahydropyrido[4,3-d]pyrimidin-4-yl)(phenyl)amino)ethanol (40 mg, 0.09 mmol) was dissolved in methanol (2 mL). Acetic acid (1.037 µL, 0.02 mmol) was added followed by formaldehyde (0.014 mL, 0.18 mmol). The reaction mixture was stirred at room temperature for 30 minutes before sodium cyanoborohydride (11.39 mg, 0.18 mmol) was added. After 20 minutes the solvent was evaporated under reduced pressure, the crude dissolved in few drops of DMF and acetonitrile, filtered and purified by preparative HPLC yielding 2-((6-methyl-2-(4-(1-methyl-1H-pyrazol-4-yl)phenylamino)-5,6,7,8-tetrahydropyrido[4,3-d]pyrimidin-4-yl)(phenyl)amino)ethanol (9.8 mg, 21%) as acetic acid salt. MS (ESI) (M+H) m/z 456;
$^1$H NMR (500 MHz, Chloroform-d) δ ppm 2.05 (s, 3 H) 2.23 (br. s., 3 H) 2.70 (m, 4 H) 2.91 (br. s., 2 H) 3.74 (t, 2 H) 3.95 (s, 3 H) 4.17 (t, 2 H) 7.16-7.25 (m, 3 H) 7.36 (t, 2 H) 7.44 (d, 2 H) 7.57-7.62 (m, 3 H) 7.74 (s, 1 H)

Example 38a 2-((2-(4-(1-Methyl-1H-pyrazol-4-yl)phenylamino)-5,6,7,8-tetrahydropyrido[4,3-d]pyrimidin-4-yl)(phenyl)amino)ethanol

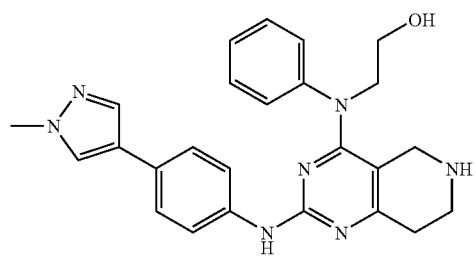

tert-Butyl 4-((2-hydroxyethyl)(phenyl)amino)-2-(4-(1-methyl-1H-pyrazol-4-yl)phenylamino)-7,8-dihydropyrido[4,3-d]pyrimidine-6(5H)-carboxylate (882 mg, 1.63 mmol) was dissolved in methanol (5 mL). Hydrochloric acid (0.136 mL, 1.63 mmol) was added and the reaction mixture was stirred at 70° C. for 1 h. The solvent was evaporated under reduced pressure and the crude was used in the next step without further purification.

MS (ESI) (M+H) m/z 442

Example 38b tert-Butyl 4-((2-hydroxyethyl)(phenyl)amino)-2-(4-(1-methyl-1H-pyrazol-4-yl)phenylamino)-7,8-dihydropyrido[4,3-d]pyrimidine-6(5H)-carboxylate

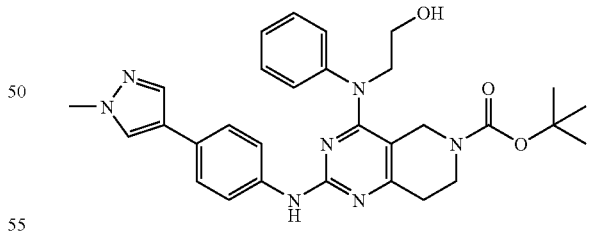

tert-Butyl 2-(4-(1-methyl-1H-pyrazol-4-yl)phenylamino)-4-(trifluoromethylsulfonyloxy)-7,8-dihydropyrido[4,3-d]pyrimidine-6(5H)-carboxylate (1 g, 1.80 mmol) and 2-(phenylamino)ethanol (0.228 mL, 1.80 mmol) in dimethylsulfoxide (3 mL) were charged in a thick wall glass, which was sealed and heated under microwave irradiation at 70° C. for 7 h. The solvent was evaporated together with toluene, the crude impregnated in silica gel and purified by flash chromatography (ISCO) using dichloromethane/methanol (0-10%) as eluent and the solvent evaporated under reduced pressure yielding tert-butyl 4-((2-hydroxyethyl)

(phenyl)amino)-2-(4-(1-methyl-1H-pyrazol-4-yl)phenylamino)-7,8-dihydropyrido[4,3-d]pyrimidine-6(5H)-carboxylate (0.882 g, 90%). MS (ESI) (M+H) m/z 542

Example 38c tert-Butyl 2-(4-(1-methyl-1H-pyrazol-4-yl)phenylamino)-4-(trifluoromethylsulfonyloxy)-7,8-dihydropyrido[4,3-d]pyrimidine-6(5H)-carboxylate

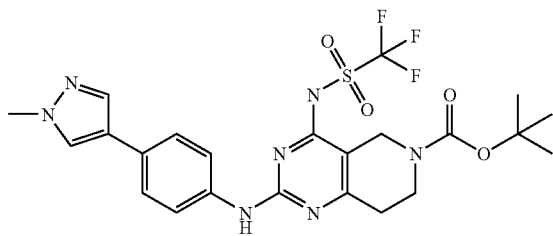

tert-Butyl 4-hydroxy-2-(4-(1-methyl-1H-pyrazol-4-yl)phenylamino)-7,8-dihydropyrido[4,3-d]pyrimidine-6(5H)-carboxylate (1 g, 2.37 mmol) was dissolved in dichloromethane (25 mL). 2,3,4,6,7,8,9,10-octahydropyrimido[1,2-a]azepine (0.360 g, 2.37 mmol) was added followed by 1,1,1-trifluoro-N-phenyl-N-(trifluoromethylsulfonyl)-methanesulfonamide (0.846 g, 2.37 mmol). Few crystals of 4-dimethylaminopyridine was added and the reaction mixture was stirred for 4 h. The solvent was evaporated under reduced pressure and the crude purified by flash chromatography (ISCO) using dichlorometane and methanol (0-10%) as eluent and the solvent was evaporated under reduced pressure yielding tert-butyl 2-(4-(1-methyl-1H-pyrazol-4-yl)phenylamino)-4-(trifluoromethylsulfonyloxy)-7,8-dihydropyrido[4,3-d]pyrimidine-6(5H)-carboxylate (1.020 g, 78%). MS (ESI) (M+H) m/z 555

Example 38d tert-Butyl 4-hydroxy-2-(4-(1-methyl-1H-pyrazol-4-yl)phenylamino)-7,8-dihydropyrido[4,3-d]pyrimidine-6(5H)-carboxylate

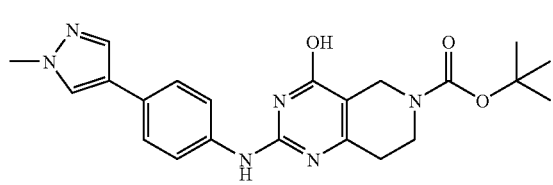

tert-Butyl 2-(4-bromophenylamino)-4-hydroxy-7,8-dihydropyrido[4,3-d]pyrimidine-6(5H)-carboxylate (1.4 g, 3.32 mmol), 1-methyl-4-(4,4,5,5-tetramethyl-1,3,2-dioxoborolan-2-yl)-1H pyrazole (0.691 g, 3.32 mmol), dichloro[1,1'-bis(di-tert-butylphosphino)ferrocene]palladium (II), Pd-118 (0.108 g, 0.17 mmol) and potassium carbonate (1.837 g, 13.29 mmol) in DMF (5 mL), water (2.5 mL) and ethanol (0.833 mL) were charged in a thick wall glass, which was sealed and heated at 110° C. for 20 minutes. The raction mixture was allowed to cool down, the crude was filtered through celite and the filtercake washed with ethanol. The solvent was evaporated under reduced pressure. The crude was used in the next step without further purification. MS (ESI) (M+1) m/z 423

Example 38e tert-Butyl 2-(4-bromophenylamino)-4-hydroxy-7,8-dihydropyrido[4,3-d]pyrimidine-6(5H)-carboxylate

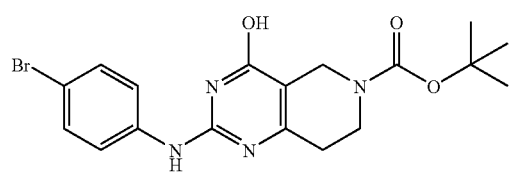

1-tert-Butyl 3-methyl 4-oxopiperidine-1,3-dicarboxylate (1 g, 3.89 mmol), 1-(4-bromophenyl)guanidine (0.832 g, 3.89 mmol) and sodium ethoxide (0.264 g, 3.89 mmol) in ethanol (8 mL) were heated to 100° C. in a microwave reactor for 15 minutes. The reaction mixture was allowed to reach room temperature, the solid obtained was filtered and washed with cold ethanol and dried in a vacuum oven yielding tert-butyl 2-(4-bromophenylamino)-4-hydroxy-7,8-dihydropyrido[4,3-d]pyrimidine-6(5H)-carboxylate (1.45 g, 72%). The compound was used in the next step without purification. MS (ESI) (M+H) m/z 423

Example 38f 1-(4-Bromophenyl)guanidine

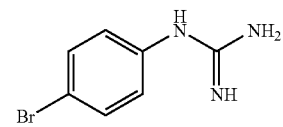

Hydrochloric acid (1.503 mL, 9.07 mmol) was added to 4-bromoaniline (2 g, 11.63 mmol) and carbodiimide (0.538 g, 12.79 mmol) in ethanol (10 mL) heated to reflux for 90 min. The solvent was removed under reduced pressure and potassium carbonate (0.964 g, 6.98 mmol) in water (10.00 mL) was added. Crystals were filtered off and washed with several portions of DCM to give the title compound (1.9 g, 60%).

MS (ES+) m/z 214 (M+H)+

Example 39

2-((2-(4-(1-Methyl-1H-pyrazol-4-yl)phenylamino)-6-propyl-5,6,7,8-tetrahydropyrido[4,3-d]pyrimidin-4-yl)(phenyl)amino)ethanol

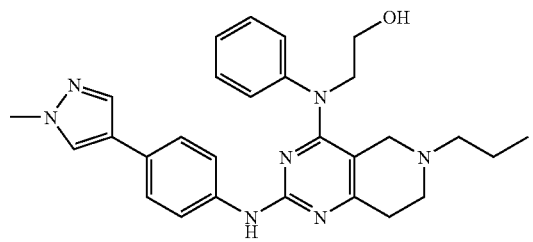

2-((2-(4-(1-Methyl-1H-pyrazol-4-yl)phenylamino)-5,6,7,8-tetrahydropyrido[4,3-d]pyrimidin-4-yl)(phenyl)amino)ethanol (40 mg, 0.09 mmol, Example 38a) was dissolved in methanol (2 mL). Acetic acid (1.037 µL, 0.02 mmol) was added followed by propionaldehyde (0.013 mL, 0.18 mmol). The reaction mixture was stirred for 30 minutes at room temperature before sodium cyanoborohydride (11.39 mg, 0.18 mmol) was added. The solvent was evaporated under reduced pressure, the crude dissolved in few drops of dimethylformamide and acetonitrile, filtered and purified by preparative HPLC yielding 2-((2-(4-(1-methyl-1H-pyrazol-4-yl)phenylamino)-6-propyl-5,6,7,8-tetrahydropyrido[4,3-d]pyrimidin-4-yl)(phenyl)amino)ethanol (7.6 mg, 15.4%) as acetic acid salt.

MS (ESI) (M+1) m/z 484

$^1$H NMR (500 MHz, chloroform-d) δ ppm 0.82 (t, 3 H) 1.30-1.40 (m, 2 H) 2.02 (s, 3 H) 2.21-2.28 (m, 2 H) 2.68 (s, 2 H) 2.72 (t, 2 H) 2.87 (t, 2 H) 3.75 (t, 2 H) 3.95 (s, 3 H) 4.17 (t, 2 H) 7.18-7.25 (m, 3 H) 7.37 (t, 2 H) 7.43 (d, 2 H) 7.57-7.61 (m, 3 H) 7.74 (s, 1 H) 8.13 (br. s., 1 H)

Example 41

2-(4-Benzyl-2-(4-(2-methyl-1H-imidazol-1-yl)phenylamino)-7,8-dihydropyrido[4,3-d]pyrimidin-6(5H)-yl)ethanol

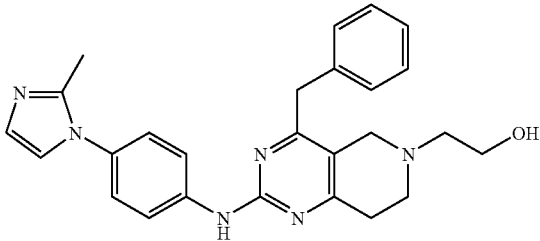

4-Benzyl-N-(4-(2-methyl-1H-imidazol-1-yl)phenyl)-5,6,7,8-tetrahydropyrido[4,3-d]pyrimidin-2-amine (75 mg, 0.19 mmol) was dissolved in methanol (2 mL). Acetic acid (10.83 µL, 0.19 mmol) was added followed by glycoaldehyde (11.36 mg, 0.19 mmol) and sodium cyanoborohydride (11.89 mg, 0.19 mmol). The reaction mixture was stirred at room temperature for 1 h and the solvent was evaporated under reduced pressure. The crude was dissolved in methanol, filtered and purified by preparative HPLC yielding 2-(4-benzyl-2-(4-(2-methyl-1H-imidazol-1-yl)phenylamino)-7,8-dihydropyrido[4,3-d]pyrimidin-6(5H)-yl)ethanol (18.10 mg, 19.7%). MS (ES+) (M+H)+=441.3

$^1$H NMR (400 MHz, chloroform-d) δ ppm 2.36 (s, 3 H) 2.72-2.80 (m, 2 H) 2.89 (dd, 4 H) 3.61 (s, 2 H) 3.68-3.75 (m, 2 H) 3.98 (s, 2 H) 6.98 (d, 1 H) 7.04 (d, 1 H) 7.14 (m, 2 H) 7.23-7.27 (m, 2 H) 7.27-7.31 (m, 1 H) 7.31-7.38 (m, 2 H) 7.67 (m, 2 H) 7.90 (s, 1 H)

Example 41a

4-Benzyl-N-(4-(2-methyl-1H-imidazol-1-yl)phenyl)-5,6,7,8-tetrahydropyrido[4,3-d]pyrimidin-2-amine

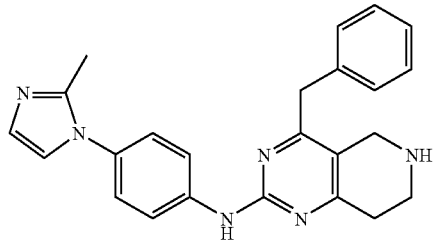

tert-Butyl 4-benzyl-2-(4-(2-methyl-1H-imidazol-1-yl)phenylamino)-7,8-dihydropyrido[4,3-d]pyrimidine-6(5H)-carboxylate (270 mg, 0.54 mmol) was dissolved in methanol (3 mL). Hydrochloric acid (0.017 mL, 0.54 mmol) was added and the reaction mixture was stirred at 75° C. for 1 h. The solvent was evaporated under reduced pressure yielding 4-benzyl-N-(4-(2-methyl-1H-imidazol-1-yl)phenyl)-5,6,7,8-tetrahydropyrido[4,3-d]pyrimidin-2-amine (150 mg, 69.6%) which was used in the subsequent step as such.

MS m/z (ES+), (M+H)+=397.2

$^1$H NMR (400 MHz, chloroform-d) δ ppm 2.34 (s, 3 H) 2.81 (t, 2 H) 3.16 (t, 2 H) 3.91 (s, 2H) 3.94 (s, 2 H) 6.98 (dd, 3 H) 7.12 (d, 2 H) 7.21-7.26 (m, 3 H) 7.28-7.34 (m, 2 H)

Example 41b tert-Butyl 4-benzyl-2-(4-(2-methyl-1H-imidazol-1-yl)phenylamino)-7,8-dihydropyrido[4,3-d]pyrimidine-6(5H)-carboxylate

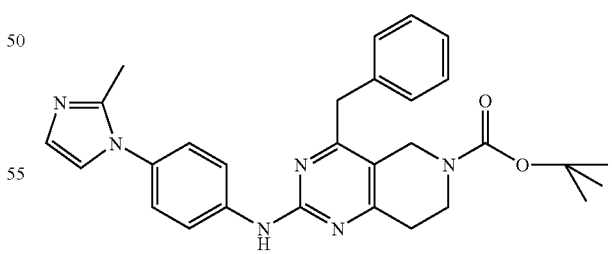

1-(4-(2-Methyl-1H-imidazol-1-yl)phenyl)guanidine (224 mg, 1.04 mmol), tert-butyl 4-oxo-3-(2-phenylacetyl)piperidine-1-carboxylate (330 mg, 1.04 mmol) and sodium ethoxide (70.8 mg, 1.04 mmol) in ethanol (5 mL) were heated to 110° C. in a microwave reactor for 1 h 20 min. The reaction was allowed to reach room temperature and the solvent was evaporated under reduced pressure. The crude was dissolved in ethyl acetate and washed with water. The organic phase was dried under MgSO₄ and the solvent evaporated under reduced pressure yielding tert-butyl 4-benzyl-2-(4-(2-methyl-1H-imidazol-1-yl)phenylamino)-7,8-dihydropyrido[4,3-d]pyrimidine-6(5H)-carboxylate (280 mg, 54.2%) which was used in the subsequent step as such.

MS m/z (ES+) 497 (M+H)+

Example 41c 1-(4-(2-Methyl-1H-imidazol-1-yl)phenyl)guanidine

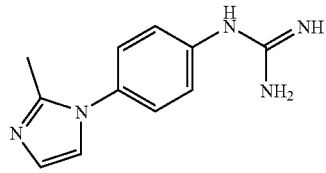

4-(2-Methylimidazol-1-yl)phenylamine (10 g, 57.73 mmol) was dissolved in ethanol (100 mL). Nitric acid (3.96 mL, 57.73 mmol) was carefully added followed by cyanamide (2.427 g, 57.73 mmol). The reaction mixture was heated to reflux overnight. Extra cyanamide (1.942 g, 46.19 mmol) and nitric acid (2.98 mL, 46.19 mmol) were added and then the reaction mixture was refluxed for 16 hours. The reaction mixture was allowed to reach room temperature and ethyl ether (100 mL) was added. The mixture was refrigerated for 2 h and the solid obtained was filtered off and washed with ethyl ether yielding 1-(4-(2-methyl-1H-imidazol-1-yl)phenyl)guanidine (9.40 g, 76%).

MS m/z (ES+) 216 (M+H)+
¹ H NMR (500 MHz, DMSO-d₆) δ ppm 2.53 (s, 3 H) 7.49 (m, 2 H) 7.60 (s, 4 H) 7.68 (m, 2H) 7.81 (dd, 2 H) 9.90 (s, 1 H)

Example 41d tert-Butyl 4-oxo-3-(2-phenylacetyl)piperidine-1-carboxylate

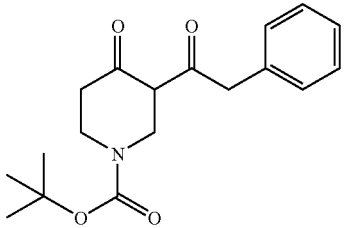

tert-Butyl 4-morpholino-5,6-dihydropyridine-1(2H)-carboxylate (6.7 g, 24.97 mmol) was dissolved in dioxane (60 mL) under an atmosphere of argon. 2-Phenylacetyl chloride (3.64 mL, 27.46 mmol) was added dropwise and the reaction mixture was refluxed overnight.

The reaction was allowed to reach room temperature and the solid was filtered off. The filtrated was concentrated under reduced pressure and purified by flash chromatography using dichlorometane and methanol as eluent, yielding tert-butyl 4-oxo-3-(2-phenylacetyl)piperidine-1-carboxylate (0.510 g, 6.44%).

MS m/z (ES−) 316 (M−H)−

¹H NMR (400 MHz, chloroform-d) δ ppm 3.57 (t, 2 H) 3.72 (br. s., 2 H) 3.86-3.90 (m, 1H) 4.39 (s, 1 H) 4.47-4.53 (m, 1 H) 7.25 (s, 1 H) 7.28-7.37 (m, 5 H)

Example 41e tert-Butyl 4-morpholino-5,6-dihydropyridine-1(2H)-carboxylate

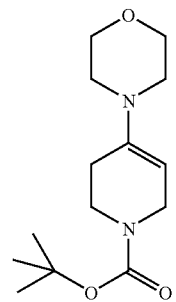

tert-Butyl 4-oxopiperidine-1-carboxylate (5 g, 25.09 mmol) was dissolved in toluene (25 mL). Morpholine (2.186 mL, 25.09 mmol) was added and the reaction mixture was heated overnight in a atmosphere of argon in a Dean-Stark reflux apparatus. The mixture was allowed to reach room temperature and it was evaporated to dryness yielding tert-butyl 4-morpholino-5,6-dihydropyridine-1(2H)-carboxylate (6.70 g, 99%).

¹H NMR (400 MHz, chloroform-d) δ ppm 1.46 (s, 9 H) 2.16 (br. s., 2 H) 2.77-2.82 (m, 4 H) 3.54 (t, 2 H) 3.72-3.77 (m, 4 H) 3.94 (br. s., 2 H) 4.56 (br. s., 1 H)

Example 42

4-Benzyl-6-methyl-N-(4-(2-methyl-1H-imidazol-1-yl)phenyl)-5,6,7,8-tetrahydropyrido[4,3-d]pyrimidin-2-amine

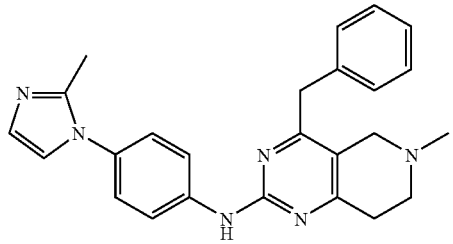

4-benzyl-N-(4-(2-methyl-1H-imidazol-1-yl)phenyl)-5,6,7,8-tetrahydropyrido[4,3-d]pyrimidin-2-amine (75 mg, 0.19 mmol, Example 41a) was dissolved in methanol (2 mL). Acetic acid (10.83 μL, 0.19 mmol) was added followed by formaldehyde (0.014 mL, 0.19 mmol). The reaction mixture was stirred at room temperature for 15 minutes and MP-CNBH₃ was added. The reaction was stirred for 1 h, the MP-CNBH₃ was filtered off and the solvent was evaporated under reduced pressure. The crude was dissolved in methanol, filtered and purified by preparative HPLC yielding 4-benzyl-6-methyl-N-(4-(2-methyl-1H-imidazol-1-yl)phenyl)-5,6,7,8-tetrahydropyrido[4,3-d]pyrimidin-2-amine (23.00 mg, 27%).

MS m/z (ES+) 411 (M+H)+

¹H NMR (400 MHz, chloroform-d) δ ppm 2.36 (s, 3 H) 2.50 (s, 3 H) 2.72-2.81 (m, 2 H) 2.92 (t, 2 H) 3.51 (s, 2 H) 3.98 (s, 2 H) 6.97 (d, 1 H) 7.04 (d, 1 H) 7.09-7.17 (m, 2 H) 7.23-7.30 (m, 3 H) 7.30-7.38 (m, 2 H) 7.61-7.70 (m, 2 H) 7.99 (s, 1 H)

Example 43

4-Benzyl-N-(3-methoxy-4-(4-methyl-1H-imidazol-1-yl)phenyl)-7,8-dihydro-5H-pyrano[4,3-d]pyrimidin-2-amine

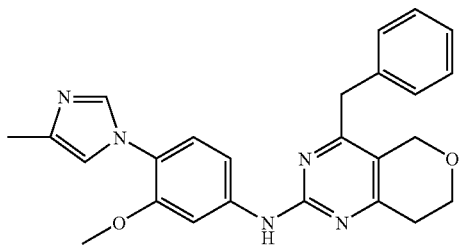

4-Benzyl-N-(3-methoxy-4-(4-methyl-1H-imidazol-1-yl)phenyl)-7,8-dihydro-5H-pyrano[4,3-d]pyrimidin-2-amine (16.00 mg, 3.7%) was obtained from 3-(2-phenylacetyl)dihydro-2H-pyran-4(3H)-one and 1-(3-methoxy-4-(4-methyl-1H-imidazol-1-yl)phenyl)guanidine by the general procedure for pyrimidine preparation.

MS (ES+) m/z 428.2 (M+H)+

1H NMR (500 MHz, CHLOROFORM-d) δ ppm 2.10 (s, 2 H) 2.30 (s, 3 H) 2.86 (t, 2 H) 3.77 (s, 3 H) 3.91 (s, 2 H) 4.00 (t, 2 H) 4.66 (s, 2 H) 6.86 (s, 1 H) 7.05-7.08 (m, 1 H) 7.11-7.14 (m, 1 H) 7.22-7.26 (m, 2 H) 7.32 (t, 2 H) 7.66 (s, 1 H) 7.74 (s, 1 H) 7.77 (d, 1 H)

Example 43a 1-(3-Methoxy-4-(4-methyl-1H-imidazol-1-yl)phenyl)guanidine

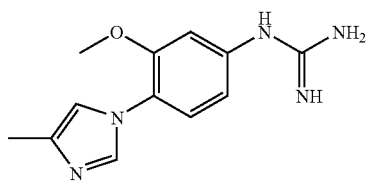

3-Methoxy-4-(4-methyl-1H-imidazol-1-yl)aniline hydrochloride (3 g, 12.52 mmol), cyanamide (0.684 g, 16.27 mmol) and hydrochloric acid (1.564 mL, 18.77 mmol) in ethanol (20 mL) were heated to reflux o.n. The reaction mixture was concentrated under reduced pressure before the residue was poured on potassium carbonate (1.730 g, 12.52 mmol) in water (60 mL) and then put in refrigerator o.n. The formed carbonate-salt was filtered off, and dried in vacuum oven o.n. The solid was washed with several portions of DCM, dried and used as such in next step (52.3%). MS (ES+) m/z 246.2 (M+H)+

Example 43b 3-(2-Phenylacetyl)dihydro-2H-pyran-4(3H)-one

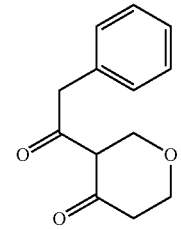

3-(2-Phenylacetyl)dihydro-2H-pyran-4(3H)-one (0.538 g, 49.4%) was synthesised from tetrahydro-4H-pyran-4-one (0.923 mL, 9.99 mmol) and phenylacetyl chloride (0.660 mL, 4.99 mmol) by the general procedure for the preparation of ketones.

MS (ES+) m/z 219.2 (M+H)+

Example 44

4-(4-Fluorobenzyl)-N-[3-methoxy-4-(4-methyl-1H-imidazol-1-yl)phenyl]-7,8-dihydro-5H-thiopyrano[4,3-d]pyrimidin-2-amine 6-oxide

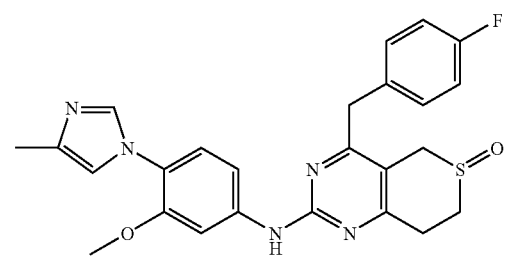

4-(4-Fluorobenzyl)-N-(3-methoxy-4-(4-methyl-1H-imidazol-1-yl)phenyl)-7,8-dihydro-5H-thiopyrano[4,3-d]pyrimidin-2-amine (254 mg, 0.55 mmol) and meta-chloroperbenzoic acid (95 mg, 0.55 mmol) was slurrified in DCM (4 mL). Saturated NaHCO₃ and water were added to the reaction mixture, the organic phase was separated and the solvent was evaporated. The crude product was purified on preparative HPLC yielding 4-(4-fluorobenzyl)-N-[3-methoxy-4-(4-methyl-1H-imidazol-1-yl)phenyl]-7,8-dihydro-5H-thiopyrano[4,3-d]pyrimidin-2-amine 6-oxide (49.0 mg, 18%).

MS (ES+) m/z 478.1 (M+H)+

Mixture of rotamers:

1H NMR (500 MHz, CHLOROFORM-d) δ ppm 2.31 (s) 2.92-3.00 (m) 3.06 (dt) 3.24-3.31 (m) 3.56 (ddd) 3.71 (d) 3.82 (s) 3.91 (dd) 4.03 (s) 6.88 (s) 7.02 (t) 7.08 (dd) 7.14-7.17 (m) 7.19 (dd) 7.36 (s) 7.66 (s) 7.69 (d)

Total no of protons in spectrum: 24

Ratio major:minor: 1:1

Example 44a 4-(4-Fluorobenzyl)-N-(3-methoxy-4-(4-methyl-1H-imidazol-1-yl)phenyl)-7,8-dihydro-5H-thiopyrano[4,3-d]pyrimidin-2-mine

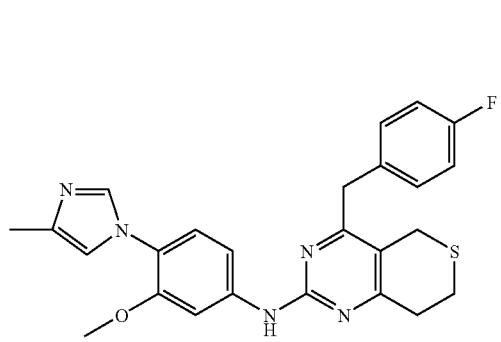

3-(2-(4-Fluorophenyl)acetyl)dihydro-2H-thiopyran-4(3H)-one (200 mg, 0.79 mmol), 1-(3-methoxy-4-(4-methyl-1H-imidazol-1-yl)phenyl)guanidine (194 mg, 0.79 mmol) and potassium carbonate (200 mg, 1.45 mmol) was slurrified in EtOH (5 mL) and heated to 60° C. for 16 h. DCM and water were added to the cooled reaction mixture. The organic phase was separated and dried with $Mg_2SO_4$ and then the solvent was evaporated. The crude product was used as such in next step. MS (ES+) m/z 462.2 (M+H)+

Example 44b 3-(2-(4-Fluorophenyl)acetyl)dihydro-2H-thiopyran-4(3H)-one

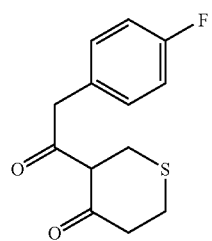

3-(2-(4-Fluorophenyl)acetyl)dihydro-2H-thiopyran-4(3H)-one (508 mg, 78%) was obtained from tetrahydrothiopyran-4-one and 4-fluorophenylacetyl chloride by the general procedure for the preparation of diketones. MS (ES+) m/z 253.1 (M+H)+

Example 45

4-Benzyl-N-(4-(2-methyl-1H-imidazol-1-yl)phenyl)-7,8-dihydro-5H-pyrano[4,3-d]pyrimidin-2-amine

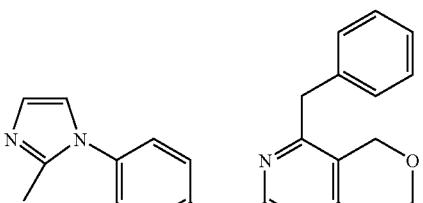

4-Benzyl-N-(4-(2-methyl-1H-imidazol-1-yl)phenyl)-7,8-dihydro-5H-pyrano[4,3-d]pyrimidin-2-amine (42.0 mg, 11.5%) was obtained from 1-(4-(2-methyl-1H-imidazol-1-yl)phenyl)guanidine and 3-(2-phenylacetyl)dihydro-2H-pyran-4(3H)-one by general procedure for the preparation of pyrimidines. The crude product was purified by preparative HPLC twice. Purification using ammoniumacetate buffer was followed by purification using a 0.1% TFA. MS (ES+) m/z 398.1 (M+H)+

1H NMR (500 MHz, CHLOROFORM-d) δ ppm 2.66 (s, 3 H) 3.07 (t, 2 H) 4.02-4.05 (m, 2 H) 4.05 (s, 2 H) 4.73 (s, 2 H) 7.14 (s, 1 H) 7.21 (d, 2 H) 7.25 (d, 2 H) 7.35-7.42 (m, 3H) 7.43 (s, 1 H) 7.83 (d, 2 H) 11.78 (br. s., 1 H)

EXAMPLE 45a 3-(2-Phenylacetyl)dihydro-2H-pyran-4(3H)-one

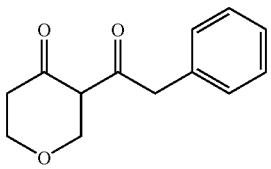

3-(2-Phenylacetyl)dihydro-2H-pyran-4(3H)-one (0.855 g, 61%) was obtained from tetrahydro-4H-pyran-4-one and phenylacetyl chloride using the general procedure for the preparation of diketones. MS (ES+) m/z 219.1 (M+H)+

Example 46

N-(4-(2-Methyl-1H-imidazol-1-yl)phenyl)-4-((tetrahydro-2H-pyran-4-yl)methyl)-7,8-dihydro-5H-thiopyrano[4,3-d]pyrimidin-2-amine

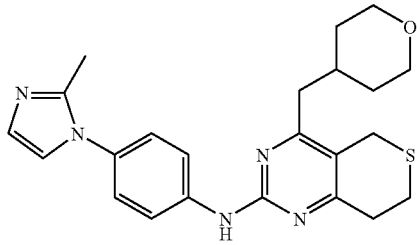

N-(4-(2-Methyl-1H-imidazol-1-yl)phenyl)-4-((tetrahydro-2H-pyran-4-yl)methyl)-7,8-dihydro-5H-thiopyrano[4,3-d]pyrimidin-2-amine was synthesised from 3-(2-(tetrahydro-2H-pyran-4-yl)acetyl)dihydro-2H-thiopyran-4(3H)-one according to the general procedure for the preparation of pyrimidines. MS (ES+) m/z 422.1 (M+H)+

1H NMR (400 MHz, CHLOROFORM-d) δ ppm 1.41-1.53 (m, 2 H) 1.68 (dd, 2 H) 2.18 (ddd, 1 H) 2.39 (s, 3 H) 2.65 (d, 2 H) 2.97 (t, 2 H) 3.12 (t, 2 H) 3.42 (td, 2 H) 3.72 (s, 2 H) 4.00 (dd, 2 H) 7.04 (d, 2 H) 7.25 (m, 2 H) 7.59 (s, 1 H) 7.81 (m, 2 H)

Example 46a

3-(2-(Tetrahydro-2H-pyran-4-yl)acetyl)dihydro-2H-thiopyran-4(3H)-one

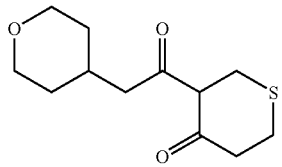

3-(2-(Tetrahydro-2H-pyran-4-yl)acetyl)dihydro-2H-thiopyran-4(3H)-one (0.300 g, 83%) was synthesised according to the general procedure for diketone synthesis.

Example 47

2-(4-(2-Cyclohexylethyl)-2-(4-(2-methyl-1H-imidazol-1-yl)phenylamino)-7,8-dihydropyrido[4,3-d]pyrimidin-6(5H)-yl)ethanol

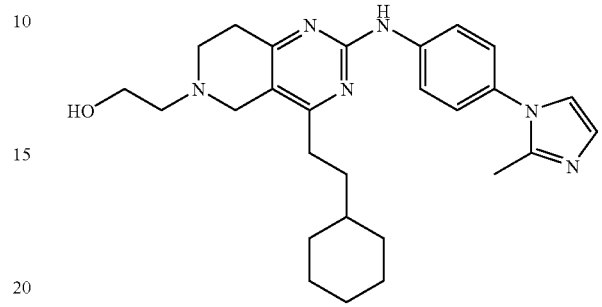

2-(4-(2-Cyclohexylethyl)-2-(4-(2-methyl-1H-imidazol-1-yl)phenylamino)-7,8-dihydropyrido[4,3-d]pyrimidin-6(5H)-yl)ethanol was synthesised from 4-(2-cyclohexylethyl)-N-(4-(2-methyl-1H-imidazol-1-yl)phenyl)-5,6,7,8-tetrahydropyrido[4,3-d]pyrimidin-2-amine (example 47a) and glycol aldehyde according to the general procedure for reductive amination.

1H NMR (500 MHz, DMSO-$d_6$) δ ppm 0.87-1.0 (m, 2 H) 1.10-1.27 (m, 4 H) 1.32 (m, 1 H) 1.53-1.65 (m, 2 H) 1.65-1.73 (m, 2 H) 1.73-1.82 (m, 2H) 2.25 (s, 3 H) 2.55-2.60 (m, 2 H) 2.62 (t, 2 H) 2.77 (m, 4 H) 3.53 (s, 2 H) 3.60 (q, 2 H) 4.49 (t, 1 H) 6.87 (d, 1 H) 7.20 (d, 1 H) 7.28 (m, 2 H) 7.93 (m, 2 H) 9.58 (s, 1 H)

Example 47a

4-(2-Cyclohexylethyl)-N-(4-(2-methyl-1H-imidazol-1-yl)phenyl)-5,6,7,8-tetrahydropyrido[4,3-d]pyrimidin-2-amine

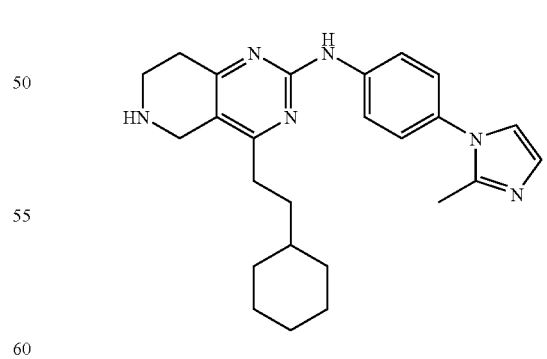

4-(2-Cyclohexylethyl)-N-(4-(2-methyl-1H-imidazol-1-yl)phenyl)-5,6,7,8-tetrahydropyrido[4,3-d]pyrimidin-2-amine (655 mg, 99%) was prepared according to the general procedure for boc deprotection of amines MS (ES+) m/z 417.3 (M+H)+

Example 47b tert-Butyl 4-(2-cyclohexylethyl)-2-(4-(2-methyl-1H-imidazol-1-yl)phenylamino)-7,8-dihydropyrido[4,3-d]pyrimidine-6(5H)-carboxylate

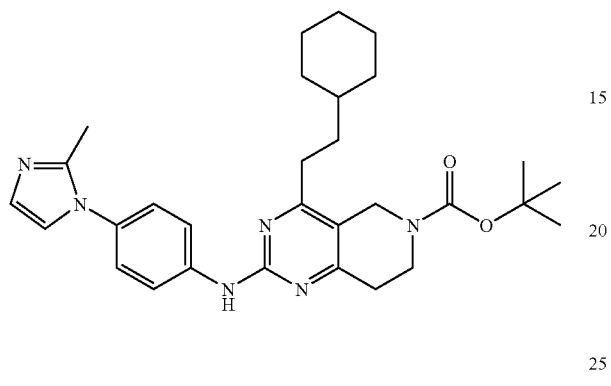

tert-Butyl 4-(2-cyclohexyl ethyl)-2-(4-(2-methyl-1H-imidazol-1-yl)phenylamino)-7,8-dihydropyrido[4,3-d]pyrimidine-6(5H)-carboxylate (393 mg, 45%) was synthesised from tert-Butyl 3-(3-cyclohexylpropanoyl)-4-oxopiperidine-1-carboxylate and 1-(4-(2-methyl-1H-imidazol-1-yl)phenyl)guanidine (Example 41c) according to the general procedure for the synthesis of pyrimidines. MS (ES+) m/z 517.1 (M+H)+

Example 47c tert-Butyl 3-(3-cyclohexylpropanoyl)-4-oxopiperidine-1-carboxylate

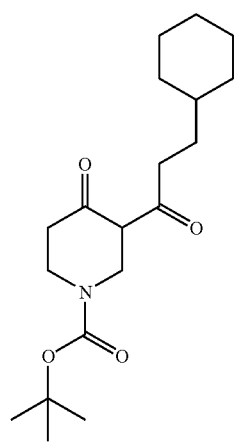

tert-Butyl 3-(3-cyclohexylpropanoyl)-4-oxopiperidine-1-carboxylate (570 mg, 99%) was synthesised from tert-butyl 4-oxopiperidine-1-carboxylate and 2-(3-methoxy-phenyl)acetyl chloride according to the general procedure for the preparation of diketones. MS (ES−) m/z 337 (M−H)−

Example 48

2-(2-(4-(2-Methyl-1H-imidazol-1-yl)phenylamino)-4-(4-methylbenzyl)-7,8-dihydropyrido[4,3-d]pyrimidin-6(5H)-yl)ethanol

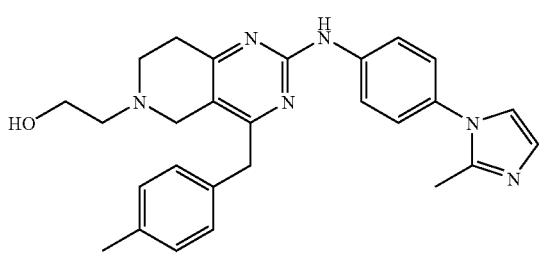

2-(2-(4-(2-Methyl-1H-imidazol-1-yl)phenylamino)-4-(4-methylbenzyl)-7,8-dihydropyrido[4,3-d]pyrimidin-6(5H)-yl)ethanol was synthesised according to the general procedure for reductive amination.

1H NMR (500 MHz, DMSO-$d_6$) d ppm 2.25 (s, 3 H) 2.27 (s, 3 H) 2.58 (t, 2 H) 2.75 (dd, 4 H) 3.53 (s, 2 H) 3.57 (q, 2 H) 3.91 (s, 2 H) 4.47 (t, 1 H) 6.87 (d, 1 H) 7.15 (m, 4 H) 7.18-7.24 (m, 3 H) 7.83 (d, 2 H) 9.64 (s, 1 H)

Example 48a

N-(4-(2-Methyl-1H-imidazol-1-yl)phenyl)-4-(4-methylbenzyl)-5,6,7,8-tetrahydropyrido[4,3-d]pyrimidin-2-amine

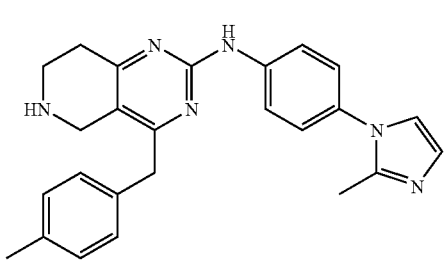

4-(2-Cyclohexylethyl)-N-(4-(2-methyl-1H-imidazol-1-yl)phenyl)-5,6,7,8-tetrahydropyrido[4,3-d]pyrimidin-2-amine was synthesised according to the general procedure for boc deprotection of amines.

Example 48b tert-Butyl 2-(4-(2-methyl-1H-imidazol-1-yl)phenylamino)-4-(4-methylbenzyl)-7,8-dihydropyrido[4,3-d]pyrimidine-6(5H)-carboxylate

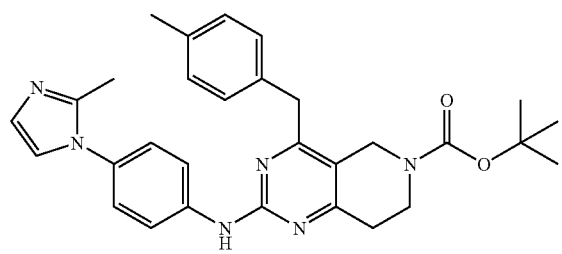

tert-Butyl 2-(4-(2-methyl-1H-imidazol-1-yl)phenylamino)-4-(4-methylbenzyl)-7,8-dihydropyrido[4,3-d]pyrimidine-6(5H)-carboxylate (236 mg, 44%) was synthesised from tert-butyl 4-oxo-3-(2-p-tolylacetyl)piperidine-1-carboxylate and 1-(4-(2-methyl-1H-imidazol-1-yl)phenyl)guanidine (Example 41c) according to the general procedure for synthesis of pyrimidines. MS (ES+) m/z 511.1 (M+H)+

Example 48c tert-Butyl 4-oxo-3-(2-p-tolylacetyl)piperidine-1-carboxylate

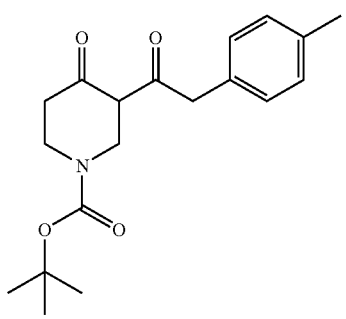

tert-Butyl 4-oxo-3-(2-p-tolylacetyl)piperidine-1-carboxylate was synthesised from tert-butyl 4-oxopiperidine-1-carboxylate and 2-p-tolylacetyl chlorides according to the general procedure for the preparation of diketones.

Example 49

2-(4-(3-Fluorophenethyl)-2-(4-(2-methyl-1H-imidazol-1-yl)phenylamino)-7,8-dihydropyrido[4,3-d]pyrimidin-6(5H)-yl)ethanol

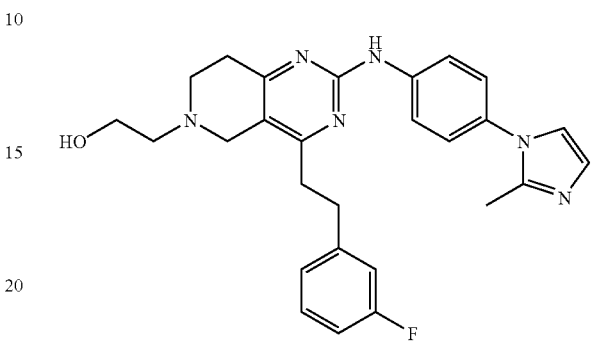

2-(4-(3-Fluorophenethyl)-2-(4-(2-methyl-1H-imidazol-1-yl)phenylamino)-7,8-dihydropyrido[4,3-d]pyrimidin-6(5H)-yl)ethanol was synthesised according to the general procedure for reductive amination.

1H NMR (500 MHz, DMSO-$d_6$) d ppm 2.26 (s, 3 H) 2.60 (t, 2 H) 2.71-2.80 (m, 4 H) 2.89 (t, 2 H) 3.07 (t, 2 H) 3.49 (s, 2 H) 3.59 (q, 2 H) 4.47 (t, 1 H) 6.87 (s, 1 H) 7.08-7.16 (m, 2 H) 7.20 (s, 1 H) 7.27-7.35 (m, 3 H) 7.90 (d, 2 H) 9.62 (s, 1 H)

Example 49a 4-(3-Fluorophenethyl)-N-(4-(2-methyl-1H-imidazol-1-yl)phenyl)-5,6,7,8-tetrahydropyrido[4,3-d]pyrimidin-2-amine

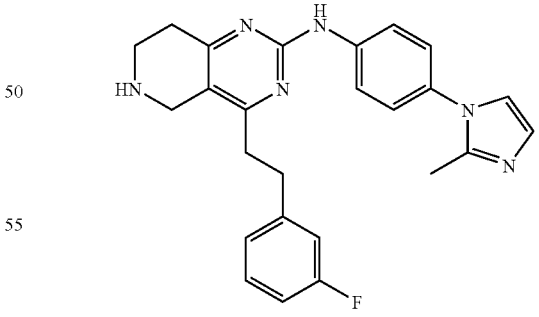

tert-Butyl 4-(3-fluorophenethyl)-2-(4-(2-methyl-1H-imidazol-1-yl)phenylamino)-7,8-dihydropyrido[4,3-d]pyrimidine-6(5H)-carboxylate (295 mg, 55%) was deprotected according to the general procedure for boc deprotection of amines. MS (ES+) m/z 429.3 (M+H)+

Example 49b nylamino)-7,8-dihydropyrido[4,3-d]pyrimidine-6(5H)-carboxylate

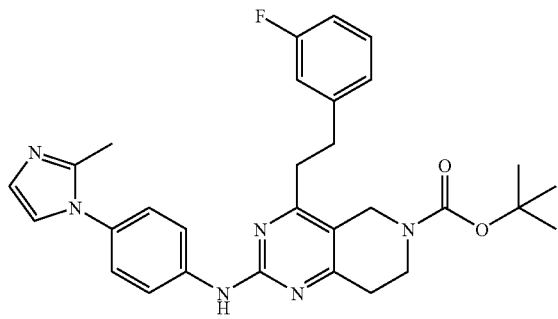

tert-Butyl 4-(3-fluorophenethyl)-2-(4-(2-methyl-1H-imidazol-1-yl)phenylamino)-7,8-dihydropyrido[4,3-d]pyrimidine-6(5H)-carboxylate (430 mg, 67%) was synthesised according to the general procedure for synthesis of pyrimidines. MS (ES+) m/z 528.0 (M+H)+

Example 49c tert-Butyl 3-(3-(3-fluorophenyl)propanoyl)-4-oxopiperidine-1-carboxylate

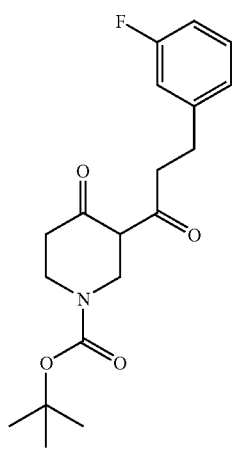

tert-Butyl 3-(3-(3-fluorophenyl)propanoyl)-4-oxopiperidine-1-carboxylate (285 mg, 48%) was synthesised from tert-butyl 4-oxopiperidine-1-carboxylate and 3-(3-fluorophenyl)propanoyl chloride according to the general procedure for the preparation of diketones. MS (ES+) m/z 250 (M+H)+

Example 50

6-Methyl-N-(4-(2-methyl-1H-imidazol-1-yl)phenyl)-4-(4-methylbenzyl)-5,6,7,8-tetrahydropyrido[4,3-d]pyrimidin-2-amine

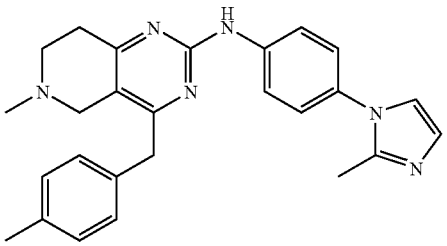

6-Methyl-N-(4-(2-methyl-1H-imidazol-1-yl)phenyl)-4-(4-methylbenzyl)-5,6,7,8-tetrahydropyrido[4,3-d]pyrimidin-2-amine (3.5 mg, 3.5%, Example 48a) was synthesised according to the general procedure for reductive amination. MS (ES+) m/z 425.3 (M+H)+

1H NMR (500 MHz, DMSO-d$_6$) δ ppm 2.25 (s, 3 H) 2.27 (s, 3 H) 2.36 (s, 3 H) 2.60-2.68 (m, 2 H) 2.75-2.82 (m, 2 H) 3.42 (s, 2 H) 3.91 (s, 2 H) 6.87 (s, 1 H) 7.11-7.18 (m, 4 H) 7.18-7.26 (m, 3 H) 7.83 (d, 2 H) 9.65 (s, 1 H)

Example 51

4-(3-Fluorophenethyl)-6-methyl-N-(4-(2-methyl-1H-imidazol-1-yl)phenyl)-5,6,7,8-tetrahydropyrido[4,3-d]pyrimidin-2-amine 4-(3-Fluorophenethyl)-6-methyl-N-(4-(2-methyl-1H-imidazol-1-yl)phenyl)-5,6,7,8-tetrahydropyrido[4,3-d]pyrimidin-2-amine (5.92 mg, 4.7%, Example 49a) was synthesised from 4-(3-fluorophenethyl)-N-(4-(2-methyl-1H-imidazol-1-yl)phenyl)-5,6,7,8-tetrahydropyrido[4,3-d]pyrimidin-2-amine and formaldehyde according to the general procedure for reductive amination. MS (ES+) m/z 443.3 (M+H)+

1H NMR (500 MHz, DMSO-d$_6$) d ppm 2.26 (s, 3 H) 2.37 (s, 3 H) 2.60-2.67 (m, 2 H) 2.75-2.81 (m, 2 H) 2.89 (t, 2 H) 3.07 (t, 2 H) 3.40 (s, 2 H) 6.87 (d, 1 H) 7.02 (d, 1 H), 7.08-7.15 (m, 2 H) 7.20 (d, 1 H) 7.27-7.35 (m, 3 H) 7.90 (d, 2 H) 9.63 (s, 1 H)

Example 52

4-(2-Fluorobenzyl)-6-methyl-N-(4-(2-methyl-1H-imidazol-1-yl)phenyl)-5,6,7,8-tetrahydropyrido[4,3-d]pyrimidin-2-ame

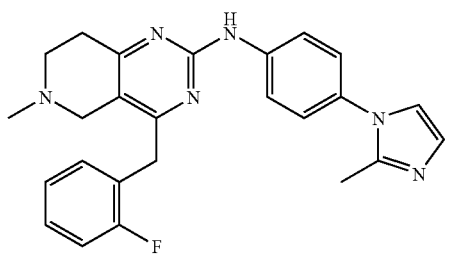

4-(2-Fluorobenzyl)-6-methyl-N-(4-(2-methyl-1H-imidazol-1-yl)phenyl)-5,6,7,8-tetrahydropyrido[4,3-d]pyrimidin-2-amine (3.8 mg, 4%) was synthesised from 4-(2-fluorobenzyl)-N-(4-(2-methyl-1H-imidazol-1-yl)phenyl)-5,6,7,8-tetrahydropyrido[4,3-d]pyrimidin-2-amine and formaldehyde according to the general procedure for reductive amination. MS (ES+) m/z 429.3 (M+H)+

1H NMR (500 MHz, DMSO-$d_6$) δ ppm 2.22 (s, 3 H) 2.41 (s, 3 H) 2.68 (t, 2 H) 2.80 (t, 2 H) 3.50 (s, 2 H) 4.01 (s, 2 H) 6.86 (s, 1 H) 7.08 (m, 2 H) 7.16 (d, 1 H) 7.18-7.26 (m, 2 H) 7.29-7.40 (m, 2 H) 7.60 (m, 2 H) 9.60 (s, 1 H)

Example 52a 4-(2-Fluorobenzyl)-N-(4-(2-methyl-1H-imidazol-1-yl)phenyl)-5,6,7,8-tetrahydropyrido[4,3-d]pyrimidin-2-amine

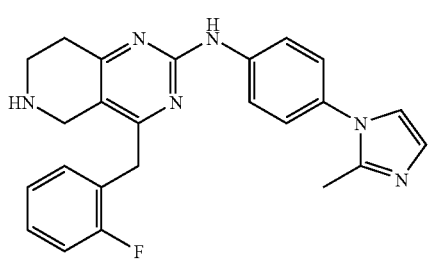

tert-Butyl 4-(2-fluorobenzyl)-2-(4-(2-methyl-1H-imidazol-1-yl)phenylamino)-7,8-dihydropyrido[4,3-d]pyrimidine-6(5H)-carboxylate (186 mg, 53%) was deprotected according the procedure for boc deprotection of amines MS (ES+) m/z 414.7 (M+H)+

Example 52b tert-Butyl 4-(2-fluorobenzyl)-2-(4-(2-methyl-1H-imidazol-1-yl)phenylamino)-7,8-dihydropyrido[4,3-d]pyrimidine-6(5H)-caboxylate

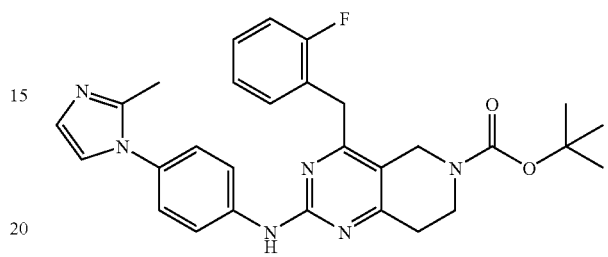

tert-Butyl 3-(2-(2-fluorophenyl)acetyl)-4-oxopiperidine-1-carboxylate (292 mg, 65%) was synthesised from tert-butyl 3-(2-(2-fluorophenyl)acetyl)-4-oxopiperidine-1-carboxylate and 1-(4-(2-methyl-1H-imidazol-1-yl)phenyl)guanidine (Example 41c) according to the general procedure for synthesis of pyrimidines. MS (ES−) m/z 513.1 (M−H)−

Example 52c tert-Butyl 3-(2-(2-fluorophenyl)acetyl)-4-oxopiperidine-1-carboxylate

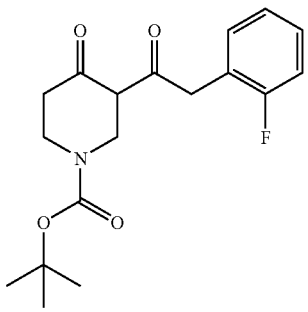

tert-Butyl 3-(2-(2-fluorophenyl)acetyl)-4-oxopiperidine-1-carboxylate (295 mg, 52%) was synthesised from tert-butyl 4-oxopiperidine-1-carboxylate and 2-(2-fluorophenyl)acetyl chloride according to the general procedure for the preparation of diketones. MS (ES−) m/z 334.1(M−H)−

Example 53

4-(3-Methoxybenzyl)-6-methyl-N-(4-(2-methyl-1H-imidazol-1-yl)phenyl)-5,6,7,8-tetrahydropyrido[4,3-d]pyrimidin-2-amine

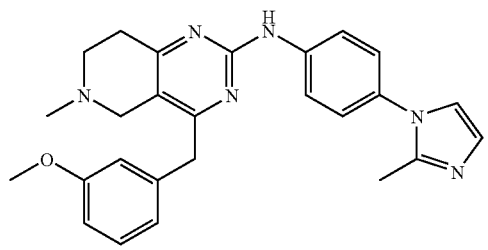

4-(3-Methoxybenzyl)-6-methyl-N-(4-(2-methyl-1H-imidazol-1-yl)phenyl)-5,6,7,8-tetrahydropyrido[4,3-d]pyrimidin-2-amine (14.3 mg, 10.4%) was synthesised from 4-(3-methoxybenzyl)-N-(4-(2-methyl-1H-imidazol-1-yl)phenyl)-5,6,7,8-tetrahydropyrido[4,3-d]pyrimidin-2-amine and formaldehyde according to the general procedure for reductive amination. MS (ES+) m/z 441.3 (M+H)+

1H NMR (500 MHz, DMSO-$d_6$) d ppm 2.24 (s, 3 H) 2.37 (s, 3 H) 2.61-2.69 (m, 2 H) 2.79 (t, 2 H) 3.44 (s, 2 H) 3.71 (s, 3 H) 3.94 (s, 2 H) 6.80-6.85 (m, 2 H) 6.87 (s, 2 H), 7.16-7.28 (m, 4 H) 7.83 (d, 2 H) 9.67 (s, 1 H)

Example 53a 4-(3-Methoxybenzyl)-N-(4-(2-methyl-1H-imidazol-1-yl)phenyl)-5,6,7,8-tetrahydropyrido[4,3-d]pyrimidin-2-amine

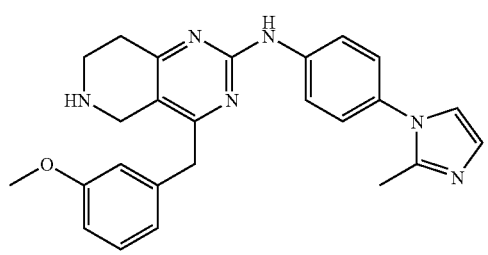

4-(3-Methoxybenzyl)-N-(4-(2-methyl-1H- imidazol-1-yl)phenyl)-5,6,7,8-tetrahydropyrido[4,3-d]pyrimidin-2-amine (268 mg, 54%) was prepared according to the general procedure for boc deprotection of amines MS (ES+) m/z 426.9 (M+H)+

Example 53b tert-Butyl 4-(3-methoxybenzyl)-2-(4-(2-methyl-1H-imidazol-1-yl)phenylamino)-7,8-dihydropyrido[4,3-d]pyrimidine-6(5H)-carboxylate

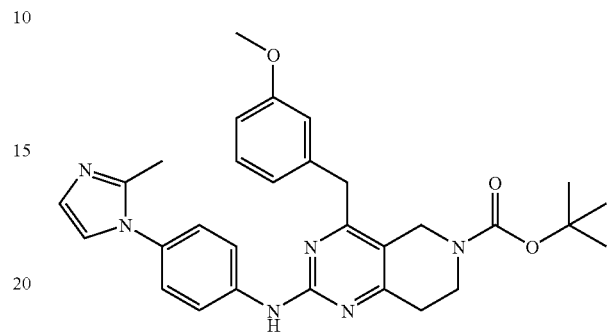

tert-Butyl 4-(3-methoxybenzyl)-2-(4-(2-methyl-1H-imidazol-1-yl)phenylamino)-7,8-dihydropyrido[4,3-d]pyrimidine-6(5H)-carboxylate (373 mg, 62%) was synthesised from tert-butyl 3-(2-(3-methoxyphenyl)acetyl)-4-oxopiperidine-1-carboxylate and 1-(4-(2-methyl-1H-imidazol-1-yl)phenyl)guanidine (Example 41c) according to the general procedure for synthesis of pyrimidines. MS (ES+) m/z 527.1 (M+H)+

Example 53c tert-Butyl 3-(2-(3-methoxyphenyl)acetyl)-4-oxopiperidine-1-carboxylate

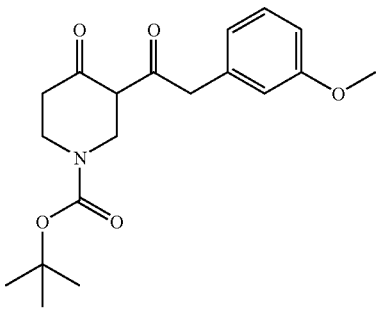

tert-Butyl 3-(2-(3-methoxyphenyl)acetyl)-4-oxopiperidine-1-carboxylate (388 mg, 66%) was synthesised from tert-butyl 4-oxopiperidine-1-carboxylate and 2-(3-methoxy-phenyl)acetyl chloride according to the general procedure for the preparation of diketones.

MS (ES−) m/z 346.1 (M−H)−

Example 54

4-(2-Cyclohexylethyl)-6-methyl-N-(4-(2-methyl-1H-imidazol-1-yl)phenyl)-5,6,7,8-tetrahydropyrido[4,3-d]pyrimidin-2-amine

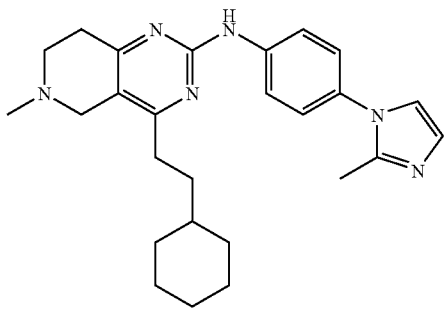

4-(2-Cyclohexylethyl)-6-methyl-N-(4-(2-methyl-1H-imidazol-1-yl)phenyl)-5,6,7,8-tetrahydropyrido[4,3-d]pyrimidin-2-amine (20.0 mg, 10.4%) was synthesised from 4-(2-cyclohexylethyl)-N-(4-(2-methyl-1H-imidazol-1-yl)phenyl)-5,6,7,8-tetrahydropyrido[4,3-d]pyrimidin-2-amine and formaldehyde according to the general procedure for reductive amination. MS (ES+) m/z 431.4 (M+H)+

1H NMR (500 MHz, DMSO-d$_6$) d ppm 0.88-0.99 (m, 2 H) 1.11-1.26 (m, 4 H) 1.31 (m, 1 H) 1.53-1.64 (m, 2 H) 1.67 (br. s., 2 H) 1.77 (d, 2 H) 2.25 (s, 3 H) 2.39 (s, 3 H), 2.54-2.60 (m, 2 H) 2.60-2.69 (m, 2 H) 2.78 (t, 2 H) 3.42 (s, 2 H) 6.87 (d, 1 H) 7.20 (d, 1 H) 7.28 (m, 2 H) 7.94 (m, 2 H) 9.59 (s, 1 H)

Example 55

4-(Cyclopentylmethyl)-6-methyl-N-(4-(2-methyl-1H-imidazol-1-yl)phenyl)-5,6,7,8-tetrahydropyrido[4,3-d]pyrimidin-2-amine

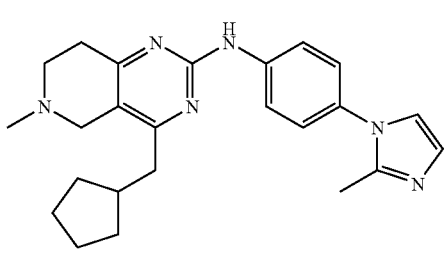

4-(Cyclopentylmethyl)-6-methyl-N-(4-(2-methyl-1H-imidazol-1-yl)phenyl)-5,6,7,8-tetrahydropyrido[4,3-d]pyrimidin-2-amine (5.7 mg, 6%) was synthesised from 4-(cyclopentylmethyl)-N-(4-(2-methyl-1H-imidazol-1-yl)phenyl)-5,6,7,8-tetrahydropyrido[4,3-d]pyrimidin-2-amine and formaldehyde according to the general procedure for reductive amination. MS (ES+) m/z 403.4 (M+H)+

1H NMR (500 MHz, DMSO-d$_6$) d ppm 1.19-1.28 (m, 2 H) 1.52 (dd, 2 H) 1.63 (m, 2 H) 1.74 (m, 2 H) 2.25 (s, 3 H) 2.32-2.38 (m, 1 H) 2.39 (s, 3 H) 2.58 (d, 2 H) 2.62-2.69 (m, 2 H) 2.79 (t, 2 H) 3.42 (s, 2 H) 6.87 (d, 1 H) 7.20 (d, 1 H) 7.29 (m, 2 H) 7.94 (m, 2 H), 9.58 (s, 1 H)

Example 55a 4-(Cyclopentylmethyl)-N-(4-(2-methyl-1H-imidazol-1-yl)phenyl)-5,6,7,8-tetrahydropyrido[4,3-d]pyrimidin-2-amine

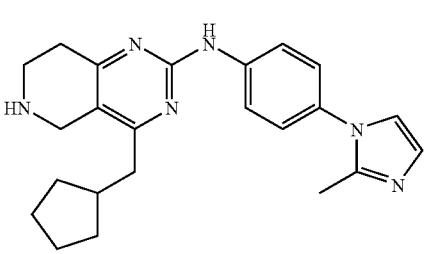

4-(Cyclopentylmethyl)-N-(4-(2-methyl-1H-imidazol-1-yl)phenyl)-5,6,7,8-tetrahydropyrido[4,3-d]pyrimidin-2-amine (187 mg, 51%) was prepared according to the general procedure for boc deprotection of amines MS (ES+) m/z 389.3 (M+H)+

Example 55b tert-Butyl 4-(cyclopentylmethyl)-2-(4-(2-methyl-1H-imidazol-1-yl)phenylamino)-7,8-dihydropyrido[4,3-d]pyrimidine-6(5H)-carboxylate

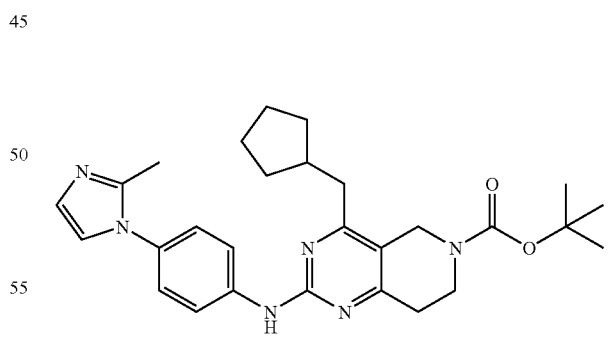

tert-Butyl 4-(cyclopentylmethyl)-2-(4-(2-methyl-1H-imidazol-1-yl)phenylamino)-7,8-dihydropyrido[4,3-d]pyrimidine-6(5H)-carboxylate (199 mg, 39%) was synthesised from tert-butyl 3-(2-cyclopentylacetyl)-4-oxopiperidine-1-carboxylate and 1-(4-(2-methyl-1H-imidazol-1-yl)phenyl)

guanidine (Example 41c) according to the general procedure for the synthesis of pyrimidines. MS (ES+) m/z 489.1 (M+H)+

Example 55c tert-Butyl 3-(2-cyclopentylacetyl)-4-oxopiperidine-1-carboylate

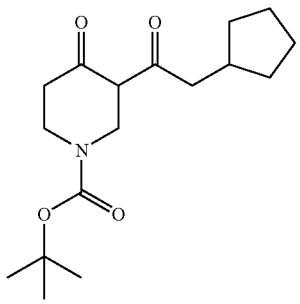

tert-Butyl 3-(2-cyclopentylacetyl)-4-oxopiperidine-1-carboxylate (311 mg, 59%) was synthesised from tert-butyl 4-oxopiperidine-1-carboxylate and 2-cyclopentylacetyl chloride according to the general procedure for the preparation of diketones. MS (ES–) m/z 308.1 (M–H)–

Example 56

2-(4-(2-Fluorobenzyl)-2-(4-(2-methyl-1H-imidazol-1-yl)phenylamino)-7,8-dihydropyrido[4,3-d]pyrimidin-6(5H)-yl)ethanol

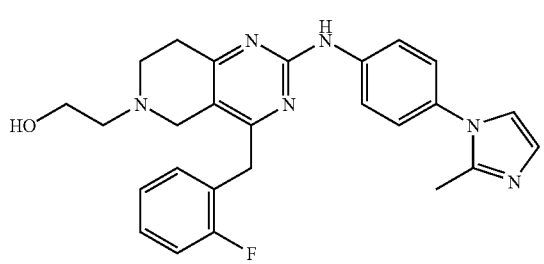

2-(4-(2-Fluorobenzyl)-2-(4-(2-methyl-1H-imidazol-1-yl)phenylamino)-7,8-dihydropyrido[4,3-d]pyrimidin-6(5H)-yl)ethanol (4.7 mg, 4.5%) was synthesised from 4-(2-fluorobenzyl)-N-(4-(2-methyl-1H-imidazol-1-yl)phenyl)-5,6,7,8-tetrahydropyrido[4,3-d]pyrimidin-2-amine (Example 52a) and glycolaldehyde according to the general procedure for reductive amination. MS (ES+) m/z 459.3 (M+H)+

1H NMR (500 MHz, DMSO-$d_6$) δ ppm 2.22 (s, 3 H) 2.60-2.67 (m, 2 H) 2.79 (s, 4 H) 3.58-3.64 (m, 4 H) 4.01 (s, 2 H) 4.50 (t, 1 H) 6.86 (s, 1 H) 7.08 (m, 2 H) 7.16 (s, 1 H), 7.18-7.26 (m, 2 H) 7.29-7.40 (m, 2 H) 7.60 (m, 2 H) 9.59 (s, 1 H)

Example 57

2-(4-(3-Methoxybenzyl)-2-(4-(2-methyl-1H-imidazol-1-yl)phenylamino)-7,8-dihydropyrido[4,3-d]pyrimidin-6(5H)-yl)ethanol

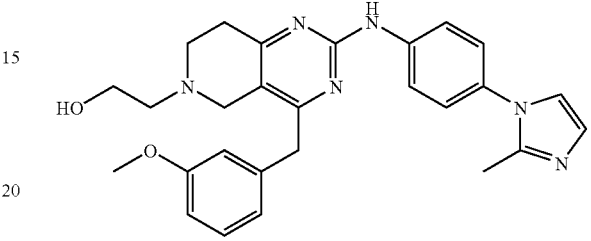

2-(4-(3-Methoxybenzyl)-2-(4-(2-methyl-1H-imidazol-1-yl)phenylamino)-7,8-dihydropyrido[4,3-d]pyrimidin-6(5H)-yl)ethanol (19.6 mg, 13%) was synthesised from 4-(3-methoxybenzyl)-N-(4-(2-methyl-1H-imidazol-1-yl)phenyl)-5,6,7,8-tetrahydropyrido[4,3-d]pyrimidin-2-amine (Example 53a) and glycolaldehyde according to the general procedure for reductive amination. MS (ES+) m/z 471.3 (M+H)+

1H NMR (500 MHz, DMSO-$d_6$) δ ppm 2.24 (s, 3 H) 2.60 (t, 2 H) 2.72-2.81 (m, 4 H) 3.52-3.62 (m, 4 H) 3.71 (s, 3 H) 3.93 (s, 2 H) 4.48 (t, 1 H) 6.80-6.86 (m, 2 H) 6.87 (s, 2 H) 7.16-7.28 (m, 4 H) 7.83 (d, 2 H) 9.66 (s, 1 H)

Example 58

1-(4-(2-Cyclohexylethyl)-2-(4-(2-methyl-1H-imidazol-1-yl)phenylamino)-7,8-dihydropyrido[4,3-d]pyrimidin-6(5H)-yl)ethanone

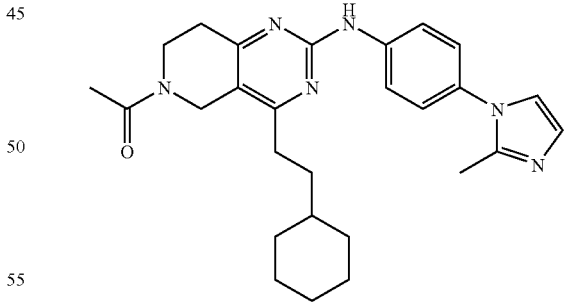

1-(4-(2-Cyclohexylethyl)-2-(4-(2-methyl-1H-imidazol-1-yl)phenylamino)-7,8-dihydropyrido[4,3-d]pyrimidin-6(5H)-yl)ethanone (51 mg, 26%) was synthesised from 4-(2-cyclohexylethyl)-N-(4-(2-methyl-1H-imidazol-1-yl)phenyl)-5,6,7,8-tetrahydropyrido[4,3-d]pyrimidin-2-amine (Example 54a) and acetic anhydride according to the general procedure for N-acetylation. MS (ES+) m/z 459.4 (M+H)+

Mixture of Rotamers:

1H NMR (500 MHz, DMSO-$d_6$) δ ppm 0.87-1.01 (m) 1.12-1.28 (m) 1.31-1.40 (m) 1.55-1.64 (m) 1.68 (dd) 1.78 (d)

2.08-2.15 (m) 2.25 (s) 2.57-2.68 (m) 2.71 (t) 2.85 (t) 3.74 (m) 4.50-4.59 (m) 6.87 (s) 7.20 (d) 7.30 (d) 7.94 (d) 9.68 (s)

Total no of protons in spectrum: 34
Ratio major:minor: 1.7:1

Example 59

1-(2-(4-(2-Methyl-1H-imidazol-1-yl)phenylamino)-4-(4-methylbenzyl)-7,8-dihydropyrido[4,3-d]pyrimidin-6(5H)-yl)ethanone

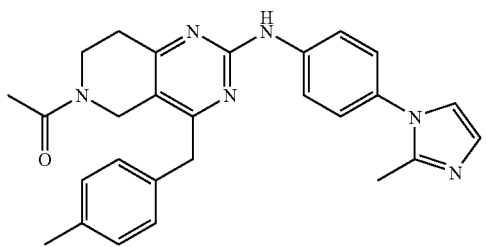

1-(2-(4-(2-Methyl-1H-imidazol-1-yl)phenylamino)-4-(4-methylbenzyl)-7,8-dihydropyrido[4,3-d]pyrimidin-6(5H)-yl)ethanone (11.3 mg, 10.6%) was synthesised from N-(4-(2-methyl-1H-imidazol-1-yl)phenyl)-4-(4-methylbenzyl)-5,6,7,8-tetrahydropyrido[4,3-d]pyrimidin-2-amine (Example 50a) and acetic anhydride according to the general procedure for N-acetylation. MS (ES+) m/z 453.2 (M+H)+

1H NMR (500 MHz, DMSO-$d_6$) δ ppm 1.93 (d) 2.02 (s) 2.23-2.29 (m) 2.77-2.90 (m) 3.72 (m) 3.96 (d) 4.54 (s) 4.62 (d) 6.87 (d) 7.07 (d) 7.11-7.25 (m) 7.83 (dd) 9.74 (d)

Example 60

1-(4-(3-Fluorophenethyl)-2-(4-(2-methyl-1H-imidazol-1-yl)phenylamino)-7,8-dihydropyrido[4,3-d]pyrimidin-6(5H)-yl)ethanone

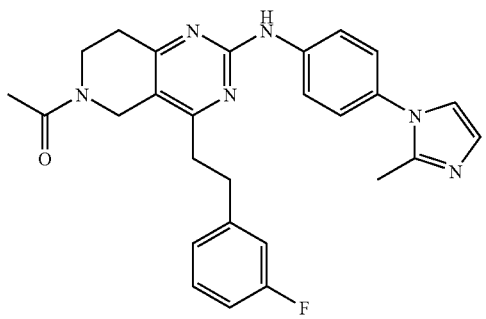

1-(4-(3-Fluorophenethyl)-2-(4-(2-methyl-1H-imidazol-1-yl)phenylamino)-7,8-dihydropyrido[4,3-d]pyrimidin-6(5H)-yl)ethanone (15.8 mg, 12%) was synthesised from 4-(3-fluorophenethyl)-N-(4-(2-methyl-1H-imidazol-1-yl)phenyl)-5,6,7,8-tetrahydropyrido[4,3-d]pyrimidin-2-amine (Example 51a) and acetic anhydride according to the general procedure for N-acetylation. MS (ES+) m/z 471.3 (M+H)+

Mixture of Rotamers:

1H NMR (500 MHz, DMSO-$d_6$) δ ppm 2.10 (d) 2.26 (s) 2.34-2.38 (m) 2.62-2.66 (m) 2.69-2.74 (m) 2.86 (t) 2.92-3.01 (m) 3.09 (d) 3.71 (q) 4.50 (d) 6.87 (d) 7.02 (br. s) 7.10-7.19 (m) 7.21 (d) 7.28-7.36 (m) 7.90 (dd) 9.72 (d)

Total no of protons in spectrum: 27
Ratio major:minor: 1.5:1

Example 61

6-Methyl-N-(4-(2-methyl-1H-imidazol-1-yl)phenyl)-4-((tetrahydro-2H-pyran-4-yl)methyl)-5,6,7,8-tetrahydropyrido[4,3-d]pyrimidin-2-amine

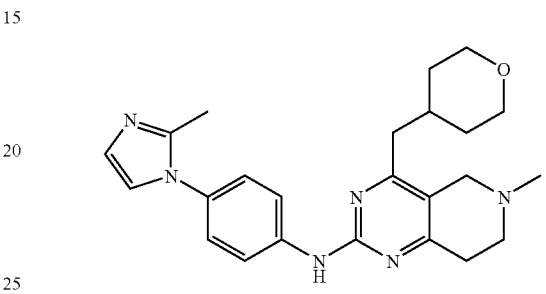

6-Methyl-N-(4-(2-methyl-1H-imidazol-1-yl)phenyl)-4-((tetrahydro-2H-pyran-4-yl)methyl)-5,6,7,8-tetrahydropyrido[4,3-d]pyrimidin-2-amine (8 mg, 5%) was synthesised from N-(4-(2-methyl-1H-imidazol-1-yl)phenyl)-4-((tetrahydro-2H-pyran-4-yl)methyl)-5,6,7,8-tetrahydropyrido[4,3-d]pyrimidin-2-amine and formaldehyde according to the general procedure for reductive amination. MS (ES+) m/z 419.2 (M+H)+

1H NMR (400 MHz, CHLOROFORM-d) δ ppm 1.39-1.52 (m, 2 H) 1.67 (dd, 2 H) 2.13-2.26 (m, 4 H) 2.36 (br. s., 2 H) 2.55 (s, 3 H) 2.81 (t, 2 H) 2.95 (t, 2 H) 3.42 (td, 2 H) 3.53 (s, 2 H) 3.99 (dd, 2 H) 7.10 (br. s., 1 H) 7.23 (m, 2 H) 7.85 (m, 2 H) 8.51 (s, 1 H)

Example 61a

N-(4-(2-Methyl-1H-imidazol-1-yl)phenyl)-4-((tetrahydro-2H-pyran-4-yl)methyl)-5,6,7,8-tetrahydropyrido[4,3-d]pyrimidin-2-amine

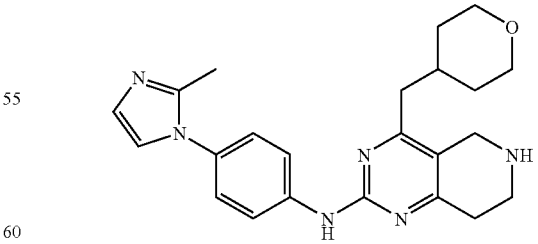

N-(4-(2-Methyl-1H-imidazol-1-yl)phenyl)-4-((tetrahydro-2H-pyran-4-yl)methyl)-5,6,7,8-tetrahydropyrido[4,3-d]pyrimidin-2-amine (480 mg, 80%) was prepared from tert-butyl 2-(4-(2-methyl-1H-imidazol-1-yl)phenylamino)-4-((tetrahydro-2H-pyran-4-yl)methyl)-7,8-dihydropyrido[4,3- d]pyrimidine-6(5H)-carboxylate according to the procedure for boc deprotection of amines MS (ES+) m/z 405.0 (M+H)+

Example 61b tert-Butyl 2-(4-(2-methyl-1H-imidazol-1-yl)phenylamino)-4-((tetrahydro-2H-pyran-4-yl)methyl)-7,8-dihydropyrido[4,3-d]pyrimidine-6(5H)-carboxylate

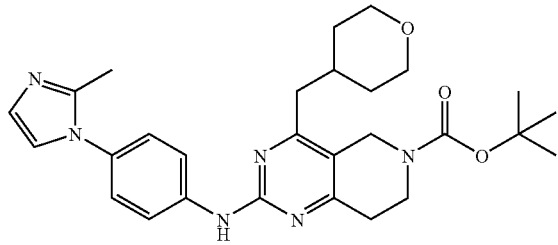

tert-Butyl 2-(4-(2-methyl-1H-imidazol-1-yl)phenylamino)-4-((tetrahydro-2H-pyran-4-yl)methyl)-7,8-dihydropyrido[4,3-d]pyrimidine-6(5H)-carboxylate (745 mg, 86%) was synthesised from tert-butyl 4-oxo-3-(2-(tetrahydro-2H-pyran-4-yl)acetyl)piperidine-1-carboxylate and 1-(4-(2-methyl-1H-imidazol-1-yl)phenyl)guanidine (Example 41c) according to the general procedure for the synthesis of pyrimidines. MS (ES−) m/z 503.3 (M−H)−

Example 61c tert-Butyl 4-oxo-3-(2-(tetrahydro-2H-pyran-4-yl)acetyl)piperidine-1-carboxylate

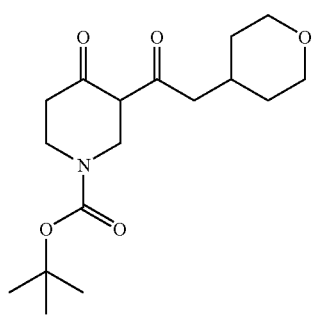

tert-Butyl 4-oxo-3-(2-(tetrahydro-2H-pyran-4-yl)acetyl)piperidine-1-carboxylate (510 mg, 78%) was synthesised from tetrahydropyranacetyl chloride according to the general procedure for the preparation of diketones. MS (ES−) m/z 324.2 (M−H)−

Example 62

2-(2-(4-(2-Methyl-1H-imidazol-1-yl)phenylamino)-4-((tetrahydro-2H-pyran-4-yl)methyl)-7,8-dihydropyrido[4,3-d]pyrimidin-6(5H)-yl)ethanol

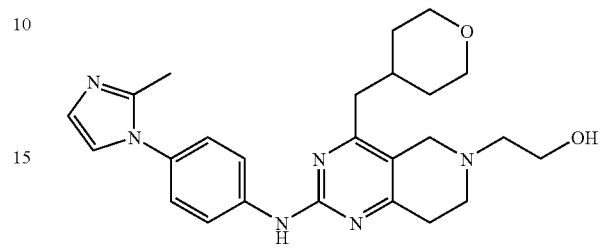

2-(2-(4-(2-Methyl-1H-imidazol-1-yl)phenylamino)-4-((tetrahydro-2H-pyran-4-yl)methyl)-7,8-dihydropyrido[4,3-d]pyrimidin-6(5H)-yl)ethanol (20.00 mg, 11.3%) was synthesised from N-(4-(2-methyl-1H-imidazol-1-yl)phenyl)-4-((tetrahydro-2H-pyran-4-yl)methyl)-5,6,7,8-tetrahydropyrido[4,3-d]pyrimidin-2-amine (Example 61a) and glycol aldehyde according to the general procedure for reductive amination.

MS (ES+) m/z 449.2 (M+H)+

1H NMR (400 MHz, CHLOROFORM-d) δ ppm 1.38-1.53 (m, 2 H) 1.68 (dd, 2 H) 2.14-2.27 (m, 4 H) 2.37 (br. s., 3 H) 2.54 (d, 2 H) 2.83 (br. s., 1 H) 2.93 (br. s., 3 H) 3.42 (td, 2 H) 3.66 (br. s., 2 H) 3.80 (br. s., 2 H) 3.99 (dd, 2 H) 7.10 (br. s., 1 H) 7.23 (d, 2 H) 7.85 (d, 2 H) 8.49 (s, 1 H)

Example 63

1-(2-(4-(2-Methyl-1H-imidazol-1-yl)phenylamino)-4-((tetrahydro-2H-pyran-4-yl)methyl)-7,8-dihydropyrido[4,3-d]pyrimidin-6(5H)-yl)ethanone

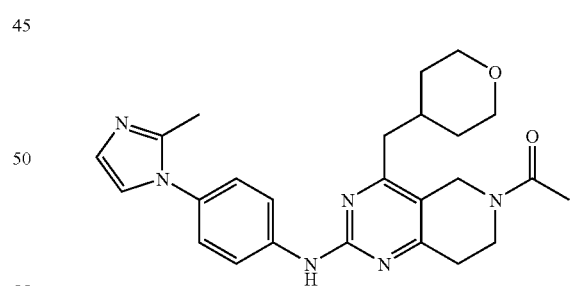

1-(2-(4-(2-Methyl-1H-imidazol-1-yl)phenylamino)-4-((tetrahydro-2H-pyran-4-yl)methyl)-7,8-dihydropyrido[4,3-d]pyrimidin-6(5H)-yl)ethanone (27.0 mg, 15.3%) was synthesised from N-(4-(2-methyl-1H-imidazol-1-yl)phenyl)-4-((tetrahydro-2H-pyran-4-yl)methyl)-5,6,7,8-tetrahydropyrido[4,3-d]pyrimidin-2-amine (Example 61a) and acetic anhydride according to the general procedure for N-acetylation. MS (ES+) m/z 447.2 (M+H)+

Example 64

4-(4-Fluorobenzyl)-N-[4-(2-methyl-1H-imidazol-1-yl)phenyl]-7,8-dihydro-5H-thiopyrano[4,3-d]pyrimidin-2-amine 6-oxide

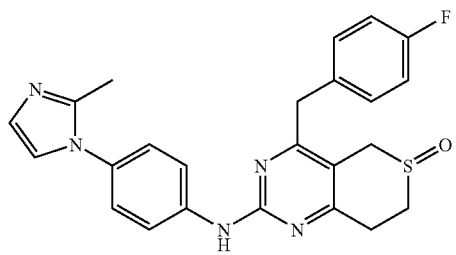

4-(4-Fluorobenzyl)-N-(4-(2-methyl-1H-imidazol-1-yl)phenyl)-7,8-dihydro-5H-thiopyrano[4,3-d]pyrimidin-2-amine (103 mg, 0.24 mmol) was dissolved in DCM (3 mL). mCPBA (61.8 mg, 0.36 mmol) was added and the reaction was stirred at rt for 2 h. Water was added and the product was obtained by separating the organic phase and evaporating the solvent. The crude product was purified using preparative HPLC yielding 4-(4-fluorobenzyl)-N-[4-(2-methyl-1H-imidazol-1-yl)phenyl]-7,8-dihydro-5H-thiopyrano[4,3-d]pyrimidin-2-amine 6-oxide (21.0 mg, 18.9%). MS (ES+) m/z 448.1 (M+H)+

Mixture of Rotamers:

1H NMR (400 MHz, CHLOROFORM-d) δ ppm 2.39 (s) 2.92-3.02 (m) 3.08 (dt) 3.25-3.35 (m) 3.58 (ddd) 3.74 (d) 3.94 (dd) 4.04 (d) 6.99-7.09 (m) 7.17-7.24 (m) 7.54 (s) 7.66-7.69 (m) 7.69-7.72 (m)

Total no of protons in spectrum: 22

Ratio major:minor: 1.25:1

Example 64a 4-(4-Fluorobenzyl)-N-(4-(2-methyl-1H-imidazol-1-yl)phenyl)-7,8-dihydro-5H-thiopyrano[4,3-d]pyrimidin-2-amine

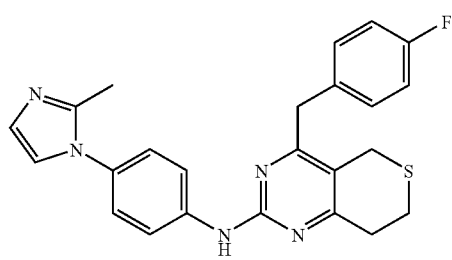

4-(4-Fluorobenzyl)-N-(4-(2-methyl-1H-imidazol-1-yl)phenyl)-7,8-dihydro-5H-thiopyrano[4,3-d]pyrimidin-2-amine (103 mg, 78%) was synthesised from 3-(2-(4-fluorophenyl)acetyl)dihydro-2H-thiopyran-4(3H)-one and 1-(4-(2-methyl-1H-imidazol-1-yl)phenyl)guanidine (Example 41c) according to the general procedure for the synthesis of pyrimidines. MS (ES+) m/z 432.2 (M+H)+

Example 64b 3-(2-(4-Fluorophenyl)acetyl)dihydro-2H-thiopyran-4(3H)-one

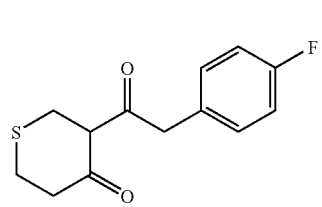

3-(2-(4-Fluorophenyl)acetyl)dihydro-2H-thiopyran-4(3H)-one (77 mg, 61%) was synthesised from 4-fluorophenylacetyl chloride according to the general procedure for the preparation of diketones. MS (ES+) m/z 253.1 (M+H)+

Example 65

4-(Methoxy(phenyl)methyl)-N-(4-(2-methyl-1H-imidazol-1-yl)phenyl)-7,8-dihydro-5H-pyrano[4,3-d]pyrimidin-2-amine

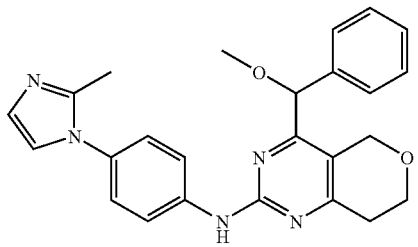

3-(2-Methoxy-2-phenylacetyl)dihydro-2H-pyran-4(3H)-one (100 mg, 0.40 mmol), 1-(4-(2-methyl-1H-imidazol-1-yl)phenyl)guanidine (Example 41c) (87 mg, 0.40 mmol) and potassium carbonate (55.7 mg, 0.40 mmol) was slurrified in EtOH (4 mL) and heated to 50° C. for 15 h. DCM and water were added. The organic phase was separated, dried with MgSO$_4$ concentrated and purified by preparative HPLC yielding 4-(methoxy(phenyl)methyl)-N-(4-(2-methyl-1H-imidazol-1-yl)phenyl)-7,8-dihydro-5H-pyrano[4,3-d]pyrimidin-2-amine (10.0 mg, 5.7%). MS (ES+) m/z 428.1 (M+H)+

1H NMR (500 MHz, CHLOROFORM-d) δ ppm 2.43 (s, 3 H) 2.89-2.94 (m, 2 H) 3.48 (s, 3 H) 3.98-4.05 (m, 2 H) 4.75 (d, 2 H) 5.27 (s, 1 H) 7.02 (s, 1 H) 7.09 (br. s., 1 H) 7.21 (m, 2 H) 7.32-7.46 (m, 6 H) 7.72 (m, 2 H)

Example 65a 3-(2-Methoxy-2-phenylacetyl)dihydro-2H-pyran-4(3H)-one

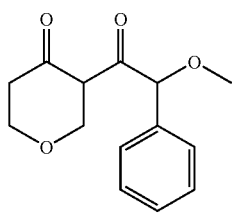

3-(2-Methoxy-2-phenylacetyl)dihydro-2H-pyran-4(3H)-one (54 mg, 14.5%) was synthesised from 2-methoxy-2-phenylacetyl chloride and dihydro-2H-pyran-4(3H)-one according to the general procedure for the preparation of diketones. MS (ES−) m/z 247.1 (M−H)−

Example 66

4-[Methoxy(phenyl)methyl]-N-[4-(2-methyl-1H-imidazol-1-yl)phenyl]-7,8-dihydro-5H-thiopyrao[4,3-d]pyrimidin-2-amine 6,6-dioxide

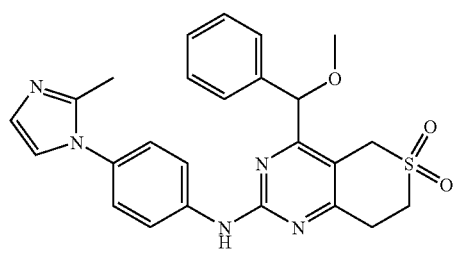

4-(Methoxy(phenyl)methyl)-N-(4-(2-methyl-1H-imidazol-1-yl)phenyl)-7,8-dihydro-5H-thiopyrano[4,3-d]pyrimidin-2-amine (105 mg, 0.24 mmol) was dissolved in DCM (4 mL). mCPBA (230 mg, 1.33 mmol) was added portionwise, 2 eq at a time. The mCPBA was extracted using sat NaHCO$_3$ and the organic phase was reduced by evaporation. The crude product was purified using preparative HPLC yielding 44-[methoxy(phenyl)methyl]-N-[4-(2-methyl-1H-imidazol-1-yl)phenyl]-7,8-dihydro-5H-thiopyrano[4,3-d]pyrimidin-2-amine 6,6-dioxide (12.0 mg, 10.7%). MS (ES+) m/z 476.1 (M+H)+

1H NMR (400 MHz, CHLOROFORM-d) δ ppm 2.39 (s, 3 H) 3.31-3.37 (m, 2 H) 3.44-3.49 (m, 2 H) 3.50 (s, 3 H) 4.07 (d, 1 H) 4.55 (d, 1 H) 5.39 (s, 1 H) 7.02 (br. s., 1 H) 7.07 (br. s., 1 H) 7.23 (m, 2 H) 7.32-7.39 (m, 2 H) 7.40 (m, 2 H) 7.41 (s, 1 H) 7.58 (s, 1 H) 7.71 (m, 2 H)

Example 66a 4-(Methoxy(phenyl)methyl)-N-(4-(2-methyl-1H-imidazol-1-yl)phenyl)-7,8-dihydro-5H-thiopyrano[4,3-4]pyrimidin-2-amine

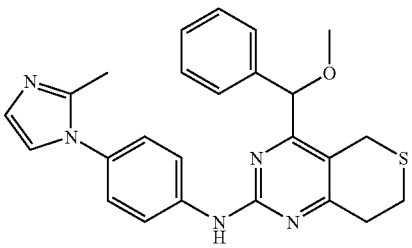

4-(Methoxy(phenyl)methyl)-N-(4-(2-methyl-1H-imidazol-1-yl)phenyl)-7,8-dihydro-5H-thiopyrano[4,3-d]pyrimidin-2-amine (31.5 mg, 11%) was synthesised from 3-(2-methoxy-2-phenylacetyl)dihydro-2H-thiopyran-4(3H)-one and 1-(4-(2-methyl-1H-imidazol-1-yl)phenyl)guanidine (Example 41c) according to the general procedure for the synthesis of pyrimidines. MS (ES+) m/z 444.0 (M+H)+

Example 66b 3-(2-Methoxy-2-phenylacetyl)dihydro-2H-thiopyran-4(3H)-one

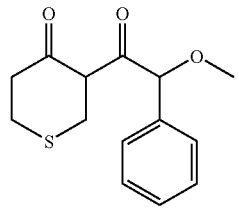

3-(2-Methoxy-2-phenylacetyl)dihydro-2H-pyran-4(3H)-one (54 mg, 14.5%) was synthesised from 2-methoxy-2-phenylacetyl chloride and dihydro-2H-thiopyran-4(3H)-one according to the general procedure for the preparation of diketones. MS (ES−) m/z 263.1 (M−H)−

Example 67

N-(4-(2-Methyl-1H-imidazol-1-yl)phenyl)-4-((tetrahydro-2H-pyran-4-yl)methyl)-7,8-dihydro-5H-pyrano[4,3-d]pyrimidin-2-amine

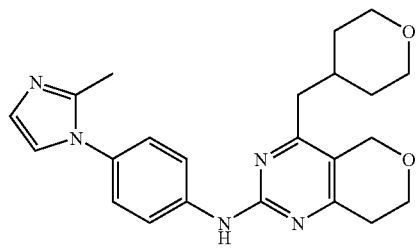

3-(2-(Tetrahydro-2H-pyran-4-yl)acetyl)dihydro-2H-pyran-4(3H)-one (200 mg, 0.88 mmol), 1-(4-(2-methyl-1H-imidazol-1-yl)phenyl)guanidine (190 mg, 0.88 mmol, Example 41c) and potassium carbonate (122 mg, 0.88 mmol) was slurrified in EtOH (4 mL) and heated to 50° C. for 15 h. DCM and water were added. The organic phase was separated, dried with MgSO₄ and the solvent was evaporated. The crude product was purified using preparative HPLC yielding N-(4-(2-methyl-1H-imidazol-1-yl)phenyl)-4-((tetrahydro-2H-pyran-4-yl)methyl)-7,8-dihydro-5H-pyrano[4,3-d]pyrimidin-2-amine (15.0 mg, 4.0%).

MS (ES+) m/z 406.2 (M+H)+

1H NMR (400 MHz, CHLOROFORM-d) δ ppm 1.37-1.50 (m, 2 H) 1.66 (dd, 2 H) 2.17 (ddd, 1 H) 2.38 (s, 3 H) 2.45 (d, 2 H) 2.89 (t, 2 H) 3.41 (td, 2 H) 3.98 (dd, 2 H) 4.04 (t, 2 H) 4.71 (s, 2 H) 7.00 (s, 1 H) 7.04 (s, 1 H) 7.24 (m, 2 H) 7.42 (s, 1 H) 7.79 (m, 2 H)

Example 67a 3-(2-Ttetrahydro-2H-pyran-4-yl)acetyl)dihydro-2H-pyran-4(3H)-one

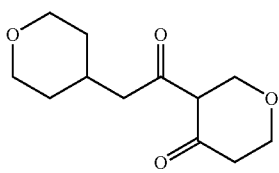

3-(2-(tetrahydro-2H-pyran-4-yl)acetyl)dihydro-2H-pyran-4(3H)-one (170 mg, 50%) was synthesised from 2-(tetrahydro-2H-pyran-4-yl)acetyl chloride and dihydro-2H-pyran-4(3H)-one according to the general procedure for the preparation of diketones.

MS (ES+) m/z 227.1 (M+H)+

Example 68

4-Benzyl-N-(3-methoxy-4-(4-methyl-1H-imidazol-1-yl)phenyl)-6-methyl-5,6,7,8-tetrahydropyrido[4,3-d]pyrimidin-2-amine

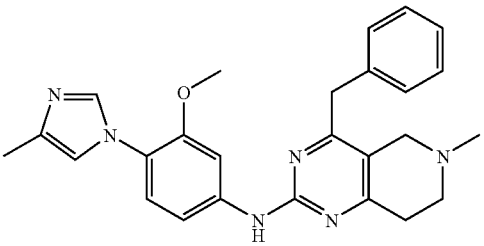

4-Benzyl-N-(3-methoxy-4-(4-methyl-1H-imidazol-1-yl)phenyl)-5,6,7,8-tetrahydropyrido[4,3-d]pyrimidin-2-amine (400 mg, 0.94 mmol, example 106) was is dissolved in methanol (5 mL). Acetic acid (0.054 mL, 0.94 mmol) was added followed by formaldehyde (0.070 mL, 0.94 mmol). The reaction mixture was stirred at room temperature for 15 minutes and sodium cyanoborohydride (58.9 mg, 0.94 mmol) was added. LCMS analysis showed full conversion after 1 h. The solvent was evaporated under reduced pressure, the crude redissolved in methanol, filtered and purified by preparative HPLC yielding 4-benzyl-N-(3-methoxy-4-(4-methyl-1H-imidazol-1-yl)phenyl)-6-methyl-5,6,7,8-tetrahydropyrido[4,3-d]pyrimidin-2-amine (74.0 mg, 17.60%). MS (ES+) m/z 441.3 (M+H)+

1H NMR (600 MHz, CHLOROFORM-d) δ ppm 2.32 (s, 3 H) 2.50 (s, 3 H) 2.76 (t, 2 H) 2.93 (t, 2 H) 3.50 (s, 2 H) 3.76 (s, 3 H) 3.98 (s, 2 H) 6.87 (s, 1 H) 7.00 (dd, 1 H) 7.11 (d, 1 H) 7.24 (d, 3 H) 7.31 (t, 2 H) 7.67 (s, 1 H) 7.77 (d, 1 H)

Example 69

N4-Cyclohexyl-6-methyl-N2-(4-(2-methyl-1H-imidazol-1-yl)phenyl)-5,6,7,8-tetrahydropyrido[4,3-d]pyrimidine-2,4-diamine N4-Cyclohexyl-N2-(4-(2-methyl-1H-imidazol-1-yl)phenyl)-5,6,7,8-tetrahydropyrido[4,3-d]pyrimidine-2,4-diamine (93 mg, 0.23 mmol) was dissolved in methanol (3 mL). Acetic acid (0.013 mL, 0.23 mmol) was added followed by formaldehyde (0.017 mL, 0.23 mmol) and sodium cyanoborohydride (14.48 mg, 0.23 mmol). The reaction mixture was stirred at room temperature for 1 h and the solvent was evaporated under reduced pressure. The crude material was dissolved in few drops of methanol, filtered and purified by preparative HPLC (acidic system) yielding N4-cyclohexyl-6-methyl-N2-(4-(2-methyl-1H-imidazol-1-yl)phenyl)-5,6,7,8-tetrahydropyrido[4,3-d]pyrimidine-2,4-diamine (15.00 mg, 15.59%). MS (ES+) m/z 418.2 (M+H)+

1H NMR (600 MHz, MeOD) δ ppm 1.22-1.31 (m, 1 H) 1.36-1.44 (m, 4 H) 1.72 (d, 1 H) 1.87 (d, 2 H) 2.05 (d, 2 H) 2.59 (s, 3 H) 3.09 (d, 5 H) 3.61 (br. s., 2 H) 4.04-4.17 (m, 3 H) 7.52-7.58 (m, 2 H) 7.60 (d, 1 H) 7.65-7.68 (m, 1 H) 7.97 (d, 2 H)

Example 69a

N4-Cyclohexyl-N2-(4-(2-methyl-1H-imidazol-1-yl)phenyl)-5,6,7,8-tetrahydropyrido[4,3-d]pyrimidine-2,4-diamine

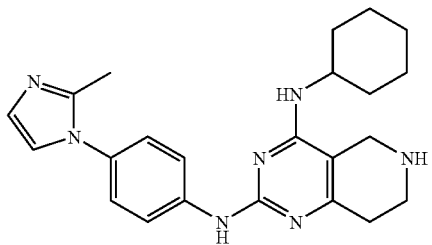

tert-Butyl 4-(cyclohexylamino)-2-(4-(2-methyl-1H-imidazol-1-yl)phenylamino)-7,8-dihydropyrido[4,3-d]pyrimidine-6(5H)-carboxylate (124 mg, 0.25 mmol) was dissolved in methanol (2 mL). Hydrochloric acid (7.48 μL, 0.25 mmol) was added and the reaction mixture was stirred at 75° C. for 1 h. The solvent was evaporated under reduced pressure and the crude N4-cyclohexyl-N2-(4-(2-methyl-1H-imidazol-1-yl)phenyl)-5,6,7,8-tetrahydropyrido[4,3-d]pyrimidine-2,4-diamine (93 mg, 94%) was used as such in the subsequent step. MS (ES+) m/z 404.3 (M+H)+

Example 69b tert-butyl 4-(cyclohexylamino)-2-(4-(2-methyl-1H-imidazol-1-yl)phenylamino)-7,8-dihydropyrido[4,3-d]pyrimidine-6(5H)-carboxylate

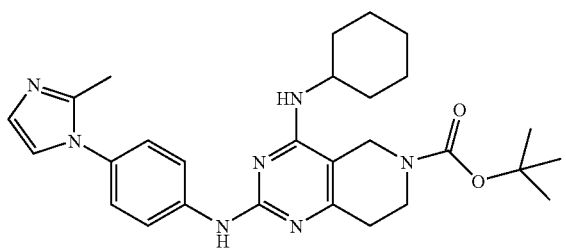

tert-Butyl 2-(4-(2-methyl-1H-imidazol-1-yl)phenylamino)-4-(trifluoromethylsulfonyloxy)-7,8-dihydropyrido[4,3-d]pyrimidine-6(5H)-carboxylate (250 mg, 0.45 mmol) was dissolved in DMF (2 mL). Cyclohexanamine (44.7 mg, 0.45 mmol) was added and the reaction mixture was heated at 85° C. overnight. The reaction mixture was allowed to reach room temperature, the solvent was evaporated under reduced pressure and the crude was purified by flash chromatography using dichloromethane and methanol as eluent yielding tert-butyl 4-(cyclohexylamino)-2-(4-(2-methyl-1H-imidazol-1-yl)phenylamino)-7,8-dihydropyrido[4,3-d]pyrimidine-6(5H)-carboxylate (124 mg, 54.6%). MS (ES+) m/z 504.4 (M+H)+

1H NMR (600 MHz, CHLOROFORM-d) δ ppm 1.40-1.45 (m, 4 H) 1.52 (s, 9 H) 1.82 (dd, 4 H) 2.10 (d, 3 H) 2.39 (s, 3 H) 2.72 (t, 2 H) 3.70 (t, 2 H) 4.02 (br. s., 1 H) 4.13 (q, 1 H) 4.20 (br. s., 2 H) 7.01 (d, 1 H) 7.06 (d, 1 H) 7.21 (d, 2 H) 7.77 (d, 2 H)

Example 69c tert-Butyl 2-(4-(2-methyl-1H-imidazol-1-yl)phenylamino)-4-(trifluoromethylsulfonyloxy)-7,8-dihydropyrido[4,3-d]pyrimidine-6(5H)-carboxylate

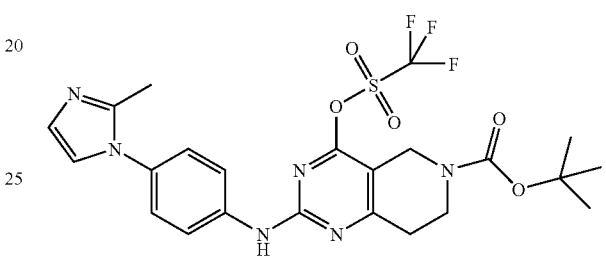

tert-Butyl 4-hydroxy-2-(4-(2-methyl-1H-imidazol-1-yl)phenylamino)-7,8-dihydropyrido[4,3-d]pyrimidine-6(5H)-carboxylate (1.97 g, 4.66 mmol) was dissolved in dichloromethane (10 mL). 1,8-diazabicyclo[5.4.0]undec-7-ene (0.697 mL, 4.66 mmol) was added followed by N-phenyltrifluoromethanesulfonimide (1.666 g, 4.66 mmol) and 4-dimethylaminopyridine (0.570 mg, 4.66 μmol). The reaction was stirred at room temperature for 2 h and the solvent was evaporated under reduced pressure. Purification by flash column chromatography using dichloromethane and methanol as eluent gave tert-butyl 2-(4-(2-methyl-1H-imidazol-1-yl)phenylamino)-4-(trifluoromethylsulfonyloxy)-7,8-dihydropyrido[4,3-d]pyrimidine-6(5H)-carboxylate (2.56 g, 99%). MS (ES+) m/z 555.0 (M+H)+

Example 69d tert-Butyl 4-hydroxy-2-(4-(2-methyl-1H-imidazol-1-yl)phenylamino)-7,8-dihydropyrido[4,3-d]pyrimidine-6(5H)-carboxylate

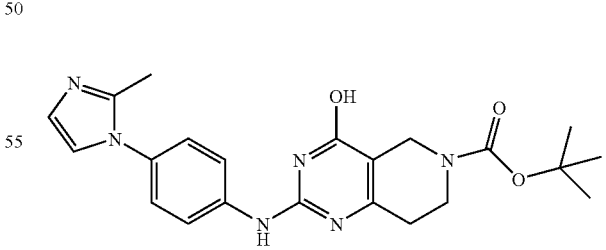

1-(4-(2-Methyl-1H-imidazol-1-yl)phenyl)guanidine (1.8 g, 8.36 mmol, example 9e), 1-tert-butyl 3-methyl 4-oxopiperidine-1,3-dicarboxylate (2.151 g, 8.36 mmol) and sodium ethoxide (0.569 g, 8.36 mmol) in ethanol (10 mL) were charged in a thick glass vial, which was sealed and heated under microwave irradiation at 110° C. for 2 h. The reaction mixture was allowed to reach room temperature and the solvent was evaporated under reduced pressure. The crude was dissolved in ethyl acetate and washed with water. The organic phase was dried under MgSO$_4$ and concentrated under reduced pressure yielding tert-butyl 4-hydroxy-2-(4-(2-methyl-1H-imidazol-1-yl)phenylamino)-7,8-dihydropyrido[4,3-d]pyrimidine-6(5H)-carboxylate (1.970 g, 55.8%). The product was used as such in the subsequent step. MS (ES+) m/z 423.3 (M+H)+

Example 69e 1-tert-Butyl 3-methyl 4-oxopiperidine-1,3-dicarboxylate

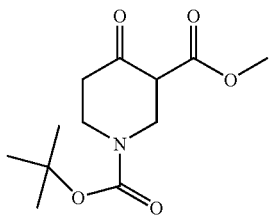

Methyl 4-oxo-3-piperidinecarboxylate hydrochloride (5 g, 25.82 mmol) was dissolved in dichloromethane (50 mL) and triethylamine (3.60 mL, 25.82 mmol). Di-tert-butyl dicarbonate (5.93 mL, 25.82 mmol) was carefully added and the reaction mixture was stirred at room temperature for 2 h. The reaction mixture was washed with 2M HCl (aq.) and brine. The organic phase was dried under MgSO$_4$ and concentrated under reduced pressure yielding 1-tert-butyl 3-methyl 4-oxopiperidine-1,3-dicarboxylate (6.55 g, 99%).

MS (ES+) m/z 256.1 (M–H)–

1H NMR (400 MHz, CHLOROFORM-d) δ ppm 1.48 (s, 9 H) 1.49 (s, 3 H) 2.38 (t, 2 H) 3.57 (t, 2 H) 3.77 (s, 1 H) 3.78 (s, 3 H) 4.06 (br. s., 2 H) 11.98 (s, 1 H)

Example 70

6-Methyl-N-(4-(2-methyl-1H-imidazol-1-yl)phenyl)-4-(1-phenylethyl)-5,6,7,8-tetrahydropyrido[4,3-d]pyrimidin-2-mine

ISOMER 1

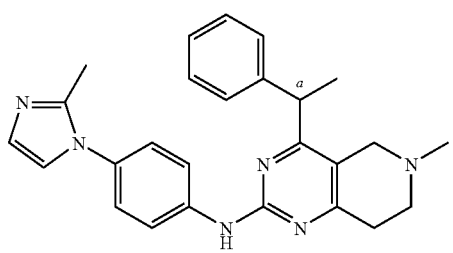

a = unknown absolute

Chiral separation gave isomer 1 (P1)=(−) optical rotation (PDR-Chiral Detector)

1H NMR (600 MHz, CHLOROFORM-d) δ ppm 1.66 (d, 3 H) 2.35 (s, 3 H) 2.45 (s, 3 H) 2.60-2.67 (m, 1 H) 2.73 (dt, 1 H) 2.82-2.95 (m, 2 H) 3.27 (d, 1 H) 3.58 (d, 1 H) 4.14 (q, 1 H) 6.98 (s, 1 H) 7.01 (s, 1 H) 7.19 (d, 4 H) 7.28 (d, 3 H) 7.76 (d, 2 H)

MS (ES+) m/z 425.3 (M+H)+

Example 71

6-Methyl-N-(4-(2-methyl-1H-imidazol-1-yl)phenyl)-4-(1-phenylethyl)-5,6,7,8-tetrahydropyrido[4,3-d]pyrimidin-2-amine

ISOMER 2

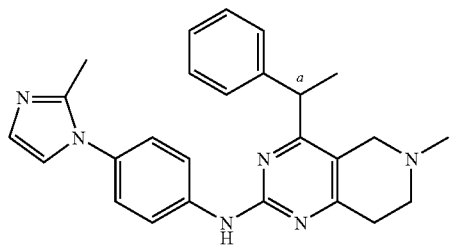

a = unknown absolute

Chiral separation gave isomer 2 (P2)=(+) optical rotation (PDR-Chiral Detector)

1H NMR (600 MHz, CHLOROFORM-d) δ ppm 1.66 (d, 3 H) 2.35 (s, 3 H) 2.44 (s, 3 H) 2.59-2.68 (m, 1 H) 2.73 (dt, 1 H) 2.81-2.96 (m, 2 H) 3.27 (d, 1 H) 3.58 (d, 1 H) 4.14 (q, 1 H) 6.99 (d, 2 H) 7.14-7.23 (m, 4 H) 7.28 (br. s., 3 H) 7.76 (d, 2 H)

MS (ES+) m/z 425.2 (M+H)+

Example 71a

N-(4-(2-Methyl-1H-imidazol-1-yl)phenyl)-4-(1-phenylethyl)-5,6,7,8-tetrahydropyrido[4,3-d]pyrimidin-2-amine

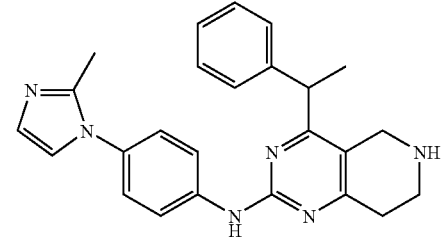

tert-Butyl 2-(4-(2-methyl-1H-imidazol-1-yl)phenylamino)-4-(1-phenylethyl)-7,8-dihydropyrido[4,3-d]pyrimidine-6(5H)-carboxylate (612 mg, 1.20 mmol) was dissolved in methanol (10 mL). Hydrochloric acid (0.098 mL, 1.20 mmol) was added and the reaction mixture was stirred at 75° C. for 1 h. The solvent was evaporated under reduced pressure and the crude N-(4-(2-methyl-1H-imidazol-1-yl)phenyl)-4-(1-phenylethyl)-5,6,7,8-tetrahydropyrido[4,3-d]pyrimidin-2-amine (490 mg, 100%) was used as such in the subsequent step. MS (ES+) m/z 411 (M+H)+

Example 71b tert-Butyl 2-(4-(2-methyl-1H-imidazol-1-yl)phenylamino)-4-(1-phenylethyl)-7,8-dihydropyrido[4,3-d]pyrimidine-6(5H)-carboxylate

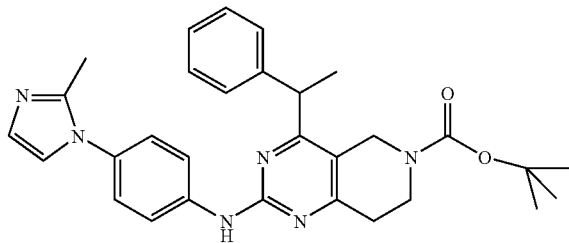

1-(4-(2-Methyl-1H-imidazol-1-yl)phenyl)guanidine (700 mg, 3.25 mmol, example 9e), tert-butyl 4-oxo-3-(2-phenylpropanoyl)piperidine-1-carboxylate (1293 mg, 3.90 mmol) and sodium ethoxide (221 mg, 3.25 mmol) in ethanol (6 mL) were heated to 110° C. in a microwave reactor for 4 h. The solvent was evaporated and the crude was dissolved in ethyl acetate and washed with water. The organic phase was dried under MgSO₄ and the solvent was evaporated under reduced pressure. Purification by flash chromatography using dichloromethane and methanol (0-10%) as eluent gave tert-butyl 2-(4-(2-methyl-1H-imidazol-1-yl)phenylamino)-4-(1-phenylethyl)-7,8-dihydropyrido[4,3-d]pyrimidine-6(5H)-carboxylate (612 mg, 36.9%). MS (ES+) m/z 511 (M+H)+

Example 71c tert-Butyl 4-oxo-3-(2-phenylpropanoyl)piperidine-1-carboxylate

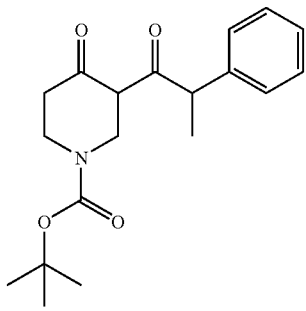

tert-Butyl 4-oxopiperidine-1-carboxylate (2.363 g, 11.86 mmol) was dissolved in toluene (7 mL) and cooled to 0° C. LHMDS (12.45 mL, 12.45 mmol) in THF was added. After 2 min 2-phenylpropanoyl chloride (0.855 mL, 5.93 mmol) was added. After 2 min the cooling bath was removed and after 5 min 1:1 acetic acid:water (3 ml) was added. The water phase was separated after hard stirring and the organic phase was dried with MgSO₄ and the solvent was evaporated. Purification by flash column chromatography (0-25% EtOAc in heptane) yielded tert-butyl 4-oxo-3-(2-phenylpropanoyl)piperidine-1-carboxylate (1.319 g, 67.1%). MS (ES−) m/z 330.1 (M−H)−

Example 72

(S)-(1-(6-Methyl-2-(4-(2-methyl-1H-imidazol-1-yl)phenylamino)-5,6,7,8-tetrahydropyrido[4,3-d]pyrimidin-4-yl)indolin-2-yl)methanol

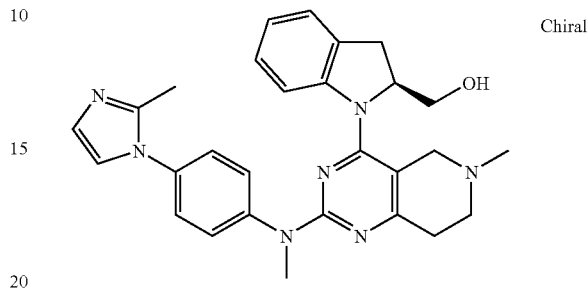

(S)-(1-(2-(4-(2-Methyl-1H-imidazol-1-yl)phenylamino)-5,6,7,8-tetrahydropyrido[4,3-d]pyrimidin-4-yl)indolin-2-yl)methanol (49 mg, 0.11 mmol) was dissolved in methanol (3 mL). Acetic acid (6.18 µL, 0.11 mmol) was added followed by formaldehyde (0.016 mL, 0.22 mmol). The reaction mixture was allowed to stirred at room temperature for 15 minutes and sodium cyanoborohydride (13.58 mg, 0.22 mmol) was added. After 1 h the solvent was evaporated and the crude dissolved in few drops of methanol, filtered and purified by preparative HPLC to give (S)-(1-(6-methyl-2-(methyl(4-(2-methyl-1H-imidazol-1-yl)phenyl)amino)-5,6,7,8-tetrahydropyrido[4,3-d]pyrimidin-4-yl)indolin-2-yl)methanol (14.80 mg, 26.2%) and (S)-(1-(6-methyl-2-(4-(2-methyl-1H-imidazol-1-yl)phenylamino)-5,6,7,8-tetrahydropyrido[4,3-d]pyrimidin-4-yl)indolin-2-yl)methanol (4.60 mg, 8.07%) were obtained as acetate salt.

MS (ES+) m/z 482.2 (M+H)+

1H NMR (600 MHz, CHLOROFORM-d) δ ppm 2.38 (s, 3 H) 2.50 (s, 3 H) 2.78 (d, 2 H) 2.85-2.92 (m, 6 H) 3.26 (dd, 1 H) 3.33 (s, 2 H) 3.82-3.90 (m, 1 H) 4.56-4.62 (m, 2 H) 6.48 (d, 1 H) 6.70 (t, 1 H) 6.99 (s, 1 H) 7.05 (d, 1 H) 7.08 (d, 1 H) 7.11 (t, 1 H) 7.22 (m, 2H) 7.75 (m, 2 H)

Example 72a (S)-(1-(2-(4-(2-Methyl-1H-imidazol-1-yl)phenylamino)-5,6,7,8-tetrahydropyrido[4,3-d]pyrimidin-4-yl)indolin-2-yl)methanol

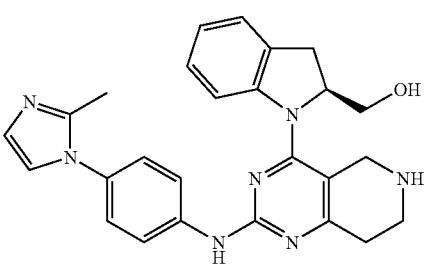

(S)-tert-Butyl 4-(2-(hydroxymethyl)indolin-1-yl)-2-(4-(2-methyl-1H-imidazol-1-yl)phenylamino)-7,8-dihydropyrido[4,3-d]pyrimidine-6(5H)-carboxylate (65.3 mg, 0.12 mmol) was dissolved in methanol (3 mL). Hydrochloric acid (9.69 μL, 0.12 mmol) was added and the reaction mixture was stirred at 75° C. for 1 h. The solvent was evaporated under reduced pressure and the crude was used as such in the subsequent step. MS (ES+) m/z 454.3 (M+H)+

Example 72b (S)-tert-Butyl 4-(2-(hydroxymethyl)indolin-1-yl)-2-(4-(2-methyl-1H-imidazol-1-yl)phenylamino)-7,8-dihydropyrido[4,3-d]pyrimidine-6(5H)-carboxylate

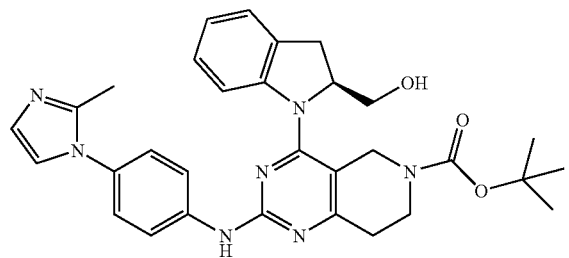

tert-Butyl 2-(4-(2-methyl-1H-imidazol-1-yl)phenylamino)-4-(trifluoromethylsulfonyloxy)-7,8-dihydropyrido[4,3-d]pyrimidine-6(5H)-carboxylate (250 mg, 0.45 mmol, example 69c) was dissolved in DMF (2 mL). (S)-indolin-2-ylmethanol (67.3 mg, 0.45 mmol) was added and the reaction mixture was heated at 85° C. overnight. The reaction was allowed to reach room temperature, the solvent was evaporated under reduced pressure and the crude was purified by flash column chromatography using dichloromethane and methanol as eluent and gave (S)-tert-butyl 4-(2-(hydroxymethyl)indolin-1-yl)-2-(4-(2-methyl-1H-imidazol-1-yl)phenylamino)-7,8-dihydropyrido[4,3-d]pyrimidine-6(5H)-carboxylate (65.3 mg, 26.2%). MS (ES+) m/z 554.4 (M+H)+

Example 73

(S)-6-Methyl-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine

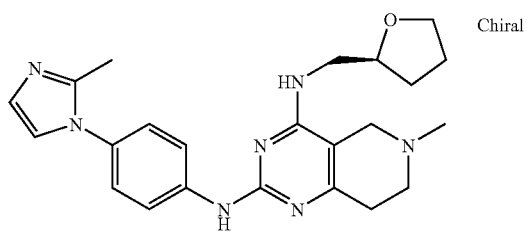

(S)-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine (55 mg, 0.14 mmol) was dissolved in methanol (3 mL). Acetic acid (7.76 μL, 0.14 mmol) was added followed by formaldehyde (10.10 μL, 0.14 mmol) and sodium cyanoborohydride (8.52 mg, 0.14 mmol). The reaction mixture was stirred for 1 h at room temperature and the solvent was evaporated under reduced pressure. The crude was purified by preparative HPLC yielding (S)-6-methyl-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine (19.30 mg, 33.9%). MS (ES+) m/z 417.8 (M−H)−

1H NMR (600 MHz, MeOD) δ ppm 1.64-1.71 (m, 1 H) 1.89-1.97 (m, 2 H) 2.01-2.08 (m, 1 H) 2.60 (s, 3 H) 3.12 (s, 3 H) 3.15 (t, 2 H) 3.61-3.69 (m, 4 H) 3.73-3.78 (m, 1 H) 3.85-3.89 (m, 1 H) 4.13-4.24 (m, 3 H) 7.59 (s, 1 H) 7.60 (d, 2 H) 7.68 (d, 1 H) 7.96 (d, 2 H)

Example 73a (S)-N2-(4-(2-Methyl-1H-imidazol-1-yl)phenyl)-N4-((tetrahydrofuran-2-yl)methyl)-5,6,7,8-tetrahydropyrido[4,3-d]pyrimidine-2,4-diamine

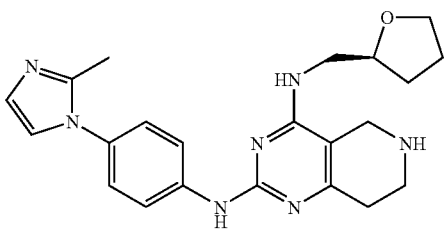

(S)-tert-Butyl 2-(4-(2-methyl-1H-imidazol-1-yl)phenylamino)-4-((tetrahydrofuran-2-yl)methylamino)-7,8-dihydropyrido[4,3-d]pyrimidine-6(5H)-carboxylate (75 mg, 0.15 mmol) was dissolved in methanol (3 mL). Hydrochloric acid (4.51 μL, 0.15 mmol) was added and the reaction mixture was stirred at 75° C. for 1 h. The solvent was evaporated under reduced pressure and the crude (S)-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine (55.0 mg, 91%) was used as such in the subsequent step. MS (ES+) m/z 406.3 (M+H)+

Example 73b (S)-tert-butyl 2-(4-(2-methyl-1H-imidazol-1-yl)phenylamino)-4-((tetrahydrofuran-2-yl)methylamino)-7,8-dihydropyrido[4,3-d]pyrimidine-6(5H)-carboxylate

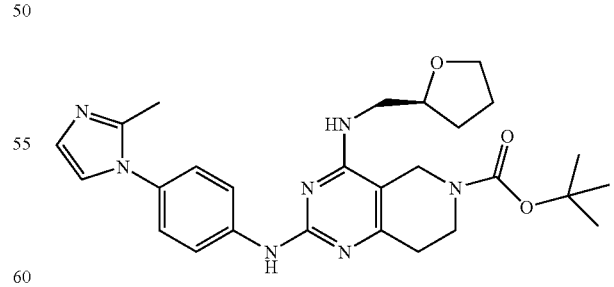

tert-Butyl 2-(4-(2-methyl-1H-imidazol-1-yl)phenylamino)-4-(trifluoromethylsulfonyloxy)-7,8-dihydropyrido[4,3-d]pyrimidine-6(5H)-carboxylate (250 mg, 0.45 mmol, example 69c) was dissolved in DMF (2 mL). (S)-(tetrahydrofuran-2-yl)methanamine (45.6 mg, 0.45 mmol) was added and the reaction mixture was stirred at 85° C. overnight. The solvent was evaporated under reduced pressure and the crude was purified by flash column chromatography using dichloromethane and methanol as eluent. The fractions containing the title compound were pulled together and the solvent was evaporated yielding (S)-tert-butyl 2-(4-(2-methyl-1H-imidazol-1-yl)phenylamino)-4-((tetrahydrofuran-2-yl)methylamino)-7,8-dihydropyrido[4,3-d]pyrimidine-6(5H)-carboxylate (50.0 mg, 21.94%). MS (ES+) m/z 506.4 (M+H)+

Example 74

(R)-6-Methyl-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine

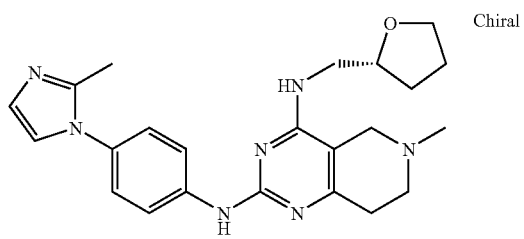

(R)-N2-(4-(2-Methyl-1H-imidazol-1-yl)phenyl)-N4-((tetrahydrofuran-2-yl)methyl)-5,6,7,8-tetrahydropyrido[4,3-d]pyrimidine-2,4-diamine (56 mg, 0.14 mmol) was dissolved in methanol (3 mL). Acetic acid (7.91 µL, 0.14 mmol) was added followed by formaldehyde (10.28 µL, 0.14 mmol) and sodium cyanoborohydride (8.68 mg, 0.14 mmol). The reaction mixture was stirred at room temperature for 1 h and the solvent was evaporated under reduced pressure. The crude was purified by preparative HPLC yielding (R)-6-methyl-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine (18.70 mg, 32.3%).

MS (ES+) m/z 419.9 (M+H)+

1H NMR (600 MHz, MeOD) δ ppm 1.63-1.72 (m, 1 H) 1.89-1.98 (m, 2 H) 2.01-2.07 (m, 1 H) 2.60 (s, 3 H) 3.12 (s, 3 H) 3.14 (t, 2 H) 3.61-3.69 (m, 4 H) 3.73-3.77 (m, 1 H) 3.84-3.90 (m, 1 H) 4.15-4.22 (m, 3 H) 7.59 (d, 2 H) 7.60 (d, 1 H) 7.67 (d, 1 H) 7.96 (d, 2 H)

Example 74a (R)-N2-(4-(2-Methyl-1H-imidazol-1-yl)phenyl)-N4-((tetrahydrofuran-2-yl)methyl)-5,6,7,8-tetrahydropyrido[4,3-d]pyrimidine-2,4-diamine

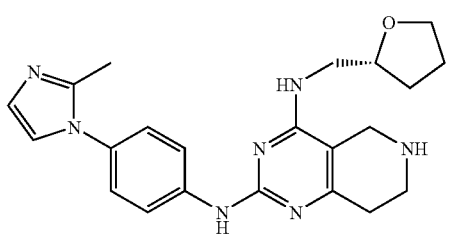

(R)-tert-Butyl 2-(4-(2-methyl-1H-imidazol-1-yl)phenylamino)-4-((tetrahydrofuran-2-yl)methylamino)-7,8-dihydropyrido[4,3-d]pyrimidine-6(5H)-carboxylate (75 mg, 0.15 mmol) was dissolved in methanol (2 mL). Hydrochloric acid (4.51 µL, 0.15 mmol) was added and the reaction mixture was stirred at 75° C. for 30 minutes. The solvent was evaporated under reduced pressure and the crude (R)-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine (56.0 mg, 93%) was used as such in the subsequent step. MS (ES+) m/z 406.3 (M+H)+

Example 74b (R)-tert-Butyl 2-(4-(2-methyl-1H-imidazol-1-yl)phenylamino)-4-((tetrahydrofuran-2-yl)methylamino)-7,8-dihydropyrido[4,3-d]pyrimidine-6(5H)-carboxylate

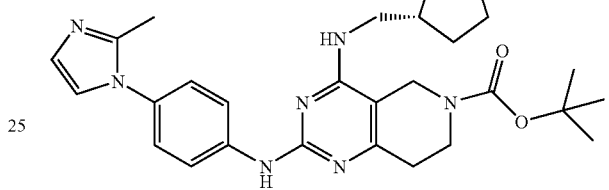

tert-Butyl 2-(4-(2-methyl-1H-imidazol-1-yl)phenylamino)-4-(trifluoromethylsulfonyloxy)-7,8-dihydropyrido[4,3-d]pyrimidine-6(5H)-carboxylate (250 mg, 0.45 mmol, example 69c) was dissolved in DMF (2 mL). (R)-(tetrahydrofuran-2-yl)methanamine (45.6 mg, 0.45 mmol) was added and the reaction mixture was stirred overnight at 85° C. The solvent was evaporated under reduced pressure and the crude crude was purified by flash column chromatography using dichloromethane and methanol as eluent and gave (R)-tert-butyl 2-(4-(2-methyl-1H-imidazol-1-yl)phenylamino)-4-((tetrahydrofuran-2-yl)methylamino)-7,8-dihydropyrido[4,3-d]pyrimidine-6(5H)-carboxylate (75 mg, 33%). MS (ES+) m/z 506.4 (M+H)+

Example 75

2-(4-Benzyl-2-(3-methoxy-4-(4-methyl-1H-imidazol-1-yl)phenylamino)-7,8-dihydropyrido[4,3-d]pyrimidin-6(5H)-yl)ethanol

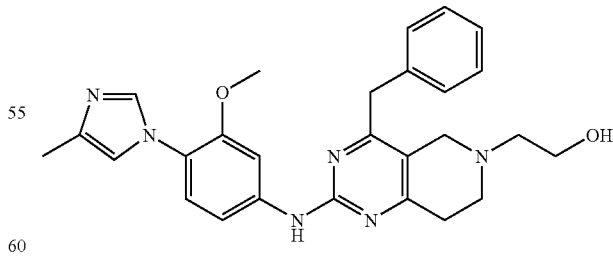

4-Benzyl-N-(3-methoxy-4-(4-methyl-1H-imidazol-1-yl)phenyl)-5,6,7,8-tetrahydropyrido[4,3-d]pyrimidin-2-amine (400 mg, 0.94 mmol, example 106) was dissolved in methanol (10 mL). Acetic acid (0.054 mL, 0.94 mmol) was added followed by glycoaldehyde (56.3 mg, 0.94 mmol). The reaction mixture was stirred at room temperature for 15 minutes and sodium cyanoborohydride (58.9 mg, 0.94 mmol) was added. After 1 h the solvent was evaporated, the crude purified by preparative HPLC yielding 2-(4-benzyl-2-(3-methoxy-4-(4-methyl-1H-imidazol-1-yl)phenylamino)-7,8-dihydropyrido[4,3-d]pyrimidin-6(5H)-yl)ethanol (112 mg, 25.2%). MS (ES+) m/z 471.3 (M+H)+

1H NMR (600 MHz, CHLOROFORM-d) δ ppm 2.31 (s, 3 H) 2.75 (t, 2 H) 2.83-2.89 (m, 2 H) 2.89-2.93 (m, 2 H) 3.59 (s, 2 H) 3.70 (t, 2 H) 3.76 (s, 3 H) 3.97 (s, 2 H) 6.86 (s, 1 H) 7.01 (dd, 1 H) 7.11 (d, 1 H) 7.22-7.25 (m, 3 H) 7.29-7.34 (m, 2 H) 7.64 (s, 1 H) 7.76 (d, 1 H)

Example 76

2-(Benzyl(6-methyl-2-(4-(2-methyl-1H-imidazol-1-yl)phenylamino)-5,6,7,8-tetrahydropyrido[4,3-d]pyrimidin-4-yl)amino)ethanol

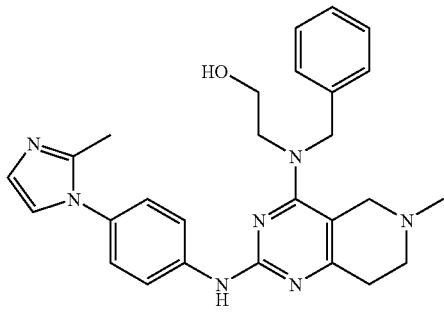

2-(Benzyl(2-(4-(2-methyl-1H-imidazol-1-yl)phenylamino)-5,6,7,8-tetrahydropyrido[4,3-d]pyrimidin-4-yl)amino)ethanol (95 mg, 0.21 mmol) was dissolved in methanol (3 mL). Acetic acid (0.012 mL, 0.21 mmol) was added followed by formaldehyde (0.016 mL, 0.21 mmol). The reaction mixture was stirred at room temperature for 15 minutes and sodium cyanoborohydride (13.10 mg, 0.21 mmol) was added. The solvent was evaporated after 1 h and the crude purified by preparative HPLC yielding 2-(benzyl(6-methyl-2-(4-(2-methyl-1H-imidazol-1-yl)phenylamino)-5,6,7,8-tetrahydropyrido[4,3-d]pyrimidin-4-yl)amino)ethanol (8.60 mg, 7.8%) as acetate salt. MS (ES+) m/z 470.3 (M+H)+

1H NMR (600 MHz, CHLOROFORM-d) δ ppm 2.10 (s, 3 H) 2.42 (d, 6 H) 2.79-2.85 (m, 2 H) 2.96 (t, 2 H) 3.56 (br. s., 2 H) 3.69 (t, 2 H) 3.86 (t, 2 H) 4.76 (s, 2 H) 7.00 (s, 1 H) 7.09 (d, 1 H) 7.17 (m, 2 H) 7.31 (t, 2 H) 7.38 (t, 3 H) 7.67 (m, 2 H)

Example 76a 2-(Benzyl(2-(4-(2-methyl-1H-imidazol-1-yl)phenylamino)-5,6,7,8-tetrahydropyrido[4,3-d]pyrimidin-4-yl)amino)ethanol

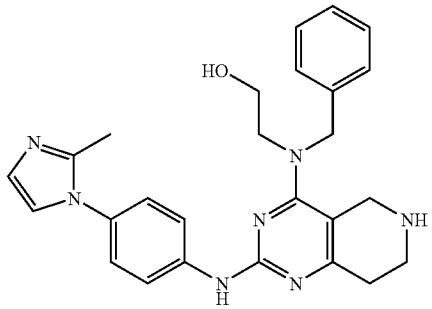

tert-Butyl 4-(benzyl(2-hydroxyethyl)amino)-2-(4-(2-methyl-1H-imidazol-1-yl)phenylamino)-7,8-dihydropyrido[4,3-d]pyrimidine-6(5H)-carboxylate (121 mg, 0.22 mmol) was dissolved methanol (2 mL). Hydrochloric acid (0.018 mL, 0.22 mmol) was added and the reaction was stirred at 75° C. for 1 h. The solvent was evaporated under reduced pressure and the crude 2-(benzyl(2-(4-(2-methyl-1H-imidazol-1-yl)phenylamino)-5,6,7,8-tetrahydropyrido[4,3-d]pyrimidin-4-yl)amino)ethanol (95 mg, 96%) was used as such in the subsequent step. MS (ES+) m/z 456.3 (M+H)+

Example 76b tert-Butyl 4-(benzyl(2-hydroxyethyl)amino)-2-(4-(2-methyl-1H-imidazol-1-yl)phenylamino)-7,8-dihydropyrido[4,3-d]pyrimidine-6(5H)-carboxylate

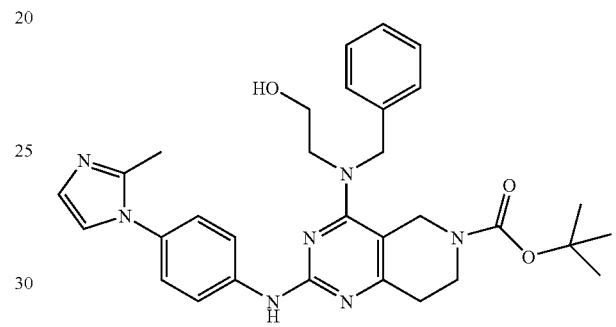

tert-Butyl 2-(4-(2-methyl-1H-imidazol-1-yl)phenylamino)-4-(trifluoromethylsulfonyloxy)-7,8-dihydropyrido[4,3-d]pyrimidine-6(5H)-carboxylate (250 mg, 0.45 mmol, example 69c) was dissolved in DMF (2 mL). 2-(benzylamino)ethanol (68.2 mg, 0.45 mmol) was added and the reaction was stirred at 85° C. overnight. The solvent was evaporated under reduced pressure and the crude was purified by flash column chromatography using dichloromethane and methanol as eluent yielding tert-butyl 4-(benzyl(2-hydroxyethyl)amino)-2-(4-(2-methyl-1H-imidazol-1-yl)phenylamino)-7,8-dihydropyrido[4,3-d]pyrimidine-6(5H)-carboxylate (121 mg, 48.3%). MS (ES-) m/z 554 (M-H)-

Example 77

2-(4-(Ethyl((tetrahydrofuran-2-yl)methyl)amino)-2-(4-(2-methyl-1H-imidazol-1-yl)phenylamino)-7,8-dihydropyrido[4,3-d]pyrimidin-6(5H)-yl)ethanol

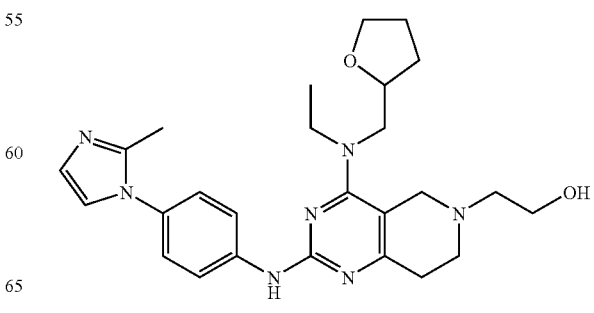

N4-Ethyl-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine (95 mg, 0.22 mmol) was dissolved in methanol (3 mL). Acetic acid (0.013 mL, 0.22 mmol) was added followed by glycoaldehyde (13.16 mg, 0.22 mmol). The reaction was stirred at room temperature for 15 minutes and sodium cyanoborohydride (13.77 mg, 0.22 mmol) was added. The reaction was stirred for 1 h, the solvent was evaporated under reduced pressure, the crude redissolved in methanol, filtered and purified twice by preparative HPLC yielding 2-(4-(ethyl((tetrahydrofuran-2-yl)methyl)amino)-2-(4-(2-methyl-1H-imidazol-1-yl)phenylamino)-7,8-dihydropyrido[4,3-d]pyrimidin-6(5H)-yl)ethanol (7.10 mg, 6.6%).

MS (ES+) m/z 478.3 (M+H)+

1H NMR (600 MHz, CHLOROFORM-d) δ ppm 1.23 (t, 3 H) 1.48-1.57 (m, 1 H) 1.81-1.96 (m, 2 H) 1.96-2.04 (m, 1 H) 2.36 (s, 3 H) 2.73-2.79 (m, 2 H) 2.83-2.92 (m, 4 H) 3.44 (dd, 1 H) 3.48-3.63 (m, 4 H) 3.68-3.77 (m, 4 H) 3.85-3.90 (m, 1 H) 4.15-4.20 (m, 1 H) 6.99 (s, 1 H) 7.03 (s, 1 H) 7.20 (d, 2 H) 7.71 (d, 2 H)

Example 77a

N4-Ethyl-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine

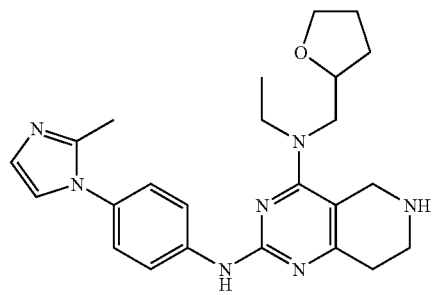

tert-Butyl 4-(ethyl((tetrahydrofuran-2-yl)methyl)amino)-2-(4-(2-methyl-1H-imidazol-1-yl)phenylamino)-7,8-dihydropyrido[4,3-d]pyrimidine-6(5H)-carboxylate (253 mg, 0.47 mmol) was dissolved in methanol (3 mL). Hydrochloric acid (0.017 mL, 0.47 mmol) was added and the reaction mixture was stirred at 80° C. for 1 h. The solvent was evaporated and the crude N4-ethyl-N2-(4-(2-methyl-1H-imidazol-1-yl)phenyl)-N4-((tetrahydrofuran-2-yl)methyl)-5,6,7,8-tetrahydropyrido[4,3-d]pyrimidine-2,4-diamine (190 mg, 92%) was used as such in the next step. MS (ES+) m/z 434.3 (M+H)+

Example 77b tert-Butyl 4-(ethyl((tetrahydrofuran-2-yl)methyl)amino)-2-(4-(2-methyl-1H-imidazol-1-yl)phenylamino)-7,8-dihydropyrido[4,3-d]pyrimidine-6(5H)-carboxylate

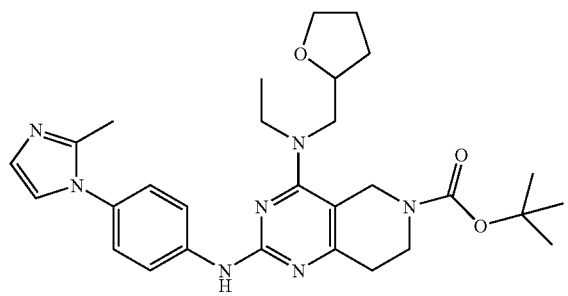

tert-Butyl 2-(4-(2-methyl-1H-imidazol-1-yl)phenylamino)-4-(trifluoromethylsulfonyloxy)-7,8-dihydropyrido[4,3-d]pyrimidine-6(5H)-carboxylate (250 mg, 0.45 mmol, example 69c) was dissolved in DMF (2 mL). N-((tetrahydrofuran-2-yl)methyl)ethanamine (58.2 mg, 0.45 mmol) was added and the reaction mixture was stirred at 85° C. overnight. The reaction was allowed to reach room temperature, the solvent was evaporated under reduced pressure and the crude was used as such in the subsequent step. MS (ES+) m/z 534.4 (M+H)+

Example 78

3-(Cyclopropyl(6-methyl-2-(4-(2-methyl-1H-imidazol-1-yl)phenylamino)-5,6,7,8-tetrahydropyrido[4,3-d]pyrimidin-4-yl)amino)propanenitrile

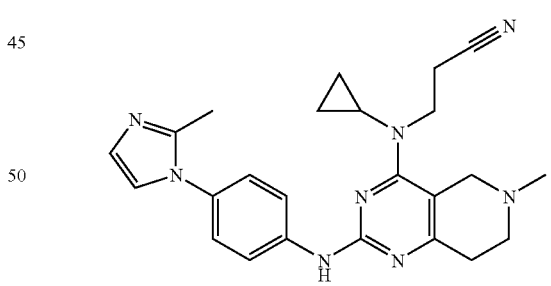

3-(Cyclopropyl(2-(4-(2-methyl-1H-imidazol-1-yl)phenylamino)-5,6,7,8-tetrahydropyrido[4,3-d]pyrimidin-4-yl)amino)propanenitrile (94 mg, 0.23 mmol) was dissolved in methanol (2 mL). Acetic acid (0.013 mL, 0.23 mmol) was added followed by formaldehyde (0.017 mL, 0.23 mmol). The reaction mixture was stirred at room s temperature for 15 minutes and sodium cyanoborohydride (14.25 mg, 0.23 mmol) was added. The reaction mixture was concentrated under reduced pressure, filtered and purified by preparative HPLC (acidic system) yielding 3-(cyclopropyl(6-methyl-2-(4-(2-methyl-1H-imidazol-1-yl)phenylamino)-5,6,7,8-tetrahydropyrido[4,3-d]pyrimidin-4-yl)amino)propanenitrile (3.50 mg, 3.16%) as acetate salt.

MS (ES+) m/z 429.3 (M+H)+

1H NMR (600 MHz, CHLOROFORM-d) δ ppm 0.68-0.74 (m, 2 H) 0.88-0.95 (m, 2 H) 2.36 (s, 3 H) 2.49 (s, 3 H) 2.71 (t, 2 H) 2.75-2.81 (m, 2 H) 2.89 (t, 2 H) 3.05-3.14 (m, 1 H) 3.64 (s, 2 H) 3.91 (t, 2 H) 6.98 (d, 1 H) 7.03 (d, 1 H) 7.21 (m, 2 H) 7.67 (m, 2 H)

Example 78a 3-(Cyclopropyl(2-(4-(2-methyl-1H-imidazol-1-yl)phenylamino)-5,6,7,8-tetrahydropyrido[4,3-d]pyrimidin-4-yl)amino)propanenitrile

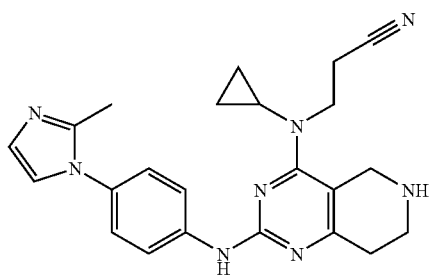

tert-Butyl 4-((2-cyanoethyl)(cyclopropyl)amino)-2-(4-(2-methyl-1H-imidazol-1-yl)phenylamino)-7,8-dihydropyrido[4,3-d]pyrimidine-6(5H)-carboxylate (240 mg, 0.47 mmol) was dissolved in methanol (5 mL). Hydrochloric acid (0.014 mL, 0.47 mmol) was added and the reaction mixture was stirred at 80° C. for 1 h. The solvent was evaporated under reduced pressure and the crude 3-(cyclopropyl(2-(4-(2-methyl-1H-imidazol-1-yl)phenylamino)-5,6,7,8-tetrahydropyrido[4,3-d]pyrimidin-4-yl)amino)propanenitrile (189 mg, 98%) was used as such in the subsequent step. MS (ES+) m/z 415.0 (M+H)+

1H NMR (400 MHz, CHLOROFORM-d) δ ppm 0.68-0.75 (m, 2 H) 0.91-0.97 (m, 2 H) 2.39 (s, 3 H) 2.75 (t, 2 H) 2.91 (t, 2 H) 3.11 (d, 1 H) 3.29-3.35 (m, 2 H) 3.92 (t, 2 H) 4.20 (s, 2 H) 6.99 (d, 1 H) 7.05 (d, 1 H) 7.19-7.24 (m, 2 H) 7.64-7.69 (m, 2 H)

Example 78b tert-Butyl 4-((2-cyanoethyl)(cyclopropyl)amino)-2-(4-(2-methyl-1H-imidazol-1-yl)phenylamino)-7,8-dihydropyrido[4,3-d]pyrimidine-6(5H)-carboxylate

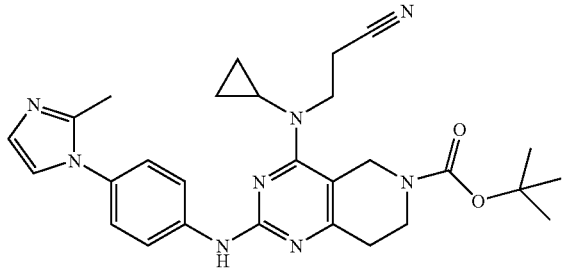

tert-Butyl 2-(4-(2-methyl-1H-imidazol-1-yl)phenylamino)-4-(trifluoromethylsulfonyloxy)-7,8-dihydropyrido[4,3-d]pyrimidine-6(5H)-carboxylate (250 mg, 0.45 mmol, example 69c) was dissolved in DMF (2 mL). 3-(cyclopropylamino)propanenitrile (49.7 mg, 0.45 mmol) was added and the reaction mixture was stirred at 85° C. overnight. The mixture was allowed to reach room temperature and the solvent was evaporated under reduced pressure. The crude tert-butyl 4-((2-cyanoethyl)(cyclopropyl)amino)-2-(4-(2-methyl-1H-imidazol-1-yl)phenylamino)-7,8-dihydropyrido[4,3-d]pyrimidine-6 (5H)-carboxylate (241 mg, 104%) was used as such in the subsequent step.

Example 79

6-Methyl-N2-(4-(2-methyl-1H-imidazol-1-yl)phenyl)-N4-((tetrahydro-2H-pyran-4-yl)methyl)-5,6,7,8-tetrahydropyrido[4,3-d]pyrimidine-2,4-diamine

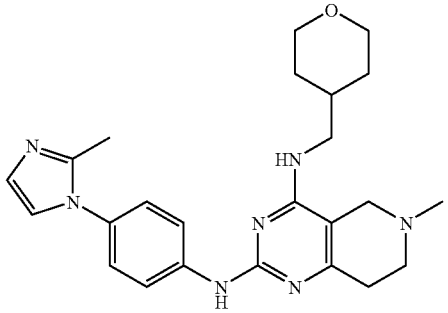

N2-(4-(2-Methyl-1H-imidazol-1-yl)phenyl)-N4-((tetrahydro-2H-pyran-4-yl)methyl)-5,6,7,8-tetrahydropyrido[4,3-d]pyrimidine-2,4-diamine (49 mg, 0.12 mmol) was dissolved in methanol (3 mL). Acetic acid (6.69 µL, 0.12 mmol) was added followed by formaldehyde (8.70 µL, 0.12 mmol). The reaction mixture was stirred at room temperature for 15 minutes and sodium cyanoborohydride (7.34 mg, 0.12 mmol) was added. After 1 h the solvent was evaporated under reduced pressure, the crude purified twice by preparative HPLC (acidic system) yielding 6-methyl-N2-(4-(2-methyl-1H-imidazol-1-yl)phenyl)-N4-((tetrahydro-2H-pyran-4-yl)methyl)-5,6,7,8-tetrahydropyrido[4,3-d]pyrimidine-2,4-diamine (16.40 mg, 32.4%). MS (ES+) m/z 434.3 (M+H)+

1H NMR (600 MHz, Acetone) δ ppm 1.26-1.34 (m, 3 H) 1.72 (d, 2 H) 2.07-2.09 (m, 1 H) 2.67 (s, 3 H) 3.02 (s, 3 H) 3.13 (t, 2 H) 3.23-3.31 (m, 2 H) 3.52-3.62 (m, 4 H) 3.84 (dd, 2 H) 4.20 (br. s., 2 H) 7.57 (s, 1 H) 7.66 (s, 1 H) 7.70 (m, 2 H) 8.06 (m, 2 H)

Example 79a

N2-(4-(2-Methyl-1H-imidazol-1-yl)phenyl)-N4-((tetrahydro-2H-pyran-4-yl)methyl)-5,6,7,8-tetrahydropyrido[4,3-d]pyrimidine-2,4-diamine

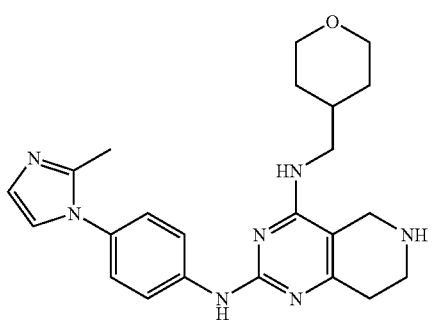

tert-Butyl 2-(4-(2-methyl-1H-imidazol-1-yl)phenylamino)-4-((tetrahydro-2H-pyran-4-yl)methylamino)-7,8-dihydropyrido[4,3-d]pyrimidine-6(5H)-carboxylate (62 mg, 0.12 mmol) was dissolved in methanol (3 mL). Hydrochloric acid (3.63 µL, 0.12 mmol) was added and the reaction mixture was stirred at 80° C. for 1 h. The solvent was evaporated under reduced pressure and the crude N2-(4-(2-methyl-1H-imidazol-1-yl)phenyl)-N4-((tetrahydro-2H-pyran-4-yl)methyl)-5,6,7,8-tetrahydropyrido[4,3-d]pyrimidine-2,4-diamine (49.0 mg, 98%) was used as such in the subsequent step. MS (ES+) m/z 420.3 (M+H)+

Example 79b tert-Butyl 2-(4-(2-methyl-1H-imidazol-1-yl)phenylamino)-4-((tetrahydro-2H-pyran-4-yl)methylamino)-7,8-dihydropyrido[4,3-d]pyrimidine-6(5H)-carboxylate

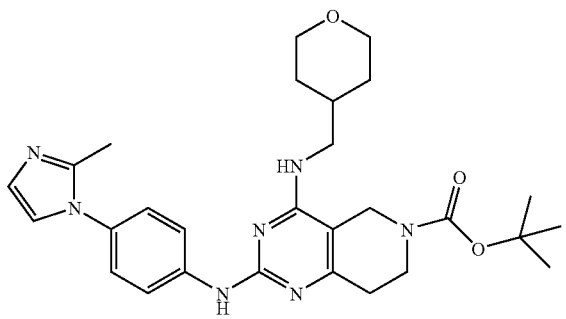

tert-Butyl 2-(4-(2-methyl-1H-imidazol-1-yl)phenylamino)-4-(trifluoromethylsulfonyloxy)-7,8-dihydropyrido[4,3-d]pyrimidine-6(5H)-carboxylate (250 mg, 0.45 mmol, example 69c) was dissolved in DMF (2 mL). 4-Aminomethyltetrahydropyran (51.9 mg, 0.45 mmol) was added and the reaction mixture was stirred at 85° C. overnight. The reaction was allowed to reach room temperature and the solvent was evaporated under reduced pressure. The crude was purified by flash column chromatography using dichloromethane and methanol as eluent yielding tert-butyl 2-(4-(2-methyl-1H-imidazol-1-yl)phenylamino)-4-((tetrahydro-2H-pyran-4-yl)methylamino)-7,8-dihydropyrido[4,3-d]pyrimidine-6(5H)-carboxylate (62.0 mg, 26.5%). MS (ES+) m/z 520.4 (M+H)+

1H NMR (400 MHz, CHLOROFORM-d) δ ppm 1.52 (s, 9 H) 2.40 (s, 3 H) 2.74 (t, 2 H) 3.23 (t, 2 H) 3.36-3.42 (m, 4 H) 3.69-3.73 (m, 2 H) 3.97-4.04 (m, 5 H) 4.22 (br. s., 2 H) 7.01 (d, 1 H) 7.06 (d, 1 H) 7.20 (s, 1 H) 7.22 (s, 1 H) 7.77 (d, 2 H) 8.23 (d, 1 H)

Example 80

(R)-2-(2-(4-(Oxazol-5-yl)phenylamino)-4-((tetrahydrofuran-2-yl)methylamino)-7,8-dihydropyrido[4,3-d]pyrimidin-6(5H)-yl)ethanol

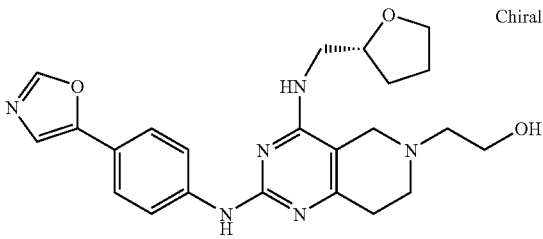

(R)-N2-(4-(Oxazol-5-yl)phenyl)-N4-((tetrahydrofuran-2-yl)methyl)-5,6,7,8-tetrahydropyrido[4,3-d]pyrimidine-2,4-diamine (135 mg, 0.34 mmol) was dissolved in methanol (3 mL). Acetic acid (0.020 mL, 0.34 mmol) was added followed by (R)-N2-(4-(oxazol-5-yl)phenyl)-N4-((tetrahydrofuran-2-yl)methyl)-5,6,7,8-tetrahydropyrido[4,3-d]pyrimidine-2,4-diamine (135 mg, 0.34 mmol). The reaction mixture was stirred at room temperature for 15 minutes and sodium cyanoborohydride (21.62 mg, 0.34 mmol) (MP—CNBH$_3$) was added and the reaction was stirred overnight. The crude was filtered, concentrated under reduced pressure, dissolved in methanol, filtered and purified by preparative HPLC yielding (R)-2-(2-(4-(oxazol-5-yl)phenylamino)-4-((tetrahydrofuran-2-yl)methylamino)-7,8-dihydropyrido[4,3-d]pyrimidin-6(5H)-yl)ethanol (31.0 mg, 18.15%) as acetate salt. MS (ES+) m/z 437.3 (M+H)+;

¹H NMR (400 MHz, CHLOROFORM-d) δ ppm 1.59-1.69 (m, 1 H) 1.90-2.02 (m, 2 H) 2.03-2.10 (m, 1 H) 2.13 (s, 3 H) 2.74-2.87 (m, 6 H) 3.36 (m, 2 H) 3.38-3.47 (m, 1 H) 3.71-3.77 (m, 2 H) 3.78-3.95 (m, 3 H) 4.10-4.20 (m, 1 H) 5.12 (t, 1 H) 7.55-7.61 (m, 2 H) 7.72-7.79 (m, 2 H) 7.89 (s, 1 H) 9.77 (br. s., 1 H)

Example 80a (R)-N2-(4-(Oxazol-5-yl)phenyl)-N4-((tetrahydrofuran-2-yl)methyl)-5,6,7,8-tetrahydropyrido[4,3-d]pyrimidine-2,4-diamine

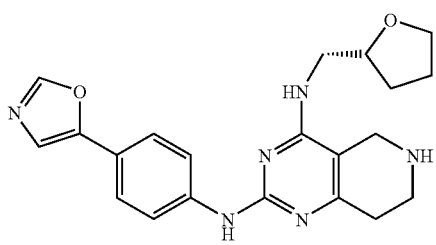

(R)-tert-Butyl 2-(4-(oxazol-5-yl)phenylamino)-4-((tetrahydrofuran-2-yl)methylamino)-7,8-dihydropyrido[4,3-d]pyrimidine-6(5H)-carboxylate (323 mg, 0.66 mmol) was dissolved in methanol (3 mL). Hydrochloric acid (0.020 mL, 0.66 mmol) was added and the reaction mixture was stirred at 80° C. for 1 h. The solvent was evaporated under reduced pressure and the crude was used as such in the subsequent step. MS (ES+) m/z 393.3 (M+H)+

Example 80b (R)-tert-Butyl 2-(4-(oxazol-5-yl)phenylamino)-4-((tetrahydrofuran-2-yl)methylamino)-7,8-dihydropyrido[4,3]pyrimidine-6(5H)-carboxylate

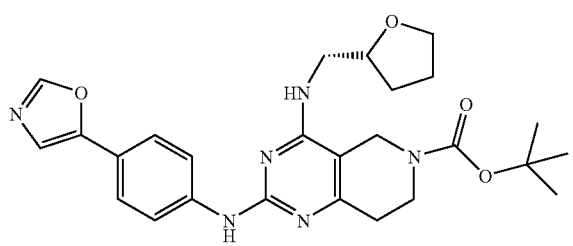

tert-Butyl 2-(4-(oxazol-5-yl)phenylamino)-4-(trifluoromethylsulfonyloxy)-7,8-dihydropyrido[4,3-d]pyrimidine-6(5H)-carboxylate (350 mg, 0.65 mmol, example 1b) was dissolved in DMF (2 mL). (R)-(−)-Tetrahydrofurfurylamine (0.067 mL, 0.65 mmol) was added and the reaction mixture was stirred at 80° C. for 6 h. The solvent was evaporated under reduced pressure and the crude was used as such in the next step. MS (ES+) m/z 493.3 (M+H)+

Example 81

2-(4-(Ethyl((tetrahydrofuran-2-yl)methyl)amino)-2-(4-(oxazol-5-yl)phenylamino)-7,8-dihydropyrido[4,3-d]pyrimidin-6(5H)-yl)ethanol

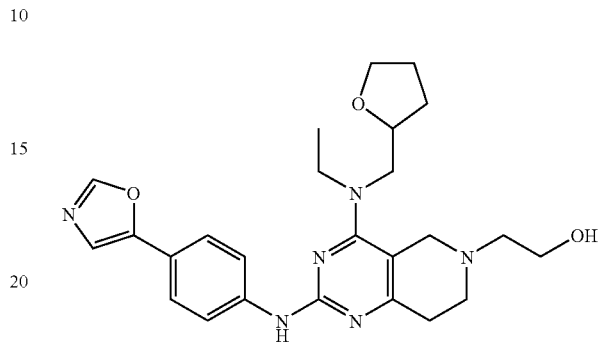

N4-Ethyl-N2-(4-(oxazol-5-yl)phenyl)-N4-((tetrahydrofuran-2-yl)methyl)-5,6,7,8-tetrahydropyrido[4,3-d]pyrimidine-2,4-diamine (125 mg, 0.30 mmol) was dissolved in methanol (3 mL). Acetic acid (0.017 mL, 0.30 mmol) was added followed by glycoaldehyde (17.85 mg, 0.30 mmol). The reaction mixture was stirred for 15 minutes at room temperature and sodium cyanoborohydride (18.68 mg, 0.30 mmol) (MP—CNBH$_3$) was added. The reaction was stirred overnight at room temperature, the MP—CNBH$_3$ was filtered off, the solvent was evaporated under reduced pressure and the crude was purified by preparative HPLC yielding 2-(4-(ethyl((tetrahydrofuran-2-yl)methyl)amino)-2-(4-(oxazol-5-yl)phenylamino)-7,8-dihydropyrido[4,3-d]pyrimidin-6(5H)-yl)ethanol (54.0 mg, 34.6%) as acetate salt. MS (ES+) m/z 465.3 (M+H)+

1H NMR (400 MHz, CHLOROFORM-d) δ ppm 1.25 (t, 3 H) 1.46-1.61 (m, 1 H) 1.80-1.97 (m, 2 H) 1.98-2.08 (m, 1 H) 2.10 (s, 3 H) 2.69-2.79 (m, 2 H) 2.82-2.94 (m, 4 H) 3.38 (dd, 1 H) 3.50-3.79 (m, 7 H) 3.79-3.92 (m, 2 H) 4.13-4.25 (m, 1 H) 7.27 (s, 1 H) 7.57 (m, 2 H) 7.71 (m, 2 H) 7.89 (s, 1 H) 10.19 (br. s., 1 H)

Example 81a

N4-Ethyl-N2-(4-(oxazol-5-yl)phenyl)-N4-((tetrahydrofuran-2-yl)methyl)-5,6,7,8-tetrahydropyrido[4,3-d]pyrimidine-2,4-diamine

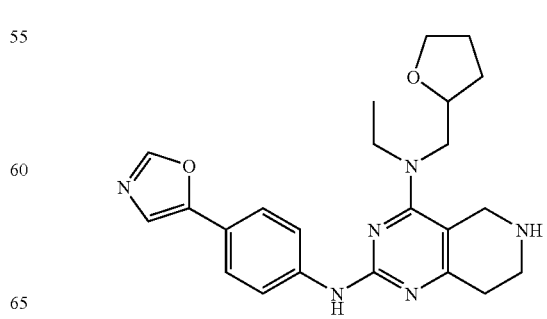

tert-Butyl 4-(ethyl((tetrahydrofuran-2-yl)methyl)amino)-2-(4-(oxazol-5-yl)phenylamino)-7,8-dihydropyrido[4,3-d]pyrimidine-6(5H)-carboxylate (320 mg, 0.61 mmol) was dissolved in methanol (5 mL). Hydrochloric acid (0.019 mL, 0.61 mmol) was added and the reaction mixture was stirred at 80° C. for 1 h. The solvent was evaporated under reduced pressure and the crude was used as such in the subsequent step. MS (ES+) m/z 421.0 (M+H)+

Example 81b tert-Butyl 4-(ethyl((tetrahydrofuran-2-yl)methyl)amino)-2-(4-(oxazol-5-yl)phenylamino)-7,8-dihydropyrido[4,3-d]pyrimidine-6(5H)-carboxylate

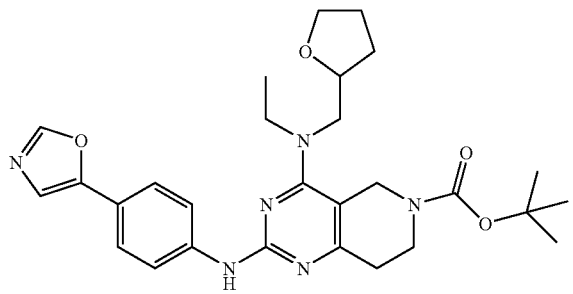

tert-Butyl 2-(4-(oxazol-5-yl)phenylamino)-4-(trifluoromethylsulfonyloxy)-7,8-dihydropyrido[4,3-d]pyrimidine-6(5H)-carboxylate (350 mg, 0.65 mmol, example 1b) was dissolved in DMF (2 mL). N-((tetrahydrofuran-2-yl)methyl) ethanamine (84 mg, 0.65 mmol) was added and the reaction was stirred at 80° C. overnight. The solvent was evaporated under reduced pressure and the crude was used as such in the subsequent step.
MS (ES+) m/z 521.1 (M+H)+

Example 82

N4-Ethyl-6-methyl-N2-(4-(oxazol-5-yl)phenyl)-N4-((tetrahydrofuran-2-yl)methyl)-5,6,7,8-tetrahydropyrido[4,3-d]pyrimidine-2,4-diamine

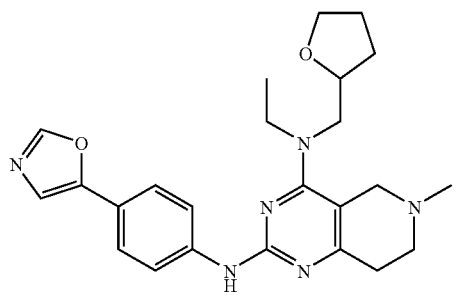

N4-Ethyl-N2-(4-(oxazol-5-yl)phenyl)-N4-((tetrahydrofuran-2-yl)methyl)-5,6,7,8-tetrahydropyrido[4,3-d]pyrimidine-2,4-diamine (125 mg, 0.30 mmol, example 81a) was dissolved in methanol (3 mL). Acetic acid (0.017 mL, 0.30 mmol) was added followed by formaldehyde (0.022 mL, 0.30 mmol). The reaction was stirred at room temperature for 15 minutes and sodium cyanoborohydride (18.7 mg, 0.30 mmol) (MP—CNBH₃) was added. The reaction was stirred overnight at room temperature. The MP—CNBH₃ was filtered, the solvent evaporated under reduced pressure, the crude dissolved in methanol and purified by preparative HPLC N4-ethyl-6-methyl-N2-(4-(oxazol-5-yl)phenyl)-N4-((tetrahydrofuran-2-yl)methyl)-5,6,7,8-tetrahydropyrido[4,3-d]pyrimidine-2,4-diamine (29.8 mg, 21.04%) as acetate salt. MS (ES+) m/z 435.2 (M+H)+

1H NMR (400 MHz, CHLOROFORM-d) δ ppm 1.24 (t, 3 H) 1.46-1.61 (m, 1 H) 1.80-1.97 (m, 2 H) 1.97-2.08 (m, 1 H) 2.11 (s, 3 H) 2.49 (s, 3 H) 2.66-2.80 (m, 2 H) 2.88 (t, 2 H) 3.35-3.50 (m, 3 H) 3.59 (tt, 2 H) 3.71-3.94 (m, 3 H) 4.11-4.24 (m, 1 H) 7.28 (s, 1 H) 7.58 (m, 2 H) 7.71 (m, 2 H) 7.90 (s, 1 H) 9.51 (br. s., 1 H)

Example 83

(S)-6-Methyl-N2-(4-(oxazol-5-yl)phenyl)-N4-((tetrahydrofuran-2-yl)methyl)-5,6,7,8-tetrahydropyrido[4,3-d]pyrimidine-2,4-diamine

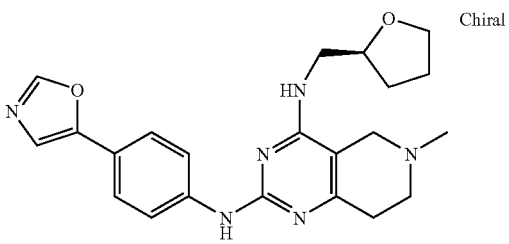

(S)-N2-(4-(Oxazol-5-yl)phenyl)-N4-((tetrahydrofuran-2-yl)methyl)-5,6,7,8-tetrahydropyrido[4,3-d]pyrimidine-2,4-diamine (120 mg, 0.31 mmol) was dissolved in methanol (3 mL). Acetic acid (0.018 mL, 0.31 mmol) was added followed by formaldehyde (0.023 mL, 0.31 mmol). The reaction mixture was stirred at room temperature for 15 minutes and sodium cyanoborohydride (19.22 mg, 0.31 mmol) MP—CNBH₃ was added. The reaction was stirred at room temperature overnight, MP—CNBH₃ was filtered off and the solvent was evaporated under reduced pressure. Purification by HPLC gave (S)-6-methyl-N2-(4-(oxazol-5-yl)phenyl)-N4-((tetrahydrofuran-2-yl)methyl)-5,6,7,8-tetrahydropyrido[4,3-d]pyrimidine-2,4-diamine (67.0 mg, 48%). MS (ES+) m/z 407.2 (M+H)+

1H NMR (400 MHz, CHLOROFORM-d) δ ppm 1.58-1.71 (m, 1 H) 1.90-2.08 (m, 2 H) 2.52 (s, 3 H) 2.72-2.86 (m, 4 H) 3.27 (s, 2 H) 3.45 (ddd, 1 H) 3.76-3.97 (m, 3 H) 4.15 (qd, 1 H) 5.19 (t, 1 H) 7.27 (s, 1 H) 7.58 (m, 2 H) 7.77 (m, 2 H) 7.89 (s, 1 H) 10.59 (br. s., 1 H)

Example 83a (S)-N2-(4-(Oxazol-5-yl)phenyl)-N4-((tetrahydrofuran-2-yl)methyl)-5,6,7,8-tetrahydropyrido[4,3-d]pyrimidine-2,4-diamine

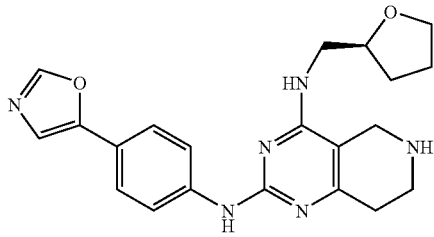

(S)-tert-Butyl 2-(4-(oxazol-5-yl)phenylamino)-4-((tetrahydrofuran-2-yl)methylamino)-7,8-dihydropyrido[4,3-d]pyrimidine-6(5H)-carboxylate was dissolved in methanol (3 mL). Hydrochloric acid was added and the reaction mixture was stirred at 75° C. for 1 h. The solvent was evaporated under reduced pressure and the crude was used as such in the next step. MS (ES+) m/z 393.2 (M+H)+

1H NMR (400 MHz, CHLOROFORM-d) δ ppm 1.58-1.70 (m, 1 H) 1.96 (qd, 2 H) 2.02-2.10 (m, 2 H) 2.11 (s, 3 H) 2.69 (t, 2 H) 3.15 (t, 2 H) 3.46 (ddd, 1 H) 3.67 (d, 2 H) 3.77-3.95 (m, 4 H) 4.14 (qd, 2 H) 5.04 (t, 1 H) 7.59 (m, 2 H) 7.77 (m, 2 H) 7.89 (s, 1 H) 9.89 (br. s., 1 H)

Example 83b (S)-tert-Butyl 2-(4-(oxazol-5-yl)phenylamino)-4-((tetrahydrofuran-2-yl)methylamino)-7,8-dihydropyrido[4,3-d]pyrimidine-6(5H)-carboxylate

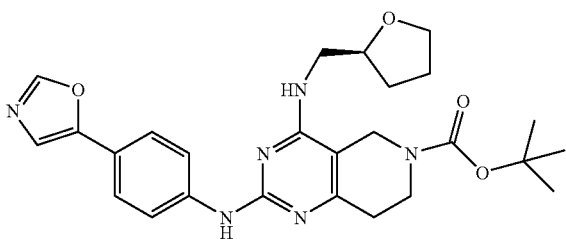

tert-Butyl 2-(4-(oxazol-5-yl)phenylamino)-4-(trifluoromethylsulfonyloxy)-7,8-dihydropyrido[4,3-d]pyrimidine-6(5H)-carboxylate (350 mg, 0.65 mmol, example 1b) was dissolved in DMF (2 mL). (S)-(tetrahydrofuran-2-yl)methanamine was added and the reaction mixture was stirred at 80° C. for 3 h. The solvent was evaporated under reduced pressure and the crude used in the subsequent step without purification. MS (ES+) m/z 493.3 (M+H)+

Example 84

(R)-6-Methyl-N2-(4-(oxazol-5-yl)phenyl)-N4-((tetrahydrofuran-2-yl)methyl)-5,6,7,8-tetrahydropyrido[4,3-d]pyrimidine-2,4-diamine

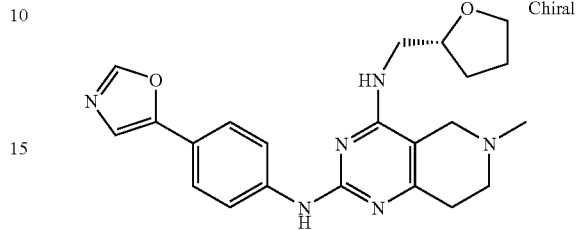

(R)-N2-(4-(Oxazol-5-yl)phenyl)-N4-((tetrahydrofuran-2-yl)methyl)-5,6,7,8-tetrahydropyrido[4,3-d]pyrimidine-2,4-diamine (135 mg, 0.34 mmol, example 80a) was dissolved in methanol (3 mL). Acetic acid (0.020 mL, 0.34 mmol) was added followed by formaldehyde (0.026 mL, 0.34 mmol). The reaction mixture was stirred at room temperature for 15 minutes and sodium cyanoborohydride (21.62 mg, 0.34 mmol) MP—CNBH$_3$ was added. The reaction was stirred overnight, the MP—CNBH$_3$ was filtered off and the solvent was evaporated under reduced pressure. The crude was dissolved in methanol, filtered and purified by HPLC yielding (R)-6-methyl-N2-(4-(oxazol-5-yl)phenyl)-N4-((tetrahydrofuran-2-yl)methyl)-5,6,7,8-tetrahydropyrido[4,3-d]pyrimidine-2,4-diamine (46.0 mg, 30.3%). MS (ES+) m/z 407.2 (M+H)+

1H NMR (400 MHz, CHLOROFORM-d) δ ppm 1.65 (dq 1 H) 1.91-2.00 (m, 2 H) 2.02-2.10 (m, 1 H) 2.52 (s, 3 H) 2.73-2.80 (m, 3 H) 3.25 (d, 2 H) 3.45 (ddd, 1 H) 3.77-3.95 (m, 4 H) 4.10-4.18 (m, 1 H) 5.01 (t, 1 H) 7.27 (s, 1 H) 7.56-7.61 (m, 2 H) 7.73-7.77 (m, 2 H) 7.89 (s, 1 H) 9.40 (br. s., 1 H)

Example 85

6-Methyl-N2-(4-(oxazol-5-yl)phenyl)-N4-((tetrahydro-2H-pyran-4-yl)methyl)-5,6,7,8-tetrahydropyrido[4,3-d]pyrimidine-2,4-diamine

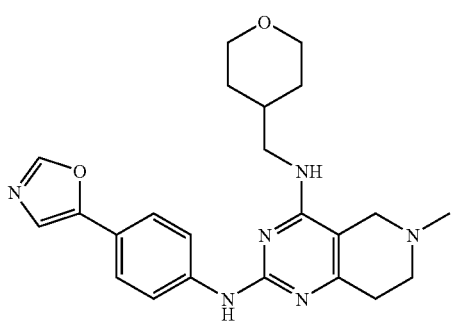

N2-(4-(Oxazol-5-yl)phenyl)-N4-((tetrahydro-2H-pyran-4-yl)methyl)-5,6,7,8-tetrahydropyrido[4,3-d]pyrimidine-2,4-diamine (134 mg, 0.33 mmol) was dissolved in methanol (3 mL). Acetic acid (0.019 mL, 0.33 mmol) was added followed by formaldehyde (0.025 mL, 0.33 mmol). The reaction mixture was stirred at room temperature for 15 minutes and MP—CNBH₃ was added. The reaction was stirred overnight. The MP—CNBH₃ was filtered off and the solvent was evaporated under reduced pressure. The crude was dissolved in methanol, filtered and purified by HPLC yielding 6-methyl-N2-(4-(oxazol-5-yl)phenyl)-N4-((tetrahydro-2H-pyran-4-yl)methyl)-5,6,7,8-tetrahydropyrido[4,3-d]pyrimidine-2,4-diamine (23.00 mg, 15.8%).

MS (ES+) m/z 421.2 (M+H)+

1H NMR (400 MHz, CHLOROFORM-d) δ ppm 1.33-1.46 (m, 2 H) 1.70 (dd, 2 H) 1.93-2.03 (m, 1 H) 2.52 (s, 3 H) 2.76 (dd, 4 H) 3.23 (s, 2 H) 3.39 (td, 2 H) 3.47 (t, 2 H) 4.02 (dd, 2 H) 4.59 (t, 1 H) 7.26 (s, 1 H) 7.57 (m, 2 H) 7.75 (m, 2 H) 7.89 (s, 1 H) 8.41 (br. s., 1 H)

Example 85a

N2-(4-(Oxazol-5-yl)phenyl)-N4-((tetrahydro-2H-pyran-4-yl)methyl)-5,6,7,8-tetrahydropyrido[4,3-d]pyrimidine-2,4-diamine

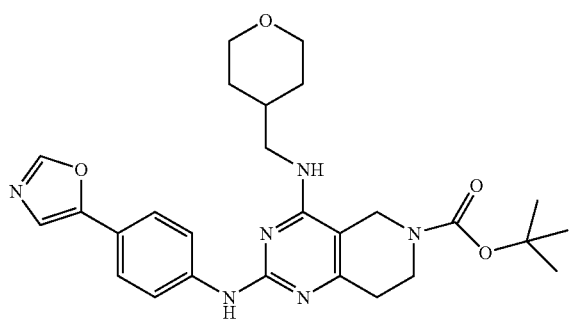

tert-Butyl 2-(4-(oxazol-5-yl)phenylamino)-4-((tetrahydro-2H-pyran-4-yl)methylamino)-7,8-dihydropyrido[4,3-d]pyrimidine-6(5H)-carboxylate (330 mg, 0.65 mmol) was dissolved in methanol (3 mL). Hydrochloric acid (0.020 mL, 0.65 mmol) was added and the reaction mixture was stirred at 80° C. for 30 minutes. The solvent was evaporated and the crude was used as such in the subsequent step. MS (ES+) m/z 407.2 (M+H)+

Example 85b tert-Butyl 2-(4-(oxazol-5-yl)phenylamino)-4-((tetrahydro-2H-pyran-4-yl)methylamino)-7,8-dihydropyrido[4,3-d]pyrimidine-6(5H)-carboxylate tert-Butyl 2-(4-(oxazol-5-yl)phenylamino)-4-(trifluoromethylsulfonyloxy)-7,8-dihydropyrido[4,3-d]pyrimidine-6(5H)-carboxylate (350 mg, 0.65 mmol, example 1b) was dissolved in DMF (2 mL). 4-Aminomethyltetrahydropyran (74.4 mg, 0.65 mmol) was added and the reaction mixture was stirred at 80° C. for 6 h. The solvent was evaporated under reduced pressure and the crude was used in the next step as such. MS (ES+) m/z 507.3 (M+H)+

Example 86

2-(2-(4-(Oxazol-5-yl)phenylamino)-4-((tetrahydro-2H-pyran-4-yl)methylamino)-7,8-dihydropyrido[4,3-d]pyrimidin-6(5H)-yl)ethanol

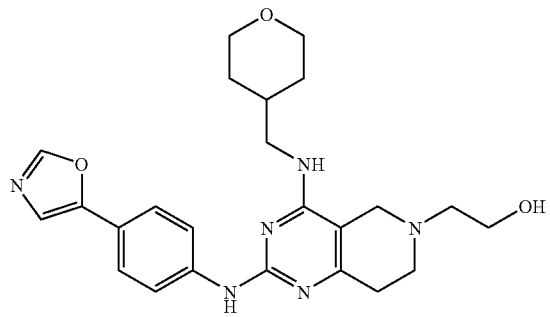

N2-(4-(Oxazol-5-yl)phenyl)-N4-((tetrahydro-2H-pyran-4-yl)methyl)-5,6,7,8-tetrahydropyrido[4,3-d]pyrimidine-2,4-diamine (134 mg, 0.33 mmol, example 85a) was dissolved in methanol (3 mL). Acetic acid (0.019 mL, 0.33 mmol) was added followed by glycoaldehyde (19.80 mg, 0.33 mmol). The reaction mixture was stirred at room temperature for 15 minutes and MP—CNBH₃ was added. The reaction mixture was stirred overnight, the MP—CNBH₃ was filtered off, the solvent was evaporated under reduced pressure, the crude was purified twice by HPLC yielding 2-(2-(4-(oxazol-5-yl)phenylamino)-4-((tetrahydro-2H-pyran-4-yl)methylamino)-7,8-dihydropyrido[4,3-d]pyrimidin-6(5H)-yl)ethanol (38.0 mg, 22.58%) as acetate salt. MS (ES+) m/z 451.3 (M+H)+

1H NMR (400 MHz, CHLOROFORM-d) δ ppm 1.31-1.47 (m, 2 H) 1.69 (dd, 2 H) 1.94-2.05 (m, 1 H) 2.11 (s, 3 H) 2.73-2.83 (m, 4 H) 2.83-2.91 (m, 2 H) 3.30-3.44 (m, 4 H) 3.47 (t, 2 H) 3.70-3.81 (m, 2 H) 4.02 (dd, 2 H) 4.77 (t, 1 H) 7.57 (m, 2 H) 7.79 (m, 2 H) 7.89 (s, 1 H) 9.80 (br. s., 1 H)

Example 87

4-Methyl-N-(4-(2-methyl-1H-imidazol-1-yl)phenyl)-6-(1-phenylethyl)pyrimidin-2-amine

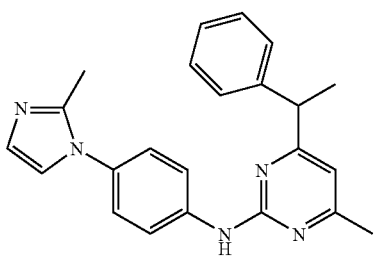

1-(4-(2-Methyl-1H-imidazol-1-yl)phenyl)guanidine (953 mg, 4.43 mmol, example 9e), 5-phenylhexane-2,4-dione (842 mg, 4.43 mmol) and sodium ethoxide (301 mg, 4.43 mmol) in ethanol (5 mL) were heated in a microwave reactor at 100° C. for 15 minutes. The mixture was allowed to reach room temperature and the crude was purified by HPLC yielding 4-methyl-N-(4-(2-methyl-1H-imidazol-1-yl)phenyl)-6-(1-phenylethyl)pyrimidin-2-amine (23.00 mg, 1.313%). MS (ES+) m/z 370.2 (M+H)+

1H NMR (400 MHz, CHLOROFORM-d) δ ppm 1.64 (d, 3 H) 2.30 (s, 3 H) 2.32 (s, 3 H) 4.04 (q, 1 H) 6.45 (s, 1 H) 6.96 (dd, 2 H) 7.09-7.24 (m, 4 H) 7.28-7.32 (m, 2 H) 7.70-7.78 (m, 2 H) 7.85 (s, 1 H)

General Procedure for Amine Substitution of Tosylate on Pyrimidines

An amine (1 eq) was added to 6-acetyl-2-(4-(oxazol-5-yl)phenylamino)-5,6,7,8-tetrahydropyrido[4,3-d]pyrimidin-4-yl trifluoromethanesulfonate (1 eq) in DMSO (1 mL) and stirred overnight at 80° C., filtered and purified by preparative HPLC.

Example 88

1-(4-(Cyclohexyl(methyl)amino)-2-(4-(oxazol-5-yl)phenylamino)-7,8-dihydropyrido[4,3-d]pyrimidin-6(5H)-yl)ethanone

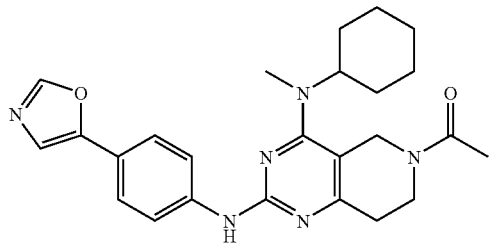

1-(4-(Cyclohexyl(methyl)amino)-2-(4-(oxazol-5-yl)phenylamino)-7,8-dihydropyrido[4,3-d]pyrimidin-6(5H)-yl)ethanone (12.6 mg, 17%) was prepared from N-methylcyclohexanamine and 6-acetyl-2-(4-(oxazol-5-yl)phenylamino)-5,6,7,8-tetrahydropyrido[4,3-d]pyrimidin-4-yl trifluoromethanesulfonate according to the general procedure for amine substitution of tosylate on pyrimidines.

Mixture of Rotamers:

1H NMR (500 MHz, DMSO-d$_6$) δ ppm 1.09-1.22 (m) 1.31-1.46 (m) 1.56-1.70 (m) 1.70-1.87 (m) 2.02-2.10 (m) 2.78 (t) 2.83-2.95 (m) 3.66-3.76 (m) 4.42-4.54 (m) 7.46-7.55 (m) 7.58 (m) 7.86 (m) 8.36 (s) 9.36 (br. s.)

Total no of protons in spectrum: 29

Ratio major:minor 3:1.4

Example 88a

6-Acetyl-2-(4-(oxazol-5-yl)phenylamino)-5,6,7,8-tetrahydropyrido[4,3-d]pyrimidin-4-yl trifluoromethanesulfonate

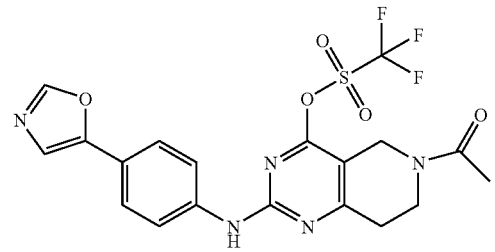

1-(4-Hydroxy-2-(4-(oxazol-5-yl)phenylamino)-7,8-dihydropyrido[4,3-d]pyrimidin-6(5H)-yl)ethanone (1.4 g, 3.98 mmol) was dissolved in dichloromethane (40 mL) and 1,8-diazabicyclo[5.4.0]undec-7-ene (0.595 mL, 3.98 mmol). 1,1,1-trifluoro-N-phenyl-N-(trifluoromethylsulfonyl)methanesulfonamide (1.566 g, 4.38 mmol) was added in small portions followed by 4-dimethylaminopyridine (0.487 mg, 3.98 μmol). The reaction mixture was stirred at room temperature for 4 h. The crude was impregnated in silica gel and purified by flash column chromatography using dichloromethane and methanol (0-10%) as eluent yielding 6-acetyl-2-(4-(oxazol-5-yl)phenylamino)-5,6,7,8-tetrahydropyrido[4,3-d]pyrimidin-4-yl trifluoromethanesulfonate (1.340 g, 69.6%). MS (ES+) m/z 484.2 (M+H)+

1H NMR (500 MHz, DMSO-d$_6$) d ppm 2.13 (br. s., 3 H) 3.34 (br. s., 2 H) 3.79 (br. s., 2 H) 4.52 (br. s., 2 H) 7.61 (br. s., 1 H) 7.67 (br. s., 3 H) 7.79 (br. s., 2 H) 8.40 (br. s., 1 H) 10.37 (br. s., 1 H)

Example 88b 1-(4-Hydroxy-2-(4-(oxazol-5-yl)phenylamino)-7,8-dihydropyrido[4,3-d]pyrimidin-6(5H)-yl)ethanone

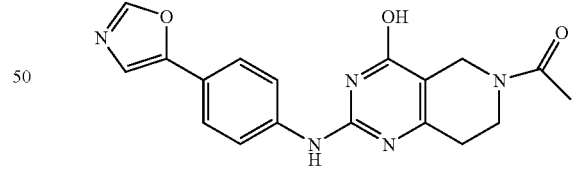

1-(4-(Oxazol-5-yl)phenyl)guanidine (2 g, 9.89 mmol, example 1e), methyl 1-acetyl-4-oxopiperidine-3-carboxylate (1.970 g, 9.89 mmol) and sodium ethoxide (0.673 g, 9.89 mmol) in ethanol were charged in a thick wall glass which was sealed and heated at 100° C. under microwave irradiation. The reaction mixture was allowed to reach room temperature and water was added until a solid was obtained. The solid was filtered and dried in a vacuum oven at 40° C. overnight yielding 1-(4-hydroxy-2-(4-(oxazol-5-yl)phenylamino)-7,8-dihydropyrido[4,3-d]pyrimidin-6(5H)-yl)ethanone (1.400 g, 40.3%).

MS (ES+) m/z 352.2 (M+H)+

Example 89

1-(4-((4-Fluorophenyl)(methyl)amino)-2-(4-(oxazol-5-yl)phenylamino)-7,8-dihydropyrido[4,3-d]pyrimidin-6(5H)-yl)ethanone

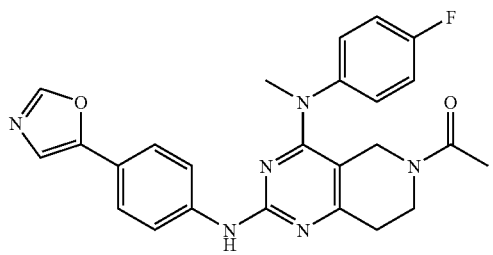

1-(4-((4-fluorophenyl)(methyl)amino)-2-(4-(oxazol-5-yl)phenylamino)-7,8-dihydropyrido[4,3-d]pyrimidin-6(5H)-yl)ethanone (15 mg, 18%) was prepared from 4-fluoro-N-methylaniline and 6-acetyl-2-(4-(oxazol-5-yl)phenylamino)-5,6,7,8-tetrahydropyrido[4,3-d]pyrimidin-4-yl trifluoromethanesulfonate (example 88a) according to the general procedure for amine substitution of tosylate on pyrimidines.

MS (ES+) m/z 459.3 (M+H)+

1H NMR (500 MHz, DMSO-$d_6$) δ ppm 1.68 (s, 1 H) 1.97 (s, 2 H) 2.60-2.67 (m, 1 H) 2.77 (t, 1 H) 3.42 (s, 3 H) 3.52-3.60 (m, 4 H) 7.18-7.36 (m, 4 H) 7.51 (s, 1 H) 7.62 (m, 2 H) 7.91 (m, 2 H) 8.35 (s, 1 H) 9.52-9.59 (m, 1 H)

Example 90

1-(4-(Indolin-1-yl)-2-(4-(oxazol-5-yl)phenylamino)-7,8-dihydropyrido[4,3-d]pyrimidin-6(5H)-yl)ethanone

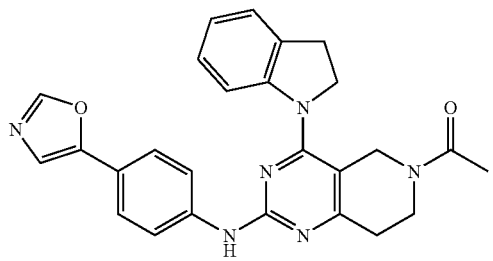

1-(4-(Indolin-1-yl)-2-(4-(oxazol-5-yl)phenylamino)-7,8-dihydropyrido[4,3-d]pyrimidin-6(5H)-yl)ethanone (14.3 mg, 19.1%) was prepared from indoline and 6-acetyl-2-(4-(oxazol-5-yl)phenylamino)-5,6,7,8-tetrahydropyrido[4,3-d]pyrimidin-4-yl trifluoromethanesulfonate (example 88a) according to the general procedure for amine substitution of tosylate on pyrimidines. MS (ES+) m/z 453.3 (M+H)+

Mixture of Rotamers:

1H NMR (500 MHz, DMSO-$d_6$) δ ppm 2.03 (s) 2.08 (s) 2.76 (s) 2.90 (t) 3.15 (t) 3.74-3.86 (m) 4.06-4.23 (m) 4.39-4.51 (m) 6.89-6.98 (m) 7.05 (d) 7.10-7.23 (m) 7.28 (d) 7.51 (s) 7.52-7.59 (m) 7.79-7.91 (m) 8.36 (s) 9.61 (s)

Total no of protons in spectrum: 24

Ratio major:minor 1.7:0.7

Example 91

1-(4-((2-(Hydroxymethyl)benzyl)(methyl)amino)-2-(4-(oxazol-5-yl)phenylamino)-7,8-dihydropyrido[4,3-d]pyrimidin-6(5H)-yl)ethanone

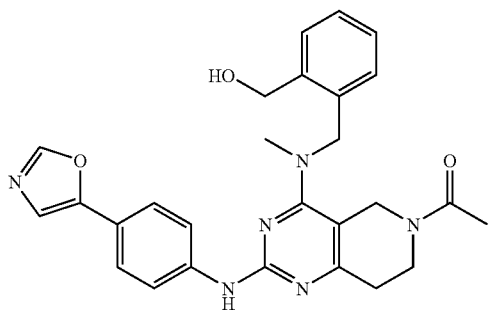

1-(4-((2-(Hydroxymethyl)benzyl)(methyl)amino)-2-(4-(oxazol-5-yl)phenylamino)-7,8-dihydropyrido[4,3-d]pyrimidin-6(5H)-yl)ethanone (12.3 mg, 15.3%) was prepared from (2-((methylamino)methyl)phenyl)methanol and 6-acetyl-2-(4-(oxazol-5-yl)phenylamino)-5,6,7,8-tetrahydropyrido[4,3-d]pyrimidin-4-yl trifluoromethanesulfonate (example 88a) according to the general procedure for amine substitution of tosylate on pyrimidines.

MS (ES+) m/z 485.3 (M+H)+

1H NMR (500 MHz, DMSO-$d_6$) δ ppm 1.67 (s, 2 H) 2.05 (s, 2 H) 2.62-2.70 (m, 1 H) 2.80 (t, 1 H) 3.03 (s, 2 H) 3.11 (s, 2 H) 3.65 (t, 1 H) 3.72 (t, 1 H) 4.39 (s, 1 H) 4.51-4.58 (m, 4 H) 4.71 (d, 2 H) 5.18 (dt, 1 H) 7.21-7.32 (m, 3 H) 7.45-7.49 (m, 3 H) 7.53 (d, 1 H) 7.72 (d, 1 H) 7.80 (d, 1 H) 8.34 (d, 1 H) 9.33 (s, 1 H)

Example 92

1-(4-(Methyl(pyridin-2-ylmethyl)amino)-2-(4-(oxazol-5-yl)phenylamino)-7,8-dihydropyrido[4,3-d]pyrimidin-6(5H)-yl)ethanone

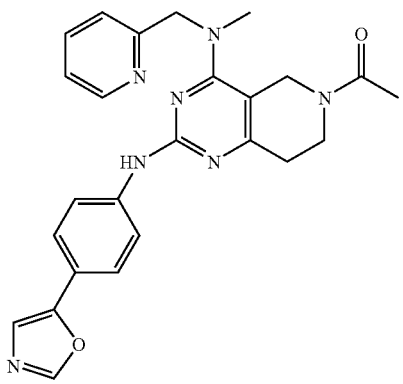

1-(4-(Methyl(pyridin-2-ylmethyl)amino)-2-(4-(oxazol-5-yl)phenylamino)-7,8-dihydropyrido[4,3-d]pyrimidin-6(5H)-yl)ethanone (8.8 mg 12%) was prepared from N-methyl-1-(pyridin-2-yl)methanamine and 6-acetyl-2-(4-(oxazol-5-yl)phenylamino)-5,6,7,8-tetrahydropyrido[4,3-d]pyrimidin-4-yl trifluoromethanesulfonate (example 88a) according to the general procedure for amine substitution of tosylate on pyrimidines.

MS (ES+) m/z 456.3 (M+H)+

1H NMR (500 MHz, DMSO-$d_6$) δ ppm 1.35 (s, 1 H) 1.89 (s, 1 H) 2.06 (s, 2 H) 2.66 (t, 1 H) 2.80 (t, 1 H) 3.12-3.17 (m, 3 H) 3.66-3.75 (m, 2 H) 4.55-4.62 (m, 2 H) 4.73-4.79 (m, 2 H) 7.26-7.34 (m, 2 H) 7.43-7.51 (m, 3 H) 7.65-7.75 (m, 2 H) 7.75-7.83 (m, 1 H) 8.32-8.35 (m, 1 H) 8.55-8.61 (m, 1 H)

Example 93

1-(4-(3-(Hydroxymethyl)piperidin-1-yl)-2-(4-(oxazol-5-yl)phenylamino)-7,8-dihydropyrido[4,3-d]pyrimidin-6(5H)-yl)ethanone

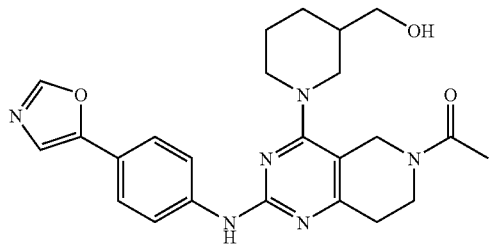

1-(4-(3-(hydroxymethyl)piperidin-1-yl)-2-(4-(oxazol-5-yl)phenylamino)-7,8-dihydropyrido[4,3-d]pyrimidin-6(5H)-yl)ethanone (25.7 mg, 34.6%) was prepared from piperidin-3-ylmethanol and 6-acetyl-2-(4-(oxazol-5-yl)phenylamino)-5,6,7,8-tetrahydropyrido[4,3-d]pyrimidin-4-yl trifluoromethanesulfonate (example 88a) according to the general procedure for amine substitution of tosylate on pyrimidines.

MS (ES+) m/z 449.3 (M+H)+

Mixture of Rotamers:

1H NMR (500 MHz, CDCl$_3$) δ ppm 1.28-1.42 (m), 1.60-2.06 (m), 2.16 (s, 3 H), 2.79-2.95 (m), 3.05-3.15 (m), 3.20-3.30 (m), 3.52-3.95 (m), 4.36-4.46 (m), 7.25 (s, 1 H), 7.56-7.73 (m), 7.87 (s, 1 H)

Total no of protons in spectrum: 27

Ratio major:minor 1:0.4

Example 94

1-(4-(2-(Hydroxymethyl)piperidin-1-yl)-2-(4-(oxazol-5-yl)phenylamino)-7,8-dihydropyrido[4,3-d]pyrimidin-6(5H)-yl)ethanone

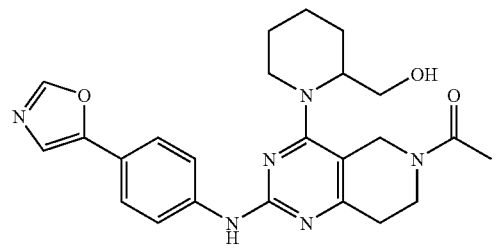

1-(4-(2-(Hydroxymethyl)piperidin-1-yl)-2-(4-(oxazol-5-yl)phenylamino)-7,8-dihydropyrido[4,3-d]pyrimidin-6(5H)-yl)ethanone (18.3 mg, 56.4%) was prepared from piperidin-2-ylmethanol and 6-acetyl-2-(4-(oxazol-5-yl)phenylamino)-5,6,7,8-tetrahydropyrido[4,3-d]pyrimidin-4-yl trifluoromethanesulfonate (example 88a) according to the general procedure for amine substitution of tosylate on pyrimidines.

MS (ES+) m/z 449.3 (M+H)+

Mixture of Rotamers:

1H NMR (500 MHz, DMSO-$d_6$) δ ppm 1.16-1.27 (m) 1.50-1.63 (m) 1.68-1.84 (m) 2.01-2.11 (m) 2.52-2.73 (m) 2.80-3.00 (m) 3.65-3.89 (m) 4.33-4.52 (m) 4.59-4.64 (m) 7.50 (s) 7.55-7.63 (m) 7.89 (d) 8.36 (s) 9.38-9.48 (m). Total number of protons in spectrum: 27

Ratio major:minor: 3:1

Example 95

N-(3-Methoxy-4-(4-methyl-1H-imidazol-1-yl)phenyl)-4-(3-methoxybenzyl)-6-methyl-5,6,7,8-tetrahydropyrido[4,3-d]pyrimidin-2-amine

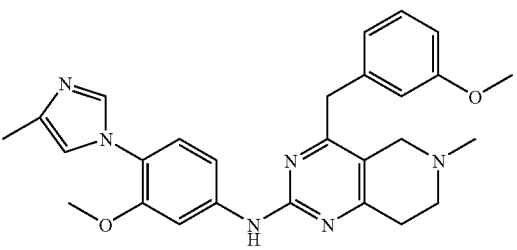

Formaldehyde (3.15 μL, 0.04 mmol) was added to a solution of N-(3-methoxy-4-(4-methyl-1H-imidazol-1-yl)phenyl)-4-(3-methoxybenzyl)-5,6,7,8-tetrahydropyrido[4,3-d]pyrimidin-2-amine (13.70 mg, 0.03 mmol) in methanol (1.5 mL). Sodium cyanoborohydride (0.943 mg, 0.02 mmol) and acetic acid (1.030 μL, 0.02 mmol) was added and the reaction mixture stirred for 2 h at rt and purified by preparative HPLC to afford the titled compound.

MS (ES+) m/z 471.3 (M+H)+

1H NMR (600 MHz, CHLOROFORM-d) δ ppm 2.31 (s, 3 H) 2.49 (s, 3 H) 2.76 (s, 2 H) 2.92 (s, 2 H) 3.50 (s, 2 H) 3.77

(d, 6 H) 3.95 (s, 2 H) 6.79 (s, 3 H) 6.86 (s, 1 H) 7.02-7.06 (m, 1 H) 7.09-7.13 (m, 1 H) 7.20-7.25 (m, 1 H) 7.67 (s, 1 H) 7.72-7.76 (m, 1 H) 7.78 (d, 1 H)

Example 95a

N-(3-Methoxy-4-(4-methyl-1H-imidazol-1-yl)phenyl)-4-(3-methoxybenzyl)-5,6,7,8-tetrahydropyrido[4,3-d]pyrimidin-2-amine

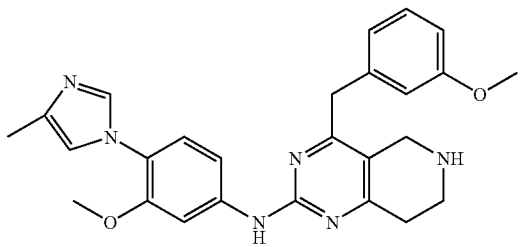

Trifluoroacetic acid (2 mL, 26.05 mmol) in dichloromethane (2 mL) was added to tert-butyl 2-(3-methoxy-4-(4-methyl-1H-imidazol-1-yl)phenylamino)-4-(3-methoxybenzyl)-7,8-dihydropyrido[4,3-d]pyrimidine-6(5H)-carboxylate (14 mg, 0.03 mmol) and stirred at rt for 1 hour. The solvents were removed under reduced pressure and the product was used without further purification. MS (ES+) m/z 457.3 (M+H)+

Example 95b tert-Butyl 2-(3-methoxy-4-(4-methyl-1H-imidazol-1-yl)phenylamino)-4-(3-methoxybenzyl)-7,8-dihydropyrido[4,3-d]pyrimidine-6(5H)-carboxylate

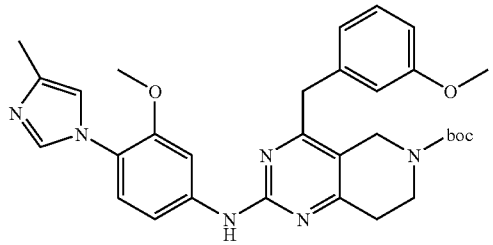

tert-Butyl 3-(2-(3-methoxyphenyl)acetyl)-4-oxopiperidine-1-carboxylate (320 mg, 0.92 mmol), 1-(3-methoxy-4-(4-methyl-1H-imidazol-1-yl)phenyl)guanidine dinitrate (342 mg, 0.92 mmol, example 43a) and potassium carbonate (382 mg, 2.76 mmol) in ethanol (4 mL) was heated in a microwave reactor to 130° C. for 3 hours. DCM and water was added and the organic phases were separated, dried with MgSO4, concentrated and purified by preparative HPLC to afford tert-butyl 2-(3-methoxy-4-(4-methyl-1H-imidazol-1-yl)phenylamino)-4-(3-methoxybenzyl)-7,8-dihydropyrido[4,3-d]pyrimidine-6(5H)-carboxylate (15.00 mg, 3%).

MS (ES+) m/z 557.4 (M+H)+

Example 95c tert-Butyl 3-(2-(3-methoxyphenyl)acetyl)-4-oxopiperidine-1-carboxylate

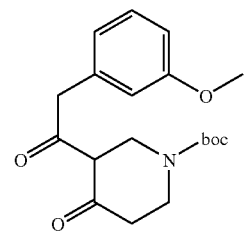

tert-Butyl 3-(2-(3-methoxyphenyl)acetyl)-4-oxopiperidine-1-carboxylate (323 mg, 74%) was prepared from 2-(3-methoxyphenyl)acetyl chloride according to the general procedure for the preparation of diketones.

MS (ES+) m/z 346.2 (M+H)+

Example 96

1-(2-(3-Methoxy-4-(4-methyl-1H-imidazol-1-yl)phenylamino)-4-(3-methoxybenzyl)-7,8-dihydropyrido[4,3-d]pyrimidin-6(5H)-yl)ethanone

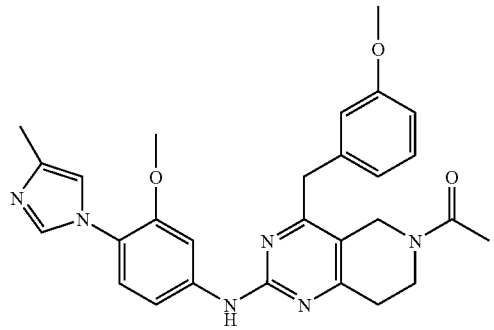

N-(3-Methoxy-4-(4-methyl-1H-imidazol-1-yl)phenyl)-4-(3-methoxybenzyl)-5,6,7,8-tetrahydropyrido[4,3-d]pyrimidin-2-amine (137 mg, 0.3 mmol, example 95a) was dissolved in DCM (3 mL) and acetic anhydride (0.028 mL, 0.30 mmol) was added. The crude product was purified by preparative HPLC yielding 1-(2-(3-methoxy-4-(4-methyl-1H-imidazol-1-yl)phenylamino)-4-(3-methoxybenzyl)-7,8-dihydropyrido[4,3-d]pyrimidin-6(5H)-yl)ethanone (25.00 mg, 16.7%).

MS (ES+) m/z 499.3 (M+H)+

Mixture of Rotamers:

1H NMR (500 MHz, CHLOROFORM-d) δ ppm 1.98 (s) 2.08 (s) 2.20 (s) 2.31 (s) 2.85 (t) 2.91 (t) 3.74 (t) 3.78 (s) 3.80 (s) 3.82 (s) 3.87 (t) 3.97-4.03 (m) 4.43 (s) 4.66 (s) 6.76-6.89 (m) 7.04-7.09 (m) 7.12-7.17 (m) 7.23 (t) 7.28 (br. s) 7.64 (d) 7.72 (d)

Total no of protons in spectrum: 30

Ratio major:minor: 2:1

Example 97

1-(4-(3-Methoxybenzyl)-2-(4-(2-methyl-1H-imidazol-1-yl)phenylamino)-7,8-dihydropyrido[4,3-d]pyrimidin-6(5H)-yl)ethanone

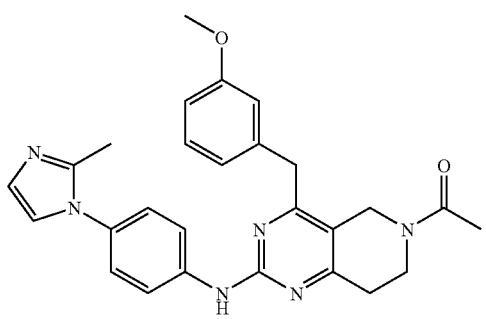

1-(4-(3-Methoxybenzyl)-2-(4-(2-methyl-1H-imidazol-1-yl)phenylamino)-7,8-dihydropyrido[4,3-d]pyrimidin-6(5H)-yl)ethanone (18.2 mg, 12.5%) was prepared from 4-(3-methoxybenzyl)-N-(4-(2-methyl-1H-imidazol-1-yl)phenyl)-5,6,7,8-tetrahydropyrido[4,3-d]pyrimidin-2-amine (example 53a) according to the general procedure for N-acetylation.

MS (ES+) m/z 469.4 (M+H)+

Mixture of Rotamers:

1H NMR (500 MHz, DMSO-$d_6$) d ppm 2.03 (s) 2.11 (s) 2.25 (s) 2.72 (t) 2.86 (t) 3.72 (m) 3.98 (s) 4.03 (s) 4.57 (s) 6.78-6.94 (m) 7.17-7.29 (m) 7.83 (dd) 9.72-9.79 (m)

Total no of protons in spectrum: 28
Ratio major:minor: 1.5:1

Example 98

1-(4-(2-Fluorobenzyl)-2-(4-(2-methyl-1H-imidazol-1-yl)phenylamino)-7,8-dihydropyrido[4,3-d]pyrimidin-6(5H)-yl)ethanone

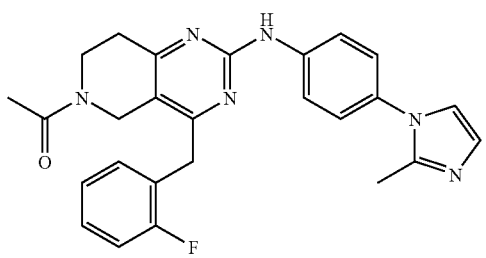

1-(4-(2-Fluorobenzyl)-2-(4-(2-methyl-1H-imidazol-1-yl)phenylamino)-7,8-dihydropyrido[4,3-d]pyrimidin-6(5H)-yl)ethanone (12 mg, 12%) was prepared from 4-(2-fluorobenzyl)-N-(4-(2-methyl-1H-imidazol-1-yl)phenyl)-5,6,7,8-tetrahydropyrido[4,3-d]pyrimidin-2-amine and acetic anhydride according to the general procedure for N-acetylation. MS (ES+) m/z 457 (M+H)+

Mixture of Rotamers:

1H NMR (500 MHz, DMSO-$d_6$) d ppm 1.95 (d) 2.10-2.15 (m) 2.23 (s) 2.74 (t) 2.87 (t) 3.76 (t) 4.05 (s) 4.11 (s) 4.62 (s) 4.65 (s) 6.87 (s) 7.06-7.15 (m) 7.17 (s) 7.23 (dd) 7.37 (d) 7.58 (m) 9.68 (d)

Total no of protons in spectrum: 25
Ratio major:minor: 1.3:1

Example 98a 4-(2-Fluorobenzyl)-N-(4-(2-methyl-1H-imidazol-1-yl)phenyl)-5,6,7,8-tetrahydropyrido[4,3-d]pyrimidin-2-amine

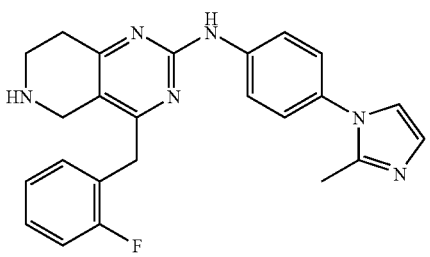

tert-Butyl 4-(2-fluorobenzyl)-2-(4-(2-methyl-1H-imidazol-1-yl)phenylamino)-7,8-dihydropyrido[4,3-d]pyrimidine-6(5H)-carboxylate was dissolved in DCM (5 mL). TFA, 10 eq, was added and the reaction was heated to reflux for 2 h. The mixture was neutralized with sat NaHCO$_3$ and the phases were separated. The organic phase was dried with MgSO$_4$ and the solvent was removed under reduced pressure to yield 4-(2-fluorobenzyl)-N-(4-(2-methyl-1H-imidazol-1-yl)phenyl)-5,6,7,8-tetrahydropyrido[4,3-d]pyrimidin-2-amine (186 mg, 53%).

MS (ES+) m/z 414.7 (M+H)+

Example 98b tert-Butyl 4-(2-fluorobenzyl)-2-(4-(2-methyl-1H-imidazol-1-yl)phenylamino)-7,8-dihydropyrido[4,3-d]pyrimidine-6(5H)-carboxylate

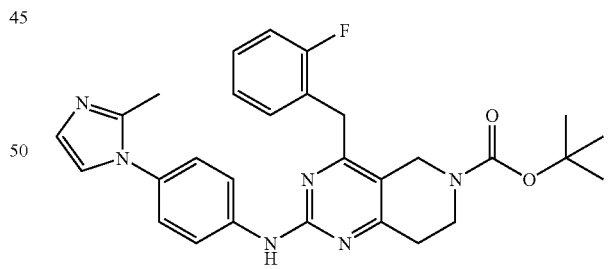

tert-Butyl 3-(2-(2-fluorophenyl)acetyl)-4-oxopiperidine-1-carboxylate, (0.88 mmol) together with 1 eq 1-(4-(2-methyl-1H-imidazol-1-yl)phenyl)guanidine and 2 eq of potassium carbonate were slurrified in 4 ml EtOH. The reactions were heated in the microwave oven to 130° C. for 3 h. DCM and water were added and the organic phases were separated, dried with MgSO$_4$ and the solvent was removed under reduced pressure tert-butyl 4-(2-fluorobenzyl)-2-(4-(2-methyl-1H-imidazol-1-yl)phenylamino)-7,8-dihydropyrido[4,3-d]pyrimidine-6(5H)-carboxylate (292 mg, 65%).

MS (ES+) m/z 515.0 (M+H)+

Example 98c tert-Butyl 3-(2-(2-fluorophenyl)acetyl)-4-oxopiperidine-1-carboxylate

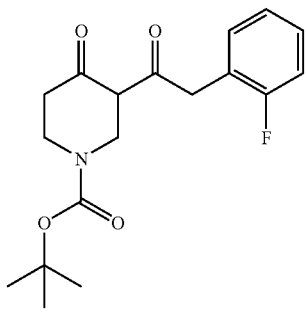

tert-Butyl 3-(2-(2-fluorophenyl)acetyl)-4-oxopiperidine-1-carboxylate (295 mg, 52%) was prepared from 2-(2-fluorophenyl)acetyl chloride according to the general procedure for the preparation of diketones.
MS (ES−) m/z 334.1 (M−H)−

Example 98d 2-(2-Fluorophenyl)acetyl chloride

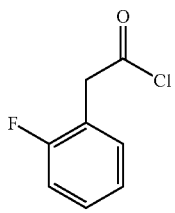

2-(2-Fluorophenyl)acetic acid, (1.7 mmol) was dissolved in thionyl chloride (0.372 ml, 5.10 mmol) and heated to reflux for 1 h. The reaction was cooled and the excess thionyl chloride was evaporated. The residue was instantly dissolved in dry THF and refridgerated until used. No purity analysis or weighing were performed.

Example 99

4-(4-Fluorobenzyl)-N-(4-(2-methyl-1H-imidazol-1-yl)phenyl)-6-(trifluoromethyl)-5,6,7,8-tetrahydroquinazolin-2-amine

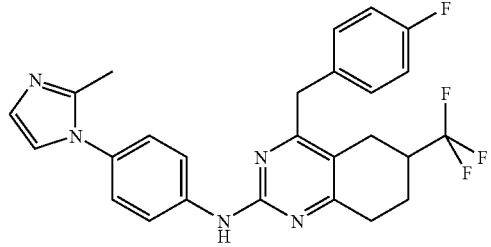

2-(2-(4-Fluorophenyl)acetyl)-4-(trifluoromethyl)cyclohexanone (75 mg, 0.25 mmol), 1-(4-(2-methyl-1H-imidazol-1-yl)phenyl)guanidine (53.4 mg, 0.25 mmol) and potassium carbonate (68.6 mg, 0.50 mmol) were added to a microwave vial. EtOH (3 mL) was added and the reaction was heated to 130° C. for 2 h. DCM (3 mL) and water (3 mL) were added. The organic phase was separated and the solvent was evaporated. The product was purified by preparative HPLC yielding 4-(4-fluorobenzyl)-N-(4-(2-methyl-1H-imidazol-1-yl)phenyl)-6-(trifluoromethyl)-5,6,7,8-tetrahydroquinazolin-2-amine (30.0 mg, 25.1%).
MS (ES+) m/z 482.1 (M+H)+;
1H NMR (500 MHz, CHLOROFORM-$d_6$) δ ppm 1.72-1.84 (m, 1 H) 2.22-2.30 (m, 1 H) 2.43 (br. s., 3 H) 2.47-2.54 (m, 1 H) 2.61 (dd, 1 H) 2.80-2.89 (m, 1 H) 2.92-3.00 (m, 2 H) 4.01 (s, 2 H) 7.04 (t, 3 H) 7.14-7.19 (m, 3 H) 7.23 (dd, 2 H) 7.67 (d, 2 H)

Example 99a 2-(2-(4-Fluorophenyl)acetyl)-4-(trifluoromethyl)cyclohexanone

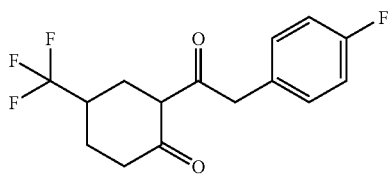

2-(2-(4-Fluorophenyl)acetyl)-4-(trifluoromethyl)cyclohexanone (75 mg, 50%) was prepared from 4-fluorophenylacetyl chloride according to the general procedure for the preparation of diketones. MS (ES+) m/z 303.1 (M+H)+

Example 100

N-(3-Methoxy-4-(4-methyl-1H-imidazol-1-yl)phenyl)-4-(3-methoxybenzyl)-7,8-dihydro-5H-pyrano[4,3-d]pyrimidin-2-amine

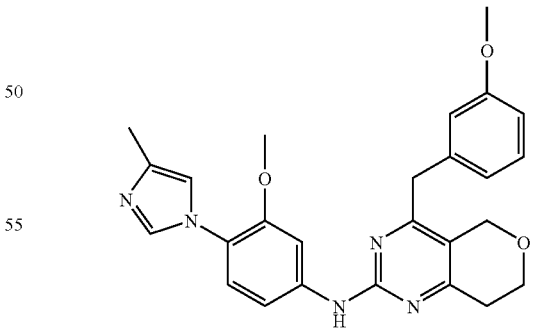

1-(3-Methoxy-4-(4-methyl-1H-imidazol-1-yl)phenyl) guanidine (85 mg, 0.35 mmol), 3-(2-(3-methoxyphenyl) acetyl)dihydro-2H-pyran-4(3H)-one (86 mg, 0.35 mmol) and potassium carbonate (47.9 mg, 0.35 mmol) in ethanol (2 mL) were heated to 60° C. over night. DCM and water were added and the organic phase was separated and the solvent was removed under reduced pressure. The crude product was purified by preparative HPLC yielding N-(3-methoxy-4-(4-methyl-1H-imidazol-1-yl)phenyl)-4-(3-methoxybenzyl)-7,8-dihydro-5H-pyrano[4,3-d]pyrimidin-2-amine (10.00 mg, 6%).

MS (ES+) m/z 458.2 (M+H)+

1H NMR (500 MHz, CHLOROFORM-d) δ ppm 2.33 (s, 3 H) 2.88 (t, 2 H) 3.80 (s, 3 H) 3.81 (s, 3 H) 3.89 (s, 2 H) 4.02 (t, 2 H) 4.68 (s, 2 H) 6.79-6.82 (m, 2 H) 6.84 (d, 2 H) 6.89 (s, 1 H) 7.06 (dd, 1 H) 7.16 (d, 1 H) 7.23 (s, 1 H) 7.66 (br. s., 1 H) 7.80 (d, 1 H)

Example 100a 3-(2-(3-Methoxyphenyl)acetyl)dihydro-2H-pyran-4(3H)-one

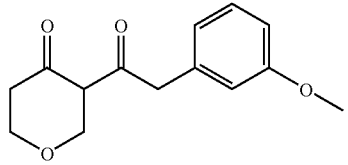

Tetrahydro-4H-pyran-4-one (0.138 mL, 1.50 mmol) was dissolved in toluene (1 mL) and cooled to 0° C. LHMDS (1.573 mL, 1.57 mmol) was added. 3-Methoxyphenylacetyl chloride (0.117 mL, 0.75 mmol) was added after 2 minutes. After 5 minutes, acetic acid (0.129 mL, 2.25 mmol) and water was added. The organic phase was separated and the crude product was purified by flash column chromatography (EtOAc 0-40% in heptane) yielding 3-(2-(3-methoxyphenyl)acetyl)dihydro-2H-pyran-4(3H)-one (86 mg, 46%).

MS (ES−) m/z 247 (M−H)−

Example 101

4-(Methoxy(phenyl)methyl)-N-(3-methoxy-4-(4-methyl-1H-imidazol-1-yl)phenyl)-7,8-dihydro-5H-pyrano[4,3-d]pyrimidin-2-amine

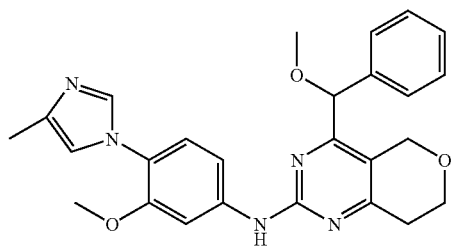

A reaction mixture of 1-(3-methoxy-4-(4-methyl-1H-imidazol-1-yl)phenyl)guanidine (0.300 g, 0.81 mmol) and potassium carbonate (0.337 g, 2.44 mmol) in ethanol (5 mL) was stirred at 50° C. for 5 minutes. 3-(2-methoxy-2-phenylacetyl)dihydro-2H-pyran-4(3H)-one (0.161 g, 0.65 mmol) in ethanol (0.5 mL) was added dropwise to the reaction mixture and the resulting mixture was stirred at 50° C. overnight. The solvent was evaporated and the residue was partitioned between water and dichloromethane. The water phase was extracted twice with dichloromethane. The combined organic layer was dried over MgSO₄, filtered, concentrated and purified by preparative HPLC yielding 4-(methoxy(phenyl)methyl)-N-(3-methoxy-4-(4-methyl-1H-imidazol-1-yl)phenyl)-7,8-dihydro-5H-pyrano[4,3-d]pyrimidin-2-amine (8.00 mg, 2%).

1H NMR (500 MHz, DMSO-d₆) δ ppm 9.86 (s, 1 H) 8.11 (d, 1 H) 7.65 (d, 1 H) 7.40-7.45 (m, 2 H) 7.37 (t, 3 H) 7.31 (d, 1 H) 7.24-7.30 (m, 2 H) 7.18 (d, 1 H) 7.03 (s, 1 H) 5.36 (s, 1 H) 4.67-4.73 (m, 1 H) 4.57 (d, 1 H) 3.95 (dt, 5.62 Hz, 1 H) 3.82-3.90 (m, 1 H) 3.79 (s, 3 H) 3.35 (s, 4 H) 2.80-2.89 (m, 1 H) 2.72-2.79 (m, 1 H) 2.12-2.17 (m, 3 H)

MS (ES+) m/z 458 (M+H)+

Example 101a 1-(1H-imidazol-1-yl)-2-methoxy-2-phenylethanone

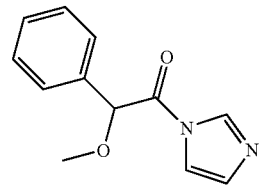

Di-(1H-imidazol-1-yl)methanone (1.073 g, 6.62 mmol) was added in small portions to a stirred solution of 2-methoxy-2-phenylacetic acid (1.047 g, 6.30 mmol) in dichloromethane (3 mL) at room temperature under argon. The reaction mixture was stirred at room temperature overnight. The mixture was washed twice with water, dried over MgSO₄ and concentrated yielding 1-(1H-imidazol-1-yl)-2-methoxy-2-phenylethanone (1.118 g, 82%).

1H NMR (400 MHz, DMSO-d₆) δ ppm 8.52-8.56 (m, 1 H), 7.76 (t, 1 H), 7.47-7.53 (m, 2 H), 7.36-7.44 (m, 3 H), 7.06 (dd, 1 H), 5.86 (s, 1 H), 3.38 (s, 3 H); (No correct MS was obtained)

Example 101b 3-(2-Methoxy-2-phenylacetyl)dihydro-2H-pyran-4(3H)-one

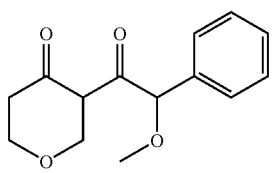

Lithium bis(trimethylsilyl)amide (2.024 mL, 10.78 mmol) was added to a stirred solution of tetrahydro-4H-pyran-4-one (0.948 mL, 10.27 mmol) in toluene (3 mL) at 0° C. After 2 minutes 1-(1H-imidazol-1-yl)-2-methoxy-2-phenylethanone (1.110 g, 5.13 mmol) was added and the mixture was stirred at 0° C. for 5 minutes. The reaction was quenched with acetic acid (0.882 mL, 15.40 mmol) in 5 mL water. The organic layer was separated and concentrated. The crude product was purified by silica flash chromatography using ethyl acetate (0 to 40%) in heptane giving 3-(2-methoxy-2-phenylacetyl)dihydro-2H-pyran-4(3H)-one (0.245 g, 19%). MS (ES−) m/z 247 (M−H)−

Example 102

N-(3-Methoxy-4-(4-methyl-1H-imidazol-1-yl)phenyl)-4-(2-(tetrahydrofuran-2-yl)ethyl)-7,8-dihydro-5H-pyrano[4,3-d]pyrimidin-2-amine

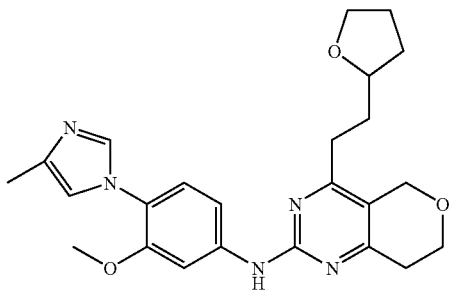

A reaction mixture of 1-(3-methoxy-4-(4-methyl-1H-imidazol-1-yl)phenyl)guanidine (0.305 g, 0.83 mmol, example 7c) and potassium carbonate (0.343 g, 2.48 mmol) in ethanol (3 mL) was stirred at 50° C. for 20 minutes under argon. 3-(3-(tetrahydrofuran-2-yl)propanoyl)dihydro-2H-pyran-4 (3H)-one (0.187 g, 0.83 mmol) was added dropwise (neat) over 2 hours and stirred at 50° C. overnight. The solvent was evporated and the residue was partitioned between water and dichloromethane. The water phase was extracted twice with dichloromethane. The combined organic layer was dried over MgSO$_4$, filtered and concentrated. ¼ of the crude was purified by preparative HPLC and concentrated. The residue was partitioned between NaHCO$_3$ (aq) and dichloromethane and the the water phase was extracted twice with dichloromethane, dried (MgSO$_4$) and concentrated giving 4 mg of the product.
MS (ES+) m/z 436 (M+H)+

Example 102a 1-(1H-Imidazol-1-yl)-3-(tetrahydrofuran-2-yl)propan-1-one

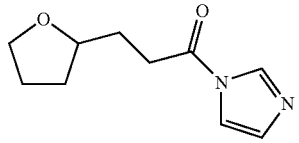

Di-(1H-imidazol-1-yl)methanone (0.554 g, 3.42 mmol) was added in small portions to a stirred solution of 3-(tetrahydrofuran-2-yl)propanoic acid (0.469 g, 3.25 mmol) in dichloromethane (3 mL) at room temperature under argon. The reaction mixture is stirred at room temperature for 2 hours. The mixture was washed twice with water, dried over MgSO$_4$ and concentrated resulting a quantitative yield of 1-(1H-imidazol-1-yl)-3-(tetrahydrofuran-2-yl)propan-1-one (632 mg, 100%).
1H NMR (500 MHz, DMSO-d$_6$) δ ppm 8.43 (s, 1 H) 7.71 (t, 1 H) 7.06 (d, 1 H) 3.76-3.85 (m, 1 H) 3.72 (td, 6.15 Hz, 1 H) 3.58 (td, 6.38 Hz, 1 H) 3.06 (td, 3.78 Hz, 2 H) 1.95 (dddd, 8.45, 6.50, 5.28 Hz, 1 H) 1.75-1.89 (m, 4 H) 1.41-1.51 (m, 1 H)
MS (ES−) m/z 194 (M−H)−

Example 102b 3-(3-(Tetrahydrofuran-2-yl)propanoyl)dihydro-2H-pyran-4(3H)-one

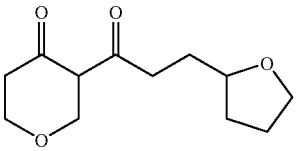

Lithium bis(trimethylsilyl)amide (1.283 ml, 6.83 mmol) was added to a stirred solution of tetrahydro-4H-pyran-4-one (0.601 ml, 6.51 mmol) in toluene (3 mL) at 0° C. and the resulting mixture was stirred for 2 minutes. 1-(1H-imidazol-1-yl)-3-(tetrahydrofuran-2-yl)propan-1-one (0.632 g, 3.25 mmol) toluene (1 mL) was added and the reaction mixture was stirred for 5 minutes before it was quenched with acetic acid (0.559 ml, 9.76 mmol) in water (4 mL). The organic layer was separated and purified by flash column chromatography (ethyl acetate in heptane, 0 to 40%) yielding 3-(3-(tetrahydrofuran-2-yl)propanoyl)dihydro-2H-pyran-4(3H)-one (117 mg, 16%).
1H NMR (500 MHz, DMSO-d$_6$) δ ppm 4.31-4.38 (m, 1 H) 3.94-4.06 (m, 1 H) 3.74-3.78 (m, 2 H) 3.68-3.74 (m, 2 H) 3.56 (td, 6.31 Hz, 1 H) 2.54-2.62 (m, 1 H) 2.34-2.45 (m, 3 H) 1.85-1.96 (m, 1 H) 1.73-1.85 (m, 2 H) 1.58-1.71 (m, 2 H) 1.33-1.45 (m, 1 H)
MS (ES−) m/z 225 (M−H)−

Example 103

2-(2-(3-Methoxy-4-(4-methyl-1H-imidazol-1-yl)phenylamino)-7,8-dihydro-5H-pyrano[4,3-d]pyrimidin-4-yl)propan-2-ol

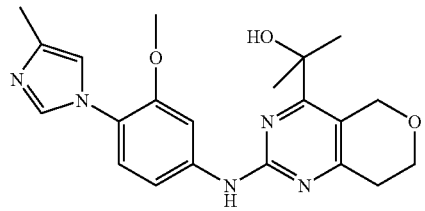

Methylmagnesium bromide (0.769 mL, 0.77 mmol) was added at 0° C. to a solution of ethyl 2-(3-methoxy-4-(4-methyl-1H-imidazol-1-yl)phenylamino)-7,8-dihydro-5H-pyrano[4,3-d]pyrimidine-4-carboxylate (150 mg, 0.37 mmol) in dry THF (5 mL). 4 eq extra equivalents of methylmagnesium bromide were added over 2 h. The crude product was partitioned between DCM and water. The organic phase was separated and the solvent was evaporated. The crude product was purification on a prepHPLC affording 2-(2-(3-methoxy-4-(4-methyl-1H-imidazol-1-yl)phenylamino)-7,8-dihydro-5H-pyrano[4,3-d]pyrimidin-4-yl)propan-2-ol (11.00 mg, 7.59%). MS (ES+) m/z 396.2 (M+H)+;

1H NMR (400 MHz, CHLOROFORM-d) δ ppm 1.56 (s, 6 H) 2.31 (s, 3 H) 2.96 (t, 2 H) 3.87 (s, 3 H) 4.05 (t, 2 H) 4.91 (s, 2 H) 6.88 (s, 1 H) 7.04 (dd, 1 H) 7.18 (d, 1 H) 7.66 (d, 2 H)

Example 103a

Ethyl 2-(3-methoxy-4-(4-methyl-1H-imidazol-1-yl) phenylamino)-7,8-dihydro-5H-pyrano[4,3-d]pyrimidine-4-carboxylate

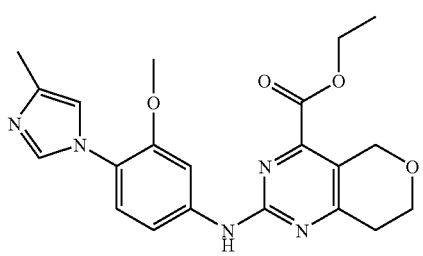

1-(3-Methoxy-4-(4-methyl-1H-imidazol-1-yl)phenyl) guanidine (418 mg, 1.36 mmol) and potassium carbonate (469 mg, 3.40 mmol) in EtOH (8mL) were stirred for 10min at 50° C. Ethyl 2-oxo-2-(4-oxotetrahydro-2H-pyran-3-yl)acetate (272 mg, 1.36 mmol) was added slowly and the reaction was stirred at 50° C. over night. The crude product was partitioned between DCM and water. The organic phase was dried and solvent evaporated and used as such in the next step. MS (ES+) m/z 410.0 (M+H)+

$^1$H NMR (500 MHz, CDCl$_3$) δ (ppm) 1.44 (t, 3 H) 2.33 (s, 3 H) 2.99 (t, 2 H) 3.91 (s, 3 H) 4.06 (t, 2 H) 4.46 (q, 2 H) 5.02 (s, 2 H) 6.89 (s, 1 H) 7.02 (dd, 1 H) 7.18 (d, 1 H) 7.37 (s, 1 H) 7.73 (s, 1 H) 7.96 (d, 1 H).

Example 103b

Ethyl 2-oxo-2-(4-oxotetrahydro-2H-pyran-3-yl)acetate

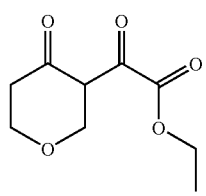

Ethyl 2-oxo-2-(4-oxotetrahydro-2H-pyran-3-yl)acetate (272 mg, 19%) was synthesised from tetrahydro-4H-pyran-4-one (1 ml, 10.83 mmol) and ethyl 2-chloro-2-oxoacetate (0.808 ml, 7.22 mmol) by the general procedure for the preparation of diketones. MS (ES−) m/z 199.1 (M−H)−

$^1$H NMR (400 MHz, CDCL$_3$) δ (ppm) 1.39 (t, 3 H) 2.65 (t, 2 H) 3.95 (t, 2 H) 4.36 (q, 2 H) 4.70 (s, 2 H) 15.44 (s, 1 H)

The compound exists in the tautomeric enol form.

Example 104

4-(1-(3,5-Dimethyl-1H-pyrazol-1-yl)ethyl)-N-(3-methoxy-4-(4-methyl-1H-imidazol-1-yl)phenyl)-7,8-dihydro-5H-pyrano[4,3-d]pyrimidin-2-amine

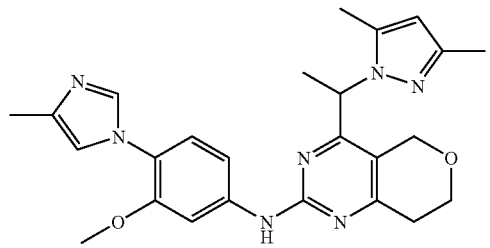

1-(3-Methoxy-4-(4-methyl-1H-imidazol-1-yl)phenyl) guanidine (86 mg, 0.28 mmol) and potassium carbonate (77 mg, 0.56 mmol) in EtOH (7 mL) were heated to 60° C. for 10 min followed by the addition of 3-(2-(3,5-dimethyl-1H-pyrazol-1-yl)propanoyl)dihydro-2H-pyran-4(3H)-one (70 mg, 0.28 mmol). The reaction was stirred over night. Solvent was evaporated and the crude product was taken up in DCM and washed with water. The product was purified on a prepHPLC yielding 4-(1-(3,5-dimethyl-1H-pyrazol-1-yl)ethyl)-N-(3-methoxy-4-(4-methyl-1H-imidazol-1-yl)phenyl)-7,8-dihydro-5H-pyrano[4,3-d]pyrimidin-2-amine (5.00 mg, 3.89%). MS (ES+) m/z 460.2 (M+H)+

Mixture of Rotamers:

1H NMR (500 MHz, CHLOROFORM-d) δ ppm 1.87 (d) 2.15 (s) 2.22 (s) 2.31 (s) 2.79-2.86 (m) 2.88-2.97 (m) 3.83-3.90 (m) 3.94 (d) 4.02 (m) 4.39 (d) 5.32 (q) 5.84 (s) 6.88 (s) 7.08 (dd) 7.16 (d) 7.34 (s) 7.65 (s) 7.76 (d)

Total no of protons in spectrum: 29

Ratio major:minor: 2:1

Example 104a 3-(2-(3,5-Dimethyl-1H-pyrazol-1-yl)propanoyl)dihydro-2H-pyran-4(3H)-one

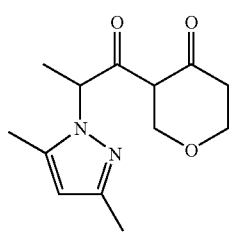

3-(2-(3,5-Dimethyl-1H-pyrazol-1-yl)propanoyl)dihydro-2H-pyran-4 (3H)-one was synthesised from 2-(3,5-dimethyl-1H-pyrazol-1-yl)propanoyl chloride (0.5 g, 2.97 mmol) and tetrahydro-4H-pyran-4-one (0.549 mL, 5.95 mmol) by the general procedure for the preparation of diketones. MS (ES+) m/z 251.1 (M+H)+

149

Example 104b 2-(3,5-Dimethyl-1H-pyrazol-1-l)propanoyl chloride

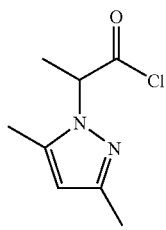

2-(3,5-Dimethyl-1H-pyrazol-1-yl)propanoyl chloride was synthesised from 243,5-dimethyl-1H-pyrazol-1-yl)propanoic acid (0.5 g, 2.97 mmol) using reaction conditions similar to the procedure described in example 98a.

Example 105

2-(4-Benzyl-2-(3-methoxy-4-(4-methyl-1H-imidazol-1-yl)phenylamino)-7,8-dihydropyrido[4,3-d]pyrimidin-6(5H)-yl)acetonitrile

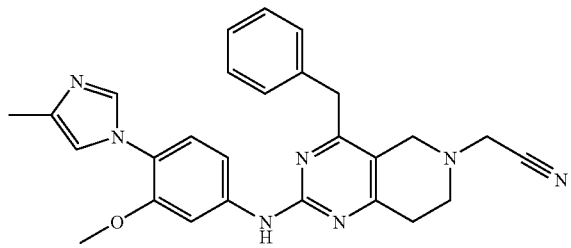

Bromoacetonitrile (0.031 mL, 0.45 mmol) was added to a solution of 4-benzyl-N-(3-methoxy-4-(4-methyl-1H-imidazol-1-yl)phenyl)-5,6,7,8-tetrahydropyrido[4,3-d]pyrimidin-2-amine (175 mg, 0.41 mmol, Example 106) and TEA (0.063 mL, 0.45 mmol) in THF (3 mL). The solution was stirred at RT for 2 hours. Solvent was evaporated and the crude product was purified on a prepHPLC yielding 2-(4-benzyl-2-(3-methoxy-4-(4-methyl-1H-imidazol-1-yl)phenylamino)-7,8-dihydropyrido[4,3-d]pyrimidin-6(5H)-yl)acetonitrile (72.0 mg, 37.7%). MS (ES+) m/z 466.3 (M+H)+

1H NMR (400 MHz, CHLOROFORM-d) δ ppm 2.30 (s, 3 H) 2.89-2.98 (m, 4 H) 3.68 (s, 2 H) 3.73 (s, 2 H) 3.76 (s, 3 H) 3.97 (s, 2 H) 6.86 (s, 1 H) 7.00-7.05 (m, 1 H) 7.09-7.13 (m, 1 H) 7.22-7.26 (m, 3 H) 7.29-7.38 (m, 3 H) 7.63 (d, 1 H) 7.72 (d, 1 H)

150

Example 106

4-Benzyl-N-(3-methoxy-4-(4-methyl-1H-imidazol-1-yl)phenyl)-5,6,7,8-tetrahydropyrido[4,3-d]pyrimidin-2-amine

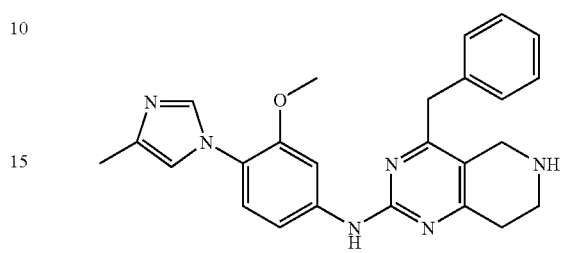

tert-Butyl 4-benzyl-2-(3-methoxy-4-(4-methyl-1H-imidazol-1-yl)phenylamino)-7,8-dihydropyrido[4,3-d]pyrimidine-6(5H)-carboxylate (1.0 g, 1.90 mmol) was dissolved in methanol (10 mL). Hydrochloric acid (0.156 mL, 1.90 mmol) was added and the reaction mixture was stirred at 80° C. for 1 h. The solvent was evaporated under reduced pressure and the crude was used in the subsequent step as such. MS (ES+) m/z 427.0 (M+H)+

1H NMR (500 MHz, MeOD) δ ppm 2.42 (s, 3 H) 3.10 (t, 2 H) 3.56 (t, 2 H) 3.85 (s, 3 H) 4.09 (s, 2 H) 4.27 (s, 2 H) 7.23-7.38 (m, 6 H) 7.42-7.46 (m, 1 H) 7.50 (s, 1 H) 7.92 (d, 1 H) 9.04 (d, 1 H)

Example 106a tert-Butyl 4-benzyl-2-(3-methoxy-4-(4-methyl-1H-imidazol-1-yl)phenylamino)-7,8-dihydropyrido[4,3-d]pyrimidine-6(5H)-carboxylate

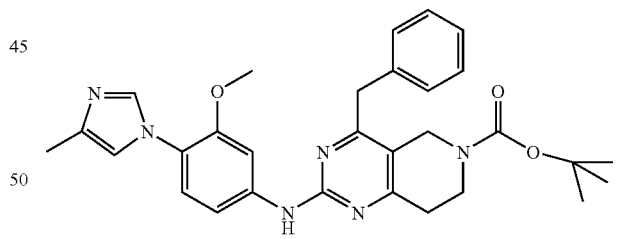

1-(3-Methoxy-4-(4-methyl-1H-imidazol-1-yl)phenyl) guanidine (300 mg, 1.22 mmol, example 43a), tert-butyl 4-oxo-3-(2-phenylacetyl)piperidine-1-carboxylate (466 mg, 1.47 mmol, example 41d) and sodium ethoxide (83 mg, 1.22 mmol) in ethanol (4 mL) were heated at 100° C. in a microwave reactor for 20 minutes. The reaction mixture was allowed to reach room temperature and the solvent was evaporated under reduced pressure. The crude was dissolved in ethyl acetate and washed with water. The organic phase was dried under MgSO₄ and the solvent was evaporated under reduced pressure yielding tert-butyl 4-benzyl-2-(3-methoxy-4-(4-methyl-1H-imidazol-1-yl)phenylamino)-7,8-dihydropyrido[4,3-d]pyrimidine-6(5H)-carboxylate (590 mg, 92%) which was used in the subsequent step as such. MS (ES+) m/z 527.3 (M+H)+

Example 107

1-(4-Benzyl-2-(3-methoxy-4-(4-methyl-1H-imidazol-1-yl)phenylamino)-7,8-dihydropyrido[4,3-d]pyrimidin-6(5H)-yl)ethanone

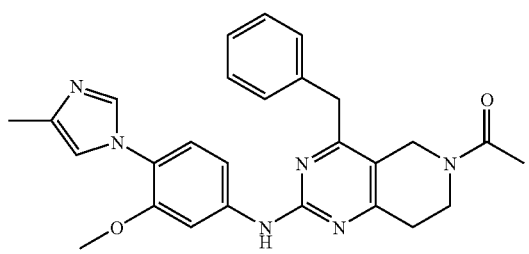

Acetic anhydride (0.039 mL, 0.41 mmol) was added to a solution of 4-benzyl-N-(3-methoxy-4-(4-methyl-1H-imidazol-1-yl)phenyl)-5,6,7,8-tetrahydropyrido[4,3-d]pyrimidin-2-amine (175 mg, 0.41 mmol, example 109) in THF (3 mL) and stirred for one hour. The solvent was evaporated under reduced pressure and the crude product purified on prepHPLC yielding 1-(4-benzyl-2-(3-methoxy-4-(4-methyl-1H-imidazol-1-yl)phenylamino)-7,8-dihydropyrido[4,3-d]pyrimidin-6(5H)-yl)ethanone (64.0 mg, 33.3%).

MS (ES+) m/z 469.1 (M+H)+

Mixture of Rotamers:

1H NMR (400 MHz, CHLOROFORM-d) δ ppm 1.95 (s), 2.21 (s), 2.26 (s), 2.38 (s), 2.85 (t), 2.92 (t), 3.71-3.77 (m), 3.79 (s), 3.82 (s), 3.87 (t), 4.02-4.06 (m), 4.43 (s), 4.66 (s), 6.90 (s), 7.03-7.18 (m), 7.25 (d), 7.28-7.37 (m), 7.76 (s), 7.83 (s), 7.87 (br. s)

Total no of protons in spectrum: 23
Ratio major:minor: 1:1

Example 108

1-(4-(1-(3,5-Dimethyl-1H-pyrazol-1-yl)ethyl)-2-(3-methoxy-4-(4-methyl-1H-imidazol-1-yl)phenylamino)-7,8-dihydropyrido[4,3-d]pyrimidin-6(5H)-yl)ethanone

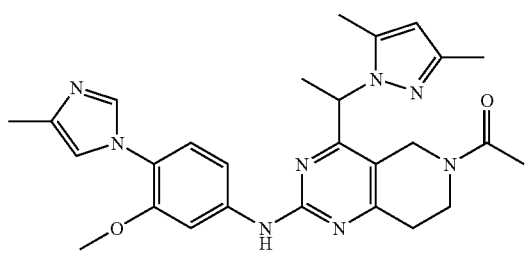

Acetic anhydride (0.016 mL, 0.17 mmol) was added to a solution of 4-(1-(3,5-dimethyl-1H-pyrazol-1-yl)ethyl)-N-(3-methoxy-4-(4-methyl-1H-imidazol-1-yl)phenyl)-5,6,7,8-tetrahydropyrido[4,3-d]pyrimidin-2-amine in DCM (1 mL) and stirred for one hour. The solvent was evaporated and the crude product was purified on prepHPLC yielding 1-(4-(1-(3,5-dimethyl-1H-pyrazol-1-yl)ethyl)-2-(3-methoxy-4-(4-methyl-1H-imidazol-1-yl)phenylamino)-7,8-dihydropyrido[4,3-d]pyrimidin-6(5H)-yl)ethanone (14.00 mg, 16.03%).

MS (ES+) m/z 501.2 (M+H)+

Mixture of Rotamers:

1H NMR (500 MHz, CHLOROFORM-d) δ ppm 1.86 (d) 1.93 (d) 1.96 (s) 2.10 (s) 2.14 (s) 2.17 (s) 2.19 (s) 2.22 (s) 2.29-2.33 (m) 2.83-2.88 (m) 2.88-2.94 (m) 3.54-3.61 (m) 3.61-3.68 (m) 3.81-3.86 (m) 3.87 (d) 3.95-4.01 (m) 4.12 (d) 5.41-5.49 (m) 5.86 (d) 6.88 (d) 7.07-7.13 (m) 7.13-7.20 (m) 7.44 (s) 7.68 (s) 7.71-7.77 (m)

Total no of protons in spectrum: 32
Ratio major:minor: 1:1

Example 108a 4-(1-(3,5-Dimethyl-1H-pyrazol-1-yl)ethyl)-N-(3-methoxy-4-(4-methyl-1H-imidazol-1-yl)phenyl)-5,6,7,8-tetrahydropyrido[4,3-d]pyrimidin-2-amine

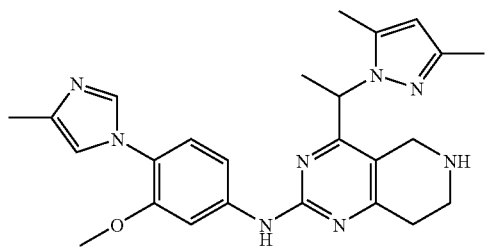

A solution of tert-butyl 4-(1-(3,5-dimethyl-1H-pyrazol-1-yl)ethyl)-2-(3-methoxy-4-(4-methyl-1H-imidazol-1-yl)phenylamino)-7,8-dihydropyrido[4,3-d]pyrimidine-6(5H)-carboxylate (397 mg, 0.71 mmol) and TFA (0.547 mL, 7.10 mmol) in DCM was stirred for one hour at 40° C. The reaction mixture was cooled and sat aqu NaHCO₃ was added until the mixture was neutralized. The organic phase was separated and the water phase was washed repeatedly with DCM yielding 4-(1-(3,5-dimethyl-1H-pyrazol-1-yl)ethyl)-N-(3-methoxy-4-(4-methyl-1H-imidazol-1-yl)phenyl)-5,6,7,8-tetrahydropyrido[4,3-d]pyrimidin-2-amine (250 mg, 77%)

MS (ES+) m/z 459.1 (M+H)+

Example 108b tert-Butyl 4-(1-(3,5-dimethyl-1H-pyrazol-1-yl)ethyl)-2-(3-methoxy-4-(4-methyl-1H-imidazol-1-yl)phenylamino)-7,8-dihydropyrido[4,3-d]pyrimidine-6(5H)-carboxylate

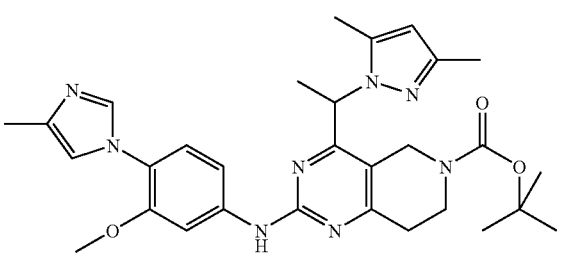

1-(3-Methoxy-4-(4-methyl-1H-imidazol-1-yl)phenyl)guanidine (175 mg, 0.57 mmol) and potassium carbonate (196 mg, 1.42 mmol) in EtOH (7 mL) were heated to 50° C. and tert-butyl 3-(2-(3,5-dimethyl-1H-pyrazol-1-yl)propanoyl)-4-oxopiperidine-1-carboxylate (248 mg, 0.71 mmol) added. The reaction mixture was stirred overnight. The solvent was evaporated and DCM added. The organic phase was washed with water and concentrated. The crude product was used as such in next step (450 mg, 113%).

MS (ES+) m/z 559.2 (M+H)+

Example 108c tert-Butyl 3-(2-(3,5-dimethyl-1H-pyrazol-1-yl)propanoyl)-4-oxopiperidine-1-carboxylate

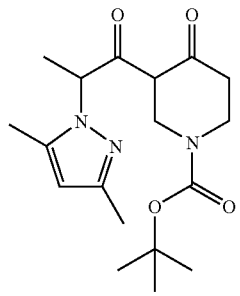

tert-Butyl 3-(2-(3,5-dimethyl-1H-pyrazol-1-yl)propanoyl)-4-oxopiperidine-1-carboxylate (0.248 g, 23.87% yield) was synthesised from 2-(3,5-dimethyl-1H-pyrazol-1-yl)propanoyl chloride (0.5 g, 2.97 mmol, example 104b) and tert-butyl 4-oxopiperidine-1-carboxylate (1.185 g, 5.95 mmo) by the general procedure for the preparation of diketones.

MS (ES−) m/z 348.7 (M−H)−

Example 109

4-(Cyclopentyloxymethyl)-N-(3-methoxy-4-(4-methyl-1H-imidazol-1-yl)phenyl)-7,8-dihydro-5H-pyrano[4,3-d]pyrimidin-2-amine

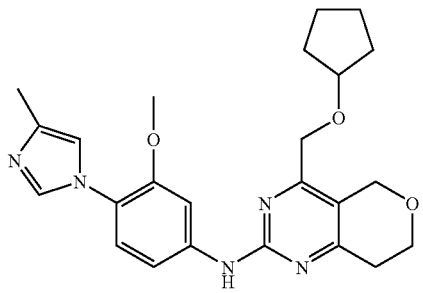

3-(2-(Cyclopentyloxy)acetyl)dihydro-2H-pyran-4(3H)-one (280 mg, 1.24 mmol), 1-(3-methoxy-4-(4-methyl-1H-imidazol-1-yl)phenyl)guanidine (1 equiv.) and potassium carbonate (2 equiv.) were heated to 50° C. over night in EtOH (5 mL). The crude product was extracted into DCM, the organic phase collected and solvent evaporated. The crude product was purified by flash chromatography (0-100% EtOAc in Heptane). The purity was not satisfactory so further purification on prepHPLC was performed to afford the title compound (83 mg, 16% yield).

MS (ES+) m/z 436.3 (M+H)+

1H NMR (500 MHz, CHLOROFORM-d) δ ppm 1.53-1.62 (m, 2 H) 1.70-1.80 (m, 6 H) 2.32 (s, 3 H) 2.91 (t, 2 H) 3.87 (s, 3 H) 4.01 (dt, 1 H) 4.05 (t, 2 H) 4.41 (s, 2 H) 4.80 (s, 2 H) 6.88 (s, 1 H) 7.06 (dd, 1 H) 7.14 (s, 1 H) 7.17 (d, 1 H) 7.68 (s, 1 H) 7.80 (d, 1 H)

Example 109a 3-(2-(Cyclopentyloxy)acetyl)dihydro-2H-pyran-4(3H)-one

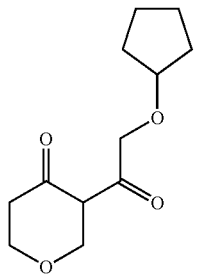

2-(Cyclopentyloxy)acetic acid (476mg, 3.3 mmol) was heated to reflux in thionyl chloride (0.365 ml, 5.00 mmol). After 30 min the excess of thionyl chloride was evaporated to afford (2-(cyclopentyloxy)acetyl chloride (3.3 mmol) that was used directly in the next step.

3-(2-(cyclopentyloxy)acetyl)dihydro-2H-pyran-4(3H)-one (280 mg, 21.5%) was synthesised from dihydro-2H-pyran-4(3H)-one (0.462 ml, 5.00 mmol) and (2-(cyclopentyloxy)acetyl chloride (3.3 mmol) by the general procedure for the preparation of diketones.

MS (ES−) m/z 225.1 (M−H)−

Example 110

1-(2-(2-(3-Methoxy-4-(4-methyl-1H-imidazol-1-yl)phenylamino)-7,8-dihydro-5H-pyrano[4,3-d]pyrimidin-4-yl)ethyl)pyrrolidin-2-one

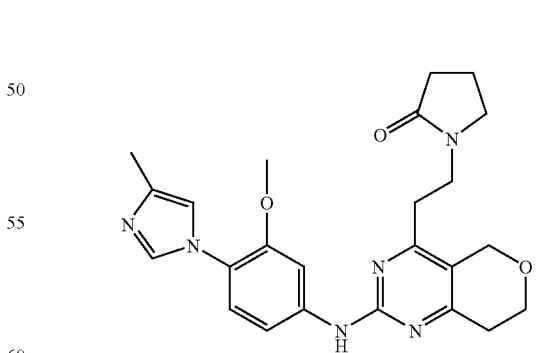

1-(3-oxo-3-(4-oxotetrahydro-2H-pyran-3-yl)propyl)pyrrolidin-2-one (202 mg, 0.84 mmol), 1-(3-methoxy-4-(4-methyl-1H-imidazol-1-yl)phenyl)guanidine (1 equiv.) and potassium carbonate (2 equiv.) were heated to 50° C. over night in EtOH (5 mL). The crude product was extracted into DCM and solvent was evaporated. The crude product was purified by flash chromatogaphy (0-100% EtOAc in heptanes) followed by prepHPLC to afford the titled compound.

MS (ES+) m/z 449.1 (M+H)+

1H NMR (500 MHz, CHLOROFORM-d) δ ppm 1.97-2.04 (m, 2 H) 2.12 (s, 3 H) 2.30 (s, 3 H) 2.36 (t, 2 H) 2.73-2.78 (m, 2 H) 2.87 (t, 2 H) 3.37-3.42 (m, 2 H) 3.73 (t, 2 H) 3.88 (s, 3 H) 4.03 (t, 2 H) 4.72 (s, 2 H) 6.87 (s, 1 H) 7.12-7.16 (m, 1 H) 7.16-7.19 (m, 1 H) 7.70 (s, 1 H) 7.74 (d, 1 H) 7.94 (br. s., 1 H)

Example 110a 1-(3-Oxo-3-(4-oxotetrahydro-2H-pyran-3-yl)propyl)pyrrolidin-2-one

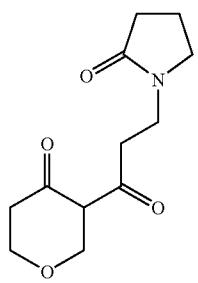

3-(2-Oxopyrrolidin-1-yl)propanoic acid (519 mg, 3.3 mmol) was heated to reflux in thionyl chloride (0.365 ml, 5.00 mmol) for 30 min. The excess of thionyl chloride was evaporated and the product, (3-(2-oxopyrrolidin-1-yl)propanoyl chloride (3.3 mmol)) used as such in the next step. 1-(3-oxo-3-(4-oxotetrahydro-2H-pyran-3-yl)propyl)pyrrolidin-2-one (202 mg, 15%) was synthesised from dihydro-2H-pyran-4 (3H)-one (0.462 ml, 5.00 mmol) and 3-(2-oxopyrrolidin-1-yl)propanoyl chloride (3.3 mmol) by the general procedure for the preparation of diketones.

MS (ES−) m/z 238.1 (M−H)−

Example 111

1-(2-(3-Methoxy-4-(4-methyl-1H-imidazol-1-yl)phenylamino)-4-(2-(tetrahydrofuran-2-yl)ethyl)-7,8-dihydropyrido[4,3-d]pyrimidin-6(5H)-yl)ethanone

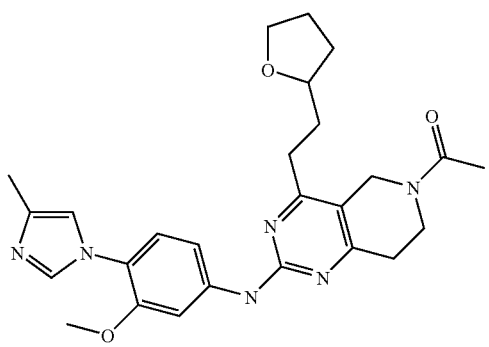

To a solution of N -(3-methoxy-4-(4-methyl-1H-imidazol-1-yl)phenyl)-4-(2-(tetrahydrofuran-2-yl)ethyl)-5,6,7,8-tetrahydropyrido[4,3-d]pyrimidin-2-amine (0.114 g, 0.26 mmol) in dichloromethane (2 mL) was added acetic anhydride (0.027 mL, 0.29 mmol) at rt. The reaction mixture was stirred for 45 minutes. The solvent was concentrated; the residue was suspended with methanol and purified by prepHPLC. Fractions were pooled and the solvent was evaporated. The residue was dissolved in water/acetonitrile-mixture (50:50) and freezedried giving 1-(2-(3-methoxy-4-(4-methyl-1H-imidazol-1-yl)phenylamino)-4-(2-(tetrahydrofuran-2-yl)ethyl)-7,8-dihydropyrido[4,3-d]pyrimidin-6(5H)-yl)ethanone (0.062 g, 49.6%).

1H NMR (400 MHz, DMSO-$d_6$) δ ppm 9.69 (s, 1 H) 7.99-8.08 (m, 1 H) 7.65 (s, 1 H) 7.24-7.34 (m, 1 H) 7.15-7.24 (m, 1 H) 7.02 (s, 1 H) 4.50-4.59 (m, 2 H) 3.81-3.85 (m, 1 H) 3.79-3.81 (m, 3 H) 3.80 (s, 3 H) 3.57-3.65 (m, 1 H) 2.82-2.89 (m, 1 H) 2.68-2.76 (m, 2 H) 2.13-2.15 (m, 3 H) 2.10-2.13 (m, 3 H) 1.86-2.04 (m, 4 H) 1.74-1.86 (m, 2 H) 1.38-1.51 (m, 1 H); MS (ES+) m/z 477 (M+H)+.

Example 111a

N-(3-Methoxy-4-(4-methyl-1H-imidazol-1-yl)phenyl)-4-(2-(tetrahydrofuran-2-yl)ethyl)-5,6,7,8-tetrahydropyrido[4,3-d]pyrimidin-2-amine

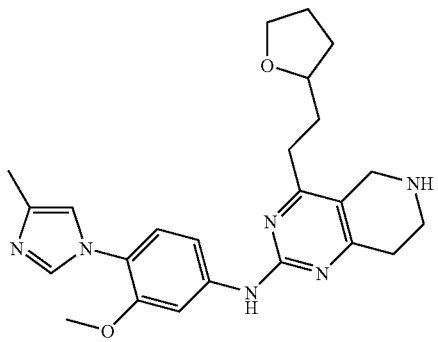

Trifluoroacetic acid (0.238 mL, 3.09 mmol) was added dropwise to a stirred solution of tert-butyl 2-(3-methoxy-4-(4-methyl-1H-imidazol-1-yl)phenylamino)-4-(2-(tetrahydrofuran-2-yl)ethyl)-7,8-dihydropyrido[4,3-d]pyrimidine-6 (5H)-carboxylate (0.330 g, 0.62 mmol) in DCM (3 mL) at rt. The reaction mixture was stirred under reflux for 1 hr. Five equivalents of trifluoroacetic acid were added and the reaction mixture was stirred at reflux for 1 hour. The reaction mixture was allowed to cool to room temperature. The organic mixture was washed with potassium carbonate (aq) and the organic layer was separated, dried (MgSO$_4$) and concentrated giving 0.247 g (92%) of N-(3-methoxy-4-(4-methyl-1H-imidazol-1-yl)phenyl)-8-phenyl-5,6,7,8-tetrahydropyrido[4,3-d]pyrimidin-2-amine.

1H NMR (500 MHz, DMSO-$d_6$) δ ppm 9.54 (s, 1 H) 8.04 (s, 1 H) 7.62 (s, 1 H) 7.24-7.26 (m, 1 H) 7.15-7.17 (m, 1 H) 7.0 (s, 1 H) 3.72-3.80 (m, 7 H) 3.57-3.60 (m, 1 H) 2.95-2.97 (m, 2 H) 2.63-2.65 (m, 2 H) 2.51-2.63 (m, 2 H) 1.90-1.99 (m, 1 H) 1.83-1.90 (m, 2 H) 1.74-1.83 (m, 2 H) 1.50-1.53 (m, 1 H) 1.36-1.46 (m, 1 H) 1.19-1.27 (m, 1 H) 0.77-0.87 (m, 1 H); MS (ES+) m/z 435 (M+H)+.

Example 111b tert-Butyl 2-(3-methoxy-4-(4-methyl-1H-imidazol-1-yl)phenylamino)-4-(2-(tetrahydrofuran-2-yl)ethyl)-7,8-dihydropyrido[4,3-d]pyrimidine-6(5H)-carboxylate

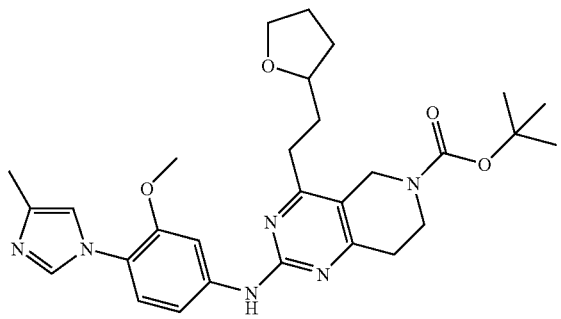

A reaction mixture of 1-(3-methoxy-4-(4-methyl-1H-imidazol-1-yl)phenyl)guanidine (0.800 g, 2.17 mmol), tert-butyl 4-oxo-3-(3-(tetrahydrofuran-2-yl)propanoyl)piperidine-1-carboxylate (0.705 g, 2.17 mmol) and potassium carbonate (0.599 g, 4.33 mmol) in ethanol (6 mL) was stirred at 60° C. overnight. The reaction mixture was transferred to a microwave vial (20 mL) and run in the microwave at 120° C. for 45 minutes. The reaction mixture was filtered and washed with dichloromethane. The filtrate was concentrated and the residue was dissolved in dichloromethane and washed with water, dried (MgSO$_4$) and concentrated. The crude product was purified by silica flash chromatography using a gradient of methanol in dichloromethane (0 to 4%) giving tert-butyl 2-(3-methoxy-4-(4-methyl-1H-imidazol-1-yl)phenylamino)-4-(2-(tetrahydrofuran-2-yl)ethyl)-7,8-dihydropyrido[4,3-d]pyrimidine-6(5H)-carboxylate (0.335 g, 28.9%) as the product.

1H NMR (500 MHz, DMSO-d$_6$) δ ppm 9.68 (s, 1 H) 8.03 (s, 1 H) 7.64 (s, 1 H) 7.27-7.29 (m, 1 H) 7.19-7.21 (m, 1 H) 7.02 (s, 1 H) 4.44 (br. s., 2 H) 4.05-4.01 (m, 1 H) 3.81-3.84 (m, 1 H) 3.80 (s, 3 H) 3.74-3.79 (m, 1 H) 3.59-3.65 (m, 3 H) 2.75-2.77 (m, 2 H) 2.66-2.72 (m, 1 H) 2.58-2.62 (m, 1 H) 2.14 (s, 3 H), 1.86-1.92 (m, 2 H) 1.78-1.86 (m, 2 H) 1.44 (s, 9 H) 1.16-1.19 (m, 1 H); MS (ES+) m/z 535 (M+H)+.

Example 111c tert-Butyl 4-oxo-3-(3-(tetrahydrofuran-2-yl)propanoyl)piperidine-1-carboxylate

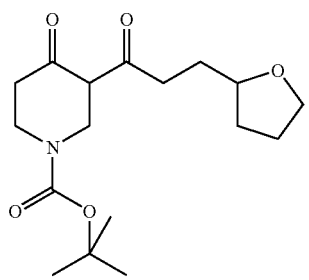

Lithium bis(trimethylsilyl)amide (2.231 ml, 11.88 mmol) was added to a stirred solution of tert-butyl 4-oxopiperidine-1-carboxylate (1.127 g, 5.66 mmol) in toluene (3 mL) at 0° C. and the resulting mixture was stirred for 2 minutes. 1-(1H-Imidazol-1-yl)-3-(tetrahydrofuran-2-yl)propan-1-one (1.099 g, 5.66 mmol) in toluene (1 mL) was added and the reaction mixture was stirred for 5 minutes before it was quenched with acetic acid (0.972 ml, 16.97 mmol) in water (4 mL). The organic layer was separated and purified by silica flash chromatography using a gradient of ethyl acetate in heptane (0 to 40%) giving tert-butyl 4-oxo-3-(3-(tetrahydrofuran-2-yl)propanoyl)piperidine-1-carboxylate (0.717 g, 38.9%) as the product.

1H NMR (400 MHz, DMSO-d$_6$) δ ppm 4.12 (s, 1 H) 3.81 (br. s., 1 H) 3.68-3.77 (m, 2 H) 3.56-3.64 (m, 5 H) 3.44-3.51 (m, 1 H) 2.37-2.43 (m, 1 H) 2.33-2.36 (m, 4 H) 1.85-1.98 (m, 2 H) 1.74-1.85 (m, 3 H) 1.59-1.74 (m, 2 H) 1.47-1.59 (m, 1 H) 1.42 (s, 9 H) 1.41 (s, 7 H) 1.40 (s, 2 H) 1.20-1.28 (m, 2 H) 0.81-0.90 (m, 2 H); MS (ES-) m/z 324 (M-H)-.

Example 111d 1-(1H-Imidazol-1-yl)-3-(tetrahydrofuran-2-yl)propan-1-one

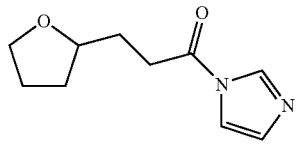

Di(1H-imidazol-1-yl)methanone (1.196 g, 7.38 mmol) was added in small portions to a stirred solution of 3-(tetrahydrofuran-2-yl)propanoic acid (1.013 g, 7.03 mmol) in dichloromethane (3 mL) at room temperature under argon. The reaction mixture was stirred at room temperature for 2 hours. The mixture was washed twice with water, dried over MgSO$_4$ and concentrated giving 1-(1H-imidazol-1-yl)-3-(tetrahydrofuran-2-yl)propan-1-one (1.099 g, 81%) as the product. 1H NMR (500 MHz, DMSO-d$_6$) δ ppm 8.34-8.51 (m, 1 H), 7.64-7.79 (m, 1 H), 6.98-7.17 (m, 1 H), 3.76-3.85 (m, 1 H), 3.66-3.76 (m, 1 H), 3.55-3.60 (m, 1 H), 3.03-3.10 (m, 2 H), 1.90-2.00 (m, 1 H), 1.73-1.90 (m, 4 H), 1.39-1.53 (m, 1 H); MS (ES-) m/z 194 (M-H)-.

Example 112

N-(3-Methoxy-4-(4-methyl-1H-imidazol-1-yl)phenyl)-6-methyl-4-(2-(tetrahydrofuran-2-yl)ethyl)-5,6,7,8-tetrahydropyrido[4,3-d]pyrimidin-2-amine

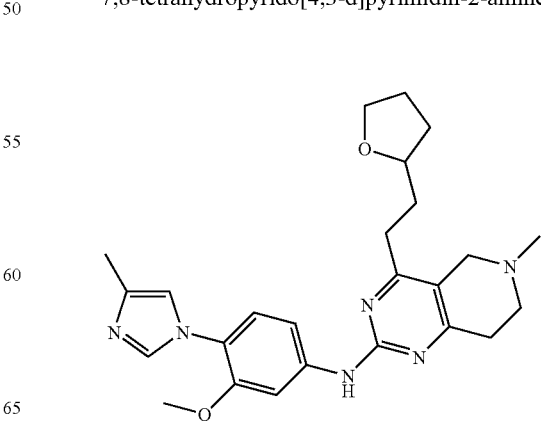

N-(3-Methoxy-4-(4-methyl-1H-imidazol-1-yl)phenyl)-4-(2-(tetrahydrofuran-2-yl)ethyl)-5,6,7,8-tetrahydropyrido[4,3-d]pyrimidin-2-amine (0.133 g, 0.31 mmol, Example 114a), formaldehyde (8.43 µL, 0.31 mmol) and acetic acid (8.76 µL, 0.15 mmol) in methanol (4 mL) was stirred at room temperature for 20 minutes. Polymer supported cyanoborohydride (0.46 g, 0.92 mmol) was added and the reaction mixture was stirred at room temperature overnight. The polymer supported cyanoborohyride was filtered off and the filtrated was purified by preparative chromatography. The product containing fractions were pooled and the solvent was evaporated. The residue was dissolved in water/acetonitrile-mixture (50:50) and freezedried giving N-(3-methoxy-4-(4-methyl-1H-imidazol-1-yl)phenyl)-6-methyl-4-(2-(tetrahydrofuran-2-yl)ethyl)-5,6,7,8-tetrahydropyrido[4,3-d]pyrimidin-2-amine (0.055 g, 40.1%).

1H NMR (400 MHz, DMSO-$d_6$) δ ppm 9.60 (s, 1 H) 8.06 (s, 1 H) 7.64 (s, 1 H) 7.22-7.30 (m, 1 H) 7.14-7.22 (m, 1 H) 7.02 (s, 1 H) 3.72-3.82 (m, 5 H) 3.57-3.63 (m, 1 H) 3.41-3.43 (m, 2 H) 2.77-2.80 (m, 2 H) 2.63-2.67 (m, 3 H) 2.62-2.57 (m, 1 H) 2.39 (s, 3 H) 2.10-2.16 (m, 3 H) 1.92-2.01 (m, 2 H) 1.74-1.89 (m, 3 H) 1.34-1.52 (m, 1 H); MS (ES+) m/z 449 (M+H)+.

Example 113

4-((1,3-Difluoropropan-2-yloxy)methyl)-N-(3-methoxy-4-(4-methyl-1H-imidazol-1-yl)phenyl)-7,8-dihydro-5H-pyrano[4,3-d]pyrimidin-2-amine

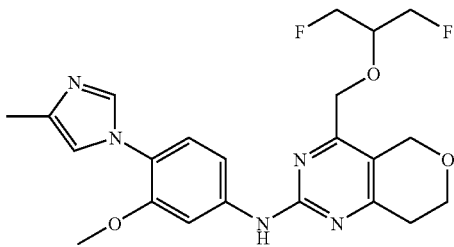

Potassium carbonate (222 mg, 1.61 mmol) was added to 1-(3-methoxy-4-(4-methyl-1H-imidazol-1-yl)phenyl)guanidine (149 mg, 0.40 mmol) in DMF (1 mL) and set under $N_2$ atmosphere. The DMF (1 mL) solution of 3-(2-(1,3-difluoropropan-2-yloxy)acetyl)dihydro-2H-pyran-4(3H)-one (95 mg, 0.40 mmol) was added dropwise to the reaction mixture and stirred for 16 hours at 50° C. The reaction mixture was cooled to room temperature and filtered. The filtrate was concentrated and the crude product was purified by silica flash chromatography using a gradient of methanol in dichloromethane (0 to 4%) affording the title compound (120 mg, 67% yield).

MS (ES+) m/z 446 [M+1].

$^1$H NMR (400 MHz, CDCl$_3$) δ (δ ppm) 7.81 (d, 2 H) 7.14-7.23 (m, 2 H) 7.09 (dd, 1 H) 6.91 (s, 1 H) 4.82 (s, 2 H) 4.66 (s, 2 H) 4.58-4.65 (m, 2 H) 4.45-4.57 (m, 2 H) 4.06 (t, 2 H) 3.90-4.05 (m, 1 H) 3.88 (s, 3 H) 2.84-3.01 (m, 2 H) 2.36 (s, 3 H).

Example 113a 3-(2-(1,3-Difluoropropan-2-yloxy)acetyl)dihydro-2H-pyran-4(3H)-one

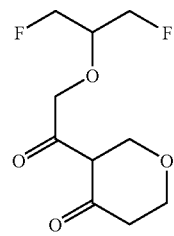

2-(1,3-Difluoropropan-2-yloxy)acetic acid (0.382 g, 2.48 mmol) in 1,2-dichloroethane (8 mL) was treated with thionyl chloride (0.542 mL, 7.44 mmol) and set under $N_2$ atmosphere. The mixture was stirred for 1 hour at 45° C. then concentrated in vacuo. The crude oil was used in the next step without further purification.

At 0° C., the toluene (5 mL) solution of tetrahydro-4H-pyran-4-one (0.344 mL, 3.72 mmol) was treated with LiHMDS, 1M solution in THF (3.97 mL, 3.97 mmol) under $N_2$ atmosphere. After 2 minutes 2-(1,3-difluoropropan-2-yloxy)acetyl chloride (428 mg, 2.48 mmol) in toluene (1 mL) was added. After 5 minutes, acetic acid (0.270 mL, 4.71 mmol) and 10 ml water were added. The phases were separated and the aqueous layer was extracted with ethyl acetate. The organic layer was dried over anhydrous sodium sulfate, filtered and concentrated. The solvent was removed in vacuo and the residual oil was purified by silica flash chromatography (EtOAc/Heptane gradient) to afford the title product (0.095 g, 16% yield).

MS (ES+) m/z 237 [M+1].

Example 113b 2-(1,3-Difluoropropan-2-yloxy)acetic acid

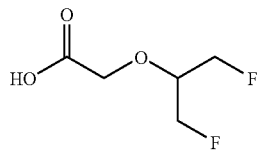

Benzyl 2-(1,3-difluoropropan-2-yloxy)acetate (0.91 g, 3.73 mmol) was dissolved in THF (14 mL)/water (7 mL) mixture and treated with lithium hydroxide monohydrate (0.469 g, 11.18 mmol) and allowed to stir for 16 hours at room temperature. The mixture was concentrated, redissolved in water and extracted with ethyl acetate. The aqueous phase was treated with 2M HCl and NaCl then extracted with ethyl acetate (3×). The organic layer was dried over anhydrous sodium sulfate, filtered and concentrated to afford the title product (0.388 g, 67% yield).

$^1$H NMR (400 MHz, CDCl$_3$) δ (ppm) 4.63-4.70 (m, 2 H) 4.50-4.59 (m, 2 H) 4.38 (s, 2 H) 3.90-4.06 (m, 1 H).

Example 113c

Benzyl 2-(1,3-difluoropropan-2-yloxy)acetate

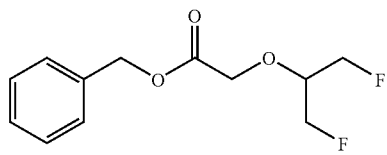

Sodium tert-butoxide (0.923 g, 9.60 mmol) in DMF (20 mL)/THF (12 mL) mixture was cooled down to 0° C. and set under N$_2$ atmosphere. 1,3-Difluoropropan-2-ol (0.717 mL, 9.25 mmol) was added via syringe and stirred for 40 min then benzyl 2-bromoacetate (1.373 mL, 8.73 mmol) was added dropwise via syringe and the mixture was stirred at rt for 16 hours. Ethyl acetate and sat NaHCO$_3$ solution were added and the phases were separated. The aqueous layer was extracted with ethyl acetate and the combined organic layer was dried over anhydrous sodium sulfate, filtered and concentrated. The crude oil was purified by silica gel chromatography (heptane/EtOAc gradient) to afford the title compound (0.91 g, 43% yield).

MS (ES$^+$) m/z 245 [M+1].

$^1$H NMR (400 MHz, CDCl$_3$) δ (ppm) 7.30-7.46 (m, 5 H) 5.21 (s, 2 H) 4.66 (d, 2 H) 4.54 (d, 2 H) 4.35 (s, 2 H) 3.84-4.07 (m, 1 H).

Example 114

4-Benzyl-N-[4-(2-methyl-1H-imidazol-1-yl)phenyl]-7,8-dihydro-5H-thiopyrano[4,3-d]pyrimidin-2-amine 6-oxide

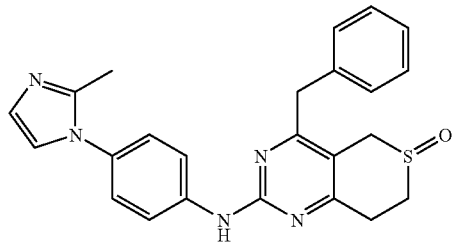

4-Benzyl-N-(4-(2-methyl-1H-imidazol-1-yl)phenyl)-7,8-dihydro-5H-thiopyrano[4,3-d]pyrimidin-2-amine (90 mg, 0.22 mmol) and mCPBA (56.3 mg, 0.33 mmol) was dissolved in DCM (4 mL). The reaction was completed after 2 h. The solvent was evaporated and the crude product was purified on preparative HPLC yielding 4-benzyl-N-[4-(2-methyl-1H-imidazol-1-yl)phenyl]-7,8-dihydro-5H-thiopyrano[4,3-d]pyrimidin-2-amine 6-oxide (13.0 mg, 13.0%). MS (ES+) m/z 430.0 (M+H)+

Mixture of Rotamers:

1H NMR (400 MHz, CHLOROFORM-d) δ ppm 2.38 (s), 2.92-3.01 (m), 3.04 (t), 3.09 (t), 3.25-3.33 (m), 3.58 (ddd), 3.72-3.81 (m), 3.91-3.98 (m), 4.02-4.13 (m), 7.00 (s), 7.06 (s), 7.17-7.41 (m), 7.69-7.75 (m), 7.83 (s)

Total no of protons in spectrum: 23
Ratio major:minor: 1:1

Example 114a

4-Benzyl-N-(4-(2-methyl-1H-imidazol-1-yl)phenyl)-7,8-dihydro-5H-thiopyrano[4,3-d]pyrimidin-2-amine

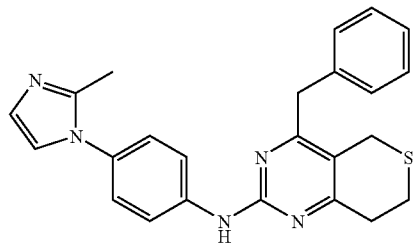

4-Benzyl-N-(4-(2-methyl-1H-imidazol-1-yl)phenyl)-7,8-dihydro-5H-thiopyrano[4,3-d]pyrimidin-2-amine (74 mg, 28%) was synthesised from 3-(2-phenylacetyl)dihydro-2H-thiopyran-4(3H)-one and 1-(4-(2-methyl-1H-imidazol-1-yl)phenyl)guanidine (Example 41c) according to the general procedure for the synthesis of pyrimidines. MS (ES+) m/z 414.2 (M+H)+

Example 114b 3-(2-Phenylacetyl)dihydro-2H-thiopyran-4(3H)-one

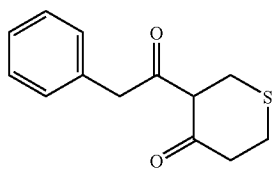

3-(2-Phenylacetyl)dihydro-2H-thiopyran-4(3H)-one (291 mg, 83%) was synthesised from 2-phenylacetyl chloride and dihydro-2H-thiopyran-4(3H)-one according to the general procedure for the preparation of diketones. MS (ES−) m/z 233 (M−H)−

Assays

The level of activity of the compounds on Aβ release was tested using the following method:

Compounds were diluted in 100% DMSO and stored at 20° C. prior to use. Human Embryonic Kidney (HEK) or Human Neuroblastoma (SH-SY5Y) cell lines stably expressing APP with the Swedish mutation (APPswe) were cultured using Dulbecco's Modified Eagles medium (DMEM) supplied with 4500 g/l glucose, Na-pyruvate and GlutaMAX with 10% FBS, 100 U/ml penicillin-streptomycin (PEST) respectively, 1× non-essential amino acids (NEAA), 10 μM Hepes, 100 μg/ml Zeocine. Cells at about 80% confluence were washed with PBS, detached from culture flasks using 1× Trypsin/EDTA diluted in PBS, re-suspended in cell media and plated in 384-well poly-d-lysine coated cell culture plates at about 10000-15000 cells/well, in 25 μL cell media. Optionally, cryo-preserved cells (frozen and stored at −140° C. in 90% cell media and 10% DMSO) were thawed, washed and plated as above. Next the cells were incubated for 15-24 h at 37° C. and 5% CO$_2$, after which cell medium was changed. Fresh medium containing test compound diluted ×200 from prepared compound plate was added to the cells before further incubation for 4-6 hours at 37° C. and 5% $CO_2$. After incubation with test compound the amount of Aβ peptides, including Aβ42, Aβ40, Aβ39, Aβ38 and Aβ37, secreted to the cell medium was analyzed using the electrochemiluminescence assay technology from Meso Scale Discovery Technology, in combination with specific antibodies raised against the different Aβ peptides. Potential cytotoxic effects of the compounds were usually assayed by measuring the ATP content (ViaLight) from cell lysate.

Results

Typical $IC_{50}$ values of Aβ42 release for the compounds of the present invention are in the range of about 1 to about 16000 nM. Biological data on final compounds are given below in Table 1.

TABLE 1

| Example number | pIC50 |
| --- | --- |
| 1 | 6.0 |
| 2 | 6.4 |
| 3 | 6.0 |
| 4 | 6.5 |
| 5 | 6.0 |
| 6 | 5.9 |
| 7 | 7.0 |
| 8 | 7.1 |
| 9 | 5.8 |
| 10 | 6.3 |
| 11 | 6.4 |
| 12 | 5.4 |
| 13 | 5.5 |
| 14 | 6.9 |
| 15 | 6.4 |
| 16 | 6.2 |
| 17 | 5.8 |
| 18 | 5.6 |
| 19 | 6.1 |
| 20 | 6.0 |
| 21 | 5.9 |
| 22 | 6.4 |
| 23 | 5.2 |
| 24 | 6.6 |
| 25 | 6.1 |
| 26 | 6.9 |
| 27 | 6.5 |
| 28 | 6.1 |
| 29 | 6.2 |
| 30 | 6.0 |
| 31 | 6.1 |
| 32 | 6.1 |
| 33 | 5.9 |
| 34 | 5.5 |
| 35 | 5.5 |
| 36 | 5.3 |
| 37 | 5.0 |
| 38 | 6.4 |
| 39 | 6.8 |
| 41 | 6.7 |
| 42 | 6.4 |
| 43 | 7.2 |
| 44 | 7.1 |
| 45 | 6.2 |
| 46 | 5.8 |
| 47 | 7.1 |
| 48 | 6.7 |
| 49 | 6.6 |
| 50 | 6.6 |
| 51 | 6.6 |
| 52 | 6.5 |
| 53 | 6.5 |
| 54 | 6.5 |
| 55 | 6.5 |
| 56 | 6.4 |
| 57 | 6.4 |
| 58 | 6.7 |

TABLE 1-continued

| Example number | pIC50 |
| --- | --- |
| 59 | 6.4 |
| 60 | 6.3 |
| 61 | 5.0 |
| 62 | 5.0 |
| 63 | 4.3 |
| 64 | 6.0 |
| 65 | 6.5 |
| 66 | 5.9 |
| 67 | 5.0 |
| 68 | 7.7 |
| 69 | 6.4 |
| 70 | 6.2 |
| 71 | 6.6 |
| 72 | 6.2 |
| 73 | 6.1 |
| 74 | 6.0 |
| 75 | 7.6 |
| 76 | 6.3 |
| 77 | 6.2 |
| 78 | 6.0 |
| 79 | 5.9 |
| 80 | 6.8 |
| 81 | 6.6 |
| 82 | 6.5 |
| 83 | 6.8 |
| 84 | 6.8 |
| 85 | 6.6 |
| 86 | 6.3 |
| 87 | 6.5 |
| 88 | 6.4 |
| 89 | 6.2 |
| 90 | 6.2 |
| 91 | 5.6 |
| 92 | 5.3 |
| 93 | 5.2 |
| 94 | 5.3 |
| 95 | 7.4 |
| 96 | 7.2 |
| 97 | 6.2 |
| 98 | 6.1 |
| 99 | 6.5 |
| 100 | 7.0 |
| 101 | 7.3 |
| 102 | 6.9 |
| 103 | 7.0 |
| 104 | 6.7 |
| 105 | 7.8 |
| 106 | 7.2 |
| 107 | 7.6 |
| 108 | 6.3 |
| 109 | 7.7 |
| 110 | 5.6 |
| 111 | 6.6 |
| 112 | 6.9 |
| 113 |  |
| 114 | 5.8 |

The invention claimed is:

1. A compound or pharmaceutically acceptable salt thereof of formula (Ia)

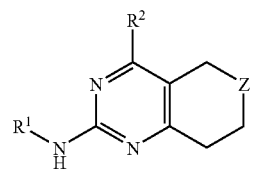

(Ia)

wherein:
R[1] is selected from phenyl substituted in the para position by a heteroaryl group and wherein the phenyl group and the heteroaryl group are optionally and independently substituted by one to three R' groups;

$R^2$ is Y—$R^7$;

Y is —C($R^{12}$)($R^{13}$)—, —N($R^8$)—, —O—, —C($R^{12}$)($R^{13}$)—N($R^8$)—, —N($R^8$)—C($R^{12}$)($R^{13}$)—, —C($R^{12}$)($R^{13}$)—O—, or —O—C($R^{12}$)($R^{13}$)—;

R' is selected from halogen, $C_{1-6}$alkyl, halogenated $C_{1-6}$alkyl, $C_{1-6}$alkoxy, halogenated $C_{1-6}$alkoxy;

$R^8$ is selected from hydrogen, $C_{1-6}$alkyl, halogenated $C_{1-6}$alkyl and $C_{3-6}$carbocyclyl, wherein said $C_{1-6}$alkyl, is optionally and independently substituted with one to three substituents selected from cyano, hydroxy or heterocyclyl;

$R^7$ is selected from hydrogen, aryl, heteroaryl, $C_{1-4}$alkylaryl, $C_{1-4}$alkylheteroaryl, $C_{1-4}$alkylheterocyclyl, halogenated $C_{1-6}$alkyl, $C_{1-6}$alkyl and $C_{3-6}$carbocyclyl, wherein said aryl, heteroaryl, $C_{1-6}$alkyl or carbocyclyl is optionally and independently substituted with one to three hydroxy, alkoxy, cyano, hydroxyalkyl, C(O)$C_{1-6}$alkyl or R' groups, wherein said C(O)$C_{1-6}$alkyl is optionally substituted with hydroxy; or $R^8$ and $R^7$ may, when Y is $NR^8$, optionally form together with the nitrogen atom a saturated, partially saturated or unsaturated ring system containing one nitrogen atom as a heteroatom, wherein said ring system is optionally and independently substituted by one to three R' groups $R^{12}$ and $R^{13}$ are independently selected from $C_{1-4}$alkyl, halogenated $C_{1-4}$alkyl, $C_{1-4}$alkoxy, halogenated $C_{1-4}$alkoxy;

Z is N—($R^{3b}$);

$R^{3b}$ is selected from hydrogen, $C_{1-6}$alkyl, cyano substituted $C_{1-6}$alkyl, halogenated $C_{1-6}$alkyl, $C_{1-6}$alkanoyl, hydroxy substituted $C_{1-6}$alkanoyl, dialkylamino substituted $C_{1-6}$alkanoyl, $C_{1-6}$alkoxy substituted $C_{1-6}$alkanoyl, $C_{3-6}$carbocyclyl-carbonyl, ($C_{1-6}$alkyl)$_2$carbamoyl, $C_{1-6}$alkylsulfonyl, and $C_{1-6}$alkoxycarbonyl;

provided that compounds according to formula (Ia), wherein Y is $NR^8$, Z is N—($R^{3b}$), $R^8$ is hydrogen, alkyl or cycloalkyl, and $R^7$ is arylalkyl are excluded.

2. A compound or salt thereof according to claim 1 wherein $R^1$ is selected from phenyl substituted in the para position by a heteroaryl group and wherein the phenyl group is further optionally substituted with a $C_{1-4}$alkoxy group or a halogenated $C_{1-4}$alkoxy group and the heteroaryl group is optionally substituted by a $C_{1-4}$alkyl group or a halogenated $C_{1-4}$alkyl group;

$R^2$ is Y—$R^7$;

Y is —C($R^{12}$)($R^{13}$)—or C($R^{12}$)($R^{13}$)—O—;

$R^7$ is selected from hydrogen, aryl, heteroaryl, $C_{1-4}$alkylaryl, $C_{1-4}$alkylheteroaryl, $C_{1-4}$alkylheterocyclyl, $C_{1-6}$alkyl, halogenated$C_{1-6}$alkyl and $C_{3-6}$carbocyclyl, wherein said aryl, heteroaryl, $C_{1-4}$alkylaryl, $C_{1-6}$alkyl, halogenated$C_{1-6}$alkyl or carbocyclyl is optionally substituted with one substituent selected from hydroxy, alkoxy, cyano, $C_{1-6}$alkyl, halogenated $C_{1-6}$alkyl and C(O)$C_{1-6}$alkyl, wherein said C(O)$C_{1-6}$alkyl is optionally substituted with hydroxy;

$R^{12}$ and $R^{13}$ independently ndependently selected from $C_{1-4}$alkyl, halogenated $C_{1-4}$alkyl, $C_{1-4}$alkoxy, halogenated $C_{1-4}$alkoxy;

Z is N—($R^{3b}$); and $R^{3b}$ is selected from hydrogen, $C_{1-6}$alkyl, cyano substituted $C_{1-6}$alkyl, $C_{1-6}$alkanoyl, hydroxy substituted $C_{1-6}$alkanoyl, dialkylamino substituted $C_{1-6}$alkanoyl, $C_{1-6}$alkoxy substituted $C_{1-6}$alkanoyl, $C_{3-6}$carbocyclyl-carbonyl, ($C_{1-6}$alkyl)$_2$carbamoyl, $C_{1-6}$alkylsulfonyl, and $C_{1-6}$alkoxycarbonyl.

3. A compound or salt thereof of formula (Ia)

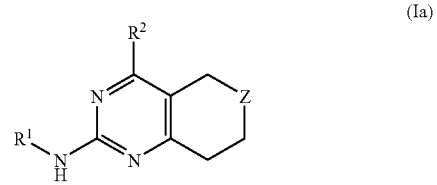

(Ia)

wherein:

$R^1$ is selected from 3-methoxy-4-(4-methylimidazol-1-yl)phenyl, 4-(1-methylpyrazol-4-yl)phenyl, 4-(2-methylimidazol-1-yl)phenyl, or 4-oxazol-5-ylphenyl;

$R^2$ is selected from the group consisting of[2-fluoro-1-(fluoromethyl)ethoxy]methyl, (2-fluorophenyl)methyl, (2-hydroxy-2-phenyl-ethyl)-methyl-amino, (2R)-2-(hydroxymethyl)indolin-1-yl, (2S)-2-(hydroxymethylindolin-1-yl, (3-acetylphenyl)amino, (3-methoxyphenyl)methyl, (4-fluorophenyl)methyl, (4-fluorophenyl)-methyl-amino,[(2R)-norbornan-2-yl]amino,[(2R)-tetrahydrofuran-2-yl]methylamino,[(2S)-tetrahydrofuran-2-yl]methylamino,[1-(hydroxymethyl)cyclopentyl]amino,[2-(hydroxymethyl)phenyl]methyl-methyl-amino,[3-(hydroxymethyl)phenyl]amino, 1-(3,5-dimethylpyrazol-1-yl)ethyl, 1-hydroxy-1-methyl-ethyl, 1-phenylethyl, 2-(2-oxopyrrolidin-1-yl)ethyl, 2-(3-fluorophenyl)ethyl, 2-(hydroxymethyl)-1-piperidyl, 2-cyanoethyl-cyclopropyl-amino, 2-cyclohexyl-ethyl, 2-hydroxyethyl-phenyl-amino, 2-tetrahydrofuran-2-ylethyl, 3-(hydroxymethyl)-1-piperidyl, 4,4-difluoro-1-piperidyl, benzyl, benzyl-(2-hydroxyethyl)amino, benzylamino, benzyloxy, cyclohexylamino, cyclohexyl-methyl-amino, cyclopentoxymethyl, cyclopentylmethyl, ethyl-(tetrahydrofuran-2-ylmethyl)amino, indolin-1-yl, methoxy-phenyl-methyl, methyl-(2-pyridylmethyl)amino, methyl-(3-pyridylmethyl)amino, p-tolylmethyl, tetrahydropyran-4-ylmethyl, and tetrahydropyran-4-ylmethylamino;

Z is N—($R^{3b}$); and $R^{3b}$ is selected from the group consisting of hydrogen, (2S)-2-hydroxypropanoyl, 2-dimethylaminoacetyl, 2-hydroxyacetyl, 2-hydroxyethyl, 2-methoxyacetyl, acetyl, cyanomethyl, cyclopropanecarbonyl, dimethylcarbamoyl, ethoxycarbonyl, ethylsulfonyl, methoxycarbonyl, methyl, methylsulfonyl, propanoyl, and propyl.

4. A compound selected from the group consisting of:
2-((2-(4-(oxazol-5-yl)phenylamino)-5,6,7,8-tetrahydropyrido[4,3-d]pyrimidin-4-yl)(phenyl)amino)ethanol;
2-((6-methyl-2-(4-(oxazol-5-yl)phenylamino)-5,6,7,8-tetrahydropyrido[4,3-d]pyrimidin-4-yl)(phenyl)amino)ethanol;
N2-(4-(oxazol-5-yl)phenyl)-N4-phenyl-5,6,7,8-tetrahydropyrido[4,3-d]pyrimidine-2,4-diamine;
6-methyl-N2-(4-(oxazol-5-yl)phenyl)-N4-phenyl-5,6,7,8-tetrahydropyrido[4,3-d]pyrimidine-2,4-diamine;
N4-benzyl-N2-(4-(oxazol-5-yl)phenyl)-5,6,7,8-tetrahydropyrido[4,3-d]pyrimidine-2,4-diamine;
N2-(3-methoxy-4-(4-methyl-1H-imidazol-1-yl)phenyl)-N4-phenyl-5,6,7,8-tetrahydropyrido[4,3-d]pyrimidine-2,4-diamine;

2-(2-(3-methoxy-4-(4-methyl-1H-imidazol-1-yl)phenylamino)-4-(phenylamino)-7,8-dihydropyrido[4,3-d]pyrimidin-6(5H)-yl)ethanol;
(S)-(1-(6-methyl-2-(4-(2-methyl-1H-imidazol-1-yl)phenylamino)-5,6,7,8-tetrahydropyrido[4,3-d]pyrimidin-4-yl)indolin-2-yl)methanol;
N4-((2R)-bicyclo[2.2.1]heptan-2-yl)-6-methyl-N2-(4-(2-methyl-1H-imidazol-1-yl)phenyl)-5,6,7,8-tetrahydropyrido[4,3-d]pyrimidine-2,4-diamine;
N4-cyclohexyl-N4,6-dimethyl-N2-(4-(2-methyl-1H-imidazol-1-yl)phenyl)-5,6,7,8-tetrahydropyrido[4,3-d]pyrimidine-2,4-diamine;
4-(benzyloxy)-N-(4-(oxazol-5-yl)phenyl)-5,6,7,8-tetrahydropyrido[4,3-d]pyrimidin-2-amine;
(R)-(1-(6-methyl-2-(4-(2-methyl-1H-imidazol-1-yl)phenylamino)-5,6,7,8-tetrahydropyrido[4,3-d]pyrimidin-4-yl)indolin-2-yl)methanol;
2-((2-(4-(oxazol-5-yl)phenylamino)-6-propyl-5,6,7,8-tetrahydropyrido[4,3-d]pyrimidin-4-yl)(phenyl)amino)ethanol;
1-(4-((2-hydroxyethyl)(phenyl)amino)-2-(4-(oxazol-5-yl)phenylamino)-7,8-dihydropyrido[4,3-d]pyrimidin-6(5H)-yl)propan-1-one;
Cyclopropyl(4-((2-hydroxyethyl)(phenyl)amino)-2-(4-(oxazol-5-yl)phenylamino)-7,8-dihydropyrido[4,3-d]pyrimidin-6(5H)-yl)methanone;
2-(dimethylamino)-1-(4-((2-hydroxyethyl)(phenyl)amino)-2-(4-(oxazol-5-yl)phenylamino)-7,8-dihydropyrido[4,3-d]pyrimidin-6(5H)-yl)ethanone;
1-(4-((2-hydroxyethyl)(phenyl)amino)-2-(4-(oxazol-5-yl)phenylamino)-7,8-dihydropyrido[4,3-d]pyrimidin-6(5H)-yl)-2-methoxyethanone;
2-hydroxy-1-(4-((2-hydroxyethyl)(phenyl)amino)-2-(4-(oxazol-5-yl)phenylamino)-7,8-dihydropyrido[4,3-d]pyrimidin-6(5H)-yl)ethanone;
(S)-2-hydroxy-1-(4-((2-hydroxyethyl)(phenyl)amino)-2-(4-(oxazol-5-yl)phenylamino)-7,8-dihydropyrido[4,3-d]pyrimidin-6(5H)-yl)propan-1-one;
2-((6-(methylsulfonyl)-2-(4-(oxazol-5-yl)phenylamino)-5,6,7,8-tetrahydropyrido[4,3-d]pyrimidin-4-yl)(phenyl)amino)ethanol;
2-((6-(ethylsulfonyl)-2-(4-(oxazol-5-yl)phenylamino)-5,6,7,8-tetrahydropyrido[4,3-d]pyrimidin-4-yl)(phenyl)amino)ethanol;
methyl 4-((2-hydroxyethyl)(phenyl)amino)-2-(4-(oxazol-5-yl)phenylamino)-7,8-dihydropyrido[4,3-d]pyrimidine-6(5H)-carboxylate;
ethyl 4-((2-hydroxyethyl)(phenyeamino)-2-(4-(oxazol-5-yl)phenylamino)-7,8-dihydropyrido[4,3-d]pyrimidine-6(5H)-carboxylate;
4-((2-hydroxyethyl)(phenyl)amino)-N,N-dimethyl-2-(4-(oxazol-5-yl)phenylamino)-7,8-dihydropyrido[4,3-d]pyrimidine-6(5H)-carboxamide;
1-(4-(cyclohexylamino)-2-(4-(oxazol-5-yl)phenylamino)-7,8-dihydropyrido[4,3-d]pyrimidin-6(5H)-yl)ethanone;
(S)-1-(2-(4-(oxazol-5-yl)phenylamino)-4-((tetrahydrofuran-2-yl)methylamino)-7,8-dihydropyrido[4,3-d]pyrimidin-6(5H)-yl)ethanone;
1-(4-((2-hydroxyethyl)(phenyl)amino)-2-(4-(oxazol-5-yl)phenylamino)-7,8-dihydropyrido[4,3-d]pyrimidin-6(5H)-yl)ethanone;
1-(4-(3-(hydroxymethyl)phenylamino)-2-(4-(oxazol-5-yl)phenylamino)-7,8-dihydropyrido[4,3-d]pyrimidin-6(5H)-yl)ethanone;
(S)-1-(4-(2-(hydroxymethyl)indolin-1-yl)-2-(4-(oxazol-5-yl)phenylamino)-7,8-dihydropyrido[4,3-d]pyrimidin-6(5H)-yl)ethanone;
3-((6-acetyl-2-(4-(oxazol-5-yl)phenylamino)-5,6,7,8-tetrahydropyrido[4,3-d]pyrimidin-4-yl)(cyclopropyl)amino)propanenitrile;
1-(4-(benzyl(2-hydroxyethyl)amino)-2-(4-(oxazol-5-yl)phenylamino)-7,8-dihydropyrido[4,3-d]pyrimidin-6(5H)-yl)ethanone;
1-(3-(6-acetyl-2-(4-(oxazol-5-yl)phenylamino)-5,6,7,8-tetrahydropyrido[4,3-d]pyrimidin-4-ylamino)phenyl)ethanone;
1-(4-((2-hydroxy-2-phenylethyl)(methyl)amino)-2-(4-(oxazol-5-yl)phenylamino)-7,8-dihydropyrido[4,3-d]pyrimidin-6(5H)-yl)ethanone;
1-(4-(1-(hydroxymethy)cyclopentylamino)-2-(4-(oxazol-5-yl)phenylamino)-7,8-dihydropyrido[4,3-d]pyrimidin-6(5H)-yl)ethanone;
1-(4-(methyl(pyridin-3-ylmethyl)amino)-2-(4-(oxazol-5-yl)phenylamino)-7,8-dihydropyrido[4,3-d]pyrimidin-6(5H)-yl)ethanone;
(R)-1-(4-(2-(hydroxymethyl)indolin-1-yl)-2-(4-(oxazol-5-yl)phenylamino)-7,8-dihydropyrido[4,3-d]pyrimidin-6(5H)-yl)ethanone;
2-((6-methyl-2-(4-(1-methyl-1H-pyrazol-4-yl)phenylamino)-5,6,7,8-tetrahydropyrido[4,3-d]pyrimidin-4-yl)(phenyl)amino)ethanol;
2-((2-(4-(1-methyl-1H-pyrazol-4-yl)phenylamino)-6-propyl-5,6,7,8-tetrahydropyrido[4,3-d]pyrimidin-4-yl)(phenyl)amino)ethanol;
2-(4-benzyl-2-(4-(2-methyl-1H-imidazol-1-yl)phenylamino)-7,8-dihydropyrido[4,3-d]pyrimidin-6(5H)-yl)ethanol;
4-benzyl-6-methyl-N-(4-(2-methyl-1H-imidazol-1-yl)phenyl)-5,6,7,8-tetrahydropyrido[4,3-d]pyrimidin-2-amine;
2-(4-(2-cyclohexylethyl)-2-(4-(2-methyl-1H-imidazol-1-yl)phenylamino)-7,8-dihydropyrido[4,3-d]pyrimidin-6(5H)-yl)ethanol;
2-(2-(4-(2-methyl-1H-imidazol-1-yl)phenylamino)-4-(4-methylbenzyl)-7,8-dihydropyrido[4,3-d]pyrimidin-6(5H)-yl)ethanol;
2-(4-(3-fluorophenethyl)-2-(4-(2-methyl-1H-imidazol-1-yl)phenylamino)-7,8-dihydropyrido[4,3-d]pyrimidin-6(5H)-yl)ethanol;
6-methyl-N-(4-(2-methyl-1H-imidazol-1-yl)phenyl)-4-(4-methylbenzyl)-5,6,7,8-tetrahydropyrido[4,3-d]pyrimidin-2-amine;
4-(3-fluorophenethyl)-6-methyl-N-(4-(2-methyl-1H-imidazol-1-yl)phenyl)-5,6,7,8-tetrahydropyrido[4,3-d]pyrimidin-2-amine;
4-(2-fluorobenzyl)-6-methyl-N-(4-(2-methyl-1H-imidazol-1-yl)phenyl)-5,6,7,8-tetrahydropyrido[4,3-d]pyrimidin-2-amine;
4-(3-methoxybenzyl)-6-methyl-N-(4-(2-methyl-1H-imidazol-1-yl)phenyl)-5,6,7,8-tetrahydropyrido[4,3-d]pyrimidin-2-amine;
4-(2-cyclohexylethyl)-6-methyl-N-(4-(2-methyl-1H-imidazol-1-yl)phenyl)-5,6,7,8-tetrahydropyrido[4,3-d]pyrimidin-2-amine;
4-(cyclopentylmethyl)-6-methyl-N-(4-(2-methyl-1H-imidazol-1-yl)phenyl)-5,6,7,8-tetrahydropyrido[4,3-d]pyrimidin-2-amine;
2-(4-(2-fluorobenzyl)-2-(4-(2-methyl-1H-imidazol-1-yl)phenylamino)-7,8-dihydropyrido[4,3-d]pyrimidin-6(5H)-yl)ethanol;

2-(4-(3-methoxybenzyl)-2-(4-(2-methyl-1H-imidazol-1-yl)phenylamino)-7,8-dihydropyrido[4,3-d]pyrimidin-6(5H)-yl)ethanol;

1-(4-(2-cyclohexylethyl)-2-(4-(2-methyl-1H-imidazol-1-yl)phenylamino)-7,8-dihydropyrido[4,3-d]pyrimidin-6(5H)-yl)ethanone;

1-(2-(4-(2-methyl-1H-imidazol-1-yl)phenylamino)-4-(4-methylbenzyl)-7,8-dihydropyrido[4,3-d]pyrimidin-6(5H)-yl)ethanone;

1-(4-(3-fluorophenethyl)-2-(4-(2-methyl-1H-imidazol-1-yl)phenylamino)-7,8-dihydropyrido[4,3-d]pyrimidin-6(5H)-yl)ethanone;

6-methyl-N-(4-(2-methyl-1H-imidazol-1-yl)phenyl)-4-((tetrahydro-2H-pyran-4-yl)methyl)-5,6,7,8-tetrahydropyrido[4,3-d]pyrimidin-2-amine;

2-(2-(4-(2-methyl-1H-imidazol-1-yl)phenylamino)-4-((tetrahydro-2H-pyran-4-yl)methyl)-7,8-dihydropyrido[4,3-d]pyrimidin-6(5H)-yl)ethanol;

1-(2-(4-(2-methyl-1H-imidazol-1-yl)phenylamino)-4-((tetrahydro-2H-pyran-4-yl)methyl)-7,8-dihydropyrido[4,3-d]pyrimidin-6(5H)-yl)ethanone;

4-benzyl-N-(3-methoxy-4-(4-methyl-1H-imidazol-1-yl)phenyl)-6-methyl-5,6,7,8-tetrahydropyrido[4,3-d]pyrimidin-2-amine;

N4-cyclohexyl-6-methyl-N2-(4-(2-methyl-1H-imidazol-1-yl)phenyl)-5,6,7,8-tetrahydropyrido[4,3-d]pyrimidine-2,4-diamine;

6-Methyl-N-(4-(2-methyl-1H-imidazol-1-yl)phenyl)-4-(1-phenylethyl)-5,6,7,8-tetrahydropyrido[4,3-d]pyrimidin-2-amine;

6-Methyl-N-(4-(2-methyl-1H-imidazol-1-yl)phenyl)-4-(1-phenylethyl)-5,6,7,8-tetrahydropyrido[4,3-d]pyrimidin-2-amine;

(S)-(1-(6-methyl-2-(methyl(4-(2-methyl-1H-imidazol-1-yl)phenyl)amino)-5,6,7,8-tetrahydropyrido[4,3-d]pyrimidin-4-yl)indolin-2-yl)methanol;

(S)-6-methyl-N2-(4-(2-methyl-1H-imidazol-1-ypphenyl)-N4-((tetrahydrofuran-2-yl)methyl)-5,6,7,8-tetrahydropyrido[4,3-d]pyrimidine-2,4-diamine;

(R)-6-methyl-N2-(4-(2-methyl-1H-imidazol-1-yl)phenyl)-N4-((tetrahydrofuran-2-ylmethyl)-5,6,7,8-tetrahydropyrido[4,3-d]pyrimidine-2,4-diamine;

2-(4-benzyl-2-(3-methoxy-4-(4-methyl-1H-imidazol-1-yl)phenylamino)-7,8-dihydropyrido[4,3-d]pyrimidin-6(5H)-yl)ethanol;

2-(benzyl(6-methyl-2-(4-(2-methyl-1H-imidazol-1-yl)phenytamino)-5,6,7,8-tetrahydropyrido[4,3-d]pyrimidin-4-yDamino)ethanol;

2-(4-(ethyl((tetrahydrofuran-2-yl)methyl)amino)-2-(4-(2-methyl-1H-imidazol-1-yl)phenylamino)-7,8-dihydropyrido[4,3-d]pyrimidin-6(5H)-yl)ethanol;

3-(cyclopropyl(6-methyl-2-(4-(2-methyl-1H-imidazol-1-yl)phenylamino)-5,6,7,8-tetrahydropyrido[4,3-d]pyrimidin-4-yl)amino)propanenitrile;

6-methyl-N2-(4-(2-methyl-1H-imidazol-1-yl)phenyl)-N4-((tetrahydro-2H-pyran-4-yl)methyl)-5,6,7,8-tetrahydropyrido[4,3-d]pyrimidine-2,4-diamine;

(R)-2-(2-(4-(oxazol-5-yl)phenylamino)-4-((tetrahydrofuran-2-yl)methylamino)-7,8-dihydropyrido[4,3-d]pyrimidin-6(5H)-yflethanol;

2-(4-(ethyl((tetrahydrofuran-2-yl)methylamino)-2-(4-(oxazol-5-yl)phenylamino)-7,8-dihydropyrido[4,3-d]pyrimidin-6(5H)-yl)ethanol;

N4-ethyl-6-methyl-N2-(4-(oxazol-5-yl)phenyl)-N4-((tetrahydrofuran-2-yl)methyl)-5,6,7,8-tetrahydropyrido[4,3-d]pyrimidine-2,4-diamine;

(S)-6-methyl-N2-(4-(oxazol-5-yl)phenyl)-N4-((tetrahydrofuran-2-yl)methyl)-5,6,7,8-tetrahydropyrido[4,3-d]pyrimidine-2,4-diamine;

(R)-6-methyl-N2-(4-(oxazol-5-yl)phenyl)-N4-((tetrahydrofuran-2-yl)methyl)-5,6,7,8-tetrahydropyrido[4,3-d]pyrimidine-2,4-diamine;

6-methyl-N2-(4-(oxazol-5-yl)phenyl)-N4-((tetrahydro-2H-pyran-4-ylmethyl)-5,6,7,8-tetrahydropyrido[4,3-d]pyrimidine-2,4-diamine;

2-(2-(4-(oxazol-5-yl)phenylamino)-4-((tetrahydro-2H-pyran-4-yl)methylamino)-7,8-dihydropyrido[4,3-d]pyrimidin-6(5H)-yl)ethanol;

1-(4-(cyclohexyl(methyl)amino)-2-(4-(oxazol-5-yl)phenylamino)-7,8-dihydropyrido[4,3-d]pyrimidin-6(5H)-yl)ethanone;

1-(4-((4-fluorophenyl)(methypamino)-2-(4-(oxazol-5-yl)phenylamino)-7,8-dihydropyrido[4,3-d]pyrimidin-6(5H)-yl)ethanone;

1-(4-(indolin-1-yl)-2-(4-(oxazol-5-yl)phenylamino)-7,8-dihydropyrido[4,3-d]pyrimidin-6(5H)-yl)ethanone;

1-(4-((2-(hydroxymethylbenzyl)(methypamino)-2-(4-(oxazol-5-yl)phenylamino)-7,8-dihydropyrido[4,3-d]pyrimidin-6(5H)-yl)ethanone;

1-(4-(methyl(pyridin-2-ylmethyDamino)-2-(4-(oxazol-5-yl)phenylamino)-7,8-dihydropyrido[4,3-d]pyrimidin-6(5H)-yl)ethanone;

1-(4-(3-(hydroxymethyl)piperidin-1-yl)-2-(4-(oxazol-5-yl)phenylamino)-7,8-dihydropyrido[4,3-d]pyrimidin-6(5H)-yl)ethanone;

1-(4-(2-(hydroxymethyl)piperidin-1-yl)-2-(4-(oxazol-5-yl)phenylamino)-7,8-dihydropyrido[4,3-d]pyrimidin-6(5H)-yDethanone;

N-(3-methoxy-4-(4-methyl-1H-imidazol-1-yl)phenyl)-4-(3-methoxybenzyl)-6-methyl-5,6,7,8-tetrahydropyrido[4,3-d]pyrimidin-2-amine;

1-(2-(3-methoxy-4-(4-methyl-1H-imidazol-1-yl)phenylamino)-4-(3-methoxybenzyl)-7,8-dihydropyrido[4,3-d]pyrimidin-6(5H)-yl)ethanone;

1-(4-(3-methoxybenzyl)-2-(4-(2-methyl-1H-imidazol-1-yl)phenylamino)-7,8-dihydropyrido[4,3-d]pyrimidin-6(5H)-yl)ethanone;

1-(4-(2-fluorobenzyl)-2-(4-(2-methyl-1H-imidazol-1-yl)phenylamino)-7,8-dihydropyrido[4,3-d]pyrimidin-6(5H)-yl)ethanone;

2-(4-benzyl-2-(3-methoxy-4-(4-methyl-1H-imidazol-1-ypphenylamino)-7,8-dihydropyrido[4,3-d]pyrimidin-6(5H)-yl)acetonitrile;

4-benzyl-N-(3-methoxy-4-(4-methyl-1H-imidazol-1-yl)phenyl)-5,6,7,8-tetrahydropyrido[4,3-d]pyrimidin-2-amine;

1-(4-benzyl-2-(3-methoxy-4-(4-methyl-1H-imidazol-1-ypphenylamino)-7,8-dihydropyrido[4,3-d]pyrimidin-6(5H)-yl)ethanone;

1-(4-(1-(3,5-dimethyl-1H-pyrazol-1-ypethyl)-2-(3-methoxy-4-(4-methyl-1H-imidazol-1-yl)phenylamino)-7,8-dihydropyrido[4,3-d]pyrimidin-6(5H)-yl)ethanone;

1-(2-(3-methoxy-4-(4-methyl-1H-imidazol-1-yl)phenylamino)-4-(2-(tetrahydrofuran-2-yl)ethyl)-7,8-dihydropyrido[4,3-d]pyrimidin-6(5H)-yl)ethanone; and N-(3-methoxy-4-(4-methyl-1H-imidazol-1-yl)phenyl)-6-methyl-4-(2-(tetrahydrofuran-2-yl)ethyl)-5,6,7,8-tetrahydropyrido[4,3-d]pyrimidin-2-amine;

as a free base or a pharmaceutically acceptable salt of any foregoing compound.

5. A pharmaceutical composition comprising as active ingredient a therapeutically effective amount of a compound according to claim 1, or a pharmaceutically acceptable salt thereof, in association with pharmaceutically acceptable excipients, carriers or diluents.

* * * * *